United States Patent
Brameld et al.

(10) Patent No.: US 9,573,958 B2
(45) Date of Patent: Feb. 21, 2017

(54) BENZIMIDAZOLE DERIVATIVES AS ITK INHIBITORS

(71) Applicant: Principia Biopharma, Inc., South San Francisco, CA (US)

(72) Inventors: Kenneth Albert Brameld, Menlo Park, CA (US); Timothy Owens, San Carlos, CA (US)

(73) Assignee: PRINCIPIA BIOPHARMA, INC., South San Francisco, CA (US)

( * ) Notice: Subject to any disclaimer, the term of this patent is extended or adjusted under 35 U.S.C. 154(b) by 23 days.

(21) Appl. No.: 14/424,480

(22) PCT Filed: Aug. 27, 2013

(86) PCT No.: PCT/US2013/056877
§ 371 (c)(1),
(2) Date: Feb. 27, 2015

(87) PCT Pub. No.: WO2014/036016
PCT Pub. Date: Mar. 6, 2014

(65) Prior Publication Data
US 2015/0225412 A1    Aug. 13, 2015

Related U.S. Application Data

(60) Provisional application No. 61/695,673, filed on Aug. 31, 2012, provisional application No. 61/728,670, filed on Nov. 20, 2012, provisional application No. 61/782,213, filed on Mar. 14, 2013.

(51) Int. Cl.
| | | |
|---|---|---|
| *C07D 487/10* | (2006.01) |
| *C07D 401/04* | (2006.01) |
| *C07D 401/14* | (2006.01) |
| *C07D 403/06* | (2006.01) |
| *C07D 409/14* | (2006.01) |
| *C07D 413/14* | (2006.01) |
| *C07D 405/14* | (2006.01) |
| *C07D 407/14* | (2006.01) |
| *C07D 491/107* | (2006.01) |
| *C07D 491/10* | (2006.01) |
| *A61K 31/4184* | (2006.01) |
| *A61K 31/422* | (2006.01) |
| *A61K 31/4439* | (2006.01) |
| *A61K 31/454* | (2006.01) |
| *A61K 31/4545* | (2006.01) |
| *A61K 31/496* | (2006.01) |
| *A61K 31/5377* | (2006.01) |
| *A61K 45/06* | (2006.01) |

(52) U.S. Cl.
CPC ......... *C07D 487/10* (2013.01); *A61K 31/4184* (2013.01); *A61K 31/422* (2013.01); *A61K 31/4439* (2013.01); *A61K 31/454* (2013.01); *A61K 31/4545* (2013.01); *A61K 31/496* (2013.01); *A61K 31/5377* (2013.01); *A61K 45/06* (2013.01); *C07D 401/04* (2013.01); *C07D 401/14* (2013.01); *C07D 403/06* (2013.01); *C07D 405/14* (2013.01); *C07D 407/14* (2013.01); *C07D 409/14* (2013.01); *C07D 413/14* (2013.01); *C07D 491/10* (2013.01); *C07D 491/107* (2013.01)

(58) Field of Classification Search
CPC ... C07D 401/04; C07D 401/14; C07D 403/06; C07D 409/14; C07D 413/14; C07D 405/14; C07D 407/14; C07D 491/107; C07D 487/10
See application file for complete search history.

(56) References Cited

U.S. PATENT DOCUMENTS

2008/0207613 A1    8/2008  Styles et al.

FOREIGN PATENT DOCUMENTS

| | | |
|---|---|---|
| JP | 2001199968 | 7/2001 |
| JP | 2005509003 | 4/2005 |
| JP | 2005536533 | 12/2005 |
| WO | 9808818 | 3/1998 |
| WO | 9943672 | 9/1999 |
| WO | 02060879 | 8/2002 |
| WO | 03030902 | 4/2003 |
| WO | 03041708 | 5/2003 |
| WO | 2004014905 | 2/2004 |
| WO | 2005070420 | 8/2005 |
| WO | 2005079791 | 9/2005 |
| WO | 2006078891 | 7/2006 |
| WO | 2007022305 | 2/2007 |
| WO | 2008039218 | 4/2008 |
| WO | 2008121742 | 10/2008 |
| WO | 2010126745 | 11/2010 |
| WO | 2011060440 | 5/2011 |
| WO | 2012158764 | 11/2012 |
| WO | 2012158795 | 11/2012 |
| WO | 2012158810 | 11/2012 |
| WO | 2012158843 | 11/2012 |
| WO | 2013184757 | 12/2013 |

(Continued)

OTHER PUBLICATIONS

Patent Cooperation Treaty, International Search Report issued Dec. 10, 2013 for PCT/US2013/056877, 4 pages.

(Continued)

*Primary Examiner* — Laura L. Stockton
(74) *Attorney, Agent, or Firm* — Bryan Cave LLP

(57) ABSTRACT

The present disclosure is directed to certain inhibitors of kinases such as ITK, BLK, BMX, BTK, JAK3, TEC, TXK, HER2 (ERBB2), or HER4 (ERBB4), in particular ITK, pharmaceutical compositions comprising such compounds, and method of treating diseases mediated by such kinases.

31 Claims, No Drawings

(56) References Cited

FOREIGN PATENT DOCUMENTS

WO  2013184766  12/2013
WO  2013191965  12/2013

OTHER PUBLICATIONS

Moriarty et al., Discovery, SAR and X-ray structure of 1H-benzimidazole-5-carboxylic acid cyclohexyl-methyl amides as inhibitors of inducible T-cell kinase (Itk), Bioorganic & Medicinal Chemistry Letters, 2008, 18, 5545-5549.
Snow et al., Hit-to-lead studies on benzimidazole inhibitors of ITK: Discovery of a novel class of kinase inhibitors, Bioorganic & Medicinal Chemistry Letters, 2007, 17, 3660-3665.
European Patent Office, Extended European Search Report for 13832770.5, EP 2890691, dated Feb. 23, 2016, 7 pages.

BENZIMIDAZOLE DERIVATIVES AS ITK INHIBITORS

FIELD OF THE DISCLOSURE

The present disclosure is directed to certain inhibitors IL2-inducible T-cell kinase (ITK), pharmaceutical compositions comprising such compounds, and method of treating diseases mediated by such kinases.

BACKGROUND

Kinases play critical roles in signaling pathways controlling fundamental cellular processes such as proliferation, differentiation, and death (apoptosis). The IL2-inducible T-cell kinase (ITK) is a member of the Tec family of kinases. ITK dysfunction (e.g., overexpression) has been implicated in lung inflammation, recruitment of eosinophils, production of mucus (see Mueller, et al., Attenuation of immunological symptoms of allergic asthma in mice lacking the tyrosine kinase ITK, *Journal of Immunology*, 170:5056-5063) as well as reduced airway hyperresponsiveness (see Ferrara, et al., Reduced airway hyperresponsiveness and tracheal responses during allergic asthma in mice lacking tyrosine kinase inducible T-cell kinase, *Journal of Allergy and Clinical Immunology*, 117:780-786). In addition, using knock-out mice, RNAi and chemical inhibitors, ITK has been implicated in T cell-driven inflammatory diseases of the skin (see von Bonin et al. Inhibition of the IL-2-inducible tyrosine kinase (Itk) activity: a new concept for the therapy of inflammatory skin diseases, *Exp Dermatol*, 20:41-47, 2010). Itk was found to be expressed in lymphoid tissue and upregulated in lesional skin from patients with allergic dermatitis, atopic dermatitis and psoriasis. Itk also plays a role in the pathophysiology of T cell malignancies (see Guo W. et. al., Molecular characteristics of CTA056, a novel Itk inhibitor which selectively targets malignant T cell and modulates oncomirs, Molecular Pharmacology, doi:10.1124/mol.112.079889).

Thus, there is a need for compounds that inhibit the activity of Itk. The present disclosure can fulfill this and related needs.

SUMMARY

In one aspect, the present disclosure provides a compound of Formula (IA):

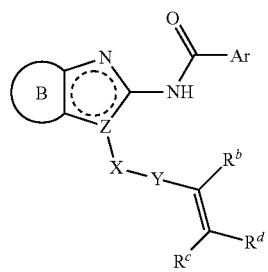

Formula (IA)

wherein:

(i) when Z is N, then ring B is:

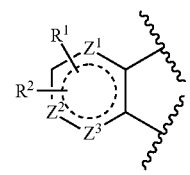

(a)

wherein:

$Z^1$, $Z^2$, and $Z^3$ are CH (or C if substituted with $R^1$ or $R^2$) or $Z^1$, $Z^2$, and $Z^3$ are independently N or CH (or C if substituted with $R^1$ or $R^2$) provided that only one of $Z^1$, $Z^2$, and $Z^3$ is N; and (ii) when Z is C, then ring B is:

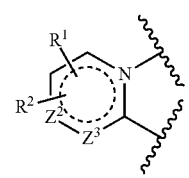

(b)

wherein:

$Z^2$ and $Z^3$ are CH (or C if substituted with $R^1$ or $R^2$) or $Z^2$ and $Z^3$ are independently N or CH (or C if substituted with $R^1$ or $R^2$) provided that only one of $Z^2$ and $Z^3$ is N;

$R^1$ is hydrogen, hydroxyalkyl, alkoxyalkyl, —$NR^3COR^4$, —$CONR^3R^5$, -(alkylene)-$NR^3R^5$ (where each $R^3$ is hydrogen, or alkyl, $R^4$ is alkyl, haloalkyl, cycloalkyl, optionally substituted aryl or optionally substituted heteroaryl, and each $R^5$ is hydrogen, alkyl, haloalkyl, hydroxyalkyl, alkoxyalkyl, acyl, cycloalkylalkyl, or heterocyclylalkyl optionally substituted with one, two, or three substituents independently selected from alkyl, halo, hydroxy, alkoxy, hydroxyalkyl, or alkoxyalkyl; or $R^3$ and $R^5$ together with the nitrogen atom to which they are attached form heterocycloamino or spiroheterocycloamino wherein the heterocycloamino ring is optionally substituted with one, two, or three substituents independently selected from alkyl, halo, hydroxyl, alkoxy, hydroxyalkyl, or alkoxyalkyl, —$NR^6R^7$ (where $R^6$ is hydrogen or alkyl and $R^7$ is hydrogen, alkyl, haloalkyl, hydroxyalkyl, alkoxyalkyl, or acyl, or $R^6$ and $R^7$ together with the nitrogen atom to which they are attached form heterocyclyl optionally substituted with one or two substituents independently selected from alkyl, halo, hydroxyl, hydroxyalkyl, or alkoxyalkyl), or —$OR^8$ (where $R^8$ is hydroxyalkyl, alkoxyalkyl, or heterocyclylalkyl optionally substituted with one, two, or three substituents independently selected from alkyl, halo, hydroxyalkyl, or alkoxyalkyl);

$R^2$ is hydrogen, alkyl, cycloalkyl, cyano, alkoxy, hydroxy, halo, haloalkyl, or haloalkoxy;

Ar is aryl or heteroaryl, each ring optionally substituted with one, two, or three substituents independently selected from alkyl, alkoxy, hydroxy, cyano, alkylthio, halo, haloalkyl, haloalkoxy, cycloalkyl, optionally substituted phenyl, or optionally substituted heteroaryl;

X is alkylene, cycloalkylene,

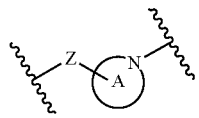

(where Z is bond or alkylene, and ring A is heterocycloamino optionally substituted with one or two substituents independently selected from alkyl, hydroxy, or fluoro), -alkylene-O—, -cycloalkylene-NR$^a$—, or -(alkylene)-NR$^a$— (where each R$^a$ is hydrogen, alkyl or cycloalkyl);

Y is —CO— or —SO$_2$—;

R$^b$ is hydrogen, cyano, nitro, halo, haloalkyl, haloalkoxy, alkylthio, or alkylsulfonyl;

R$^c$ is hydrogen, alkyl, haloalkoxy, substituted alkyl, cycloalkyl, cycloalkyleneNR$^d$R$^e$ or cycloalkylene(alkylene)NR$^d$R$^e$ (where R$^d$ and R$^e$ are independently hydrogen, alkyl, or cycloalkyl), alkoxyalkyloxyalkyl, or 3 to 6 membered saturated monocyclic heterocyclyl containing one or two heteroatoms selected from N, O, or S and optionally substituted with one or two substituents independently selected from hydroxy, alkyl or fluoro; and R$^d$ is hydrogen or alkyl, or R$^b$ and R$^d$ together form a bond; provided that when R$^b$ is other than hydrogen, then R$^c$ is not hydrogen and R$^d$ is hydrogen;

and/or a pharmaceutically acceptable salt thereof.

In another aspect, the present disclosure provides a compound of Formula (I):

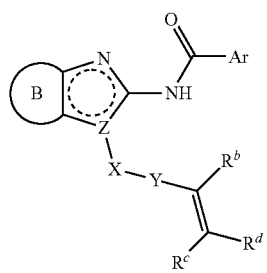

Formula (I)

wherein:

(i) when Z is N, then ring B is:

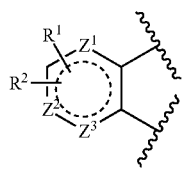

(a)

wherein:

Z$^1$, Z$^2$, and Z$^3$ are CH (or C if substituted with R$^1$ or R$^2$) or Z$^1$, Z$^2$, and Z$^3$ are independently N or CH (or C if substituted with R$^1$ or R$^2$) provided that only one of Z$^1$, Z$^2$, and Z$^3$ is N; and (ii) when Z is C, then ring B is:

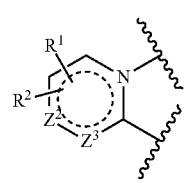

(b)

wherein:

Z$^2$ and Z$^3$ are CH (or C if substituted with R$^1$ or R$^2$) or Z$^2$ and Z$^3$ are independently N or CH (or C if substituted with R$^1$ or R$^2$) provided that only one of Z$^2$ and Z$^3$ is N;

R$^1$ is hydrogen, hydroxyalkyl, alkoxyalkyl, —NR$^3$COR$^4$, —CONR$^3$R$^5$, -(alkylene)-NR$^3$R$^5$ (where each R$^3$ is hydrogen or alkyl, R$^4$ is cycloalkyl, optionally substituted aryl or optionally substituted heteroaryl, and each R$^5$ is hydrogen, alkyl, haloalkyl, hydroxyalkyl, alkoxyalkyl, acyl, or heterocyclylalkyl optionally substituted with one or two substituents independently selected from alkyl, halo, hydroxyalkyl, or alkoxyalkyl; or R$^3$ and R$^5$ together with the nitrogen atom to which they are attached form heterocycloamino or spiro-heterocycloamino wherein the heterocycloamino ring is optionally substituted with one or two substituents independently selected from alkyl, halo, hydroxyalkyl, or alkoxyalkyl, —NR$^6$R$^7$ (where R$^6$ is hydrogen or alkyl and R$^7$ is hydrogen, alkyl, haloalkyl, hydroxyalkyl, alkoxyalkyl, or acyl, or R$^6$ and R$^7$ together with the nitrogen atom to which they are attached form heterocyclyl optionally substituted with one or two substituents independently selected from alkyl, halo, hydroxyl, hydroxyalkyl, or alkoxyalkyl), or —OR$^8$ (where R$^8$ is hydroxyalkyl, alkoxyalkyl, or heterocyclylalkyl optionally substituted with one or two substituents independently selected from alkyl, halo, hydroxyalkyl, or alkoxyalkyl);

R$^2$ is hydrogen, alkyl, cycloalkyl, cyano, alkoxy, hydroxy, halo, haloalkyl, or haloalkoxy;

Ar is aryl or heteroaryl, each ring optionally substituted with one, two, or three substituents independently selected from alkyl, alkoxy, hydroxy, cyano, alkylthio, halo, haloalkyl, haloalkoxy, cycloalkyl, optionally substituted phenyl, or optionally substituted heteroaryl;

X is alkylene, cycloalkylene,

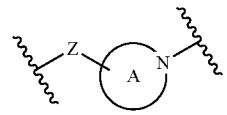

(where Z is bond or alkylene, and ring A is heterocycloamino optionally substituted with one or two substituents independently selected from alkyl, hydroxy, or fluoro), -alkylene-O—, -cycloalkylene-NR$^a$—, or (alkylene)-NR$^a$— (where each R$^a$ is hydrogen, alkyl or cycloalkyl);

Y is —CO— or —SO$_2$—;

R$^b$ is hydrogen, cyano, nitro, halo, haloalkyl, haloalkoxy, alkylthio, or alkylsulfonyl;

R$^c$ is hydrogen, alkyl, haloalkoxy, substituted alkyl, cycloalkyl, cycloalkyleneNR$^d$R$^e$ or cycloalkylene(alkylene)NR$^d$R$^e$ (where R$^d$ and R$^e$ are independently hydrogen, alkyl, or cycloalkyl), or 3 to 6 membered saturated monocyclic heterocyclyl containing one or two heteroatoms selected from N, O, or S and optionally substituted with one or two substituents independently selected from hydroxy, alkyl or fluoro; and $R^d$ is hydrogen, alkyl, or $R^b$ and $R^d$ together form a bond; provided that when $R^b$ is other than hydrogen, then $R^c$ is not hydrogen and $R^d$ is hydrogen; and/or a pharmaceutically acceptable salt thereof.

In one embodiment, the compounds of Formula (IA) and (I) and/or pharmaceutically acceptable salts thereof (and any embodiments thereof disclosed herein) where —X—Y—C($R^b$)=CR$^c$R$^d$ is —X—Y—C($R^b$)=CHR$^c$ where $R^b$ and $R^c$ are not hydrogen, the compounds of Formula (IA) and (I) can be reversible covalent inhibitors.

In one embodiment, the compounds of Formula (IA) and (I) and/or pharmaceutically acceptable salts thereof (and any embodiments thereof disclosed herein) where —X—Y—C($R^b$)=CR$^c$R$^d$ is —X—Y—C($R^b$)=CHR$^c$ where $R^b$ is cyano and $R^c$ is not hydrogen, the compounds of Formula (IA) and (I) can be reversible covalent inhibitors.

In one embodiment, the compounds of Formula (IA) and (I) and/or pharmaceutically acceptable salts thereof (and any embodiments thereof disclosed herein) where —X—Y—C($R^b$)=CR$^c$R$^d$ is —X—Y—C($R^b$)=CHR$^c$ where $R^b$ and $R^c$ are not hydrogen the compounds of Formula (IA) and (I) can be reversible covalent inhibitors where the reversibility of the covalent bond is determined by Mass spec method described in Biological Example 7 below.

In one embodiment, the compounds of Formula (IA) and (I) and/or pharmaceutically acceptable salts thereof (and any embodiments thereof disclosed herein) where —X—Y—C($R^b$)=CR$^c$R$^d$ is —X—Y—C($R^b$)=CHR$^c$ where $R^b$ is cyano and $R^c$ is not hydrogen, the compounds of Formula (IA) and (I) can be reversible covalent inhibitors where the reversibility of the covalent bond is determined by Mass spec method described in Biological Example 7 below. In another embodiment, the compounds of Formula (IA) and (I) and/or pharmaceutically acceptable salts thereof (and any embodiments thereof disclosed herein) where —X—Y—C($R^b$)=CR$^c$R$^d$ is —X—Y—C($R^b$)=CHR$^c$ where $R^b$ and $R^c$ are not hydrogen, in particular where $R^b$ is cyano, the compounds of Formula (IA) and (I) and/or pharmaceutically acceptable salts thereof can form reversible covalent bond with Cys442 of ITK.

In yet another embodiment, the compounds of Formula (IA) and (I) and/or pharmaceutically acceptable salts thereof (and any embodiments thereof disclosed herein) where —X—Y—C($R^b$)=CR$^c$R$^d$ is —X—Y—C(H)=CR$^c$R$^d$ where $R^c$ and $R^d$ are as defined above, the compounds of Formula (IA) and (I) and/or pharmaceutically acceptable salts thereof can form irreversible covalent bond with Cys442 of ITK.

In a second aspect, provided herein are pharmaceutical compositions comprising a compound disclosed herein, and/or a pharmaceutically acceptable salt thereof; and a pharmaceutically acceptable excipient.

In a third aspect, provided herein are methods of treating a disease treatable by inhibition of ITK in a patient which method comprises administering to the patient in need thereof, a pharmaceutical composition comprising a compound disclosed herein and/or a pharmaceutically acceptable salt thereof in a therapeutically effective amount and a pharmaceutically acceptable excipient. In one embodiment of the third aspect, the patient is in recognized need of such treatment. The compound disclosed herein and/or a pharmaceutically acceptable salt thereof can also inhibit one or more of ITK, BLK, BMX, BTK, JAK3, TEC, TXK (also known as RLK), HER2 (ERBB2), or HER4 (ERBB4) kinase. In one embodiment, the disease is selected from inflammatory disorders, autoimmune disorders, and lymphoproliferative disorders. In one embodiment, the inflammatory disorder, is asthma, allergic dermatitis, atopic dermatitis and psoriasis. In one embodiment, any compound of Formula (IA) or (I) is administered in combination with at least one anti-inflammatory, anti-autoimmune, or anti-lymphoproliferative agent described herein.

DESCRIPTION

Definitions:

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkylthio" means a —SR radical where R is alkyl as defined above, e.g., methylthio, ethylthio, and the like.

"Alkylsulfonyl" means a —SO$_2$R radical where R is alkyl as defined above, e.g., methylsulfonyl, ethylsulfonyl, and the like.

"Alkoxy" means a —OR radical where R is alkyl as defined above, e.g., methoxy, ethoxy, propoxy, or 2-propoxy, n-, iso-, or tert-butoxy, and the like.

"Alkylamino" means a —NHR radical where R is alkyl as defined above, e.g., methylamino, ethylamino, and the like.

"Acyl" means a —COR radical where R is alkyl, haloalkyl, optionally substituted aryl, or optionally substituted heteroaryl as defined herein, e.g., acetyl, trifluoroacetyl, benzoyl, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Alkoxyalkyloxyalkyl" means a -(alkylene)-O-(alkylene)-OR where R is alkyl as defined above, e.g., 2-methoxyethyloxyethyl, —C(CH$_3$)$_2$O—(CH$_2$)$_2$—OCH$_3$, and the like.

"Alkoxycarbonyl" means a —C(O)OR radical where R is alkyl as defined above, e.g., methoxycarbonyl, ethoxycarbonyl, and the like.

"Aminoalkyl" means a linear monovalent hydrocarbon radical of one to six carbon atoms or a branched monovalent hydrocarbon radical of three to six carbons substituted with at least one —NR$^a$R$^b$ group, preferably one or two NR$^a$R$^b$ groups, where $R^a$ and $R^b$ are independently hydrogen or alkyl, e.g., aminomethyl, methylaminomethyl, dimethylaminomethyl, 2-aminoethyl, 1-, 2-, or 3-methylaminopropyl, and the like.

"Aryl" means a monovalent monocyclic or bicyclic aromatic hydrocarbon radical of 6 to 10 ring atoms e.g., phenyl or naphthyl.

"Cycloalkyl" means a cyclic saturated monovalent hydrocarbon radical of three to ten carbon atoms, e.g., cyclopropyl, cyclobutyl, cyclopentyl, or cyclohexyl, and the like.

"Cycloalkylalkyl" means an -(alkylene)-R where R is cycloalkyl as defined above, e.g., cyclopropylmethyl, cyclobutylmethyl, cyclopentylethyl, or cyclohexylethyl, and the like.

"Cycloalkylene" means a divalent cyclic saturated monovalent hydrocarbon radical of three to ten carbon atoms, e.g., cyclopropylene, cyclobutylene, cyclopentylene, or cyclohexylene, and the like.

"CycloalkyleneNR$^d$R$^e$" and "Cycloalkylene(alkylene)NR$^d$R$^e$" means a radical of following structure:

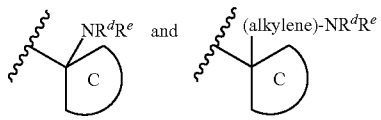

respectively, where ring C is cycloalkylene and R$^d$ and R$^e$ are independently hydrogen, alkyl, or cycloalkyl each term as defined herein.

"Dialkylamino" means a —NR$_2$ radical where each R is independently alkyl as defined above, e.g., dimethylamino, methylethylamino, and the like.

"Halo" means fluoro, chloro, bromo, or iodo, preferably fluoro or chloro.

"Haloalkyl" means alkyl radical as defined above, which is substituted with one or more halogen atoms, preferably one to five halogen atoms, preferably fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it is referred to in this Application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it is referred to in this Application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Heterocyclyl" means a saturated or unsaturated monovalent monocyclic group of 4 to 8 ring atoms in which one or two ring atoms are heteroatom selected from N, O, or S(O)n, where n is an integer from 0 to 2, the remaining ring atoms being C. The heterocyclyl ring is optionally fused to a (one) aryl or heteroaryl ring as defined herein provided the aryl and heteroaryl rings are monocyclic. The heterocyclyl ring fused to monocyclic aryl or heteroaryl ring is also referred to in this Application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds provided that the ring is not aromatic. When the heterocyclyl group is a saturated ring and is not fused to aryl or heteroaryl ring as stated above, it is also referred to herein as saturated monocyclic heterocyclyl.

"Heterocyclylalkyl" means -(alkylene)-R where R is heterocyclyl which is a saturated or unsaturated monovalent monocyclic group of 4 to 8 ring atoms in which one or two ring atoms are heteroatom selected from N, O, or S(O)n, where n is an integer from 0 to 2, the remaining ring atoms being C. Additionally, one or two ring carbon atoms in the heterocyclyl ring can optionally be replaced by a —CO— group. More specifically the term heterocyclylalkyl includes, but is not limited to, pyrrolidin-1-ylmethyl, pyrrolidinylethyl, piperidinylmethyl, piperidinylethyl, morpholinylethyl, piperazinylethyl, tetrahydropyranylethyl, thiomorpholinoethyl, and the like.

"Heterocycloamino" means a saturated or unsaturated monovalent monocyclic group of 4 to 8 ring atoms in which one or two ring atoms are heteroatom selected from N, O, or S(O)n, where n is an integer from 0 to 2, the remaining ring atoms being C provided that at least one of the ring atoms is N. Additionally, one or two ring carbon atoms in the heterocycloamino ring can optionally be replaced by a —CO— group. Unless otherwise stated, the heterocycloamino ring can optionally be substituted with one, two, or three substituents independently selected from alkyl, hydroxyl, halo, alkoxy, amino, alkylamino, or dialkylamino.

"Heteroaryl" means a monovalent monocyclic or bicyclic aromatic radical of 5 to 10 ring atoms where one or more, preferably one, two, or three, ring atoms are heteroatom selected from N, O, or S, the remaining ring atoms being carbon. Representative examples include, but are not limited to, pyrrolyl, pyrazolyl, thienyl, thiazolyl, imidazolyl, furanyl, indolyl, isoindolyl, oxazolyl, isoxazolyl, benzothiazolyl, benzoxazolyl, benzimidazolyl, quinolinyl, isoquinolinyl, pyridinyl, pyrimidinyl, pyrazinyl, pyridazinyl, triazolyl, tetrazolyl, and the like.

The present disclosure also includes the prodrugs of compounds of Formula (IA) and (I) and/or a pharmaceutically acceptable salt thereof. The term prodrug is intended to represent covalently bonded carriers, which are capable of releasing the active ingredient of Formula (IA) and (I) when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vivo or by routine manipulation. Prodrugs of compounds of Formula (IA) and (I) include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylamino-carbonyl) of hydroxy or amino functional groups in compounds of Formula (IA) and (I)), amides (e.g., trifluoroacetylamino, acetylamino, and the like), and the like. Prodrugs of compounds of Formula (IA) and (I) are also within the scope of this disclosure.

The present disclosure also includes protected derivatives of compounds of Formula (IA) and (I) and/or a pharmaceutically acceptable salt thereof. For example, when compounds of Formula (IA) and (I) contain groups such as hydroxy, carboxy, thiol or any group containing a nitrogen atom(s), these groups can be protected with a suitable protecting groups. A comprehensive list of suitable protective groups can be found in T. W. Greene, Protective Groups in Organic Synthesis, John Wiley & Sons, Inc. (1999), the disclosure of which is incorporated herein by reference in its entirety. The protected derivatives of compounds of Formula (IA) and (I) can be prepared by methods well known in the art.

The present disclosure also includes amorphous or polymorphic forms (crystalline) and deuterated forms of compounds of Formula (IA) and (I) and/or a pharmaceutically acceptable salt thereof.

A "pharmaceutically acceptable salt" of a compound means a salt that is pharmaceutically acceptable and that possesses the desired pharmacological activity of the parent compound. Such salts include: acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

The compounds of the present disclosure may have asymmetric centers. Compounds of the present disclosure containing an asymmetrically substituted atom may be isolated in optically active or racemic forms. It is well known in the art how to prepare optically active forms, such as by resolution of materials. All chiral, diastereomeric, racemic forms are within the scope of this disclosure, unless the specific stereochemistry is specifically indicated.

Certain compounds of Formula (IA) and (I) can exist as tautomers and/or geometric isomers. For example, the compound of Formula (IA) and (I) can exist in following tautomeric form:

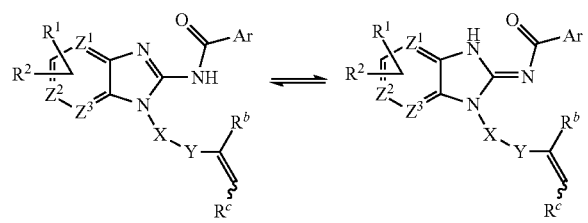

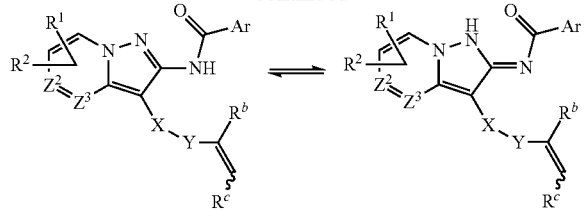

All possible tautomers are within the scope of the present disclosure. Additional, the —CR$^b$═CR$^c$R$^d$ group in the compound of Formula (IA) and (I) can exist as cis and trans isomers. The individual cis or trans forms and mixtures thereof are within the scope of the present disclosure unless a specific isomeric form is specifically indicated. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all polymorphic forms and hydrates of a compound of Formula (IA) and (I) and/or a pharmaceutically acceptable salt thereof are within the scope of this disclosure.

"Oxo" and "carbonyl" mean ═(O) and C═O, group respectively.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

"Optionally substituted aryl" means aryl as defined above which is substituted with one, two, or three substituents independently selected from alkyl, alkoxy, halo, haloalkyl, haloalkoxy, hydroxy, carboxy, alkoxycarbonyl, cyano, alkylsulfonyl, amino, alkylamino, dialkylamino, aminoalkyl or cycloalkyl.

"Optionally substituted heteroaryl" means heteroaryl as defined above which is substituted with one, two, or three substituents independently selected from alkyl, alkoxy, halo, haloalkyl, haloalkoxy, hydroxy, carboxy, alkoxycarbonyl, cyano, alkylsulfonyl, amino, alkylamino, dialkylamino, aminoalkyl or cycloalkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use.

"A pharmaceutically acceptable carrier/excipient" as used in the specification and claims includes both one and more than one such excipient.

"Spiroheterocycloamino" means a bicyclic ring of 7 to 12 ring atoms and joined through one ring atom in which one or two ring atoms are heteroatom selected from N, O, or S(O)$_n$, where n is an integer from 0 to 2, the remaining ring atoms being C provided that at least one of the ring atoms is N. Additionally, one or two ring carbon atoms in the heterocycloamino ring can optionally be replaced by a —CO— group.

"Substituted alkyl" means alkyl group as defined herein which is substituted with one, two, or three substituents independently selected from hydroxyl, alkoxy, carboxy, cyano, alkoxycarbonyl, alkylthio, alkylsulfonyl, halo, haloalkoxy, —CONRR' or —NRR' (where each R is hydrogen, alkyl, hydroxyalkyl, alkoxyalkyl, or heterocyclyl and each R' is hydrogen, alkyl, or cycloalkyl), spiroheterocycloamino, or heterocyclyl (preferably heterocycloamino) optionally substituted with one or two groups independently selected from alkyl, hydroxyl, alkoxy, alkylthio, alkylsulfonyl, halo, or —CONRR' where (where R is hydrogen, alkyl, hydroxyalkyl, or alkoxyalkyl, and R' is hydrogen, alkyl, or cycloalkyl). In one embodiment, substituted alkyl is alkyl group as defined herein which is substituted with one, two, or three substituents independently selected from hydroxyl, alkoxy, carboxy, cyano, alkoxycarbonyl, alkylthio, alkylsulfonyl, halo, haloalkoxy, —CONRR' or —NRR' (where each R is hydrogen, alkyl, hydroxyalkyl, or alkoxyalkyl, and each R' is hydrogen, alkyl, or cycloalkyl), or heterocyclyl (preferably heterocycloamino) optionally substituted with one or two groups independently selected from alkyl, hydroxyl, alkoxy, alkylthio, alkylsulfonyl, halo, or —CONRR' where (where R is hydrogen, alkyl, hydroxyalkyl, or alkoxyalkyl, and R' is hydrogen, alkyl, or cycloalkyl).

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease;
(2) inhibiting the disease, i.e., arresting or reducing the development of the disease or its clinical symptoms; or
(3) relieving the disease, i.e., causing regression of the disease or its clinical symptoms.

A "therapeutically effective amount" means the amount of a compound of Formula (IA) and (I) that, when administered to a patient for treating a disease, is sufficient to effect such treatment for the disease. The "therapeutically effective amount" will vary depending on the compound, the disease and its severity and the age, weight, etc., of the patient to be treated.

Representative compounds of the disclosure are provided in Table I below.

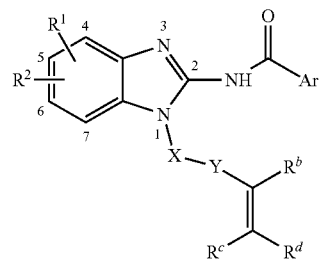

| Cpd # | $R^1$ | $R^2$ | Ar | —X—Y— | $R^b$ | $R^d$ | $R^b + R^d$ | $R^c$ |
|---|---|---|---|---|---|---|---|---|
| 1 | H | H | 4-Clphenyl | piperidin-4-yl-C(O)- | H | H | | H |
| 2 | H | H | pyridin-3-yl | piperidin-4-yl-C(O)- | H | H | | H |
| 3 | H | H | 4-Clphenyl | piperidin-3-yl-C(O)- | H | H | | H |
| 4 | H | H | 4-Clphenyl | piperidin-4-yl-C(O)- | CN | H | | isopropyl |

-continued
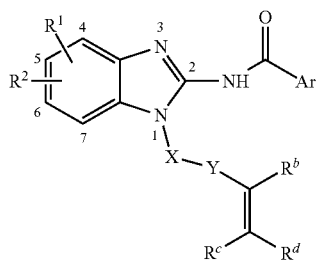
| Cpd # | R¹ | R² | Ar | —X—Y— | $R^b$ | $R^d$ | $R^b + R^d$ | $R^c$ |
|---|---|---|---|---|---|---|---|---|
| 5 | H | H | pyridin-3-yl | 3-piperidinyl-C(O)- | CN | H | | isopropyl |
| 6 | H | H | pyridin-3-yl | 3-piperidinyl-C(O)- | H | H | | H |
| 7 | H | H | 4-Clphenyl | 2-(CH₂)-pyrrolidinyl-C(O)- | CN | H | | isopropyl |
| 8 | H | H | 4-Clphenyl | 2-(CH₂)-pyrrolidinyl-C(O)- | H | H | | H |
| 9 | H | H | pyridin-3-yl | 4-piperidinyl-C(O)- | CN | H | | isopropyl |
| 10 | H | H | pyridin-3-yl | 2-(CH₂)-pyrrolidinyl-C(O)- | CN | H | | isopropyl |

-continued

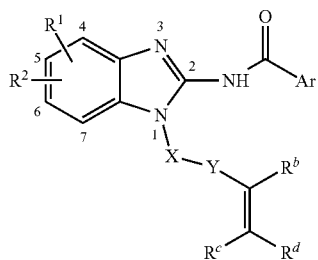

| Cpd # | R¹ | R² | Ar | —X—Y— | R$^b$ | R$^d$ | R$^b$ + R$^d$ | R$^c$ |
|---|---|---|---|---|---|---|---|---|
| 11 | H | H | pyridin-3-yl | (2-pyrrolidinyl-CH₂–, N-acyl) | H | H | | H |
| 12 | 5-(S)-CH₂NHCH(CH₃)C(CH₃)₃ | H | 4-Clphenyl | (4-piperidinyl, N-acyl) | H | H | | H |
| 13 | 5-(S)-CH₂N(COCF₃)CH(CH₃)C(CH₃)₃ | H | 4-Clphenyl | (3-piperidinyl, N-acyl) | CN | H | | isopropyl |
| 14 | 5-(S)-CH₂N(COCF₃)CH(CH₃)C(CH₃)₃ | H | 4-Clphenyl | (3-piperidinyl, N-acyl) | H | H | | H |
| 15 | 5-(S)-CH₂N(COCF₃)CH(CH₃)C(CH₃)₃ | H | 4-Clphenyl | (2-pyrrolidinyl-CH₂–, N-acyl) | CN | H | | isopropyl |
| 16 | 5-(S)-CH₂N(COCF₃)CH(CH₃)C(CH₃)₃ | H | 4-Clphenyl | (2-pyrrolidinyl-CH₂–, N-acyl) | H | H | | H |

-continued

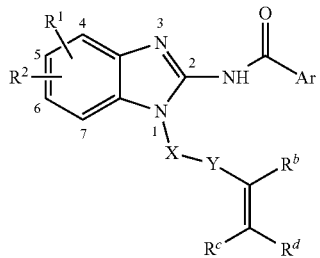

| Cpd # | R¹ | R² | Ar | —X—Y— | Rᵇ | Rᵈ | Rᵇ + Rᵈ | Rᶜ |
|---|---|---|---|---|---|---|---|---|
| 17 | 5-(S)-CH₂N(CH₃)CH(CH₃)C(CH₃)₃ | H | 4-Clphenyl | 2-pyrrolidinyl-N-C(O)- | CN | H | | isopropyl |
| 18 | 5-(S)-CH₂N(CH₃)CH(CH₃)C(CH₃)₃ | H | 4-Clphenyl | 3-piperidinyl-N-C(O)- | CN | H | | isopropyl |
| 19 | H | H | 5-(pyrazol-4-yl)-thien-2-yl | 3-piperidinyl-N-C(O)- | CN | H | | isopropyl |
| 20 | H | H | 5-(pyrazol-4-yl)-thien-2-yl | 3-piperidinyl-N-C(O)- | H | H | | H |
| 21 | H | H | 5-(pyrazol-4-yl)-thien-2-yl | 3-piperidinyl-N-C(O)- | CN | H | | —C(CH₃)₂N(CH₃)₂ |
| 22 | H | H | 5-(pyrazol-4-yl)-thien-2-yl | 3-piperidinyl-N-C(O)- | H | H | | —CH₂N(CH₃)₂ |

-continued

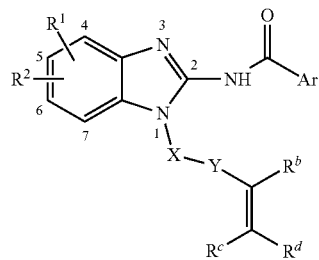

| Cpd # | R¹ | R² | Ar | —X—Y— | R$^b$ | R$^d$ | R$^b$ + R$^d$ | R$^c$ |
|---|---|---|---|---|---|---|---|---|
| 23 | 5-(S)-CH$_2$NHCH(CH$_3$)C(CH$_3$)$_3$ | H | 4-Clphenyl | 3-piperidinyl-N-C(O)- | CN | H | | isopropyl |
| 24 | 5-(S)-CH$_2$NHCH(CH$_3$)C(CH$_3$)$_3$ | H | 4-Clphenyl | 3-piperidinyl-N-C(O)- | CN | H | | —C(CH$_3$)$_2$NH$_2$ |
| 25 | 5-(S)-CH$_2$NHCH(CH$_3$)C(CH$_3$)$_3$ | H | 4-Clphenyl | 3-piperidinyl-N-C(O)- | CN | H | | —C(CH$_3$)$_2$NHCH$_3$ |
| 26 | 5-(S)-CH$_2$NHCH(CH$_3$)C(CH$_3$)$_3$ | H | 4-Clphenyl | 3-piperidinyl-N-C(O)- | CN | H | | —C(CH$_3$)$_2$N(CH$_3$)$_2$ |
| 27 | 5-(S)-CH$_2$NHCH(CH$_3$)C(CH$_3$)$_3$ | H | 4-Clphenyl | 3-piperidinyl-N-C(O)- | H | H | | H |
| 28 | 5-(S)-CH$_2$NHCH(CH$_3$)C(CH$_3$)$_3$ | H | 4-Clphenyl | 2-pyrrolidinyl-CH$_2$/N-C(O)- | CN | H | | isopropyl |

-continued

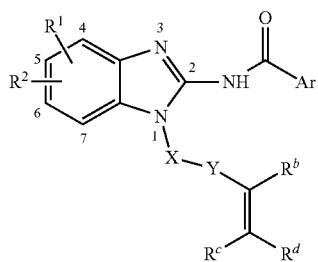

| Cpd # | R¹ | R² | Ar | —X—Y— | R$^b$ | R$^d$ | R$^b$ + R$^d$ | R$^c$ |
|---|---|---|---|---|---|---|---|---|
| 29 | 5-(S)-CH$_2$NHCH(CH$_3$)C(CH$_3$)$_3$ | H | 4-Clphenyl | pyrrolidine-acyl | CN | H | | —C(CH$_3$)$_2$NH$_2$ |
| 30 | 5-(S)-CH$_2$NHCH(CH$_3$)C(CH$_3$)$_3$ | H | 4-Clphenyl | pyrrolidine-acyl | CN | H | | —C(CH$_3$)$_2$NHCH$_3$ |
| 31 | 5-(S)-CH$_2$NHCH(CH$_3$)C(CH$_3$)$_3$ | H | 4-Clphenyl | pyrrolidine-acyl | CN | H | | —C(CH$_3$)$_2$N(CH$_3$)$_2$ |
| 32 | 5-(S)-CH$_2$NHCH(CH$_3$)C(CH$_3$)$_3$ | H | 4-Clphenyl | pyrrolidine-acyl | CN | H | | —C(CH$_3$)$_2$OC$_2$H$_5$ |
| 33 | 5-(S)-CH$_2$NHCH(CH$_3$)C(CH$_3$)$_3$ | H | 4-Clphenyl | pyrrolidine-acyl | H | H | | H |
| 34 | 5-(S)-CH$_2$NHCH(CH$_3$)C(CH$_3$)$_3$ | H | 4-Clphenyl | (R)-pyrrolidine-acyl | H | H | | H |

-continued

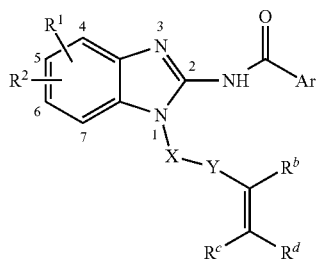

| Cpd # | R¹ | R² | Ar | —X—Y— | R$^b$ | R$^d$ | R$^b$ + R$^d$ | R$^c$ |
|---|---|---|---|---|---|---|---|---|
| 35 | 5-(S)-CH$_2$NHCH(CH$_3$)C(CH$_3$)$_3$ | H | 4-Clphenyl | (3-piperidinyl carbonyl) | CN | H | | tert-butyl |
| 36 | 5-(S)-CH$_2$NHCH(CH$_3$)C(CH$_3$)$_3$ | H | 4-Clphenyl | (2-pyrrolidinylmethyl carbonyl) | CN | H | | tert-butyl |
| 37 | 5-(S)-CH$_2$NHCH(CH$_3$)C(CH$_3$)$_3$ | H | 4-CHF$_2$phenyl | (2-pyrrolidinylmethyl carbonyl) | H | H | | H |
| 38 | 5-(S)-CH$_2$NHCH(CH$_3$)C(CH$_3$)$_3$ | H | 4-CHF$_2$phenyl | (2-pyrrolidinylmethyl carbonyl) | CN | H | | isopropyl |
| 39 | 5-(S)-CH$_2$NHCH(CH$_3$)C(CH$_3$)$_3$ | H | 5-CHF$_2$thien-2-yl | (2-pyrrolidinylmethyl carbonyl) | H | H | | H |
| 40 | 5-(S)-CH$_2$NHCH(CH$_3$)C(CH$_3$)$_3$ | H | 5-CHF$_2$thien-2-yl | (2-pyrrolidinylmethyl carbonyl) | CN | H | | isopropyl |

-continued

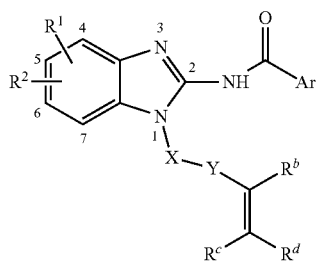

| Cpd # | R¹ | R² | Ar | —X—Y— | R$^b$ | R$^d$ | R$^b$ + R$^d$ | R$^c$ |
|---|---|---|---|---|---|---|---|---|
| 41 | H | H | 5-(pyrazol-4-yl)-thien-2-yl | (R)-pyrrolidinyl-CH₂- linker with N-C(O)- | CN | H | | isopropyl |
| 42 | H | H | 5-(pyrazol-4-yl)-thien-2-yl | azetidinyl-CH₂- linker with N-C(O)- | CN | H | | isopropyl |
| 43 | H | H | 5-(pyrazol-4-yl)-thien-2-yl | (R)-pyrrolidinyl-CH₂- linker with N-C(O)- | CN | H | | —C(CH₃)₂NH₂ |
| 44 | H | H | 5-(pyrazol-4-yl)-thien-2-yl | (R)-pyrrolidinyl-CH₂- linker with N-C(O)- | CN | H | | —C(CH₃)₂-morpholin-4-yl |
| 45 | H | H | 5-(pyrazol-4-yl)-thien-2-yl | (S)-pyrrolidinyl-CH₂- linker with N-C(O)- | CN | H | | isopropyl |
| 46 | H | H | 5-(pyrazol-4-yl)-thien-2-yl | azetidinyl-CH₂- linker with N-C(O)- | CN | H | | —C(CH₃)₂NH₂ |

-continued

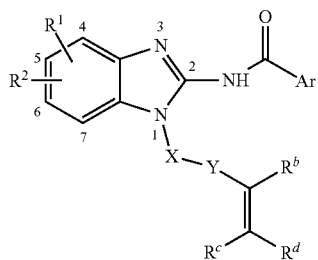

| Cpd # | R¹ | R² | Ar | —X—Y— | Rᵇ | Rᵈ | Rᵇ + Rᵈ | Rᶜ |
|---|---|---|---|---|---|---|---|---|
| 47 | H | H | 5-(pyrazol-4-yl)-thien-2-yl | (S)-pyrrolidine-CH₂/C(O) linker | CN | H | | —C(CH₃)₂NH₂ |
| 48 | H | H | 5-(pyrazol-4-yl)-thien-2-yl | (S)-pyrrolidine-CH₂/C(O) linker | CN | H | | —C(CH₃)₂-morpholin-4-yl |
| 49 | H | H | 5-(pyrazol-4-yl)-thien-2-yl | —(CH₂)₂NHCO— | CN | H | | isopropyl |
| 50 | H | H | 5-(pyrazol-4-yl)-thien-2-yl | azetidine-CH₂/C(O) linker | CN | H | | —C(CH₃)₂-morpholin-4-yl |
| 51 | H | H | 5-(pyrazol-4-yl)-thien-2-yl | —(CH₂)₂NHCO— | CN | H | | —C(CH₃)₂NH₂ |
| 52 | H | H | 5-(pyrazol-4-yl)-thien-2-yl | —(CH₂)₂NHCO— | CN | H | | —C(CH₃)₂-morpholin-4-yl |
| 53 | H | H | 5-CHF₂thien-2-yl | (R)-pyrrolidine-CH₂/C(O) linker | CN | H | | isopropyl |
| 54 | H | H | 5-CHF₂thien-2-yl | (S)-pyrrolidine-CH₂/C(O) linker | CN | H | | isopropyl |
| 55 | H | H | 5-(pyrazol-4-yl)-thien-2-yl | —(CH₂)₂N(CH₃)CO— | CN | H | | isopropyl |
| 56 | H | H | 5-(pyrazol-4-yl)-thien-2-yl | —(CH₂)₂N(CH₃)CO— | CN | H | | —C(CH₃)₂-morpholin-4-yl |

-continued

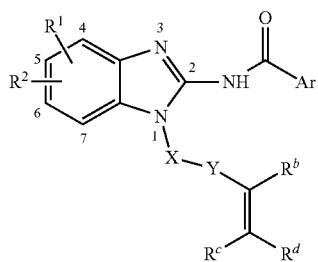

| Cpd # | R¹ | R² | Ar | —X—Y— | Rᵇ | Rᵈ | Rᵇ + Rᵈ | Rᶜ |
|---|---|---|---|---|---|---|---|---|
| 57 | 5-(S)-CH$_2$NHCH(CH$_3$)C(CH$_3$)$_3$ | H | 4-Clphenyl | (S)-pyrrolidinyl-C(O)- | H | H | | H |
| 58 | 5-(S)-CH$_2$NHCH(CH$_3$)C(CH$_3$)$_3$ | H | 4-Clphenyl | (R)-pyrrolidinyl-C(O)- | H | H | | H |
| 59 | 5-(S)-CH$_2$NHCH(CH$_3$)C(CH$_3$)$_3$ | H | 5-CHF$_2$thien-2-yl | (R)-pyrrolidinyl-C(O)- | H | H | | H |
| 60 | 5-(S)-CH$_2$NHCH(CH$_3$)C(CH$_3$)$_3$ | H | 5-CHF$_2$thien-2-yl | (R)-pyrrolidinyl-C(O)- | CN | H | | isopropyl |
| 61 | 5-(S)-CH$_2$NHCH(CH$_3$)C(CH$_3$)$_3$ | H | 5-CHF$_2$thien-2-yl | (R)-pyrrolidinyl-C(O)- | CN | H | | tert-butyl |
| 62 | 5-(S)-CH$_2$NHCH(CH$_3$)C(CH$_3$)$_3$ | H | 5-CHF$_2$thien-2-yl | (R)-pyrrolidinyl-C(O)- | CN | H | | cyclopropyl |

-continued

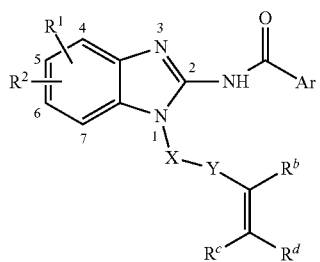

| Cpd # | R¹ | R² | Ar | —X—Y— | R^b | R^d | R^b + R^d | R^c |
|---|---|---|---|---|---|---|---|---|
| 63 | 5-(S)-CH$_2$NHCH(CH$_3$)C(CH$_3$)$_3$ | H | 5-CHF$_2$thien-2-yl | (R)-pyrrolidinyl-CH$_2$-C(O)- | CN | H | | 3-methyloxetan-3-yl |
| 64 | 5-(S)-CH$_2$NHCH(CH$_3$)C(CH$_3$)$_3$ | H | 5-CHF$_2$thien-2-yl | (R)-pyrrolidinyl-CH$_2$-C(O)- | CN | H | | —C(CH$_3$)$_2$OC$_2$H$_5$ |
| 65 | H | H | 5-CHF$_2$thien-2-yl | (R)-pyrrolidinyl-CH$_2$-C(O)- | CN | H | | tert-butyl |
| 66 | H | H | 5-CHF$_2$thien-2-yl | (R)-pyrrolidinyl-CH$_2$-C(O)- | CN | H | | —C(CH$_3$)$_2$N(CH$_3$)$_2$ |
| 67 | H | H | 5-CHF$_2$thien-2-yl | (R)-pyrrolidinyl-CH$_2$-C(O)- | H | H | | H |
| 68 | H | H | 5-CHF$_2$thien-2-yl | —(CH$_2$)$_2$—N(CH$_3$)CO— | CN | H | | tert-butyl |
| 69 | H | H | isoxazol-5-yl | (R)-pyrrolidinyl-CH$_2$-C(O)- | CN | H | | isopropyl |

-continued

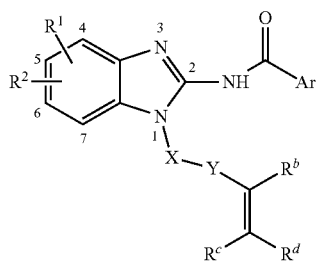

| Cpd # | R¹ | R² | Ar | —X—Y— | R$^b$ | R$^d$ | R$^b$ + R$^d$ | R$^c$ |
|---|---|---|---|---|---|---|---|---|
| 70 | H | H | 3-CHF$_2$phenyl | (R)-pyrrolidine-2-ylmethyl-carbonyl | CN | H | | isopropyl |
| 71 | H | H | 3-CF$_3$phenyl | (R)-pyrrolidine-2-ylmethyl-carbonyl | CN | H | | isopropyl |
| 72 | H | H | 3-CH$_3$phenyl | (R)-pyrrolidine-2-ylmethyl-carbonyl | CN | H | | isopropyl |
| 73 | H | H | 3,4-diFphenyl | (R)-pyrrolidine-2-ylmethyl-carbonyl | CN | H | | isopropyl |
| 74 | H | H | 5-CHF$_2$thien-2-yl | (R)-pyrrolidine-2-ylmethyl-carbonyl | CN | H | | —C(CH$_3$)$_2$CH$_2$OH |
| 75 | H | H | 5-CHF$_2$thien-2-yl | (R)-pyrrolidine-2-ylmethyl-carbonyl | CN | H | | —C(CH$_3$)$_2$NH$_2$ |

-continued

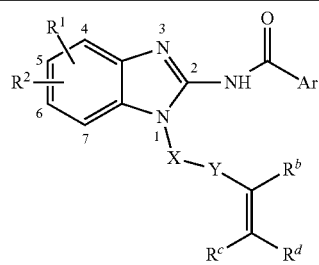

| Cpd # | R¹ | R² | Ar | —X—Y— | R$^b$ | R$^d$ | R$^b$ + R$^d$ | R$^c$ |
|---|---|---|---|---|---|---|---|---|
| 76 | H | H | 5-CHF$_2$thien-2-yl | (S)-pyrrolidine N-acetyl | CN | H | | —C(CH$_3$)$_2$NH$_2$ |
| 77 | H | H | 5-CHF$_2$thien-2-yl | azetidine N-acetyl | CN | H | | —C(CH$_3$)$_2$NH$_2$ |
| 78 | H | H | 5-CHF$_2$thien-2-yl | (R)-pyrrolidine N-acetyl | CN | H | | isopropyl |
| 79 | H | H | 5-CHF$_2$thien-2-yl | (S)-pyrrolidine N-acetyl | CN | H | | isopropyl |
| 80 | H | H | 5-CHF$_2$thien-2-yl | —(CH$_2$)$_2$—N(CH$_3$)CO— | CN | H | | —C(CH$_3$)$_2$-morpholin-4-yl |
| 81 | H | H | 5-CHF$_2$thien-2-yl | —(CH$_2$)$_2$—N(CH$_3$)CO— | CN | H | | —C(CH$_3$)$_2$N(CH$_3$)$_2$ |
| 82 | H | H | 5-CHF$_2$thien-2-yl | azetidine N-acetyl | CN | H | | —C(CH$_3$)$_2$N(CH$_3$)$_2$ |
| 83 | H | H | 5-CHF$_2$thien-2-yl | azetidine N-acetyl | CN | H | | —C(CH$_3$)$_2$-morpholin-4-yl |

-continued

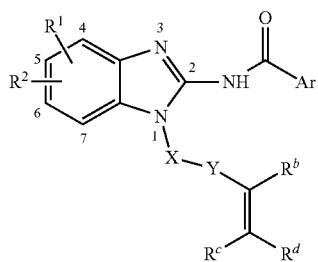

| Cpd # | R¹ | R² | Ar | —X—Y— | R$^b$ | R$^d$ | R$^b$ + R$^d$ | R$^c$ |
|---|---|---|---|---|---|---|---|---|
| 84 | 5-CH$_2$OH | H | 5-CHF$_2$thien-2-yl | (R)-pyrrolidine-CH$_2$-C(O) | CN | H | | isopropyl |
| 85 | 5-CH$_2$NHCH$_2$C(CH$_3$)$_3$ | H | 5-CHF$_2$thien-2-yl | (R)-pyrrolidine-CH$_2$-C(O) | CN | H | | isopropyl |
| 86 | 5-CH$_2$-morpholin-4-yl | H | 5-CHF$_2$thien-2-yl | (R)-pyrrolidine-CH$_2$-C(O) | CN | H | | isopropyl |
| 87 | 5-CH$_2$-2,6-dimehtylmorpholin-4-yl | H | 5-CHF$_2$thien-2-yl | (R)-pyrrolidine-CH$_2$-C(O) | CN | H | | isopropyl |
| 88 | 5-CH$_2$NHCH$_2$CF$_3$ | H | 5-CHF$_2$thien-2-yl | (R)-pyrrolidine-CH$_2$-C(O) | CN | H | | isopropyl |
| 89 | 5-CH$_2$-4-methylpiperazin-yl | H | 5-CHF$_2$thien-2-yl | (R)-pyrrolidine-CH$_2$-C(O) | CN | H | | isopropyl |

-continued

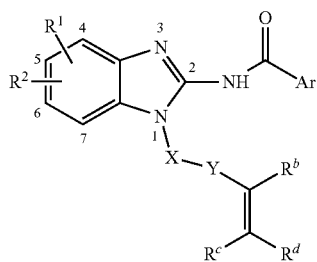

| Cpd # | R$^1$ | R$^2$ | Ar | —X—Y— | R$^b$ | R$^d$ | R$^b$ + R$^d$ | R$^c$ |
|---|---|---|---|---|---|---|---|---|
| 90 | 6-CH$_2$NHCH$_2$C(CH$_3$)$_3$ | H | 5-CHF$_2$thien-2-yl | (R)-pyrrolidine-CH$_2$/C(O) | CN | H | | isopropyl |
| 91 | 6-CH$_2$-morpholin-4-yl | H | 5-CHF$_2$thien-2-yl | (R)-pyrrolidine-CH$_2$/C(O) | CN | H | | isopropyl |
| 92 | 6-CH$_2$-2,6-dimethyl-morpholin-4-yl | H | 5-CHF$_2$thien-2-yl | (R)-pyrrolidine-CH$_2$/C(O) | CN | H | | isopropyl |
| 93 | 6-(S)-CH$_2$NHCH(CH$_3$)C(CH$_3$)$_3$ | H | 5-CHF$_2$thien-2-yl | (R)-pyrrolidine-CH$_2$/C(O) | CN | H | | isopropyl |
| 94 | 6-(R)-CH$_2$NHCH(CH$_3$)C(CH$_3$)$_3$ | H | 5-CHF$_2$thien-2-yl | (R)-pyrrolidine-CH$_2$/C(O) | CN | H | | isopropyl |
| 95 | H | H | 5-CHF$_2$thien-2-yl | (R)-pyrrolidine-CH$_2$/C(O) | CN | H | | —C(CH$_3$)$_2$CH$_2$NH$_2$ |

-continued

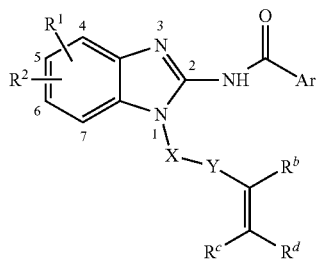

| Cpd # | R¹ | R² | Ar | —X—Y— | R$^b$ | R$^d$ | R$^b$ + R$^d$ | R$^c$ |
|---|---|---|---|---|---|---|---|---|
| 96 | 5-CH$_2$NHCH$_2$C(CH$_3$)$_3$ | H | 5-CHF$_2$thien-2-yl | (R)-pyrrolidin-2-ylmethyl-C(O)- | CN | H | | tert-butyl |
| 97 | 5-CH$_2$-morpholin-4-yl | H | 5-CHF$_2$thien-2-yl | (R)-pyrrolidin-2-ylmethyl-C(O)- | CN | H | | tert-butyl |
| 98 | 5-CH$_2$-2,6-dimehtylmorpholin-4-yl | H | 5-CHF$_2$thien-2-yl | (R)-pyrrolidin-2-ylmethyl-C(O)- | CN | H | | tert-butyl |
| 99 | 5-CH$_2$NHCH$_2$C(CH$_3$)$_3$ | H | 5-CHF$_2$thien-2-yl | (R)-pyrrolidin-2-ylmethyl-C(O)- | CN | H | | 3-methyloxetan-3-yl |
| 100 | 5-CH$_2$-morpholin-4-yl | H | 5-CHF$_2$thien-2-yl | (R)-pyrrolidin-2-ylmethyl-C(O)- | CN | H | | 3-methyloxetan-3-yl |
| 101 | 5-CH$_2$-2,6-dimethylmorpholin-4-yl | H | 5-CHF$_2$thien-2-yl | (R)-pyrrolidin-2-ylmethyl-C(O)- | CN | H | | 3-methyloxetan-3-yl |

-continued

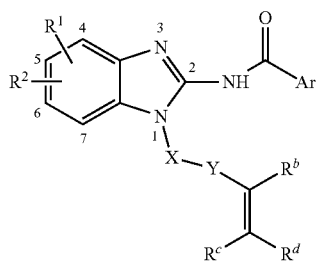

| Cpd # | R¹ | R² | Ar | —X—Y— | Rᵇ | Rᵈ | Rᵇ + Rᵈ | Rᶜ |
|---|---|---|---|---|---|---|---|---|
| 102 | 5-CH$_2$NHCH$_2$CH(CH$_3$)$_3$ | H | 5-CHF$_2$thien-2-yl | (R)-2-(pyrrolidinyl)methyl-N-acyl | CN | H | | isopropyl |
| 103 | 5-CH$_2$NHCH$_2$CH(CH$_3$)$_3$ | H | 5-CHF$_2$thien-2-yl | (R)-2-(pyrrolidinyl)methyl-N-acyl | CN | H | | tert-butyl |
| 104 | 5-CH$_2$NHCH$_2$CH(CH$_3$)$_3$ | H | 5-CHF$_2$thien-2-yl | (R)-2-(pyrrolidinyl)methyl-N-acyl | CN | H | | 3-methyloxetan-3-yl |
| 105 | 5-O-(3-methyloxetan-3-yl)methylamino | H | 5-CHF$_2$thien-2-yl | (R)-2-(pyrrolidinyl)methyl-N-acyl | CN | H | | isopropyl |
| 106 | 5-O-(3-methyloxetan-3-yl)methylamino | H | 5-CHF$_2$thien-2-yl | (R)-2-(pyrrolidinyl)methyl-N-acyl | CN | H | | tert-butyl |
| 107 | 5-O-(3-methyloxetan-3-yl)methylamino | H | 5-CHF$_2$thien-2-yl | (R)-2-(pyrrolidinyl)methyl-N-acyl | CN | H | | 3-methyloxetan-3-yl |

-continued

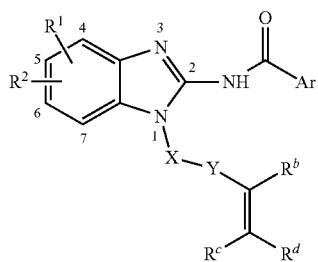

| Cpd # | R¹ | R² | Ar | —X—Y— | $R^b$ | $R^d$ | $R^b + R^d$ | $R^c$ |
|---|---|---|---|---|---|---|---|---|
| 108 | 5-O-(spiro azetidine-oxetane)-N-CH₂- | H | 5-CHF₂thien-2-yl | (R)-pyrrolidine-CH₂-C(O)- | CN | H | | isopropyl |
| 109 | 5-(S)-CH₂NHCH(CH₃)C(CH₃)₃ | H | 5-CHF₂thien-2-yl | (R)-pyrrolidine-CH₂-C(O)- | | | bond | methyl |
| 110 | 5-(S)-CH₂NHCH(CH₃)C(CH₃)₃ | H | 4-Clphenyl | (R)-pyrrolidine-CH₂-C(O)- | | | bond | methyl |
| 111 | 5-(S)-CH₂NHCH(CH₃)C(CH₃)₃ | H | 5-CHF₂thien-2-yl | (S)-pyrrolidine-CH₂-C(O)- | | | bond | methyl |
| 112 | 5-(S)-CH₂NHCH(CH₃)C(CH₃)₃ | H | 4-Clphenyl | (S)-pyrrolidine-CH₂-C(O)- | | | bond | methyl |
| 113 817 | 5-CH₂NHCH₂CH(CH₃)₃ | H | 5-CHF₂thien-2-yl | (R)-pyrrolidine-CH₂-C(O)- | CN | H | | 3-methyloxetan-3-yl |

-continued

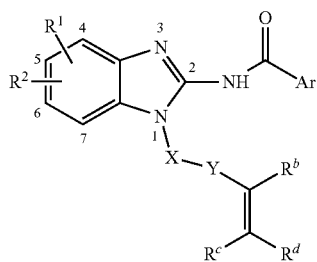

| Cpd # | R¹ | R² | Ar | —X—Y— | R$^b$ | R$^d$ | R$^b$ + R$^d$ | R$^c$ |
|---|---|---|---|---|---|---|---|---|
| 114 | H | H | 5-CHF$_2$thien-2-yl | (R)-pyrrolidinyl-C(O)- | CN | H | | —C(CH$_3$)$_2$CH$_2$NH$_2$ |
| 115 | 6-CH$_2$NHCH$_2$CH(CH$_3$)$_3$ | H | 5-CHF$_2$thien-2-yl | (R)-pyrrolidinyl-C(O)- | CN | H | | isopropyl |
| 116 | 6-CH$_2$NHCH$_2$CH(CH$_3$)$_3$ | H | 5-CHF$_2$thien-2-yl | (R)-pyrrolidinyl-C(O)- | CN | H | | 3-methyloxetan-3-yl |
| 117 | 5-CH$_2$NHCH$_2$C(CH$_3$)$_2$OH | H | 5-CHF$_2$thien-2-yl | (R)-pyrrolidinyl-C(O)- | CN | H | | isopropyl |
| 118 | 5-CH$_2$NHCH$_2$cyclopropyl | H | 5-CHF$_2$thien-2-yl | (R)-pyrrolidinyl-C(O)- | CN | H | | isopropyl |
| 119 | 5-CONHCH$_2$C(CH$_3$)$_3$ | H | 5-CHF$_2$thien-2-yl | (R)-pyrrolidinyl-C(O)- | CN | H | | isopropyl |

-continued

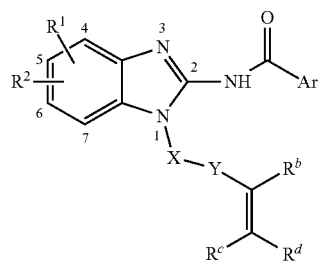

| Cpd # | R¹ | R² | Ar | —X—Y— | R$^b$ | R$^d$ | R$^b$ + R$^d$ | R$^c$ |
|---|---|---|---|---|---|---|---|---|
| 120 | 5-CONHCH$_2$C(CH$_3$)$_3$ | H | 5-CHF$_2$thien-2-yl | (R)-pyrrolidine-2-ylmethyl, N-acyl | CN | H | | 3-methyloxetan-3-yl |
| 121 | 5-CH$_2$-(3-(2-hydroxypropan-2-yl)azetidin-1-yl) | H | 5-CHF$_2$thien-2-yl | (R)-pyrrolidine-2-ylmethyl, N-acyl | CN | H | | isopropyl |
| 122 | 5-CH$_2$-(3-hydroxyazetidin-1-yl) | H | 5-CHF$_2$thien-2-yl | (R)-pyrrolidine-2-ylmethyl, N-acyl | CN | H | | isopropyl |
| 123 | 5-CH$_2$-(4-(2-hydroxypropan-2-yl)piperidin-1-yl) | H | 5-CHF$_2$thien-2-yl | (R)-pyrrolidine-2-ylmethyl, N-acyl | CN | H | | isopropyl |
| 124 | H | H | 5-CHF$_2$thien-2-yl | (R)-cyclohexane-1,3-diyl acyl | CN | H | | tert-butyl |
| 125 | H | H | 5-CHF$_2$thien-2-yl | (S)-cyclohexane-1,3-diyl acyl | CN | H | | tert-butyl |
| 126 | 5-CH$_2$OH | H | 5-CHF$_2$thien-2-yl | (R)-pyrrolidine-2-ylmethyl, N-acyl | CN | H | | —C(CH$_3$)$_2$—CH$_2$morpholin-4-yl |

-continued

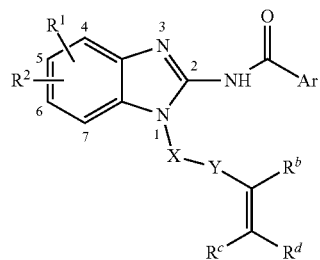

| Cpd # | R¹ | R² | Ar | —X—Y— | $R^b$ | $R^d$ | $R^b + R^d$ | $R^c$ |
|---|---|---|---|---|---|---|---|---|
| 127 | 5-CONHCH$_2$C(CH$_3$)$_3$ | H | 5-CHF$_2$thien-2-yl | (R)-pyrrolidine-CH$_2$CH$_2$-/C(O)- | H | H | | H |
| 128 | 5-(S)-CH$_2$NHCH(CH$_3$)C(CH$_3$)$_3$ | H | 5-CHF$_2$thien-2-yl | (R)-pyrrolidine-CH$_2$CH$_2$-/C(O)- | CN | H | | —C(CH$_3$)$_2$O(CH$_2$)$_2$OCH$_3$ |
| 129 | 5-(S)-CH$_2$NHCH(CH$_3$)C(CH$_3$)$_3$ | H | 5-CHF$_2$thien-2-yl | (R)-pyrrolidine-CH$_2$CH$_2$-/C(O)- | H | H | | H |
| 130 | 5-(S)-CH$_2$NHCH(CH$_3$)C(CH$_3$)$_3$ | H | 5-CHF$_2$thien-2-yl | azetidine-CH$_2$-/C(O)- | CN | H | | —C(CH$_3$)$_3$ |
| 131 | 5-(S)-CH$_2$NHCH(CH$_3$)C(CH$_3$)$_3$ | H | 5-CHF$_2$thien-2-yl | (R)-pyrrolidine-CH$_2$CH$_2$-/C(O)- | CN | H | | tert-butyl |
| 132 | 5-C(OH)(CH$_2$CH$_3$)$_2$ | H | 5-CHF$_2$thien-2-yl | (R)-pyrrolidine-CH$_2$CH$_2$-/C(O)- | CN | | | isopropyl |
| 133 | 5-(S)-CH$_2$NHCH(CH$_3$)C(CH$_3$)$_3$ | H | 5-CHF$_2$thien-2-yl | pyrrolidine-3-CH$_2$CH$_2$-/C(O)- | CN | | | tert-butyl |

-continued

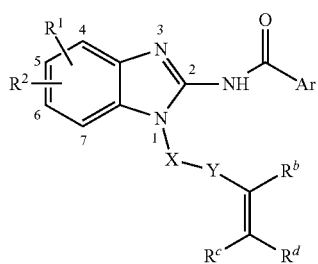

| Cpd # | R¹ | R² | Ar | —X—Y— | R$^b$ | R$^d$ | R$^b$ + R$^d$ | R$^c$ |
|---|---|---|---|---|---|---|---|---|
| 134 | 5-CH$_2$NHCH$_2$CH(CH$_3$)$_3$ | H | 5-CHF$_2$thien-2-yl | (R)-2-pyrrolidinyl-CH$_2$/C(O) | CN | H | | —C(CH$_3$)$_2$OCH$_2$CH$_3$ |
| 135 | 5-CH$_2$NHCH$_2$CH(CH$_3$)$_3$ | H | isoxazol-5-yl | (R)-2-pyrrolidinyl-CH$_2$/C(O) | CN | H | | isopropyl |
| 136 | 5-CH$_2$NHCH$_2$CH(CH$_3$)$_3$ | H | isoxazol-5-yl | (R)-2-pyrrolidinyl-CH$_2$/C(O) | CN | H | | tert-butyl |
| 137 | 5-CH$_2$NHCH$_2$CH(CH$_3$)$_3$ | H | isoxazol-5-yl | (R)-2-pyrrolidinyl-CH$_2$/C(O) | CN | H | | 3-methyloxetan-3-yl |
| 138 | 5-CH$_2$NHCH$_2$CH(CH$_3$)$_3$ | H | pyridin-3-yl | (R)-2-pyrrolidinyl-CH$_2$/C(O) | CN | H | | isopropyl |
| 139 | 5-CH$_2$NHCH$_2$CH(CH$_3$)$_3$ | H | 3-CHF$_2$phenyl | (R)-2-pyrrolidinyl-CH$_2$/C(O) | CN | H | | isopropyl |

-continued

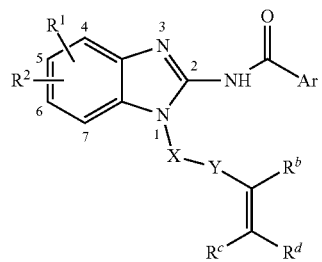

| Cpd # | R¹ | R² | Ar | —X—Y— | R$^b$ | R$^d$ | R$^b$ + R$^d$ | R$^c$ |
|---|---|---|---|---|---|---|---|---|
| 140 | 5-(S)-CH$_2$NHCH(CH$_3$)C(CH$_3$)$_3$ | H | isoxazol-5-yl | (R)-pyrrolidine-CH$_2$-/C(O)- | CN | H | | tert-butyl |
| 141 | 5-(S)-CH$_2$NHCH(CH$_3$)C(CH$_3$)$_3$ | H | isoxazol-5-yl | (R)-pyrrolidine-CH$_2$-/C(O)- | CN | H | | —C(CH$_3$)$_2$OCH$_2$CH$_3$ |
| 142 | 5-(S)-CH$_2$NHCH(CH$_3$)C(CH$_3$)$_3$ | H | isoxazol-5-yl | (R)-3-pyrrolidinyl-CH$_2$-/C(O)- | CN | H | | tert-butyl |
| 143 | 5-(S)-CH$_2$NHCH(CH$_3$)C(CH$_3$)$_3$ | H | isoxazol-5-yl | (R)-3-pyrrolidinyl-CH$_2$-/C(O)- | CN | H | | —C(CH$_3$)$_2$OCH$_2$CH$_3$ |
| 144 | 5-(S)-CH$_2$NHCH(CH$_3$)C(CH$_3$)$_3$ | H | isoxazol-5-yl | (S)-3-pyrrolidinyl-CH$_2$-/C(O)- | CN | H | | tert-butyl |
| 145 | 5-(S)-CH$_2$NHCH(CH$_3$)C(CH$_3$)$_3$ | H | isoxazol-5-yl | (S)-3-pyrrolidinyl-CH$_2$-/C(O)- | CN | H | | —C(CH$_3$)$_2$OCH$_2$CH$_3$ |
| 146 | 5-(S)-CH$_2$NHCH(CH$_3$)C(CH$_3$)$_3$ | H | 5-CHF$_2$thien-2-yl | (S)-3-pyrrolidinyl-CH$_2$-/C(O)- | CN | H | | tert-butyl |
| 147 | 5-(S)-CH$_2$NHCH(CH$_3$)C(CH$_3$)$_3$ | H | 5-CHF$_2$thien-2-yl | (S)-3-pyrrolidinyl-CH$_2$-/C(O)- | CN | H | | —C(CH$_3$)$_2$OCH$_2$CH$_3$ |
| 148 | 5-(S)-CH$_2$NHCH(CH$_3$)C(CH$_3$)$_3$ | H | 5-CHF$_2$thien-2-yl | (R)-3-pyrrolidinyl-CH$_2$-/C(O)- | CN | H | | tert-butyl |

-continued

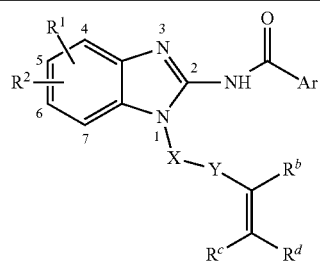

| Cpd # | R¹ | R² | Ar | —X—Y— | Rᵇ | Rᵈ | Rᵇ + Rᵈ | Rᶜ |
|---|---|---|---|---|---|---|---|---|
| 149 | 5-(S)-CH$_2$NHCH(CH$_3$)C(CH$_3$)$_3$ | H | 5-CHF$_2$thien-2-yl | (R)-3-pyrrolidinyl-CH$_2$, N-acyl | CN | H | | —C(CH$_3$)$_2$OCH$_2$CH$_3$ |
| 150 | 5-(S)-CH$_2$NHCH(CH$_3$)C(CH$_3$)$_3$ | H | 5-CHF$_2$thien-2-yl | (R)-3-pyrrolidinyl, N-acyl | CN | H | | tert-butyl |
| 151 | 5-(S)-CH$_2$NHCH(CH$_3$)C(CH$_3$)$_3$ | H | 3-CHF$_2$phenyl | (R)-2-pyrrolidinyl-CH$_2$CH$_2$, N-acyl | CN | H | | tert-butyl |
| 152 | 5-(S)-CH$_2$NHCH(CH$_3$)C(CH$_3$)$_3$ | H | 3-CHF$_2$phenyl | (R)-2-pyrrolidinyl-CH$_2$CH$_2$, N-acyl | CN | H | | isopropyl |
| 153 | 5-(S)-CH$_2$NHCH(CH$_3$)C(CH$_3$)$_3$ | H | 3-CHF$_2$phenyl | (R)-2-pyrrolidinyl-CH$_2$CH$_2$, N-acyl | CN | H | | —C(CH$_3$)$_2$OCH$_2$CH$_3$ |
| 154 | 5-CH$_2$OH | H | 5-CHF$_2$thien-2-yl | (R)-cyclohexyl | CN | H | | tert-butyl |
| 155 | 5-(S)-CH$_2$NHCH(CH$_3$)C(CH$_3$)$_3$ | H | 5-CHF$_2$thien-2-yl | (R)-3-pyrrolidinyl, N-acyl | CN | H | | —C(CH$_3$)$_2$OCH$_2$CH$_3$ |
| 156 | 5-(S)-CH$_2$NHCH(CH$_3$)C(CH$_3$)$_3$ | H | 5-CHF$_2$thien-2-yl | (R)-3-pyrrolidinyl, N-acyl | CN | H | | isopropyl | or an individual E or Z isomers thereof and are named as:

N-(1-(1-acryloylpiperidin-4-yl)-1H-benzo[d]imidazol-2 (3H)-ylidene)-4-chlorobenzamide;

N-(1-(1-acryloylpiperidin-4-yl)-1H-benzo[d]imidazol-2 (3H)-ylidene)nicotinamide;

N-(1-(1-acryloylpiperidin-3-yl)-1H-benzo[d]imidazol-2 (3H)-ylidene)-4-chlorobenzamide;

4-chloro-N-(1-(1-(2-cyano-4-methylpent-2-enoyl)piperidin-4-yl)-1H-benzo[d]imidazol-2(3H)-ylidene)benzamide;

N-(1-(1-(2-cyano-4-methylpent-2-enoyl)piperidin-3-yl)-1H-benzo[d]imidazol-2(3H)-ylidene)nicotinamide;

N-(1-(1-acryloylpiperidin-3-yl)-1H-benzo[d]imidazol-2 (3H)-ylidene)nicotinamide;

4-chloro-N-(1-((1-(2-cyano-4-methylpent-2-enoyl)pyrrolidin-2-yl)methyl)-1H-benzo[d]imidazol-2(3H)-ylidene) benzamide;

N-(1-((1-acryloylpyrrolidin-2-yl)methyl)-1H-benzo[d]imidazol-2(3H)-ylidene)-4-chlorobenzamide;

N-(1-(1-(2-cyano-4-methylpent-2-enoyl)piperidin-4-yl)-1H-benzo[d]imidazol-2(3H)-ylidene)nicotinamide;

N-(1-((1-(2-cyano-4-methylpent-2-enoyl)pyrrolidin-2-yl) methyl)-1H-benzo[d]imidazol-2(3H)-ylidene)nicotinamide;

N-(1-((1-acryloylpyrrolidin-2-yl)methyl)-1H-benzo[d]imidazol-2(3H)-ylidene)nicotinamide;

(S)-N-(1-(1-acryloylpiperidin-4-yl)-5-(((3,3-dimethylbutan-2-yl)amino)methyl)-1H-benzo[d]imidazol-2(3H)-ylidene)-4-chlorobenzamide;

4-chloro-N-(1-(1-(2-cyano-4-methylpent-2-enoyl)piperidin-3-yl)-5-((N-((S)-3,3-dimethylbutan-2-yl)-2,2,2-trifluoroacetamido)methyl)-1H-benzo[d]imidazol-2(3H)-ylidene) benzamide;

N-(1-(1-acryloylpiperidin-3-yl)-5-((N-((S)-3,3-dimethylbutan-2-yl)-2,2,2-trifluoroacetamido)methyl)-1H-benzo[d] imidazol-2(3H)-ylidene)-4-chlorobenzamide;

4-chloro-N-(1-((1-(2-cyano-4-methylpent-2-enoyl)pyrrolidin-2-yl)methyl)-5-((N-((S)-3,3-dimethylbutan-2-yl)-2,2, 2-trifluoroacetamido)methyl)-1H-benzo[d]imidazol-2 (3H)-ylidene)benzamide;

N-(1-((1-acryloylpyrrolidin-2-yl)methyl)-5-((N-((S)-3,3-dimethylbutan-2-yl)-2,2,2-trifluoroacetamido)methyl)-1H-benzo[d]imidazol-2(3H)-ylidene)-4-chlorobenzamide;

4-chloro-N-(1-((1-(2-cyano-4-methylpent-2-enoyl)pyrrolidin-2-yl)methyl)-5-((((S)-3,3-dimethylbutan-2-yl) (methyl)amino)methyl)-1H-benzo[d]imidazol-2(3H)-ylidene)benzamide;

4-chloro-N-(1-(1-(2-cyano-4-methylpent-2-enoyl)piperidin-3-yl)-5-((((S)-3,3-dimethylbutan-2-yl)(methyl)amino) methyl)-1H-benzo[d]imidazol-2(3H)-ylidene)benzamide;

N-(1-(1-(2-cyano-4-methylpent-2-enoyl)piperidin-3-yl)-1H-benzo[d]imidazol-2(3H)-ylidene)-5-(1H-pyrazol-4-yl)thiophene-2-carboxamide N-(1-(1-acryloylpiperidin-3-yl)-1H-benzo[d]imidazol-2 (3H)-ylidene)-5-(1H-pyrazol-4-yl)thiophene-2-carboxamide;

N-(1-(1-(2-cyano-4-(dimethylamino)-4-methylpent-2-enoyl)piperidin-3-yl)-1H-benzo[d]imidazol-2(3H)-ylidene)-5-(1H-pyrazol-4-yl)thiophene-2-carboxamide;

N-(1-(1-(4-(dimethylamino)but-2-enoyl)piperidin-3-yl)-1H-benzo[d]imidazol-2(3H)-ylidene)-5-(1H-pyrazol-4-yl)thiophene-2-carboxamide;

4-chloro-N-(1-(1-(2-cyano-4-methylpent-2-enoyl)piperidin-3-yl)-5-((((S)-3,3-dimethylbutan-2-yl)amino)methyl)-1H-benzo[d]imidazol-2(3H)-ylidene)benzamide;

N-(1-(1-(4-amino-2-cyano-4-methylpent-2-enoyl)piperidin-3-yl)-5-((((S)-3,3-dimethylbutan-2-yl)amino)methyl)-1H-benzo[d]imidazol-2(3H)-ylidene)-4-chlorobenzamide;

4-chloro-N-(1-(1-(2-cyano-4-methyl-4-(methylamino)pent-2-enoyl)piperidin-3-yl)-5-((((S)-3,3-dimethylbutan-2-yl) amino)methyl)-1H-benzo[d]imidazol-2-yl)benzamide;

4-chloro-N-(1-(1-(2-cyano-4-(dimethylamino)-4-methylpent-2-enoyl)piperidin-3-yl)-5-((((S)-3,3-dimethylbutan-2-yl)amino)methyl)-1H-benzo[d]imidazol-2-yl)benzamide;

N-(1-(1-acryloylpiperidin-3-yl)-5-((((S)-3,3-dimethylbutan-2-yl)amino)methyl)-1H-benzo[d]imidazol-2-yl)-4-chlorobenzamide;

4-chloro-N-(1-((1-(2-cyano-4-methylpent-2-enoyl)pyrrolidin-2-yl)methyl)-5-((((S)-3,3-dimethylbutan-2-yl)amino) methyl)-1H-benzo[d]imidazol-2-yl)benzamide;

N-(1-((1-(4-amino-2-cyano-4-methylpent-2-enoyl)pyrrolidin-2-yl)methyl)-5-((((S)-3,3-dimethylbutan-2-yl)amino) methyl)-1H-benzo[d]imidazol-2-yl)-4-chlorobenzamide;

4-chloro-N-(1-((1-(2-cyano-4-methyl-4-(methylamino) pent-2-enoyl)pyrrolidin-2-yl)methyl)-5-((((S)-3,3-dimethylbutan-2-yl)amino)methyl)-1H-benzo[d]imidazol-2-yl)benzamide;

4-chloro-N-(1-((1-(2-cyano-4-(dimethylamino)-4-methylpent-2-enoyl)pyrrolidin-2-yl)methyl)-5-((((S)-3,3-dimethylbutan-2-yl)amino)methyl)-1H-benzo[d]imidazol-2-yl)benzamide;

4-chloro-N-(1-((1-(2-cyano-4-ethoxy-4-methylpent-2-enoyl)pyrrolidin-2-yl)methyl)-5-((((S)-3,3-dimethylbutan-2-yl)amino)methyl)-1H-benzo[d]imidazol-2-yl)benzamide;

N-(1-((1-acryloylpyrrolidin-2-yl)methyl)-5-((((S)-3,3-dimethylbutan-2-yl)amino)methyl)-1 H-benzo[d]imidazol-2-yl)-4-chlorobenzamide;

N-(1-(((R)-1-acryloylpyrrolidin-2-yl)methyl)-5-((((S)-3,3-dimethylbutan-2-yl)amino)methyl)-1H-benzo[d]imidazol-2-yl)-4-chlorobenzamide;

4-chloro-N-(1-(1-(2-cyano-4,4-dimethylpent-2-enoyl)piperidin-3-yl)-5-((((S)-3,3-dimethylbutan-2-yl)amino) methyl)-1H-benzo[d]imidazol-2-yl)benzamide;

4-chloro-N-(1-((1-(2-cyano-4,4-dimethylpent-2-enoyl)pyrrolidin-2-yl)methyl)-5-((((S)-3,3-dimethylbutan-2-yl) amino)methyl)-1H-benzo[d]imidazol-2-yl)benzamide;

N-(1-((1-acryloylpyrrolidin-2-yl)methyl)-5-((((S)-3,3-dimethylbutan-2-yl)amino)methyl)-1H-benzo[d]imidazol-2-yl)-4-(difluoromethyl)benzamide;

N-(1-((1-(2-cyano-4-methylpent-2-enoyl)pyrrolidin-2-yl) methyl)-5-((((S)-3,3-dimethylbutan-2-yl)amino)methyl)-1H-benzo[d]imidazol-2-yl)-4-(difluoromethyl)benzamide;

N-(1-((1-acryloylpyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide;

N-(1-((1-(2-cyano-4-methylpent-2-enoyl)pyrrolidin-2-yl) methyl)-5-((((S)-3,3-dimethylbutan-2-yl)amino)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-1H-benzo[d]imidazol-2-yl)-5-(1H-pyrazol-4-yl)thiophene-2-carboxamide;

N-(1-((1-(2-cyano-4-methylpent-2-enoyl)azetidin-3-yl) methyl)-1H-benzo[d]imidazol-2-yl)-5-(1H-pyrazol-4-yl) thiophene-2-carboxamide;

(R)-N-(1-((1-(4-amino-2-cyano-4-methylpent-2-enoyl)pyrrolidin-2-yl)methyl)-1H-benzo[d]imidazol-2-yl)-5-(1H-pyrazol-4-yl)thiophene-2-carboxamide;

(R)-N-(1-((1-(2-cyano-4-methyl-4-morpholinopent-2-enoyl)pyrrolidin-2-yl)methyl)-1H-benzo[d]imidazol-2-yl)-5-(1H-pyrazol-4-yl)thiophene-2-carboxamide;

(S)-N-(1-((1-(2-cyano-4-methylpent-2-enoyl)pyrrolidin-2-yl)methyl)-1H-benzo[d]imidazol-2-yl)-5-(1H-pyrazol-4-yl)thiophene-2-carboxamide;

N-(1-((1-(4-amino-2-cyano-4-methylpent-2-enoyl)azetidin-3-yl)methyl)-1H-benzo[d]imidazol-2-yl)-5-(1H-pyrazol-4-yl)thiophene-2-carboxamide;

(S)-N-(1-((1-(4-amino-2-cyano-4-methylpent-2-enoyl)pyrrolidin-2-yl)methyl)-1H-benzo[d]imidazol-2-yl)-5-(1H-pyrazol-4-yl)thiophene-2-carboxamide;

(S)-N-(1-((1-(2-cyano-4-methyl-4-morpholinopent-2-enoyl)pyrrolidin-2-yl)methyl)-1H-benzo[d]imidazol-2-yl)-5-(1H-pyrazol-4-yl)thiophene-2-carboxamide;

N-(1-(2-(2-cyano-4-methylpent-2-enamido)ethyl)-1H-benzo[d]imidazol-2-yl)-5-(1H-pyrazol-4-yl)thiophene-2-carboxamide;

N-(1-((1-(2-cyano-4-methyl-4-morpholinopent-2-enoyl)azetidin-3-yl)methyl)-1H-benzo[d]imidazol-2-yl)-5-(1H-pyrazol-4-yl)thiophene-2-carboxamide;

N-(1-(2-(4-amino-2-cyano-4-methylpent-2-enamido)ethyl)-1H-benzo[d]imidazol-2-yl)-5-(1H-pyrazol-4-yl)thiophene-2-carboxamide;

N-(1-(2-(2-cyano-4-methyl-4-morpholinopent-2-enamido)ethyl)-1H-benzo[d]imidazol-2-yl)-5-(1H-pyrazol-4-yl)thiophene-2-carboxamide;

(R)-N-(1-((1-(2-cyano-4-methylpent-2-enoyl)pyrrolidin-2-yl)methyl)-1H-benzo[d]imidazol-2-yl)-5-(difluoromethyl)thiophene-2-carboxamide;

(S)-N-(1-((1-(2-cyano-4-methylpent-2-enoyl)pyrrolidin-2-yl)methyl)-1H-benzo[d]imidazol-2-yl)-5-(difluoromethyl)thiophene-2-carboxamide;

N-(1-(2-(2-cyano-N,4-dimethylpent-2-enamido)ethyl)-1H-benzo[d]imidazol-2-yl)-5-(1H-pyrazol-4-yl)thiophene-2-carboxamide;

N-(1-(2-(2-cyano-N,4-dimethyl-4-morpholinopent-2-enamido)ethyl)-1H-benzo[d]imidazol-2-yl)-5-(1H-pyrazol-4-yl)thiophene-2-carboxamide;

N-(1-(((S)-1-acryloylpyrrolidin-2-yl)methyl)-5-((((S)-3,3-dimethylbutan-2-yl)amino)methyl)-1H-benzo[d]imidazol-2-yl)-4-chlorobenzamide;

N-(1-(((R)-1-acryloylpyrrolidin-2-yl)methyl)-5-((((S)-3,3-dimethylbutan-2-yl)amino)methyl)-1H-benzo[d]imidazol-2-yl)-4-chlorobenzamide;

N-(1-(((R)-1-acryloylpyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide;

N-(1-(((R)-1-(2-cyano-4-methylpent-2-enoyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide;

N-(1-(((R)-1-(2-cyano-4,4-dimethylpent-2-enoyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide;

N-(1-(((R)-1-(2-cyano-3-cyclopropylacryloyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide;

N-(1-(((R)-1-(2-cyano-3-(3-methyloxetan-3-yl)acryloyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide;

N-(1-(((R)-1-(2-cyano-4-ethoxy-4-methylpent-2-enoyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide;

(R)-N-(1-((1-(2-cyano-4,4-dimethylpent-2-enoyl)pyrrolidin-2-yl)methyl)-1H-benzo[d]imidazol-2-yl)-5-(difluoromethyl)thiophene-2-carboxamide;

(R)-N-(1-((1-(2-cyano-4-(dimethylamino)-4-methylpent-2-enoyl)pyrrolidin-2-yl)methyl)-1H-benzo[d]imidazol-2-yl)-5-(difluoromethyl)thiophene-2-carboxamide;

(R)-N-(1-((1-acryloylpyrrolidin-2-yl)methyl)-1H-benzo[d]imidazol-2-yl)-5-(difluoromethyl)thiophene-2-carboxamide;

N-(1-(2-(2-cyano-N,4,4-trimethylpent-2-enamido)ethyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-1H-benzo[d]imidazol-2-yl)isoxazole-5-carboxamide;

(R)-N-(1-((1-(2-cyano-4-methylpent-2-enoyl)pyrrolidin-2-yl)methyl)-1H-benzo[d]imidazol-2-yl)-3-(difluoromethyl)benzamide;

(R)-N-(1-((1-(2-cyano-4-methylpent-2-enoyl)pyrrolidin-2-yl)methyl)-1H-benzo[d]imidazol-2-yl)-3-(trifluoromethyl)benzamide;

(R)-N-(1-((1-(2-cyano-4-methylpent-2-enoyl)pyrrolidin-2-yl)methyl)-1H-benzo[d]imidazol-2-yl)-3-methylbenzamide;

(R)-N-(1-((1-(2-cyano-4-methylpent-2-enoyl)pyrrolidin-2-yl)methyl)-1H-benzo[d]imidazol-2-yl)-3,4-difluorobenzamide;

(R)-N-(1-((1-(2-cyano-5-hydroxy-4,4-dimethylpent-2-enoyl)pyrrolidin-2-yl)methyl)-1H-benzo[d]imidazol-2-yl)-5-(difluoromethyl)thiophene-2-carboxamide.

(R)-N-(1-((1-(4-amino-2-cyano-4-methylpent-2-enoyl)pyrrolidin-2-yl)methyl)-1H-benzo[d]imidazol-2-yl)-5-(difluoromethyl)thiophene-2-carboxamide;

(S)-N-(1-(1-(4-amino-2-cyano-4-methylpent-2-enoyl)pyrrolidin-3-yl)-1H-benzo[d]imidazol-2-yl)-5-(difluoromethyl)thiophene-2-carboxamide;

N-(1-((1-(4-amino-2-cyano-4-methylpent-2-enoyl)azetidin-3-yl)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-1H-benzo[d]imidazol-2-yl)-5-(difluoromethyl)thiophene-2-carboxamide;

(S)-N-(1-((1-(2-cyano-4-methylpent-2-enoyl)pyrrolidin-2-yl)methyl)-1H-benzo[d]imidazol-2-yl)-5-(difluoromethyl)thiophene-2-carboxamide;

N-(1-(2-(2-cyano-N,4-dimethyl-4-morpholinopent-2-enamido)ethyl)-1H-benzo[d]imidazol-2-yl)-5-(difluoromethyl)thiophene-2-carboxamide;

N-(1-(2-(2-cyano-4-(dimethylamino)-N,4-dimethylpent-2-enamido)ethyl)-1H-benzo[d]imidazol-2-yl)-5-(difluoromethyl)thiophene-2-carboxamide;

N-(1-((1-(2-cyano-4-(dimethylamino)-4-methylpent-2-enoyl)azetidin-3-yl)methyl)-1H-benzo[d]imidazol-2-yl)-5-(difluoromethyl)thiophene-2-carboxamide;

N-(1-((1-(2-cyano-4-methyl-4-morpholinopent-2-enoyl)azetidin-3-yl)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-(hydroxymethyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-((neopentylamino)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-(morpholinomethyl)-1H-benzo[d]imidazol-2-yl)-5-(difluoromethyl)thiophene-2-carboxamide;

N-(1-(((R)-1-(2-cyano-4-methylpent-2-enoyl)pyrrolidin-2-yl)methyl)-5-((2,6-dimethylmorpholino)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-(((2,2,2-trifluoroethyl)amino)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-(4-methylpiperazin-1-yl)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-6-((neopentylamino)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-6-(morpholinomethyl)-1H-benzo[d]imidazol-2-yl)-5-(difluoromethyl)thiophene-2-carboxamide;

N-(1-(((R)-1-(2-cyano-4-methylpent-2-enoyl)pyrrolidin-2-yl)methyl)-6-((2,6-dimethylmorpholino)methyl)-1H-benzo[d]imidazol-2-yl)-5-(difluoromethyl)thiophene-2-carboxamide;

N-(1-(((R)-1-(2-cyano-4-methylpent-2-enoyl)pyrrolidin-2-yl)methyl)-6-((((S)-3,3-dimethylbutan-2-yl)amino)methyl)-1H-benzo[d]imidazol-2-yl)-5-(difluoromethyl)thiophene-2-carboxamide;

N-(1-(((R)-1-(2-cyano-4-methylpent-2-enoyl)pyrrolidin-2-yl)methyl)-6-((((R)-3,3-dimethylbutan-2-yl)amino)methyl)-1H-benzo[d]imidazol-2-yl)-5-(difluoromethyl)thiophene-2-carboxamide;

(R)-N-(1-((1-(5-amino-2-cyano-4,4-dimethylpent-2-enoyl)pyrrolidin-2-yl)methyl)-1H-benzo[d]imidazol-2-yl)-5-(difluoromethyl)thiophene-2-carboxamide;

(R)-N-(1-((1-(2-cyano-4,4-dimethylpent-2-enoyl)pyrrolidin-2-yl)methyl)-5-((neopentylamino)methyl)-1H-benzo[d]imidazol-2-yl)-5-(difluoromethyl)thiophene-2-carboxamide;

(R)-N-(1-((1-(2-cyano-4,4-dimethylpent-2-enoyl)pyrrolidin-2-yl)methyl)-5-(morpholinomethyl)-1H-benzo[d]imidazol-2-yl)-5-(difluoromethyl)thiophene-2-carboxamide; 97

N-(1-(((R)-1-(2-cyano-4,4-dimethylpent-2-enoyl)pyrrolidin-2-yl)methyl)-5-((2,6-dimethylmorpholino)methyl)-1H-benzo[d]imidazol-2-yl)-5-(difluoromethyl)thiophene-2-carboxamide;

(R)-N-(1-((1-(2-cyano-3-(3-methyloxetan-3-yl)acryloyl)pyrrolidin-2-yl)methyl)-5-((neopentylamino)methyl)-1H-benzo[d]imidazol-2-yl)-5-(difluoromethyl)thiophene-2-carboxamide;

(R)-N-(1-((1-(2-cyano-3-(3-methyloxetan-3-yl)acryloyl)pyrrolidin-2-yl)methyl)-5-(morpholinomethyl)-1H-benzo[d]imidazol-2-yl)-5-(difluoromethyl)thiophene-2-carboxamide; 100

N-(1-(((R)-1-(2-cyano-3-(3-methyloxetan-3-yl)acryloyl)pyrrolidin-2-yl)methyl)-5-((2,6-dimethylmorpholino)methyl)-1H-benzo[d]imidazol-2-yl)-5-(difluoromethyl)thiophene-2-carboxamide, (R)-N-(1-((1-(2-cyano-4-methylpent-2-enoyl)pyrrolidin-2-yl)methyl)-5-((isobutylamino)methyl)-1H-benzo[d]imidazol-2-yl)-5-(difluoromethyl)thiophene-2-carboxamide; 102

(R)-N-(1-((1-(2-cyano-4,4-dimethylpent-2-enoyl)pyrrolidin-2-yl)methyl)-5-((isobutylamino)methyl)-1H-benzo[d]imidazol-2-yl)-5-(difluoromethyl)thiophene-2-carboxamide;

(R)-N-(1-((1-(2-cyano-3-(3-methyloxetan-3-yl)acryloyl)pyrrolidin-2-yl)methyl)-5-((isobutylamino)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-((((3-methyloxetan-3-yl)methyl)amino)methyl)-1H-benzo[d]imidazol-2-yl)-5-(difluoromethyl)thiophene-2-carboxamide; 105

(R)-N-(1-((1-(2-cyano-4,4-dimethylpent-2-enoyl)pyrrolidin-2-yl)methyl)-5-((((3-methyloxetan-3-yl)methyl)amino)methyl)-1H-benzo[d]imidazol-2-yl)-5-(difluoromethyl)thiophene-2-carboxamide;

(R)-N-(1-((1-(2-cyano-3-(3-methyloxetan-3-yl)acryloyl)pyrrolidin-2-yl)methyl)-5-((((3-methyloxetan-3-yl)methyl)amino)methyl)-1H-benzo[d]imidazol-2-yl)-5-(difluoromethyl)thiophene-2-carboxamide; 107

(R)-N-(5-(2-oxa-6-azaspiro[3.3]heptan-6-ylmethyl)-1-((1-(2-cyano-4-methylpent-2-enoyl)pyrrolidin-2-yl)methyl)-1H-benzo[d]imidazol-2-yl)-5-(difluoromethyl)thiophene-2-carboxamide; 108

N-(1-(((R)-1-(but-2-ynoyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide;

N-(1-(((R)-1-(but-2-ynoyl)pyrrolidin-2-yl)methyl)-5-((((S)-3,3-dimethylbutan-2-yl)amino)methyl)-1H-benzo[d]imidazol-2-yl)-4-chlorobenzamide;

N-(1-(1-(but-2-ynoyl)piperidin-3-yl)-5-((((S)-3,3-dimethylbutan-2-yl)amino)methyl)-1H-benzo[d]imidazol-2-yl)-5-(difluoromethyl)thiophene-2-carboxamide; N-(1-(1-(but-2-ynoyl)piperidin-3-yl)-5-((((S)-3,3-dimethylbutan-2-yl)amino)methyl)-1H-benzo[d]imidazol-2-yl)-4-chlorobenzamide;

(R)-N-(1-((1-(2-cyano-3-(3-methyloxetan-3-yl)acryloyl)pyrrolidin-2-yl)methyl)-5-((neopentylamino)methyl)-1H-benzo[d]imidazol-2-yl)-5-(difluoromethyl)thiophene-2-carboxamide.

(R)-N-(1-((1-(5-amino-2-cyano-4,4-dimethylpent-2-enoyl)pyrrolidin-2-yl)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-6-((neopentylamino)methyl)-1H-benzo[d]imidazol-2-yl)-5-(difluoromethyl)thiophene-2-carboxamide;

(R)-N-(1-((1-(2-cyano-3-(3-methyloxetan-3-yl)acryloyl)pyrrolidin-2-yl)methyl)-6-((neopentylamino)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-(((2-hydroxy-2-methylpropyl)amino)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-(((cyclopropylmethyl)amino)methyl)-1H-benzo[d]imidazol-2-yl)-5-(difluoromethyl)thiophene-2-carboxamide;

(R)-1-((1-(2-cyano-4-methylpent-2-enoyl)pyrrolidin-2-yl)methyl)-2-(5-(difluoromethyl)thiophene-2-carboxamido)-N-neopentyl-1H-benzo[d]imidazole-5-carboxamide;

(R)-1-((1-(2-cyano-3-(3-methyloxetan-3-yl)acryloyl)pyrrolidin-2-yl)methyl)-2-(5-(difluoromethyl)thiophene-2-carboxamido)-N-neopentyl-1H-benzo[d]imidazole-5-carboxamide;

(R)-N-(1-((1-(2-cyano-4-methylpent-2-enoyl)pyrrolidin-2-yl)methyl)-5-((3-(2-hydroxypropan-2-yl)azetidin-1-yl)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-((3-hydroxyazetidin-1-yl)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-((4-(2-hydroxypropan-2-yl)piperidin-1-yl)methyl)-1H-benzo[d]imidazol-2-yl)-5-(difluoromethyl)thiophene-2-carboxamide;

(R)-N-(1-(1-(2-cyano-4,4-dimethylpent-2-enoyl)piperidin-3-yl)-1H-benzo[d]imidazol-2-yl)-5-(difluoromethyl)thiophene-2-carboxamide;

(S)-N-(1-(1-(2-cyano-4,4-dimethylpent-2-enoyl)piperidin-3-yl)-1H-benzo[d]imidazol-2-yl)-5-(difluoromethyl)thiophene-2-carboxamide;

(R)-N-(1-((1-(2-cyano-4,4-dimethyl-5-morpholinopent-2-enoyl)pyrrolidin-2-yl)methyl)-5-(hydroxymethyl)-1H-benzo[d]imidazol-2-yl)-5-(difluoromethyl)thiophene-2-carboxamide;

(R)-1-((1-acryloylpyrrolidin-2-yl)methyl)-2-(5-(difluoromethyl)thiophene-2-carboxamido)-N-neopentyl-1H-benzo[d]imidazole-5-carboxamide;

N-(3-(((R)-1-(2-cyano-4-(2-methoxyethoxy)-4-methylpent-2-enoyl)pyrrolidin-2-yl)methyl)-6-((((S)-3,3-dimethylbutan-2-yl)amino)methyl)-3H-imidazo[4,5-b]pyridin-2-yl)-5-(difluoromethyl)thiophene-2-carboxamide;

1-(((R)-1-acryloylpyrrolidin-2-yl)methyl)-2-(5-(difluoromethyl)thiophene-2-carboxamido)-N-((S)-3,3-dimethylbutan-2-yl)-1H-benzo[d]imidazole-5-carboxamide;

(S)-N-(1-((1-(2-cyano-4,4-dimethylpent-2-enoyl)azetidin-3-yl)methyl)-5-(((3,3-dimethylbutan-2-yl)amino)methyl)-1H-benzo[d]imidazol-2-yl)-5-(difluoromethyl)thiophene-2-carboxamide;

1-(((R)-1-(2-cyano-4,4-dimethylpent-2-enoyl)pyrrolidin-2-yl)methyl)-2-(5-(difluoromethyl)thiophene-2-carboxamido)-N-((S)-3,3-dimethylbutan-2-yl)-1H-benzo[d]imidazole-5-carboxamide;

(R)-N-(1-((1-(2-cyano-4-methylpent-2-enoyl)pyrrolidin-2-yl)methyl)-5-(3-hydroxypentan-3-yl)-1H-benzo[d]imidazol-2-yl)-5-(difluoromethyl)thiophene-2-carboxamide;

N-(1-((1-(2-cyano-4,4-dimethylpent-2-enoyl)pyrrolidin-3-yl)methyl)-5-((((S)-3,3-dimethylbutan-2-yl)amino)methyl)-1H-benzo[d]imidazol-2-yl)-5-(difluoromethyl)thiophene-2-carboxamide;

(R)-N-(1-((1-(2-cyano-4-ethoxy-4-methylpent-2-enoyl)pyrrolidin-2-yl)methyl)-5-((neopentylamino)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-((neopentylamino)-methyl)-1H-benzo[d]imidazol-2-yl)isoxazole-5-carboxamide;

(R)-N-(1-((1-(2-cyano-4,4-dimethylpent-2-enoyl)pyrrolidin-2-yl)methyl)-5-((neopentylamino)methyl)-1H-benzo[d]imidazol-2-yl)isoxazole-5-carboxamide;

(R)-N-(1-((1-(2-cyano-3-(3-methyloxetan-3-yl)acryloyl)pyrrolidin-2-yl)methyl)-5-((neopentylamino)methyl)-1H-benzo[d]imidazol-2-yl)isoxazole-5-carboxamide;

(R)-N-(1-((1-(2-cyano-4-methylpent-2-enoyl)pyrrolidin-2-yl)methyl)-5-((neopentylamino)methyl)-1H-benzo[d]imidazol-2-yl)nicotinamide;

(R)-N-(1-((1-(2-cyano-4-methylpent-2-enoyl)pyrrolidin-2-yl)methyl)-5-((neopentylamino)methyl)-1H-benzo[d]imidazol-2-yl)-3-(difluoromethyl)benzamide;

N-(1-(((R)-1-(2-cyano-4,4-dimethylpent-2-enoyl)pyrrolidin-2-yl)methyl)-5-((((S)-3,3-dimethylbutan-2-yl)amino)methyl)-1H-benzo[d]imidazol-2-yl)isoxazole-5-carboxamide;

N-(1-(((R)-1-(2-cyano-4-ethoxy-4-methylpent-2-enoyl)pyrrolidin-2-yl)methyl)-5-((((S)-3,3-dimethylbutan-2-yl)amino)methyl)-1H-benzo[d]imidazol-2-yl)isoxazole-5-carboxamide;

N-(1-(((R)-1-(2-cyano-4,4-dimethylpent-2-enoyl)pyrrolidin-3-yl)methyl)-5-((((S)-3,3-dimethylbutan-2-yl)amino)methyl)-1H-benzo[d]imidazol-2-yl)isoxazole-5-carboxamide;

N-(1-(((R)-1-(2-cyano-4-ethoxy-4-methylpent-2-enoyl)pyrrolidin-3-yl)methyl)-5-((((S)-3,3-dimethylbutan-2-yl)amino)methyl)-1H-benzo[d]imidazol-2-yl)isoxazole-5-carboxamide;

N-(1-(((S)-1-(2-cyano-4,4-dimethylpent-2-enoyl)pyrrolidin-3-yl)methyl)-5-((((S)-3,3-dimethylbutan-2-yl)amino)methyl)-1H-benzo[d]imidazol-2-yl)isoxazole-5-carboxamide;

N-(1-(((S)-1-(2-cyano-4-ethoxy-4-methylpent-2-enoyl)pyrrolidin-3-yl)methyl)-5-((((S)-3,3-dimethylbutan-2-yl)amino)methyl)-1H-benzo[d]imidazol-2-yl)isoxazole-5-carboxamide;

N-(1-(((S)-1-(2-cyano-4,4-dimethylpent-2-enoyl)pyrrolidin-3-yl)methyl)-5-((((S)-3,3-dimethylbutan-2-yl)amino)methyl)-1H-benzo[d]imidazol-2-yl)-5-(difluoromethyl)thiophene-2-carboxamide;

N-(1-(((S)-1-(2-cyano-4-ethoxy-4-methylpent-2-enoyl)pyrrolidin-3-yl)methyl)-5-((((S)-3,3-dimethylbutan-2-yl)amino)methyl)-1H-benzo[d]imidazol-2-yl)-5-(difluoromethyl)thiophene-2-carboxamide;

N-(1-(((R)-1-(2-cyano-4,4-dimethylpent-2-enoyl)pyrrolidin-3-yl)methyl)-5-((((S)-3,3-dimethylbutan-2-yl)amino)methyl)-1H-benzo[d]imidazol-2-yl)-5-(difluoromethyl)thiophene-2-carboxamide;

N-(1-(((R)-1-(2-cyano-4-ethoxy-4-methylpent-2-enoyl)pyrrolidin-3-yl)methyl)-5-((((S)-3,3-dimethylbutan-2-yl)amino)methyl)-1H-benzo[d]imidazol-2-yl)-5-(difluoromethyl)thiophene-2-carboxamide; N-(1-((R)-1-(2-cyano-4,4-dimethylpent-2-enoyl)pyrrolidin-3-yl)-5-((((S)-3,3-dimethylbutan-2-yl)amino)methyl)-1H-benzo[d]imidazol-2-yl)-5-(difluoromethyl)thiophene-2-carboxamide;

N-(1-(((R)-1-(2-cyano-4,4-dimethylpent-2-enoyl)pyrrolidin-2-yl)methyl)-5-((((S)-3,3-dimethylbutan-2-yl)amino)methyl)-1H-benzo[d]imidazol-2-yl)-3-(difluoromethyl)benzamide;

N-(1-(((R)-1-(2-cyano-4-methylpent-2-enoyl)pyrrolidin-2-yl)methyl)-5-((((S)-3,3-dimethylbutan-2-yl)amino)methyl)-1H-benzo[d]imidazol-2-yl)-3-(difluoromethyl)benzamide;

N-(1-(((R)-1-(2-cyano-4-ethoxy-4-methylpent-2-enoyl)pyrrolidin-2-yl)methyl)-5-((((S)-3,3-dimethylbutan-2-yl)amino)methyl)-1H-benzo[d]imidazol-2-yl)-3-(difluoromethyl)benzamide;

(R)-N-(1-(1-(2-cyano-4,4-dimethylpent-2-enoyl)piperidin-3-yl)-5-(hydroxymethyl)-1H-benzo[d]imidazol-2-yl)-5-(difluoromethyl)thiophene-2-carboxamide;

N-(1-((R)-1-(2-cyano-4-ethoxy-4-methylpent-2-enoyl)pyrrolidin-3-yl)-5-((((S)-3,3-dimethylbutan-2-yl)amino)methyl)-1H-benzo[d]imidazol-2-yl)-5-(difluoromethyl)thiophene-2-carboxamide;

N-(1-((R)-1-(2-cyano-4-methylpent-2-enoyl)pyrrolidin-3-yl)-5-((((S)-3,3-dimethylbutan-2-yl)amino)methyl)-1H-benzo[d]imidazol-2-yl)-5-(difluoromethyl)thiophene-2-carboxamide;
or an individual E or Z isomers thereof Other representative compounds of the disclosure are:

N-(3-(((R)-1-(2-cyano-4,4-dimethylpent-2-enoyl)pyrrolidin-2-yl)methyl)-6-((((S)-3,3-dimethylbutan-2-yl)amino)methyl)-3H-imidazo[4,5-b]pyridin-2-yl)-5-(difluoromethyl)thiophene-2-carboxamide; or N-(3-(((R)-1-(2-cyano-4-ethoxy-4-methylpent-2-enoyl)pyrrolidin-2-yl)methyl)-6-((((S)-3,3-dimethylbutan-2-yl)amino)methyl)-3H-imidazo[4,5-b]pyridin-2-yl)-5-(difluoromethyl)thiophene-2-carboxamide;

(R)-N-(3-((1-(2-cyano-4,4-dimethylpent-2-enoyl)pyrrolidin-2-yl)methyl)-6-((neopentylamino)methyl)-3H-imidazo[4,5-b]pyridin-2-yl)-5-(difluoromethyl)thiophene-2-carboxamide; or (R)-N-(3-((1-(2-cyano-4-ethoxy-4-methylpent-2-enoyl)pyrrolidin-2-yl)methyl)-6-((neopentylamino)methyl)-3H-imidazo[4,5-b]pyridin-2-yl)-5-(difluoromethyl)thiophene-2-carboxamide;
or an individual E or Z isomers thereof.

Embodiments
Embodiment 1

In one embodiment, the compound of Formula (IA) and (I) or a salt thereof has the structure (Ia):

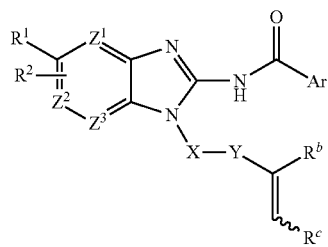

wherein the groups are as defined in Formula (IA) and (I) respectively, in the Summary. Within embodiment 1, in one group of compounds $Z^1$, $Z^2$, and $Z^3$ are CH (or C if substituted with $R^2$).

Embodiment 2

In another embodiment, the compound of Formula (IA) and (I) or a salt thereof has the structure (Ib):

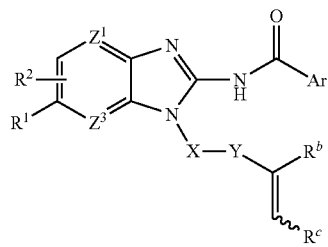

wherein the groups are as defined in Formula (IA) and (I) respectively, in the Summary. Within embodiment 2, in one group of compounds $Z^1$ and $Z^3$ are CH (or C if substituted with $R^2$).

Embodiment 3

In yet another embodiment, the compound of Formula (IA) and (I) or a salt thereof has the structure (Ic):

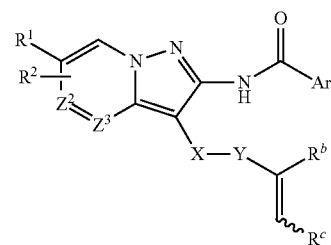

wherein the groups are as defined in Formula (IA) and (I) respectively, in the Summary. Within embodiment 3, in one group of compounds $Z^2$ and $Z^3$ are CH (or C if substituted with $R^2$).

Embodiment 4

(i) The compounds or salt thereof as defined in Formula (IA) and (I) in the Summary and embodiments 1, 2, and 3, and groups contained therein, wherein $R^b$ and $R^c$ are hydrogen.

Embodiment 5

The compounds or a salt thereof as defined in Formula (IA) and (I) in the Summary and embodiments 1, 2, and 3, and groups contained therein, wherein $R^b$ is cyano and $R^c$ is alkyl, substituted alkyl, cycloalkyl, or 3 to 6 membered saturated monocyclic heterocyclyl containing one or two heteroatoms selected from N, O, or S and optionally substituted with one or two substituents independently selected from hydroxy, alkyl or fluoro.

(a) Within the groups in embodiment 5, in one group of compounds $R^c$ is alkyl. Within this group of compounds, in one group of compounds $R^c$ is isopropyl or tert-butyl.

(b) Within the groups in embodiment 5, in another group of compounds $R^c$ is cycloalkyl. Within this group of compounds, in one group of compounds $R^c$ is cyclopropyl, cyclobutyl, cyclopentyl, or cyclohexyl. Within this group of compounds, in another group of compounds $R^c$ is cyclopropyl.

(c) Within the groups in embodiment 5, in yet another group of compounds $R^c$ is substituted alkyl. Within this group of compounds, in one group of compounds $R^c$ is alkyl substituted with hydroxy, alkoxy, —NRR' (where R is hydrogen, alkyl, hydroxyalkyl, or alkoxyalkyl and R' is hydrogen or alkyl) or heterocyclyl which is optionally substituted with one or two groups independently selected from alkyl or hydroxyl. (i) Within this group of compounds, in another group of compounds $R^c$ is —C(CH$_3$)$_2$NH$_2$, —C(CH$_3$)$_2$NHCH$_3$, —C(CH$_3$)$_2$N(CH$_3$)$_2$, —C(CH$_3$)$_2$NHCH$_2$CH$_3$, —C(CH$_3$)$_2$NHCH(CH$_3$)$_2$, —C(CH$_3$)$_2$NH(CH$_2$)$_2$OCH$_3$, —C(CH$_3$)$_2$—NH-(3-methyloxetan-3-yl), —C(CH$_3$)$_2$—N(CH$_3$)(3-methyloxetan-3-yl), —C(CH$_3$)$_2$OCH$_2$CH$_3$, —C(CH$_3$)$_2$OH, —C(CH$_3$)$_2$morpholin-4-yl, —C(CH$_3$)$_2$-(3-methyloxetan-3-yl), —C(CH$_3$)$_2$azetidin-3-yl, —C(CH$_3$)$_2$(1-methylazetidin-3-yl), —C(CH$_3$)$_2$piperazin-1-yl, —C(CH$_3$)$_2$pyrrolidin-1-yl, or —C(CH$_3$)$_2$-(3-methylpiperazin-1-yl). (ii) Within this group of compounds, in another group of compounds $R^c$ is —C(CH$_3$)$_2$CH$_2$NH$_2$ or —C(CH$_3$)$_2$CH$_2$OH. (iii) Within this group of compounds, in another group of compounds $R^c$ is —C(CH$_3$)$_2$OCH$_2$CH$_3$.

(d) Within the groups in embodiment 5, in one group of compounds $R^c$ is 3 to 6 membered saturated monocyclic heterocyclyl containing one or two heteroatoms selected from N, O, or S and optionally substituted with one or two substituents independently selected from hydroxy, alkyl or fluoro. Within this group of compounds, in one group of compounds $R^c$ is 2-pyrrolidinyl, 3- or 4-piperidinyl, 1-methylpiperidin-4-yl, 1-methylpiperidin-3-yl, azetidin-3-yl, oxetan-3-yl, 3-methyloxetan-3-yl, or 4-tetrahydropyranyl.

Embodiment 6

(a) The compounds or a salt thereof as defined in the in Formula (IA) and (I) in the Summary and embodiments 1, 2, 3, 4 and 5 and groups contained therein, wherein —X—Y— is

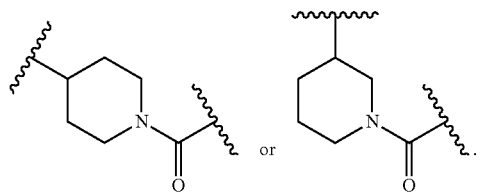 [SMILES: *C(=O)N1CCC(*)CC1 ; *C(=O)N1CCCC(*)C1]

In one embodiment it is

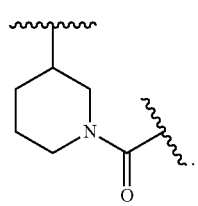 [SMILES: *C(=O)N1CCCC(*)C1]

In another embodiment it is

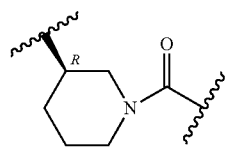

(b) The compounds or a salt thereof as defined in the in Formula (IA) and (I) in the Summary and embodiments 1, 2, 3, 4 and 5 and groups contained therein wherein —X—Y— is

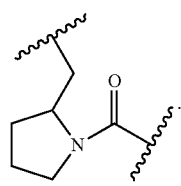 [SMILES: *CC1CCCN1C(*)=O]

Within the groups in (b), in one group of compounds —X—Y— is

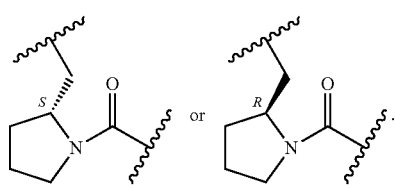

(c) The compounds or a salt thereof as defined in the in Formula (IA) and (I) in the Summary and embodiments 1, 2, 3, 4 and 5 and groups contained therein wherein —X—Y— is -alkylene-NHCO— or -alkylene-NHSO$_2$—. Within the groups in (c), in one group of compounds —X—Y— is -alkylene-NHCO—. Within the groups in (c), in one group of compounds —X—Y— is —(CH$_2$)$_2$NHCO— or —(CH$_2$)$_2$N(CH$_3$)CO—.

(d) The compounds or a salt thereof as defined in the in Formula (IA) and (I) in the Summary and embodiments 1, 2, 3, 4 and 5 and groups contained therein wherein —X—Y— is

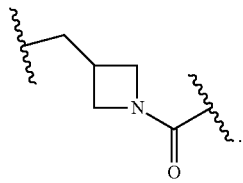 [SMILES: *CC1CN(C(*)=O)C1]

(e) The compounds or a salt thereof as defined in the in Formula (IA) and (I) in the Summary and embodiments 1, 2, 3, 4 and 5 and groups contained therein wherein —X—Y— is.

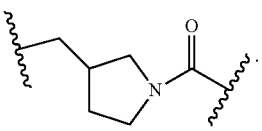 [SMILES: *CC1CCN(C(*)=O)C1]

Within the groups in (b), in one group of compounds —X—Y— is

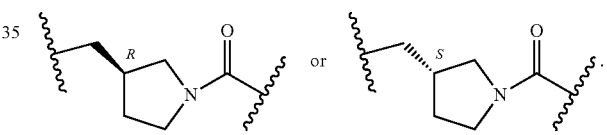

(f) The compounds or a salt thereof as defined in the in Formula (IA) and (I) in the Summary and embodiments 1, 2, 3, 4 and 5 and groups contained therein wherein —X—Y— is.

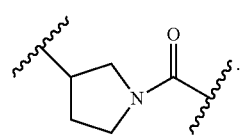 [SMILES: *C(=O)N1CCC(*)C1]

Within the groups in (b), in one group of compounds —X—Y— is (IA)

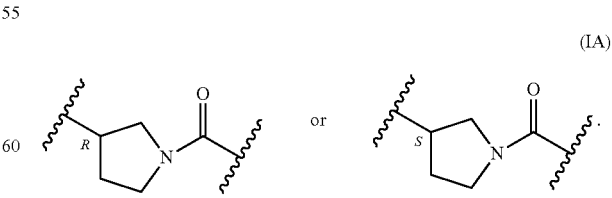

and

Embodiment 7

The compounds or a salt thereof as defined in Formula (IA) and (I) in the Summary and embodiments 1, 2, 3, 4, 5, and 6 and groups contained therein, wherein $R^1$ is hydrogen, —$NR^3COR^4$, or -(alkylene)-$NR^3R^5$ where $R^3$ is hydrogen or alkyl, $R^4$ is optionally substituted aryl or heteroaryl, and $R^5$ is hydrogen, alkyl, haloalkyl, or acyl or $R^3$ and $R^5$ together with the nitrogen atom to which they are attached from heterocycloamino optionally substituted with one or two substituents independently selected from alkyl, halo, hydroxyalkyl, or alkoxyalkyl.

(a) Within the groups in embodiment 7, in one group of compounds $R^1$ is hydrogen.

(b) Within the groups in embodiment 7, in one group of compounds $R^1$ is —$NR^3COR^4$.

(c) Within the groups in embodiment 7, in one group of compounds $R^1$ is -(alkylene)-$NR^3R^5$ where $R^3$ is hydrogen or alkyl and $R^5$ is hydrogen, alkyl, haloalkyl, or acyl. Within this group of compounds, in one group of compounds, $R^1$ is (S)-$CH_2N(COCF_3)CH(CH_3)C(CH_3)_3$, (S)-$CH_2NHCH(CH_3)C(CH_3)_3$, or (S)-$CH_2N(CH_3)CH(CH_3)C(CH_3)_3$, preferably (S)—$CH_2NHCH(CH_3)C(CH_3)_3$. Within this group of compounds, in another group of compounds, $R^1$ is $CH_2NHCH_2C(CH_3)_3$, -(R)-$CH_2NHCH(CH_3)C(CH_3)_3$, -(S)-$CH_2NHCH(CH_3)C(CH_3)_3$ (d) Within the groups in embodiment 7, in another one group of compounds $R^1$ is -(alkylene)-$NR^3R^5$ where $R^3$ and $R^5$ together with the nitrogen atom to which they are attached from heterocycloamino optionally substituted with one or two substituents independently selected from alkyl, halo, hydroxyalkyl, or alkoxyalkyl. Within this group of compounds in one group of compounds $R^1$ is —$CH_2$-2,6-dimethylmorpholin-4-yl, —$CH_2$-morpholin-4-yl, —$CH_2$-4-methylpiperazin-yl, Within the groups in embodiment 7 and groups contained therein, in one group of compounds $R^2$ is hydrogen.

Embodiment 8

The compounds or a salt thereof of Formula (IA) or (I) as defined in the Summary and embodiments 1, 2, 3, 4, 5, 6, and 7 and groups contained therein wherein Ar is phenyl optionally substituted with one, two, or three substituents selected from hydrogen, alkyl, alkoxy, hydroxy, cyano, alkylthio, halo, haloalkyl, haloalkoxy, cycloalkyl, optionally substituted phenyl, or optionally substituted heteroaryl. Within the groups in embodiment 8, in one group of compounds, Ar is phenyl substituted with one, two, or three substituents independently selected from chloro, fluoro, methyl, trifluoromethyl, trifluoromethoxy, difluoromethoxy, or difluromethyl. Within the groups in embodiment 8, in one group of compounds, Ar is phenyl, 4-Clphenyl, 4-$CHF_2$phenyl, 3-$CHF_2$phenyl, 3-$CF_3$phenyl, 3-$CH_3$phenyl, or 3,4-diFphenyl. Within the groups in embodiment 8, in one group of compounds, Ar is phenyl, 4-Clphenyl, 4-$CHF_2$phenyl, 3-$CHF_2$phenyl, 3-$CF_3$phenyl, 3-$CH_3$phenyl, 3-CN-phenyl, 4-CN-phenyl, or 3,4-diFphenyl.

Embodiment 9

The compounds or a salt thereof of Formula (IA) or (I) as defined in the Summary and embodiments 1, 2, 3, 4, 5, 6, and 7 and groups contained therein wherein Ar is heteroaryl optionally substituted with one, two, or three substituents selected from hydrogen, alkyl, alkoxy, hydroxy, cyano, alkylthio, halo, haloalkyl, haloalkoxy, cycloalkyl, optionally substituted phenyl, or optionally substituted heteroaryl. Within the groups in embodiment 8, in one group of compounds, Ar is pyridin-3-yl, 5-(pyrazol-4-yl)-thien-2-yl, 5-$CHF_2$thien-2-yl, or isoxazol-5-yl. Within the groups in embodiment 8, in one group of compounds, Ar is a five membered heteroaryl ring (such as thienyl, oxazolyl, isoxazolyl, imidazolyl, pyrrolyl, triazolyl, pyrazolyl, or thiazolyl) optionally substituted with one, two, or three substituents selected from hydrogen, alkyl, alkoxy, hydroxy, cyano, alkylthio, halo, haloalkyl, haloalkoxy, cycloalkyl, optionally substituted phenyl, or optionally substituted heteroaryl (in one group methyl, ethyl, fluoro, trifluoromethyl, or difluoromethyl). Within the groups in embodiment 8, in another group of compounds, Ar is thien-2-yl, 5-chlorothien-2-yl, 5-cyanothien-2-yl, 2-oxazol-4-ylthien-5-yl, 5-$CF_3$-thien-2-yl, 1-methyl-pyrazol-3-yl, oxazol-5-yl, 2-methyl-oxazol-5-yl, 2-methyl, 1,2,3-triazol-4-yl, oxazol-5-yl, 2-methyl-oxazol-4-yl, 2-methyl-thiazol-5-yl, 5-$CHF_2$thien-2-yl, or isoxazol-5-yl.

General Synthetic Schemes

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula (IA) and (I) can be prepared as illustrated and described in Schemes 1 and 5 below.

Compounds of Formula (IA) or (I) where ring B is (a) where $Z^1$ is CH, X is a ring of formula

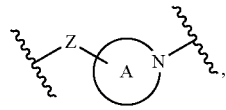

$R^b$ is cyano, and other groups are as defined in the Summary can be prepared as illustrated and described in Scheme 1 below.

Scheme 1

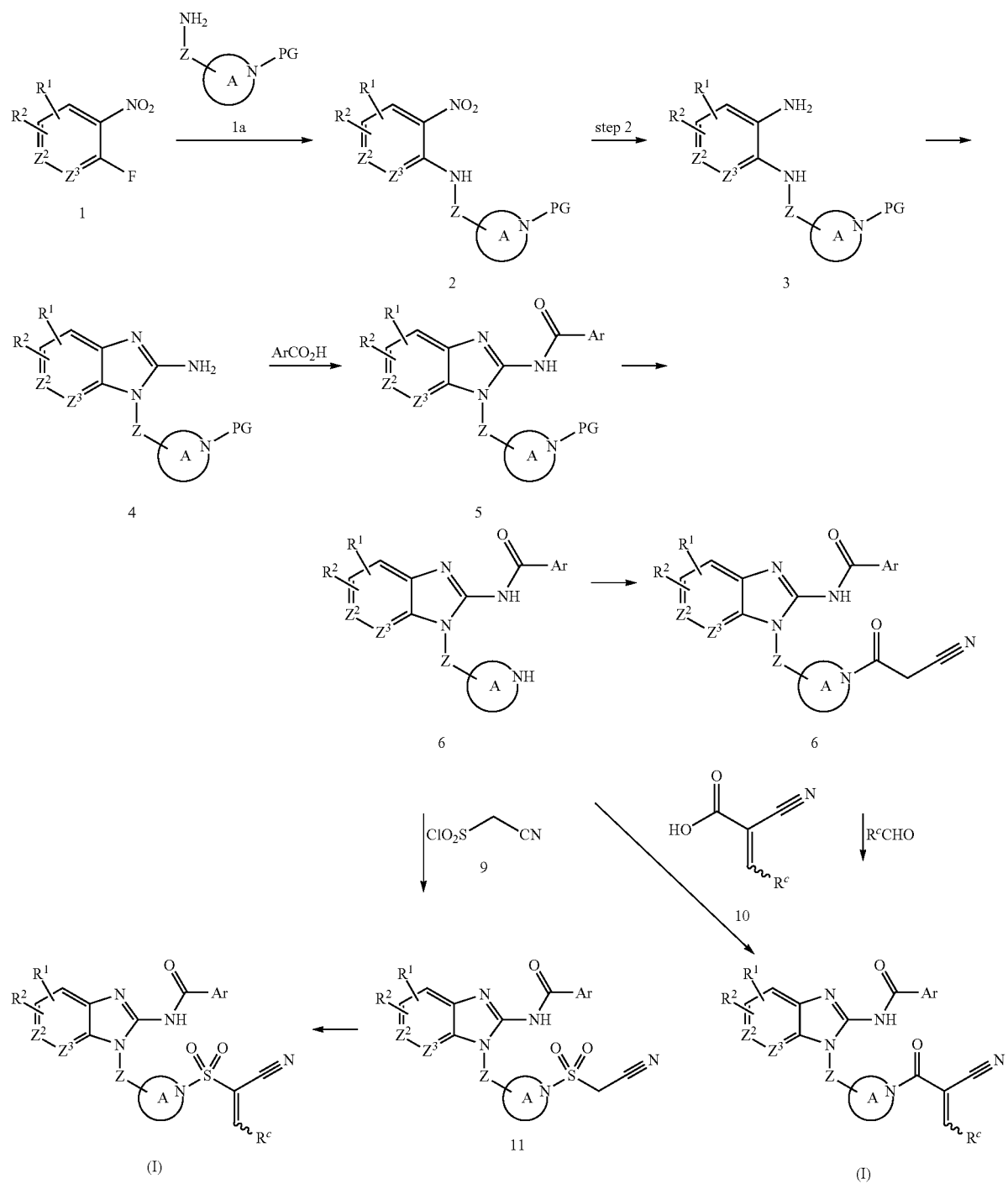

Displacement of the fluorine or other halogen group in a compound of formula 1 where $Z^2$, $Z^3$, $R^1$, and $R^2$ are as defined in the Summary, by a monoprotected diamine 1a where ring A and Z are as defined in the Summary and PG is a suitable nitrogen protecting group, in a solvent such as acetonitrile provides a compound of formula 2. Compounds of formula 1 and 1a e.g., (R)-tert-butyl 2-(aminomethyl) pyrrolidine-1-carboxylate, (S)-tert-butyl 2-(aminomethyl) pyrrolidine-1-carboxylate, tert-butyl 3-aminopiperidine-1-carboxylate, tert-butyl 4-aminopiperidine-1-carboxylate, tert-butyl 3-(aminomethyl)azetidine-1-carboxylate are commercially available or they can be prepared by methods well known in the art. Reduction of the nitro group in 2 can be accomplished by various reduction methods such as hydrogenation with Pd catalysis or by the action of elemental Zn. The resulting diamino compound 3 can be cyclized to the aminobenzimidazole compound of formula 4 by treatment with cyanogen bromide in a solvent such as ethanol. Coupling of 4 with a carboxylic acid of formula ArCOOH where Ar is as defined in the Summary occurs under standard amide coupling conditions or with an acid derivative such as a carboxylic acid chloride to provide compound of formula 5. Removal of the amino protecting group PG, followed by coupling of the resulting compound 6 with cyanoacetic acid provides a compound of formula 7. Compound 7 can be then converted to a compound of Formula (IA) or (I) by methods well known in the art. For example, compounds of Formula (IA) or (I) where X is —CO— can be prepared by condensing compound 7 with an aldehyde of formula $R^cCHO$, where $R^c$ is as defined in the Summary, under standard condensation conditions such as using a base such as piperidine and the like, in the presence or absence of acetic acid and the like in solvents such as ethanol at temperatures ranging from room temperature to reflux to afford compounds of Formula (IA) or (I). Compounds of formula $R^cCHO$ are commercially available or they can be prepared by methods well known in the art e.g. such as, e.g., acetaldehyde, cyclopropylaldehyde, isobutyraldehyde, 2-(dimethyl amino)-2-methylpropanal, and 2-methyl-2-(morpholin-4-yl)propanal are commercially available. Ethoxy-2-methylpropanal was prepared from isobutyraldehyde as described in PCT Int. Appl., 2007142576. Likewise the condensation can be performed by adding the desired aldehyde, base such as pyrrolidine or piperidine with or without chlorotrimethylsilane in dichloromethane or other suitable solvent (e.g. dioxane and ethanol).

Alternatively, compounds of Formula (IA) or (I) where X is —CO— can be prepared by reacting compound 6 with an acid of formula 10 where $R^c$ is as defined in the Summary under amide coupling conditions. Compounds of Formula (IA) or (I) where X is —SO$_2$— can be prepared by reacting amine 6 with a sulfonyl chloride of formula 9, followed by condensation of resulting compound 11 with an aldehyde of formula $R^cCHO$ as described.

It will be apparent to a person of ordinary skilled in the art, that substituting

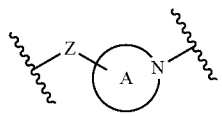

with amines of formula NH$_2$—X—NHPG where PG is a suitable amino protecting group and X is cycloalkylene or alkylene e.g., tert-butyl N-(2-aminoethyl)carbamate or NH$_2$—X—OPG$^1$ where PG$^1$ is a suitable hydroxy protecting group and X is alkylene, followed by steps described above would give compounds of Formula (IA) or (I) where X is -alkyleneNH—, -cycloalkyleneNH—, and -alkylene-O— and Y is CO or SO$_2$. Compounds of Formula (IA) or (I) where $R^b$ and $R^c$ are hydrogen, can be prepared by the addition of acryloyl chloride to amines such as 6 in a solvent such as toluene or THF.

Compounds of Formula (IA) or (I) where ring B is (b), $R^b$ is cyano and other groups are as defined in the Summary can be prepared as illustrated and described in Scheme 2 below.

Scheme 2

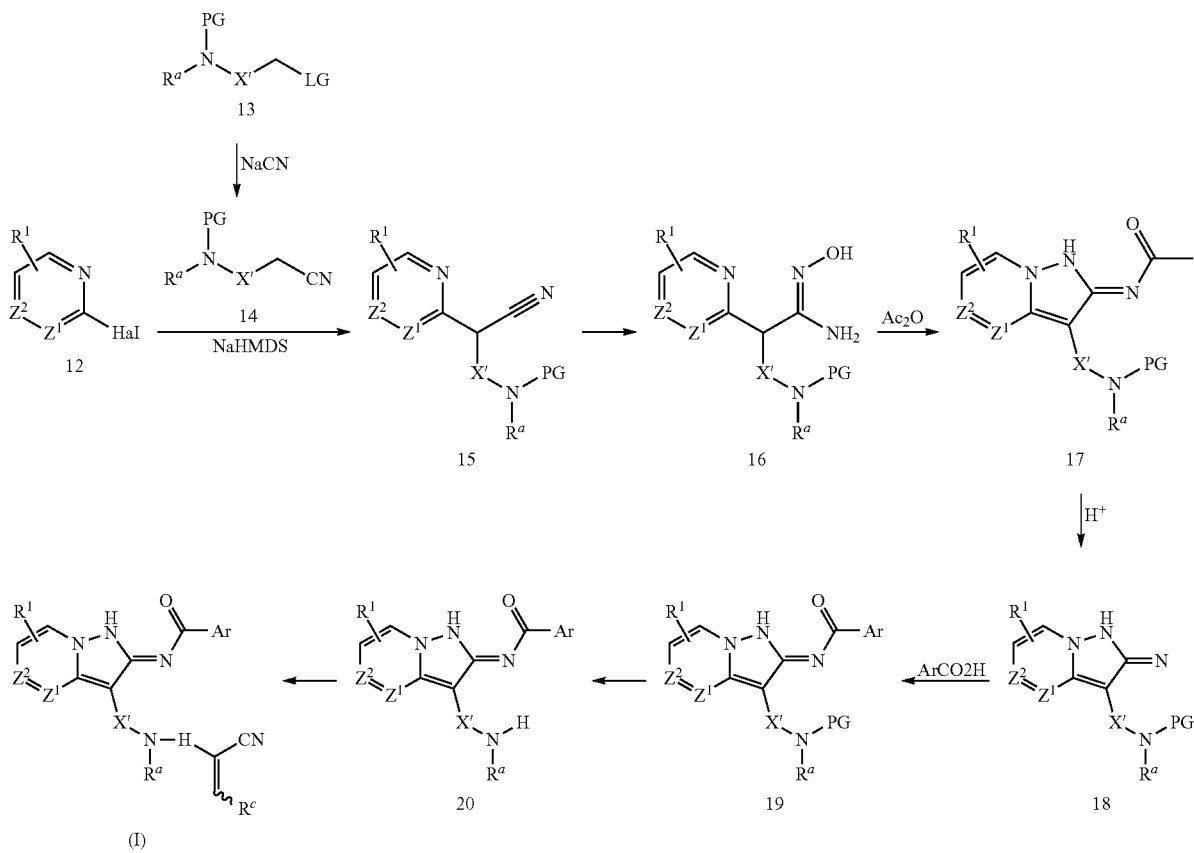

Reaction of a halopyridines, halopyrazines, or halopyrimidines 12 which are readily available from commercial suppliers with a compound of formula 14 where $R^a$ is as defined in the Summary, PG is a suitable amino protecting group and X' is alkylene or cycloalkylene in the presence of a base such as NaHMDS provides a compound of formula 15 (see J. Org. Chem, 2005, 10186-10189), Compounds 14 are either available commercially or can be prepared from a compound such as 13 where LG is a leaving group such as halogen or mesylate and sodium cyanide, PG is a suitable amino protecting group such as benzyloxy carbamate or benzyl, and $R^a$ is as defined previously or alternately a suitable amino protecting group, and X' is alkyl or cycloalkylene. Using procedures described in Chemical & Pharmaceutical Bulletin (1973), 21(10), 2146-60, addition of hydroxylamine to compound 15 affords the hydroxyamidine compound 16 which is then cyclized by the action of acetic anhydride to form compound 17. Acidic hydrolysis affords compound 18 which can be acylated as described in scheme 1 to form compound 19. Deprotection, via hydrogenation with Pd catalyst of a CBZ or benzyl protecting group for example, affords compound 20. Compound 20 can be carried forward to afford compounds of Formula (IA) or (I) as described in Scheme 1 above.

Compounds of Formula (IA) or (I) where ring B is (a) where $Z^1$ is CH (or C if substituted with $R^1$ or $R^2$), $R^1$ is —(CH$_2$)—NR$^3$R$^5$ where $R^3$ and $R^5$ are as defined in the Summary, X is a ring of formula $R^b$ is cyano, and other groups are as defined in the Summary can also be prepared as illustrated and described in Scheme 3 below.

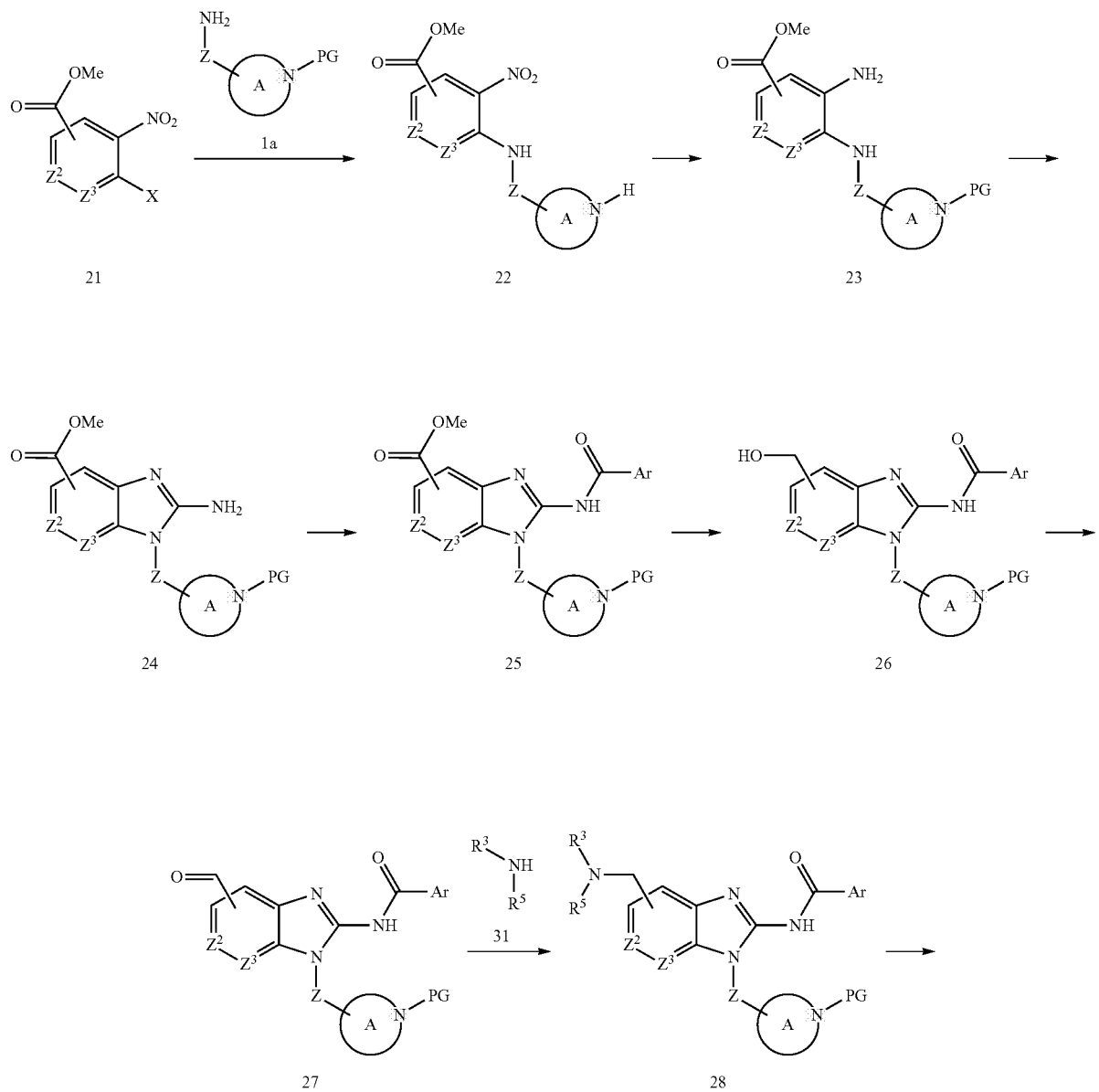

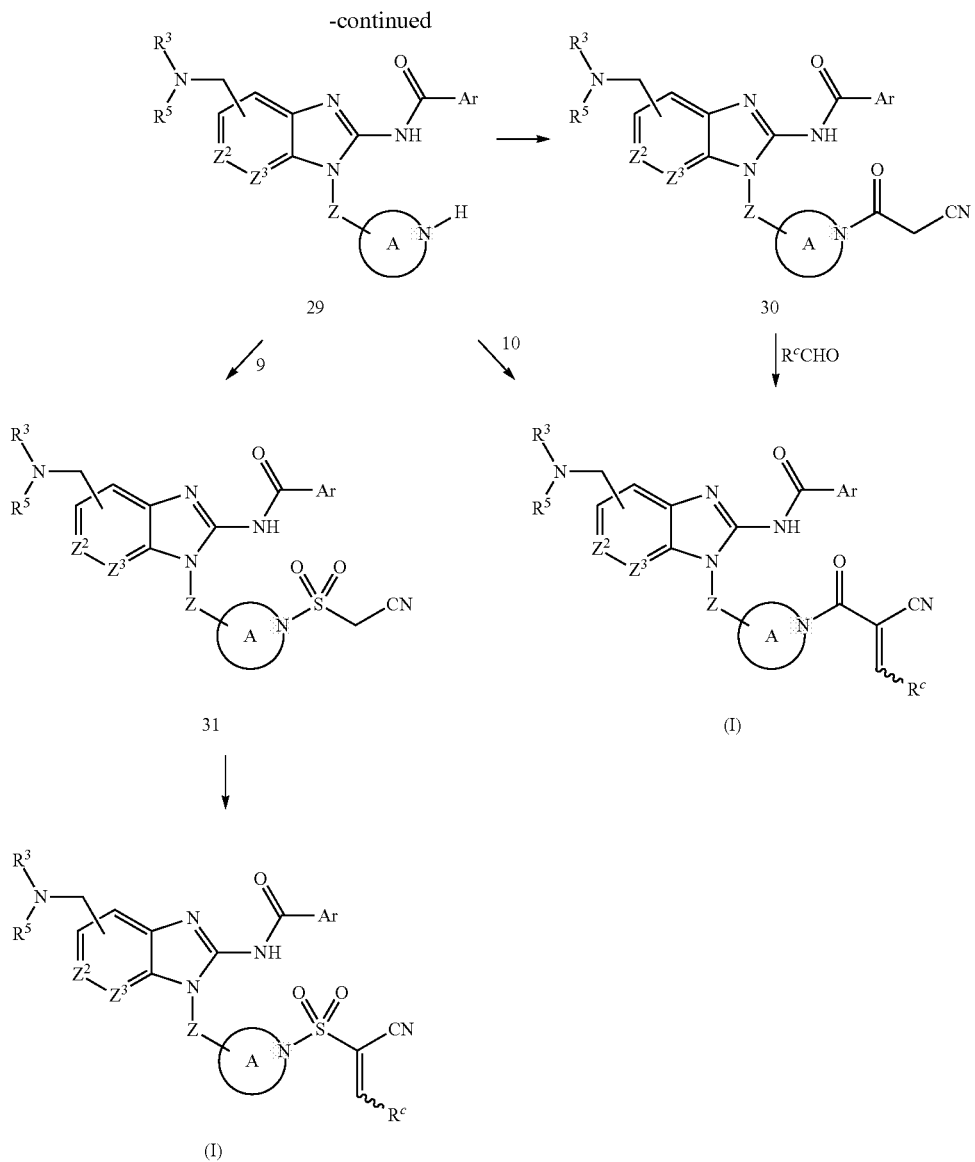

Displacement of a halogen X in a compound of formula 21 where $Z^2$ and $Z^3$ are as defined in the Summary by a monoprotected diamine 1a where Ring A and Z are as defined in the Summary, and PG is a suitable nitrogen protecting group, in a solvent such as acetonitrile provides a compound of formula 22. Compounds of formula 21 and 1a e.g., methyl 4-fluoro-3-nitrobenzoate, methyl 3-fluoro-4-nitrobenzenecarboxylate, tert-butyl(2-aminoethyl)carbamate, tert-butyl(2-aminoethyl)(methyl)-carbamate, (R)-tert-butyl 2-(aminomethyl)pyrrolidine-1-carboxylate, (S)-tert-butyl 2-(aminomethyl)pyrrolidine-1-carboxylate, tert-butyl 3-aminopiperidine-1-carboxylate, tert-butyl 4-aminopiperidine-1-carboxylate, tert-butyl 3-(aminomethyl)azetidine-1-carboxylate are commercially available or they can be prepared by methods well known in the art.

Reduction of the nitro group in 22 can be accomplished by various reduction methods such as hydrogenation with Pd catalysis or by the action of elemental Zn. The resulting diamino compound 23 can be cyclized to the aminobenzimidazole compound of formula 24 by treatment with cyanogen bromide in a solvent such as ethanol. Coupling of 24 with a carboxylic acid of formula ArCOOH where Ar is as defined in the Summary under standard amide coupling conditions or with an acid derivative such as a carboxylic acid chloride provides a compound of formula 25.

Reduction of the ester group in compound 25 with a suitable reducing agent such as lithium aluminum hydride affords alcohol 26 which can be oxidized with an oxidizing agent such as Dess-Martin Periodinane or PCC other standard oxidizing protocols such as the Swern oxidation and the like to afford aldehyde 27. Compound 27 can undergo reductive amination with amines of formula 31 where $R^3$ and $R^5$ are as described in the Summary to afford compound 28. Removal of the amino protecting group PG provides compound 29 which can be converted to a compound of Formula (IA) or (I) as described in Scheme I above.

Alternatively, compounds of Formula (IA) or (I) where ring B is (a) where $Z^1$ is CH (or C if substituted with $R^1$ or $R^2$), $R^1$ is —(CH$_2$)—NR$^3$R$^5$ where $R^3$ and $R^5$ are as defined in the Summary, X is a ring of formula

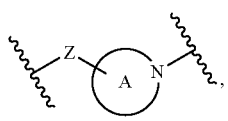

$R^b$ is cyano, and other groups are as defined in the Summary can also be prepared as illustrated and described in Scheme 4 below.

Scheme 4

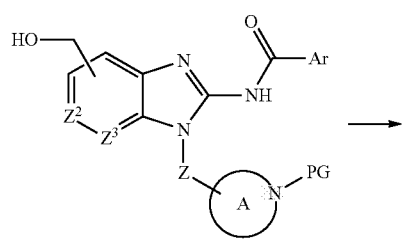

26

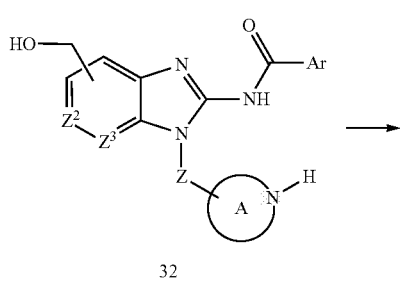

32

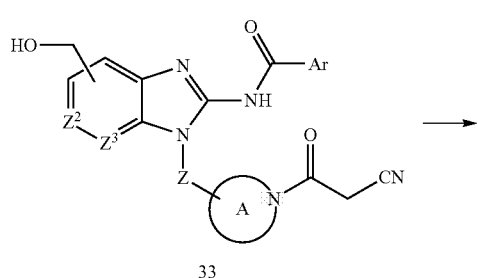

33

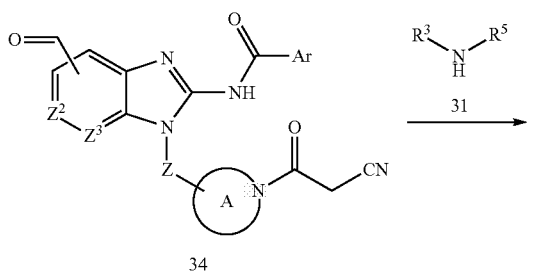

34

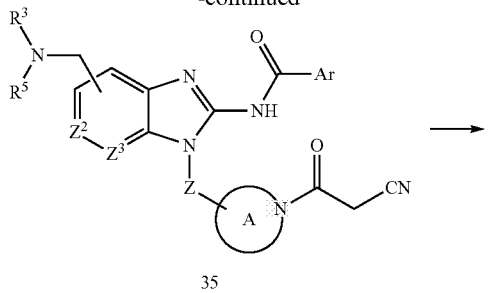

35

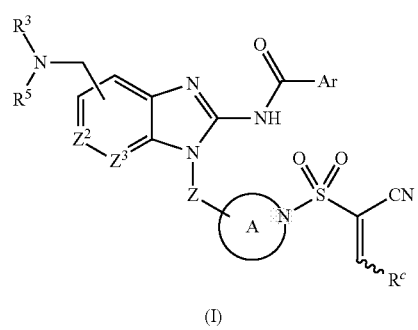

(I)

Removal of the amino protecting group PG in compound 26, followed by coupling of the resulting compound 32 with cyanoacetic acid provides a compound of formula 33. Compound 33 can be oxidized with reagents such as Dess-Martin Periodinane or PCC other standard oxidizing protocols such as the Swern oxidation and the like to afford aldehyde 34. Compound 34 can undergo reductive amination with amines 31, where $R^3$ and $R^5$ are as described in the Summary to afford compound 35. Compound 35 can be then converted to a compound of Formula (IA) and (I) as described in Scheme 1 above.

Alternatively compounds of Formula (IA) or (I) where ring B is (a) where $Z^1$ is CH (or C if substituted with $R^1$ or $R^2$), $R^1$ is —(CH$_2$)—NR$^3$R$^5$ where $R^3$ and $R^5$ are as defined in the Summary, X is a ring of formula

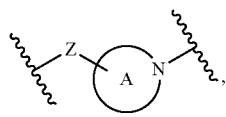

$R^b$ is cyano, and other groups are as defined in the Summary can also be prepared as illustrated and described in Scheme 5 below.

Scheme 5
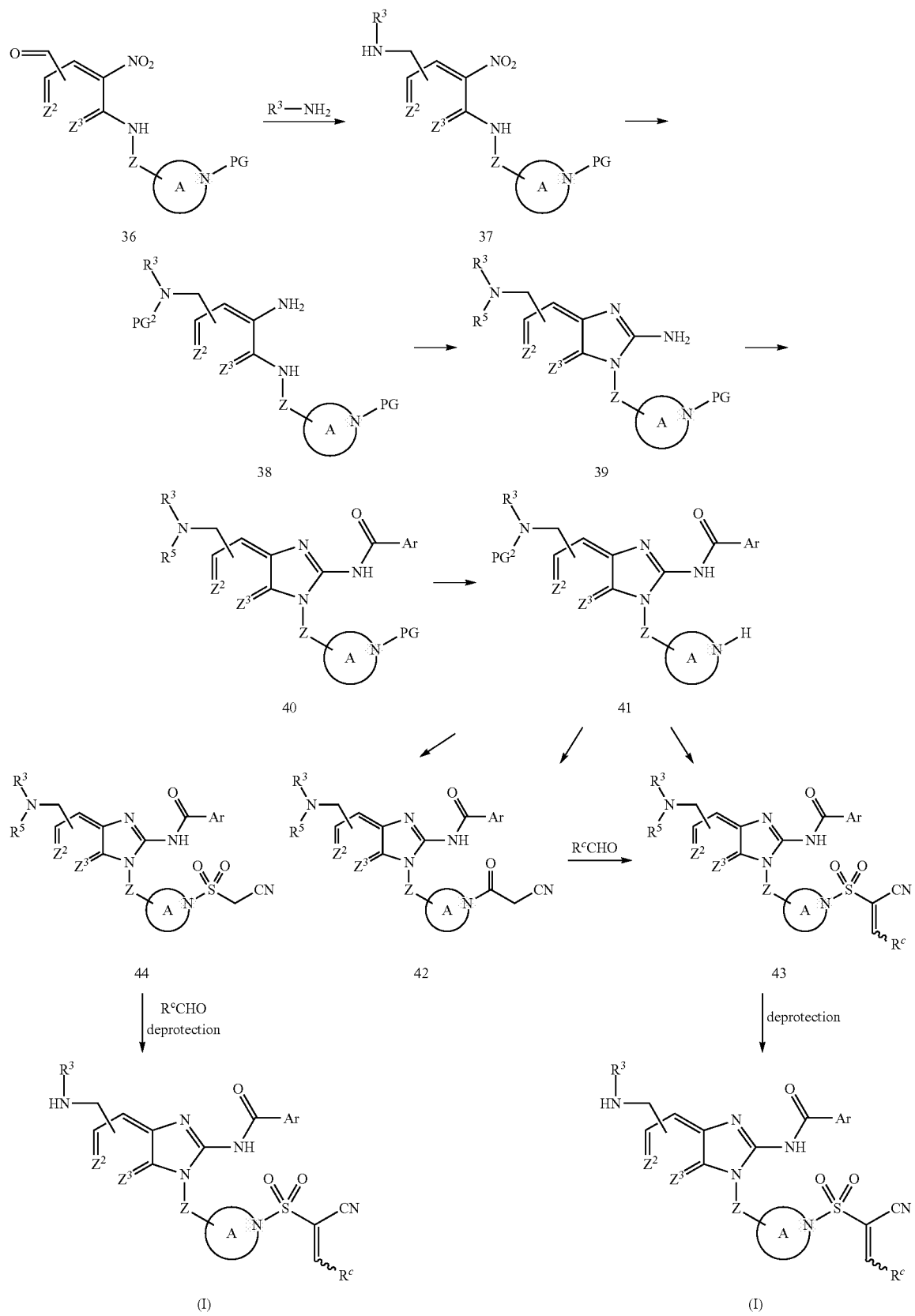

Treatment of a compound of formula 36 (prepared by reacting compound 1 where $R^1$ is aldehyde with compound 1a as described in Scheme 1) with an amine of formula $R^3NH_2$ where $R^3$ is as defined in the Summary, provides a compound of formula 37. Protection of the resultant amine 37 with a suitable orthogonal protecting group $PG^2$ such as Alloc or Cbz, can be accomplished under standard conditions as described in T. W. Greene, Protective Groups in Organic Synthesis, John Wiley & Sons, Inc. (1999) to afford a compound of formula 38 which can be converted to a compound of formula 42, 43, or 44 as described in Scheme 1 above. Removal of the amino protecting group then provides a compound of Formula (IA) or (I).

It will be apparent to a person of ordinary skilled in the art, that substituting

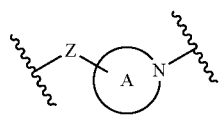

with amines of formula $NH_2$—X—NHPG where PG is a suitable amino protecting group and X is cycloalkylene or alkylene e.g., tert-butyl N-(2-aminoethyl)carbamate or $NH_2$—X—$OPG^1$ where $PG^1$ is a suitable hydroxy protecting group and X is alkylene, followed by steps described above would give compounds of Formula (I) where X is -alkyleneNH—, -cycloalkyleneNH—, and -alkylene-O— and Y is CO or $SO_2$. Compounds of Formula (IA) or (I) where $R^b$ and $R^c$ are hydrogen, can be prepared by the addition of acryloyl chloride to amines such as 41 in a solvent such as toluene or THF.

Utility

ITK dysfunction (e.g., overexpression) has been implicated in lung inflammation, recruitment of eosinophils, production of mucus (see Mueller, et al., Attenuation of immunological symptoms of allergic asthma in mice lacking the tyrosine kinase ITK, *Journal of Immunology*, 170:5056-5063) as well as reduced airway hyperresponsiveness (see Ferrara, et al., Reduced airway hyperresponsiveness and tracheal responses during allergic asthma in mice lacking tyrosine kinase inducible T-cell kinase, *Journal of Allergy and Clinical Immunology*, 117:780-786). Due to its role in the production of cytokines and T cells, inhibiting Itk function can reduce or inhibit the development and/or progression of multiple inflammatory disorders, autoimmune disorders, and lymphoproliferative disorders. Several drug therapies target Itk in order to treat inflammatory disorders, autoimmune disorders, and lymphoproliferative disorders. These drugs include, but are not limited to, BMS-488516 and BMS-509744 (see Lin, et al., Selective Itk inhibitors block T-cell activation and murine lung inflammation, *Biochemistry*, 43(34):11056-62), 2-amino-5-(thioaryl)thiazoles (Das, Discovery and SAR of 2-amino-5-(thioaryl)thiazoles as potent and selective Itk inhibitors, *Bioorganic and Medicinal Chemistry Letters*, 16(14):3706-12); 3-Aminopyrid-2-ones (see Charrier, et al., Discovery and Structure-Activity Relationship of 3-Aminopyrid-2-ones as Potent and Selective Interleukin-2 Inducible T-Cell Kinase (Itk) Inhibitors, *Journal of Medicinal Chemistry*, 54(7):2341-50).

There is evidence that ITK dysfunction plays a role in multiple inflammatory disorders that are affected by cytokine production, e.g., lung inflammation and pneumonia (see Lin, et al., Selective Itk inhibitors block T-cell activation and murine lung inflammation, *Biochemistry*, 43(34):11056-62; Das, Discovery and SAR of 2-amino-5-(thioaryl)thiazoles as potent and selective Itk inhibitors, *Bioorganic and Medicinal Chemistry Letters*, 16(14):3706-12); allergic asthma (see Mueller, et al., Attenuation of immunological symptoms of allergic asthma in mice lacking the tyrosine kinase ITK, *Journal of Immunology*, 170:5056-5063; Das, Discovery and SAR of 2-amino-5-(thioaryl)thiazoles as potent and selective Itk inhibitors, *Bioorganic and Medicinal Chemistry Letters*, 16(14):3706-12); psoriasis (see Eur. J. Pharm. Sci. 2012 October 9; 47(3):574-88. doi: 10.1016/j.ejps.2012.07.013. Epub 2012 Jul. 20 Inhibitors of interleukin-2 inducible T-cell kinase as potential therapeutic candidates for the treatment of various inflammatory disease conditions. Kaur M, Bahia M S, Silakari O. and Cold Spring Harb Perspect Biol. 2010 July; 2(7):a002287. Epub 2010 Jun. 2 T-cell signaling regulated by the Tec family kinase, Itk. Andreotti A. H, Schwartzberg P. L, Joseph R. E, Berg L. J.) and atopic dermatitis (see Exp Dermatol. 2011 January; 20 (1):41-7. doi: 10.1111/j.1600-0625.2010.01198 x. Inhibition of the IL-2-inducible tyrosine kinase (Itk) activity: a new concept for the therapy of inflammatory skin diseases. von Bonin A, Rausch A, Mengel A, Hitchcock M, Krüger M, von Ahsen O, Merz C, Röse L, Stock C, Martin S F, Leder G, Döcke W D, Asadullah K, Zügel U.

In one embodiment, a compound disclosed herein is administered to a patient in need or recognized need thereof to treat an inflammatory disorder. In another embodiment, a compound disclosed herein is administered to a patient in need or recognized need thereof to treat an inflammatory disorder characterized by excessive or undesired cytokine production or activity. In yet another embodiment, a compound disclosed herein is administered to a patient in need or recognized need thereof to treat lung inflammation, pneumonia, allergic asthma, psoriasis, atopic dermatitis, or a combination thereof. In yet another embodiment, a compound disclosed herein is administered to a patient in need or recognized need thereof to treat dry eye disease or uveitis.

Additionally, it is thought that Itk dysfunction affects the development and progression of autoimmune disorders (see Charrier, et al., Discovery and Structure-Activity Relationship of 3-Aminopyrid-2-ones as Potent and Selective Interleukin-2 Inducible T-Cell Kinase (Itk) Inhibitors, *Journal of Medicinal Chemistry*, 54(7):2341-50). In some embodiments, a compound disclosed herein is administered to a patient in need or recognized need thereof to treat an autoimmune disorder.

There is also evidence that ITK overexpression results in the development and progression of T cell malignancies (e.g., T cell lymphomas and T cell leukemia) (see Guo W. et. al., Molecular characteristics of CTA056, a novel Itk inhibitor which selectively targets malignant T cell and modulates oncomirs, Molecular Pharmacology, doi:10.1124/mol.112.079889). CTA056 was found to modulate the growth of cell lines with high ITK levels, but not those with low levels or not expressing ITK at all. In addition, normal T cell growth was not affected. The effect of ITK inhibitor was via induction of apoptosis indicating a potential therapeutic mechanism for elimination of tumor cells. In addition, inhibition of ITK modulates genes that are associated with survival pathways and oncogenesis, which also supports a mechanism to inhibit tumor cell growth. In some embodiments, a compound disclosed herein is administered to a patient in need or recognized need thereof to treat T cell malignancies, such as T cell lymphomas and T cell leukemia. In one embodiment, a compound disclosed herein is administered to a patient in need or recognized need thereof to treat PTCL, acute lymphoblastic leukemia (T-ALL), adult T cell leukemialymphoma (ATL), and Seazry syndromecutaneous T cell lymphoma (CTCL).

The effects of ITK inhibition on Th2 responses (Andreotti et al., T-cell signaling regulated by the TEC family kinase, ITK, *Cold Spring Harb Perspect Biol,* 2(7):1-21) suggest that blockade of ITK function in T cells could lead to a shift in the relative proportions (or skewing) of the Th1 and Th2 populations in patients treated with an ITK inhibitor. In animal models, this Th1/2 skewing affects the susceptibility to infectious agents such as *Listeria monocytogenes* and allergic asthma in animal models (see Mizuki et al., Interference between host resistance to *Listeria monocytogenes* infection and ovalbumin-induced allergic responses in mice, *Infection and Immunity,* 69(3): 1883-1888). Such T helper cell skewing has been suggested to play a role in the responses of chronic lymphocytic leukemia (CLL) patients to ibrutinib therapy through effects of ibrutinib on ITK (see Dubovsky et al., Ibrutinib is an irreversible molecular inhibitor ITK driving a Th1 selective pressure in T-lymphocytes, *Blood,* 2013, pre-published on line).). It was also suggested that the ITK activity of Ibrutinib was responsible for the suppression of Leishmaniasis in susceptible mice again through the Th1 skewing activity. In addition, it has been suggested that Th1 skewing may add to the therapeutic benefit of EGFR targeting in cancer patients by boosting local inflammatory response to the tumor (see Zaiss et al, Amphiregulin enhances regulatory T cell-suppressive function via epidermal growth factor receptor, *Immunity,* 38:1-10). Taken together, these data supports that inhibition of ITK in patients with CLL or other cancers, with the resultant skewing of the T helper cell population towards Th1 cells, could play a role in therapy both through anti-tumor activity as well as an adjuvant therapy to boost immune responses to pathogens that contribute to infections in these settings. In one embodiment, a compound disclosed herein is administered to a patients in need or recognized need thereof to treat CLL or other cancers or infections such as Leismaniasis that are associated with immune function suppression through skewing of T helper cell populations.

The compounds of Formula (IA) and (I) and/or pharmaceutically acceptable salts thereof (and embodiments thereof described herein) are useful in the treatment of ITK-mediated disorders described above, including disorders such as those associated with T cell and cytokine-mediated disorders.

The compounds described herein can also inhibit other kinases such as BTK, JAK3, BLK, BMX, HER2 (also known as ERBB2), HER4 (also known as ERBB4), TEC and TXK and hence can also be used for treating diseases or conditions associated with the activity of BTK, JAK3, BLK, BMX, HER2 (also known as ERBB2), HER4 (also known as ERBB4), TEC and TXK.

B lymphocyte kinase (Blk) is a tyrosine protein kinase. Specifically, it is a member of the src family of proto-oncogenes that are typically involved in cell proliferation and differentiation. In some embodiments, a compound disclosed herein inhibits or decreases the activity of Blk. In some embodiments, the inhibition or decrease of activity of Blk occurs in a human.

Blk has been implicated in B-cell receptor signaling and B-cell development. In some embodiments, a compound disclosed herein is administered to an individual in need thereof to treat a disorder characterized by undesired or excessive (or, uncontrolled) B-cell receptor signaling and B-cell development.

There is also evidence that Blk stimulates insulin synthesis and secretion in response to glucose and enhances the expression of several pancreatic beta-cell transcription factors by up-regulating the expression of PDX1 and NKX6-1. In some embodiments, a compound disclosed herein is administered to a patient in need or recognized need thereof to treat a disorder characterized by undesired or excessive (or, uncontrolled) insulin synthesis and secretion in response to glucose. In some embodiments, a compound disclosed herein is administered to a patient in need or recognized need thereof to treat diabetes.

Blk dysfunction has been implicated in multiple diseases, for example, single-nucleotide polymorphisms (SNPs) in the C8orf13 region of BLK are associated with the development of SLE in Caucasians (Ito, et al., Replication of the association between the C8orf13-BLK region and systemic lupus erythematosus in a Japanese population, Arthritis and Rheumatism, 60(2):553-8). Blk dysfunction has also been implicated in Sjogren's Syndrome (see Nordmark, et al., Association of EBF1, FAM167A(C8orf13)-BLK and TNFSF4 gene variants with primary Sjögren's syndrome, Genes and Immunity, 12(2):100-9); ulcerative colitis (see Seidelin, et al., Expression profiling of apoptosis-related genes in enterocytes isolated from patients with ulcerative colitis, APMIS, 114(7-8):508-17); rheumatoid arthritis and systemic sclerosis (see Tsuchiya, et al., Association of IRF5, STAT4 and BLK with systemic lupus erythematosus and other rheumatic diseases, Nihon Rinsho Meneki Gakkai Kaishi, 33(2):57-65). In some embodiments, a compound disclosed herein is administered to a patient in need or recognized need thereof to treat SLE, Sjogren's Syndrome, ulcerative colitis, rheumatoid arthritis, systemic sclerosis, or a combination thereof.

Blk dysfunction has also been identified in patients with lymphomas, such as cutaneous T-cell lymphoma (see Krejsgaard, et al., Ectopic expression of B-lymphoid kinase in cutaneous T-cell lymphoma, Blood, 113(23):5896-904). In some embodiments, a compound disclosed herein is administered to a patient in need or recognized need thereof to treat a lymphoma. In some embodiments, a compound disclosed herein is administered to a patient in need or recognized need thereof to treat cutaneous T-cell lymphoma. The compounds described herein can be used to treat Blk-related conditions, included those described herein.

Bone Marrow X kinase (also, Bmx, Epithelial and endothelial tyrosine kinase and ETK) is a member of Tec family non-receptor tyrosine kinase. Bmx can be activated by several extracellular stimuli, including growth factors, cytokines, extracellular matrix and hormones. Activation of Bmx kinase can be achieved by interaction of its pleckstrin homology domain either with the phosphatidylinositol 3-kinase product phosphatidylinositol 3,4,5-triphosphate or the FERM domain of FAK, which leads to plasma membrane translocation of Bmx. In some embodiments, a compound disclosed herein inhibits or decreases the activity of Bmx. In some embodiments, the inhibition or reduction of activity of Bmx occurs in a human.

Bmx has been shown to play a role in various cellular processes including cell proliferation, transformation, differentiation, migration and metastasis. Bmx is known to interact with FAK and p130Cas to regulate actin cytoskeleton and cell motility. It has also been shown that Bmx directly interacts with tumor suppress p53 and inhibit its nuclear translocation, thereby promoting chemoresistance in cancer cells.

Bmx has been implicated in several signal transduction pathways, including the Stat pathway. There is evidence that it may play a role in signal transduction (and the growth and differentiation of) hematopoietic cells, endocardial endothelial cells, and arterial endothelial cells.

Bmx dysfunction has been implicated in several types of cancer cells, such as prostate cancer (see Dai, et al., Tyrosine kinase Etk/BMX is up-regulated in human prostate cancer and its overexpression induces prostate intraepithelial neoplasia in mouse, Cancer Research, 66(16):8058-64); breast cancer (see Bagheri-Yarmand, et al., Etk/Bmx tyrosine kinase activates Pak1 and regulates tumorigenicity of breast cancer cells, *Journal of Biological Chemistry*, 276(31): 29403-9); hepatocellular carcinoma (see Guo, et al., Expression of tyrosine kinase Etk/Bmx and its relationship with AP-1- and NF-kappaB-associated proteins in hepatocellular carcinoma, *Oncology*, 72(5-6):410-6); bladder cancer (see Guo, et al., Tyrosine Kinase ETK/BMX Is Up-Regulated in Bladder Cancer and Predicts Poor Prognosis in Patients with Cystectomy, PMID: 21408190, 2011); nasopharygeal cancer (see Zhang, et al., Tyrosine kinase Etk/BMX protects nasopharyngeal carcinoma cells from apoptosis induced by radiation, Cancer Biology & Therapy, 11(7):690-8); and small cell lung cancer (see Guo, et al., Non-receptor tyrosine kinase Etk is involved in the apoptosis of small cell lung cancer cells, Experimental and Molecular Pathology, 88(3): 401-6). In some embodiments, a compound disclosed herein is administered to a patient in need or recognized need thereof to treat a cancer. In some embodiments, a compound disclosed herein is administered to a patient in need or recognized need thereof to treat prostate cancer, breast cancer, hepatocellular carcinoma, bladder cancer, nasopharygeal cancer, small cell lung cancer, or a combination thereof.

Bmx dysfunction has also been associated with multiple autoimmune disorders, such as, but not limited to, rheumatoid arthritis (see Gottar-Guillier, et al., The Tyrosine Kinase BMX Is an Essential Mediator of Inflammatory Arthritis in a Kinase-Independent Manner, Journal of Immunology, PMID: 21471444, 2011); and chronic inflammation and angiogenesis in the skin see (Paavonen, et al., Bmx tyrosine kinase transgene induces skin hyperplasia, inflammatory angiogenesis, and accelerated wound healing, Molecular Biology of the Cell, 15(9):4226-33). Accordingly, the compounds described herein can be used to treat Bmx-related conditions, included those described herein.

Human epidermal growth factor receptor 2 (HER2) is a cell-surface receptor tyrosine kinase for the epidermal growth factor receptor (EGF) family. HER2 is thought to be an orphan receptor, with none of the EGF family of ligands able to activate it; however, HER2 is the preferential dimerization partner of other members of the EGF family (see Olayioye, Update on HER-2 as a target for cancer therapy: intracellular signaling pathways of ErbB2/HER-2 and family members, Breast Cancer Res 3(6): 385-389, 2001).

Heterodimerization of the EGF family of receptors to HER2 results in stabilization of the ligand-EGF receptor interaction and enhancement of kinase-mediated activation of downstream signaling pathways. Downstream signaling pathways initiate signal transduction cascades that drive many cellular responses, including changes in gene expression, cytoskeletal rearrangement, anti-apoptosis and increased cell proliferation.

Due to its role in cell proliferation, inhibition of HER2 function should reduce or inhibit the development and/or progression of cancers Amplification and/or overexpression of the HER2 gene has been implicated in numerous cancers, including, but not limited to, breast cancer (see Konecny, et al., Her-2/neu and urokinase-type plasminogen activator and its inhibitor in breast cancer, Clin Cancer Res, 7(8):2448-57, 2001), ovarian cancer (see Lafky, et al. Clinical implications of the ErbB/epidermal growth factor (EGF) receptor family and its ligands in ovarian cancer, Biochim Biophys Acta, 178(2):232-65, 2008), gastric cancer (see Moelans, et al., Low frequency of HER2 amplification and overexpression in early onset gastric cancer, Cell Oncol (Dordr), 34(2):89-95, 2011), lung cancer (see Hirsch, et al., The role of HER2/neu expression and trastuzumab in non-small cell lung cancer, Semin Oncol, 31(1 Suppl1):75-82, 2004), glioblastoma (see Mineo, et al., Low HER2-expressing glioblastomas are more often secondary to anaplastic transformation of low-grade glioma, J Neurooncol, 85(3):281-7, 2007) and biologically aggressive forms of uterine cancer, such as uterine serous endometrial carcinoma (see Santin, et al., Trastuzumab treatment in patients with advanced or recurrent endometrial carcinoma overexpressing HER2/neu, Int J Gynaecol Obstet, 102(2): 128-31, 2008). In some embodiments, the compounds are used to treat breast cancer, ovarian cancer, gastric cancer, lung cancers, glioblastoma, and biologically aggressive forms of uterine cancer, such as uterine serous endometrial carcinoma. The compounds described herein can be used to treat HER2-related conditions, included those described herein.

Human epidermal growth factor receptor 4 (HER4) is a receptor tyrosine kinase that is a member of the epidermal growth factor receptor (ErbB) family. HER4 is a single-pass type I transmembrane protein with multiple furin-like cysteine rich domains, a tyrosine kinase domain, a phosphotidylinositol-3 kinase binding site and a PDZ domain binding motif. The protein binds to and is activated by neuregulins-2 and -3, heparin-binding EGF-like growth factor and betacellulin. Ligand binding induces a variety of cellular responses including mitogenesis and differentiation. Multiple proteolytic events allow for the release of a cytoplasmic fragment and an extracellular fragment.

The C-terminal fragment (CTF) of isoform JMA-A CYT-2 (containing E4ICD2) can stimulate transcription in the presence of YAP1. ERBB4 intracellular domain is involved in the regulation of cell growth. Overexpression studies in epithelium show growth inhibition using E4ICD1 and increased proliferation using E4ICD2. E4ICD2 has greater in vitro kinase activity than E4ICD1. This kinase activity is required for the nuclear translocation of E4ICD2. In some embodiments, a compound disclosed herein is administered to an individual in need thereof to treat a disorder characterized by undesired or excessive (or, uncontrolled) cell proliferation and differentiation.

Due to its role in cell proliferation and differentiation, inhibition of HER4 function should reduce or inhibit the development and/or progression of disorders characterized by undesired or uncontrolled cell proliferation or differentiation. In some embodiments, this disorder comprises cancers.

Mutations in and overexpression of the HER4 gene have been associated with numerous cancers, including, but not limited to, breast cancer (see Junttila, et al., Cleavable ErbB4 isoform in estrogen receptor-regulated growth of breast cancer cells, Cancer Res, 65(4):1384-93, 2005), childhood medulloblastoma (see Gilbertson, et al., Prognostic significance of HER2 and HER4 coexpression in childhood medulloblastoma., Cancer Res, 57(15):3272-80, 1997), non-small-cell lung cancer (see Starr, et al., ErbB4 increases the proliferation potential of human lung cancer cells and its blockage can be used as a target for anti-cancer therapy, Int. J. Cancer, 119(2):269-274, 2006), and melanoma (see Prickett, et al., Analysis of the tyrosine kinome in melanoma reveals recurrent mutations in ERBB4, Nat Genet, 41(10): 1127-32, 2009). In some embodiments, a compound disclosed herein is administered to a patient in need or recognized need thereof to treat a disorder characterized by uncontrolled or undesired cell proliferation or differentiation. In some embodiments, a compound disclosed herein is administered to a patient in need or recognized need thereof to treat breast cancer, lung cancer, medulloblastoma (including the childhood form), melanoma, or a combination thereof.

In addition, single-nucleotide polymorphisms and a risk haplotype have been linked to schizophrenia (see Silberberg, et al. The involvement of ErbB4 with schizophrenia: association and expression studies, Am J Med Genet B Neuropsychiatr Genet 141(B2): 142-8, 2006). In some embodiments, a compound disclosed herein is administered to a patient in need or recognized need thereof to treat schizophrenia. The compounds described herein can be used to treat HER4-related conditions, included those described herein.

Jak3 is a tyrosine kinase that belongs to the Janus family of tyrosine kinases. It is involved in cytokine receptor-mediated intracellular signal transduction. Jak3 is activated by binding to the γC chain of the type I cytokine receptor family (e.g. IL-2R, IL-4R, IL-7R, IL-9R, IL-15R, and IL-21R). Following binding, Jak3 undergoes tyrosine phosphorylation (either via autophosphorylation and/or transphosphorylation by other JAKs or other families of tyrosine kinases). Activated JAKs then phosphorylate receptors on target tyrosine residues that serve as docking sites that allow the binding of other SH2-domain containing signaling molecules such as STATs, Src-kinases, protein phosphatases and other adaptor signaling proteins such as Shc, Grb2 and PI-3 kinase (see Jatiani, et al., JAK/STAT Pathways in Cytokine Signaling and Myeloproliferative Disorders: Approaches for Targeted Therapies, Genes & Cancer, 1(10):979-993). Jak3 is predominantly expressed in immune cells and hematopoietic cells, for example, in T cells, NK cells and monocytes. It appears that Jak3 is involved in T and B cell development and function (see Cox, et al., JAK3 Specific Kinase Inhibitors: When Specificity Is Not Enough, Chemistry & Biology, 18(3):277-8). In some embodiments, a compound disclosed herein inhibits the activity of Jak3.

Jak3 contains a tyrosine kinase (JH1) domain adjacent to a catalytically inactive pseudokinase domain (JH2). The JH2 domain, which lacks any observable tyrosine kinase activity due to the absence of residues that are required for catalytic activity and nucleotide binding, negatively regulates the activity of Jak3 (see Jatiani, et al., JAK/STAT Pathways in Cytokine Signaling and Myeloproliferative Disorders: Approaches for Targeted Therapies, Genes & Cancer, 1(10): 979-993). JH2 is required for two distinct functions in cytokine signaling: (i) inhibition of the basal activity of Jak3, and (ii) cytokine-inducible activation of signaling. Jak3-JH2 deletion mutants are catalytically active, activate STAT5, and interact with other Jak kinases, but the JH2 domain is required to connect these signaling events to receptor activation. (see Saharinen, et al., The pseudokinase domain is required for suppression of basal activity of Jak2 and Jak3 tyrosine kinases and for cytokine-inducible activation of signal transduction, Journal of Biological Chemistry, 277(49):47954-63). In some embodiments, a compound disclosed herein inhibits the activity of the JH2 domain of Jak3.

Due to its role in the growth, survival, development, and differentiation of immune cells, inhibiting Jak3 function would likely reduce or inhibit the development and/or progression of immune disorders. In some embodiments, a compound disclosed herein reduces or inhibits the development and/or progression of an immune disorder.

Jak3 dysfunctions has also been implicated in inflammation and autoimmune disorders, such as arthritis (see Kim, et al., Inhibition of JAK3 alleviates inflammation in monoarthritic rats, British Journal of Pharmacology, PMID: 21434883, 2011), especially rheumatoid arthritis; transplant rejection (Flanagan, et al., Discovery of CP-690,550: a potent and selective Janus kinase (JAK) inhibitor for the treatment of autoimmune diseases and organ transplant rejection, Journal of Medicinal Chemistry, 53(24):8468-84), especially, kidney transplant rejection; psoriasis and arthritis (see West, CP-690550, a JAK3 inhibitor as an immunosuppressant for the treatment of rheumatoid arthritis, transplant rejection, psoriasis and other immune-mediated disorders, Current Opinion in Investigational Drugs, 10(5):491-504); and Type-1 diabetes (Cetkovic-Cvrlje, et al., Targeting JAK3 with JANEX-1 for prevention of autoimmune type 1 diabetes in NOD mice, Clinical Immunology, 106(3):213-25). In some embodiments, a compound disclosed herein is administered to a patient in need or recognized need thereof to treat inflammation, an autoimmune disorder, or a combination thereof. In some embodiments, a compound disclosed herein is administered to a patient in need or recognized need thereof to treat arthritis, transplant rejection, psoriasis, arthritis, type-1 diabetes, or a combination thereof.

Additionally, Jak3 dysfunction has been found in myeloproliferative and myelodisplastic syndromes (see Jatiani, et al., JAK/STAT Pathways in Cytokine Signaling and Myeloproliferative Disorders: Approaches for Targeted Therapies, Genes & Cancer, 1(10):979-993), for example, transient myeloproliferative disorder (TMD) (see Sato, et al., Functional analysis of JAK3 mutations in transient myeloproliferative disorder and acute megakaryoblastic leukemia accompanying Down syndrome, British Journal of Haemotology, 141(5):681-8). In some embodiments, a compound disclosed herein is administered to a patient in need or recognized need thereof to treat a myeloproliferative syndrome and/or a myelodisplastic syndrome. In some embodiments, a compound disclosed herein is administered to a patient in need or recognized need thereof to treat transient myeloproliferative disorder.

Roles for Jak3 dysfunction have also been found in multiple cancers, including breast adenocarcinoma (see Henkels, Cell Invasion of Highly Metastatic MTLn3 Cancer Cells Is Dependent on Phospholipase D2 (PLD2) and Janus Kinase 3 (JAK3), Journal of Molecular Biology, PMID: 21414324, 2011); T Cell Lymphoma (see Krejsgaard, t al., Malignant Cutaneous T-Cell Lymphoma Cells Express IL-17 Utilizing the Jak3/Stat3 Signaling Pathway, Journal of Investigative Dermatology, PMID: 21346774, 2011); acute megakaryoblastic leukaemia of Down syndrome (see Sato, et al., Functional analysis of JAK3 mutations in transient myeloproliferative disorder and acute megakaryoblastic leukaemia accompanying Down syndrome, British Journal of Haemotology, 141(5):681-8); B-lineage acute lymphoblastic leukemia (see Uckun, JAK3 pathway is constitutively active in B-lineage acute lymphoblastic leukemia, Expert Review of Anticancer Therapy, 11(1):37-48); colorectal cancer (see Uckun, Chemoprevention of colorectal cancer by targeting Janus kinase 3 with a rationally designed small molecule inhibitor, Nutrition and Cancer, 62(7):968-72); chronic lymphocytic leukemia (see Steele, et al., The JAK3-selective inhibitor PF-956980 reverses the resistance to cytotoxic agents induced by interleukin-4 treatment of chronic lymphocytic leukemia cells: potential for reversal of cytoprotection by the microenvironment, Blood, 116(22):4569-77); and non-melanoma skin cancer (see Uckun, et al., Prevention of UVB-induced skin inflammation, genotoxicity, and photocarcinogenesis in mice by WHI-P131, a dual-function inhibitor of Janus kinase 3 and EGF receptor kinase, Arzneimittelforschung, 60(4):218-25). In some embodiments, a compound disclosed herein is administered to a patient in need or recognized need thereof to treat a cancer. In some embodiments, a compound disclosed herein is administered to a patient in need or recognized need thereof to treat breast adenocarcinoma; T Cell Lymphoma; acute megakaryoblastic leukaemia of Down syndrome; B-lineage acute lymphoblastic leukemia; colorectal cancer; chronic lymphocytic leukemia; non-melanoma skin cancer; or a combination thereof. The compounds described herein can be used to treat Jak3-related conditions, included those described herein.

Tec protein tyrosine kinase is a member of the Tec family of non-receptor type protein tyrosine kinases. Tec family kinases are involved in the intracellular signaling mechanisms of cytokine receptors, lymphocyte surface antigens, heterotrimeric G-protein coupled receptors, and integrin molecules and are important components of antigen receptor signaling pathways in B cells, T cells, and mast cells (see Schmidt, et al., The protein tyrosine kinase Tec regulates mast cell function, Eur J Immunol, 39(11):3228-38, 2009). The domain architecture of the Tec kinases comprises a single Src homology 3 (SH3) domain, a Src homology 2 (SH2) domain, a catalytic kinase domain, a pleckstrin homology (PH) domain, and a Tec homology (TH) domain at the amino-terminus. The TH domain consists of a region unique to the Tec kinases followed by one or more proline-rich regions (see Joseph, et al., Conformational snapshots of Tec kinases during signaling, Immunol Rev, 228(1):74-92, 2009). In some embodiments, a compound disclosed herein modulates the activity of Tec.

In T cells, three members of this family, Itk, Rlk, and Tec, are expressed. They are also key players in the regulation of the immune functions. Tec kinase is an integral component of T cell signaling and has a distinct role in T cell activation. In some embodiments, a compound disclosed herein modulates the activity of Tec in T cell signaling and activation.

Aberrant expression of Tec has been implicated in various diseases, including, but not limited to, heart disease (Zhang, et al., Stress signaling by Tec tyrosine kinase in the ischemic myocardium, Am J Physiol Heart Circ Physiol, 2993(3) H713-22, 2010), myelodysplastic syndrome (see Sato, et al., Molecular cloning and analysis of the human Tec protein-tyrosine kinase, Leukemia, 8(10):1663-72, 1994), and osteoporosis (see Shinohara, et al., Tyrosine kinases Btk and Tec regulate osteoclast differentiation by linking RANK and ITAM signals, Cell, 132(5):794-806, 2008). In some embodiments, a compound disclosed herein is administered to a patient in need or recognized need thereof to treat an immune disorder. In some embodiments, a compound disclosed herein is administered to a patient in need or recognized need thereof to treat cardiovascular disease, osteoporosis, or a combination thereof. In some embodiments, a compound disclosed herein is administered to a patient in need or recognized need thereof to treat myelodysplastic syndrome thereof. The compounds described herein can be used to treat Tec-related conditions, included those described herein.

The kinase known as Txk contains several protein domains, including, a COOH-terminal kinase catalytic domain, a Src homology 2 (SH2) protein interaction domain, an SH3 domain, a palmitoylated cysteine-string motif that is required for membrane localization and a proline-rich region (see Readinger, et al., Tec kinases regulate T-lymphocyte development and function: new insights into the roles of Itk and Rlk/Txk, Immunol Rev, 228(1):93-114, 2009). Txk is expressed in Th1/Th0 cells and is an important modulator of lymphocyte development and function. In some embodiments, a compound disclosed herein inhibits or decreases or enhances the activity of Txk.

Txk is a signal-transducing molecule, which consists of the tyrosine kinase cascade downstream from the T cell receptor when an antigen is presented to the T cell through the T cell receptor. Txk is phosphorylated and activated by Fyn, one of the Srk family kinases, and it phosphorylates downstream signal molecules (see Suzuki, et al., Skewed Th1 responses caused by excessive expression of Txk, a member of the Tec family of tyrosine kinases, in patients with Behcet's disease, Clin Med Res, 4(2):147-51, 2006). Upon activation, Txk translocates from cytoplasm into nucleus and regulates specifically interferon-gamma gene transcription. Txk, poly(ADP-ribose) polymerase 1, and elongation factor 1alpha make a complex to bind to interferon-gamma gene promoter region-53/-39 (Txk responsive element) to exert positive effects on transcription as a Th1 cell-associated transcription factor (see Mihara, et al., Role of Txk, a member of the Tec family of tyrosine kinases, in immune-inflammatory diseases, Int Rev Immunol, 26(5-6): 333-48, 2007). In some embodiments, a compound disclosed herein modulates the activity of Txk.

Aberrant overexpression of Txk has been implicated in several immunopathologies, including, but not limited to, rheumatoid arthritis (see Mihara, et al., Role of Txk, a member of the Tec family of tyrosine kinases, in immune-inflammatory diseases, Int Rev Immunol, 26(5-6):333-48, 2007) and Behcet's disease (see Suzuki, et al., Skewed Th1 responses caused by excessive expression of Txk, a member of the Tec family of tyrosine kinases, in patients with Behcet's disease, Clin Med Res, 4(2):147-51, 2006). In some embodiments, a compound disclosed herein is administered to an individual in need thereof to treat an inflammatory disorder characterized by dysfunction of lymphocyte development and function. In some embodiments, a compound disclosed herein is administered to a patient in need or recognized need thereof to rheumatoid arthritis, Behcet's disease, or a combination thereof.

Additionally, a reduction in Txk expression has been implicated in bronchial asthma (see Sahu, et al., Selective expression rather than specific function of Txk and Itk regulate Th1 and Th2 responses, J. Immunol, 181(9):6125-31, 2008) and atopic dermatitis (see Arakawa, et al., Differential expression of mRNA for Th1 and Th2 cytokine-associated transcription factors and suppressors of cytokine signaling in peripheral blood mononuclear cells of patients with atopic dermatitis, Clin Exp Immunol, 135(3):505-10, 2004). In the absence of Itk and Txk, T-cell receptor signaling is impaired, with defects in mitogen-activated protein kinase activation, Ca2+ mobilization, and actin polymerization. In some embodiments, a compound disclosed herein is administered to a patient in need or recognized need thereof to treat an inflammatory disorder characterized by dysfunction of lymphocyte development and function. In some embodiments, a compound disclosed herein is administered to a patient in need or recognized need thereof to asthma, atopic dermatitis, or a combination thereof Modulation of Txk expression should lead to the correction of aberrant immunity and, consequently, disease treatment. Accordingly, there is a need for drug therapies that modulate Txk and are therefore useful in the treatment of Txk-mediated disorders, such as those associated with inflammatory immune disorders. The compounds described herein can be used to treat Txk-related conditions, included those described herein.

In one aspect, the present disclosure is directed to use of compound of Formula (IA) or I and/or a pharmaceutically acceptable salt thereof (and any embodiments thereof described herein) for use as a medicament. In one embodiment, the use of compounds of Formula (IA) or I and/or a pharmaceutically acceptable salt thereof is for treating proliferative disease (e.g., cancers). In another aspect, the present disclosure is directed to the use of a compounds of Formula (IA) or I and/or a pharmaceutically acceptable salt thereof (and any embodiments thereof described herein) for treatment of diseases associated with axonal regeneration, or spinal cord injury. In another embodiment, the disease is an inflammatory disorder chosen from asthma, allergic dermatitis, atopic dermatitis and psoriasis.

In further aspects, the present disclosure is directed to the use of a compounds of Formula (IA) or I and/or a pharmaceutically acceptable salt thereof (and any embodiments thereof described herein) for treatment of psoriasis, alleviation of inflammation during organ transplant, treatment of asthma, rheumatoid arthritis, osteoporosis, cardiovascular disease, or any other disease described above.

In any of the aforementioned aspects involving the treatment of proliferative disorders, including cancer, are further embodiments comprising administering the compound of Formula (IA) or I and/or a pharmaceutically acceptable salt thereof in combination with at least one additional agent selected from an anti-cancer agent or an agent that modulates growth or regeneration of axons. When combination therapy is used, the agents are administered simultaneously or sequentially.

Testing

The ITK inhibitory activity, residence time of the inhibitor ITK bound complex, and the ability of the of the compounds of the present disclosure to form irreversible covalent bond or reversible covalent bond with Cys 442 (UniprotKB Sequence ID Q08881) can be tested using the in vitro, in vivo assays described in working Examples below.

The kinase inhibitory activity of the compounds of the present disclosure can be tested by methods well known the art. The ITK inhibitory activity of the compounds and/or a pharmaceutically acceptable salt thereof of the present disclosure can be tested using the in vitro and in vivo assays described in Biological Examples 1, 3, 4, and 5 below. A determination of kinase inhibitory activity by any of those assays is considered to be kinase inhibitory activity within the scope of this disclosure even if any or all of the other assays do not result in a determination of kinase inhibitory activity.

Without being bound to any specific mechanistic theory, in those embodiments wherein the compound of the present disclosure is a reversible covalent inhibitor, it is believed that the cysteine sulfhydryl group and a carbon atom forming part of the carbon-carbon double bond in the group —X—Y—C($R^b$)═CHR$^c$ where $R^b$ is other than hydrogen, in particular cyano, (see Formula IA and I) of the compound of the present disclosure can form a reversible, i.e., labile, covalent bond, defined herein, such as wherein Cys 442 (UniprotKB Sequence ID Q08881) attacks an electron deficient carbon atom of the carbon-carbon double bond in the group —X—Y—C($R^b$)═CHR$^c$ in the compound of present disclosure to form a thiol adduct (e.g., Michael reaction with cysteine).

In some embodiments, the electron deficient carbon atom of the olefin is distal to the carbon attached to the $R^b$ group (where $R^b$ is not hydrogen) and to the electron withdrawing —X—Y— or —Y— moiety (see Formula (IA) and (I) in the compounds of the present disclosure. Therefore, the combination of the $R^b$ group (where $R^b$ is not hydrogen) and the "—X—Y—" or "Y" moieties and the olefinic moiety to which they are bonded in the compounds of the present disclosure can increase the reactivity of the olefin to form a thiol adduct with the active site cysteine residue in ITK.

The compounds of the present disclosure which are reversible covalent inhibitors bind with ITK in two different manners. In addition to the labile covalent binding, discussed above, they also form non-covalent binding (e.g., via van der Waals binding, hydrogen binding, hydrophobic binding, hydrophilic binding, and/or electrostatic charge binding) with ITK, the non-covalent binding being sufficient to at least partially inhibit the kinase activity of the ITK.

As disclosed herein, the labile covalent binding between the reversible covalent inhibition of the disclosure and ITK occurs between the olefin in the inhibitor and the cysteine 442 residue thiol side chain at or near the site where the inhibitor has the aforementioned non-covalent binding with the ITK.

As is evident, the compounds of the present disclosure which are reversible covalent inhibitors have both a cysteine-mediated covalent binding and a non-covalent binding with the ITK. This is in contrast with non-covalent reversible inhibitors which inhibit the ITK only via non-covalent binding and lack the cysteine-mediated covalent binding.

The binding of the compounds of the present disclosure with ITK in the two different manners mentioned above provides a reversible covalent inhibitor having a slow off-rate and a protracted duration of action, in some instances comparable to an irreversible covalent inhibitor without forming permanent irreversible protein adducts. The difference between irreversible and reversible covalent inhibitors, particularly the compounds disclosed herein, can be ascertained utilizing assays disclosed herein.

In general, the binding involved in an inhibitor that forms a reversible covalent bond with ITK is stable when the ITK is in certain configurations and susceptible to being broken when the ITK is in different configurations (in both cases under physiologic conditions), whereas the interaction between an inhibitor that forms an irreversible covalent bond is stable under physiologic conditions even when the ITK is in different configurations.

A reversible covalent bond often imparts unique properties related to the residence time of the compound within the cysteine-containing binding site. In this context, residence time refers to the temporal duration of the compound-target complex under different conditions (see Copeland R A, Pompliano D L, Meek T D. Drugtarget residence time and its implications for lead optimization. *Nat. Rev. Drug Discov.* 5(9), 730-739 (2006).

The presence of a reversible covalent bond in a reversible covalent inhibitor as disclosed herein can lead to an extended residence time when compared to a compound that does not form a covalent bond with ITK. In one embodiment disclosed herein the compounds of the present disclosure that are reversible covalent inhibitors have a residence time of at least about 1 h. Residence time may be measured using an occupancy assay in a biochemical or cellular environment (see Biological Example 2 below). Additionally, residence time may be measured using a functional assay following a defined wash-out period.

Compounds that form an irreversible covalent bond in an irreversible covalent inhibitor share these extended residence time properties but may nonetheless be differentiated from reversible covalent inhibitor using a reversibility assay. The ability of the compound of the disclosure to form reversible or irreversible covalent bond with Cys442 of ITK (UniprotKB Sequence ID Q06187) and the olefinic bond in the compound of the disclosure, can be determined by the assays described in Biological Examples 2, 6-8 below. A determination of the binding reversibility of the covalent bond between the cysteine residue and the olefinic bond of the compound of the disclosure by any of Biological Examples 2, 6-8 below is considered to be binding reversibility within the scope of this disclosure even if one or both of the other methods does not result in a determination of binding reversibility.

Administration and Pharmaceutical Composition

In general, the compounds of this disclosure will be administered in a therapeutically effective amount by any of the accepted modes of administration for agents that serve similar utilities. Therapeutically effective amounts of compounds disclosed herein may range from about 0.01 to about 200 mg per kg patient body weight per day, which can be administered in single or multiple doses. Preferably, the dosage level will be about 0.1 to about 100 mg/kg per day; more preferably about 0.5 to about 50 mg/kg per day. For oral administration, the compositions can be provided in the form of tablets containing about 1 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compounds disclosed herein, i.e., the active ingredient, will depend upon numerous factors such as the severity of the disease to be treated, the age and relative health of the subject, the potency of the compound being utilized, the route and form of administration, and other factors.

In general, compounds disclosed herein will be administered as pharmaceutical compositions by any one of the following routes: oral, systemic (e.g., transdermal, intranasal, or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compounds disclosed herein in non-toxic, aid administration, and do not adversely affect the therapeutic benefit of the compounds disclosed herein. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

The compounds of the present disclosure can also be administered intranasally. Intranasal formulations are known in the art e.g., see U.S. Pat. Nos. 4,476,116, 5,116,817 and 6,391,452, each of which is incorporated herein by reference. The choice of excipients will depend upon the nature of the nasal dosage form e.g., solutions, suspensions, or powder. For administration by inhalation, the compounds of the present disclosure may be in the form of solutions, suspensions, and powders. These formulations are administered as an aerosol, a mist or a powder and can be delivered from pressurized packs or a nebulizer with a suitable propellant such as dichlorodifluoromethane, trichlorofluoromethane, nitrogen, carbon dioxide, etc. In the case of a pressurized aerosol, the dosage unit may be determined by providing a valve to deliver a metered amount. Capsules and cartridges for use in an inhaler may be formulated containing a powder mix of the compound disclosed herein and a suitable powder base such as lactose or starch.

Topical formulation can be liquids, suspension, emulsions, and the like, and can be prepared by methods well known in the art. The formulation will contain, on a weight percent (wt %) basis, from about 0.01-99.99 wt % of a compound disclosed herein based on the total formulation, with the balance being one or more suitable pharmaceutical excipients and can be administered in single or multiple doses. Suitable excipients include polymers, surfactants, buffering or pH adjusting agents, tonicity or osmotic adjusting agent(s), preservatives, and/or dispersing agents. Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt %) basis, from about 0.01-99.99 wt % of a compound of Formula (IA) or (I) based on the total formulation, with the balance being one or more suitable pharmaceutical excipients. Preferably, the compound is present at a level of about 1-80 wt %.

The compounds of the present disclosure may be used in combination with one or more other drugs in the treatment of diseases or conditions for which compounds of the present disclosure or the other drugs may have utility, where the combination of the drugs together are safer or more effective than either drug alone. Such other drug(s) may be administered, by a route and in an amount commonly used therefore, contemporaneously or sequentially with a compound of the present disclosure. When a compound of the present disclosure is used contemporaneously with one or more other drugs, a pharmaceutical composition in unit dosage form containing such other drugs and the compound of the present disclosure is preferred. However, the combination therapy may also include therapies in which the compound of the present disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other active ingredients, in addition to a compound disclosed herein.

The above combinations include combinations of a compounds disclosed herein not only with one other active compound, but also with two or more other active compounds. Likewise, compounds disclosed herein may be used in combination with other drugs that are used in the prevention, treatment, control, amelioration, or reduction of risk of the diseases or conditions for which compounds disclosed herein are useful. Such other drugs may be administered, by a route and in an amount commonly used therefore, contemporaneously or sequentially with a compound disclosed herein. When a compound disclosed herein is used contemporaneously with one or more other drugs, a pharmaceutical composition containing such other drugs in addition to the compound disclosed herein is preferred. Accordingly, the pharmaceutical compositions of the present disclosure also include those that also contain one or more other active ingredients, in addition to a compound disclosed herein. The weight ratio of the compound disclosed herein to the second active ingredient may be varied and will depend upon the effective dose of each ingredient. Generally, an effective dose of each will be used.

Where the patient is suffering from or at risk of suffering from an autoimmune disease, an inflammatory disease, or an allergy disease, a compound disclosed herein can be used in with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, allergy vaccines, antihistamines, antileukotrienes, beta-agonists, theophylline, anticholinergics, B cell inhibitors such as anti-CD19, 20, 22 antibodies, and BTK inhibitors such as Ibrutinib.

Where the patient is suffering from or at risk of suffering from a proliferative disorder, the subject can be treated with a compound disclosed herein in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, PD184352, or Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound disclosed herein include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a compound disclosed herein include adriamycin, dactinomycin, bleomycin, vinblastine, cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound disclosed herein include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound disclosed herein include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a compound disclosed herein include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound disclosed herein include, but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, Cytarabine), purine analogs (e.g., mercaptopurine, thioguanine, pentostatin.

Examples of hormones and antagonists useful in combination a compound disclosed herein include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with a compound disclosed herein include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (-)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi). Yet another class of anticancer that can be used in combination with the compounds of the present disclosure include PD-1 inhibitors e.g, Nivolumab and MPDL3280A (Genentech).

Where the subject is suffering from or at risk of suffering from a thromboembolic disorder (e.g., stroke), the patient can be treated with a compound disclosed herein in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR1048.

EXAMPLES

The following preparations of compounds of Formula (IA) and (I) and intermediates are given to enable those skilled in the art to more clearly understand and to practice the present disclosure. They should not be considered as limiting the scope of the disclosure, but merely as being illustrative and representative thereof.

Synthetic Examples

Intermediate 1

Synthesis of tert-butyl 4-(2-imino-2,3-dihydro-1H-benzo[d]imidazol-1-yl)piperidine-1-carboxylate

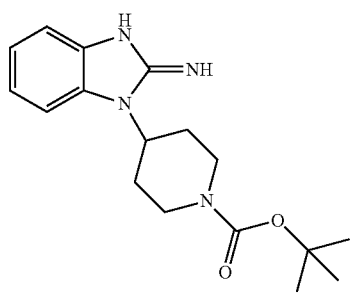 [SMILES: CC(C)(C)OC(=O)N1CCC(n2c(=N)[nH]c3ccccc32)CC1]

Step 1

In a 100 mL three necked round bottom flask, 1-fluoro-2-nitrobenzene (1.0 g, 0.0071 mole) was taken up in acetonitrile (20 mL) and DIPEA (2.75 g, 0.0213 mole) was added dropwise at room temperature. After completion of addition, the reaction mixture was stirred for 15 min at same temperature followed by slow addition of tert-butyl 4-aminopiperidine-1-carboxylate (1.71 g, 0.0085 mole) over 15 min at the same temperature. After completion of the addition, the reaction mixture was stirred for 16 h at room temperature. The completion of the reaction was monitored on TLC. After completion of the reaction, acetonitrile was distilled out and water was added to the residue. The aqueous phase was extracted with ethyl acetate and the combined organic layer was dried over Na$_2$SO$_4$, filtered and concentrated to afford crude product which was subjected for the column purification to yield 0.9 g of tert-butyl 4-(2-nitrophenylamino) piperidine-1-carboxylate.

Step 2

To a suspension of 10% dry Pd/C (0.18 g, 10% w/w) in methanol (15 mL), tert-butyl 4-(2-nitrophenylamino)piperidine-1-carboxylate (1.8 g, 0.0056 mole) in methanol (15 mL) was added under N$_2$ atmosphere. The H$_2$ gas was added to the reaction mixture for 1.5 h at room temperature. The completion of the reaction was monitored by TLC using EtOAc: hexanes (7:3). After completion of the reaction, reaction mixture was filtered through celite and washed with methanol and the filtrate was concentrated to yield 1.4 g of tert-butyl 4-(2-aminophenylamino)piperidine-1-carboxylate.

Step 3

To a flask charged with tert-butyl 4-(2-aminophenylamino)piperidine-1-carboxylate (1.4 g, 0.0048 mole) was added ethanol (25 mL). To this, cyanogen bromide (0.61 g, 0.0058 mole) was added at room temperature and the reaction mixture was stirred for 3 h. The completion of the reaction was monitored by TLC using CH$_2$Cl$_2$: methanol (9:1). After completion of the reaction, ethanol was distilled out and saturated NaHCO$_3$ solution was added to adjust pH basic. The reaction mixture was stirred for 1 h then filtered it and washed with water. The organic phase was dried over sodium sulfate, filtered and the solvent removed to afford 1.5 g of tert-butyl 4-(2-imino-2,3-dihydro-1H-benzo[d]imidazol-1-yl)piperidine-1-carboxylate.

Intermediate 2

Synthesis of 4-chloro-N-(1-(piperidin-4-yl)-1H-benzo[d]imidazol-2-yl)benzamide hydrochloride

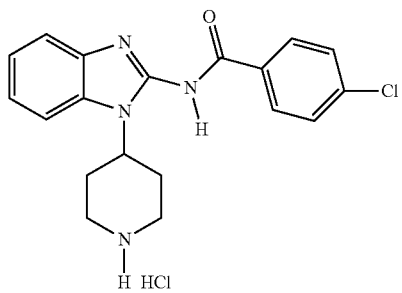 [SMILES: O=C(Nc1nc2ccccc2n1C1CCNCC1)c1ccc(Cl)cc1 ; Cl]

Step 1

To a 50 mL single neck RBF, 4-chlorobenzoic acid (0.178 g, 0.00114 mole) was added in CH$_2$Cl$_2$ (15 mL) under N$_2$ atmosphere. EDC-HCl (0.273 g, 0.00142 mole), HOBT.H$_2$O (0.219 g, 0.00142 mole) and TEA (0.4 mL, 0.00285 mole) were added to the reaction mixture at room temperature and stirred for 20 min. tert-Butyl 4-(2-imino-2,3-dihydro-1H-benzo[d]imidazol-1-yl)piperidine-1-carboxylate (0.3 g, 0.00095 mole) in CH$_2$Cl$_2$ (15 mL) was added dropwise to the reaction mixture and stirred at room temperature for 16 h. The completion of the reaction was monitored on TLC using EtOAc: Hexanes (1:1) as a mobile phase. Saturated NaHCO$_3$ solution was added to the reaction mixture and the aqueous phase was extracted with EtOAc. The combined organic layer was dried over Na$_2$SO$_4$ and evaporated to get the pure product to yield 0.41 g of tert-butyl 4-(2-(4-chlorobenzamido)-1H-benzo[d]imidazol-1-yl)piperidine-1-carboxylate.

Step 2

To a 25 mL round bottomed flaskl, tert-butyl 4-(2-(4-chlorobenzamido)-1H-benzo[d]imidazol-1-yl) piperidine-1-carboxylate (0.45 g, 0.00099 mole) was added in 1, 4 dioxane (5 mL) and the solution was cooled to 10° C. under N$_2$ atmosphere. To this, 20% HCl in 1, 4 dioxane (5 ml) was added drop wise at 10° C. and the reaction mixture was stirred for 16 h at room temperature. The completion of the reaction was monitored by TLC. After completion of the reaction, the solvent was evaporated under reduced pressure to get the crude compound which was triturated with acetone to yield 0.33 g of 4-chloro-N-(1-(piperidin-4-yl)-1H-benzo[d]imidazol-2-yl)benzamide hydrochloride.

Intermediate 3

Synthesis of 4-chloro-N-(1-(1-(2-cyanoacetyl)piperidin-4-yl)-1H-benzo[d]imidazol-2-yl)benzamide

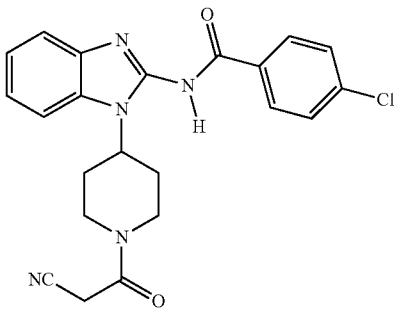 [SMILES: N#CCC(=O)N1CCC(n2c(NC(=O)c3ccc(Cl)cc3)nc3ccccc32)CC1]

2-Cyanoacetic acid (0.086 g, 0.001 mole) was taken up in CH$_2$Cl$_2$ (25 ml) and cooled to 0° C. under N$_2$ atmosphere. To this, TBTU (0.285 g, 0.0009 mole) in DMF (1 mL) was added dropwise at 0° C. After addition, the reaction mixture was allowed to attain rise to room temperature. Then, 4-chloro-N-(1-(piperidin-4-yl)-1H-benzo[d]imidazol-2-yl)benzamide hydrochloride (0.3 g, 0.00077 mole) and DIPEA (0.4 mL, 0.00255 mole) were added and the reaction mixture stirred at room temperature for 16 h. The completion of the reaction was monitored by TLC using CH$_2$Cl$_2$: MeOH (9:1) as a mobile phase. After completion of the reaction, water was added to the reaction mixture and product was extracted with CH$_2$Cl$_2$. The combined organic layer was dried over Na$_2$SO$_4$ and evaporated to get the crude product which was purified using column chromatography using 100-200 mesh size neutral silica by eluting the compound with 0.5% methanol in CH$_2$Cl$_2$ to yield 0.140 g of 4-chloro-N-(1-(1-(2-cyanoacetyl)piperidin-4-yl)-1H-benzo[d]imidazol-2-yl)benzamide.

Example 1

Synthesis of 4-chloro-N-(1-(1-(2-cyano-4-methylpent-2-enoyl)piperidin-4-yl)-1H-benzo[d]imidazol-2-yl)benzamide

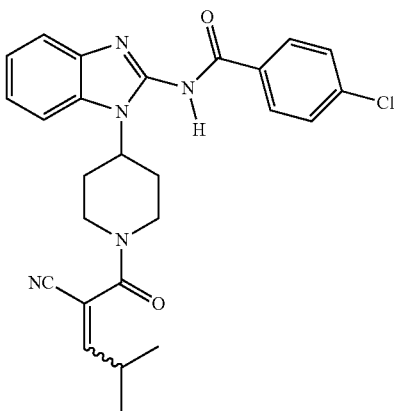 [SMILES: CC(C)C=C(C#N)C(=O)N1CCC(n2c(NC(=O)c3ccc(Cl)cc3)nc3ccccc32)CC1]

To a 25 mL round bottomed flask, 4-chloro-N-(1-(1-(2-cyanoacetyl)piperidin-3-yl)-1H-benzo[d]imidazol-2-yl)benzamide (0.14 g, 0.00033 mole) was added and dissolved in methanol (10 mL) under N$_2$ atmosphere. To this, piperidine (1 drop) and isobutyraldehyde (0.024 g, 0.00033 mole) were added at room temperature and the reaction mixture was heated to reflux for 4 h. The completion of the reaction was monitored by TLC using CH$_2$Cl$_2$: MeOH (9:1). After completion of the reaction, methanol was evaporated to get the crude product which was purified using column chromatography using 60-120 mesh size neutral silica by eluting the compound with 25% ethyl acetate in hexanes to yield 0.058 g of 4-chloro-N-(1-(1-(2-cyano-4-methylpent-2-enoyl)piperidin-4-yl)-1H-benzo[d]imidazol-2-yl)benzamide. LC-MS (ES, m/z): 476 [M+H].

Example 2

Synthesis of N-(1-(1-acryloylpiperidin-4-yl)-1H-benzo[d]imidazol-2-yl)-4-chlorobenzamide

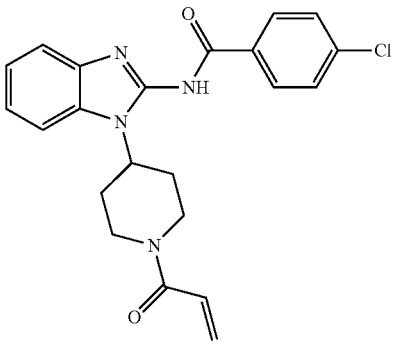 [SMILES: C=CC(=O)N1CCC(n2c(NC(=O)c3ccc(Cl)cc3)nc3ccccc32)CC1]

To a 10 mL vial, 4-chloro-N-(1-(piperidin-4-yl)-1H-benzo[d]imidazol-2-yl)benzamide hydrochloride (0.15 g, 0.0004 mole) was added in THF (5 mL) and the solution was cooled to −30° C. under N$_2$ atmosphere. Acryloyl chloride (50% solution in toluene) (0.035 g, 0.00039 mole) was added drop wise at −30° C. and the reaction mixture was stirred for 20 minutes at −30° C. The completion of the reaction was monitored by TLC using CH$_2$Cl$_2$: MeOH (9:1) as a mobile phase. After completion of the reaction, raise temperature to RT, solvent was evaporated under reduced pressure. To this, saturated NaHCO$_3$ solution was added drop wise to make pH basic, extracted with EtOAc. The combined organic layer was dried over Na$_2$SO$_4$ and evaporated to get the crude product which was subjected for the column purification. The crude compound was purified by column purification using 60-120 mesh size neutral silica by eluting the compound with 0.2% MeOH in CH$_2$Cl$_2$ to yield 0.058 g of N-(1-(1-acryloylpiperidin-4-yl)-1H-benzo[d]imidazol-2-yl)-4-chlorobenzamide. LC-MS (ES, m/z): 409.7 [M+H].

Intermediate 4

Synthesis of N-(1-(piperidin-4-yl)-1H-benzo[d]imidazol-2-yl)nicotinamide hydrochloride

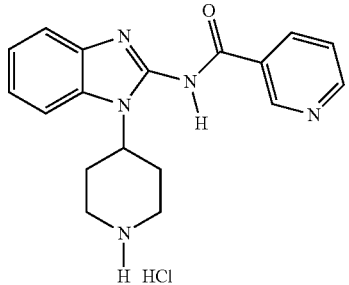 [SMILES: O=C(Nc1nc2ccccc2n1C1CCNCC1)c1cccnc1 ; Cl]

Step 1

To a 50 mL single neck round bottomed flask, nicotinic acid (0.37 g, 0.003 mole) was added in CH$_2$Cl$_2$ (10 mL) under N$_2$ atmosphere. EDC-HCl (0.72 g, 0.0037 mole), HOBT-H$_2$O (0.57 g, 0.0037 mole) and TEA (0.76 g, 0.0075 mole) were added to the reaction mixture at room temperature and stirred for 20 min tert-Butyl 4-(2-imino-2,3-dihydro-1H-benzo[d]imidazol-1-yl)piperidine-1-carboxylate (0.8 g, 0.0025 mole) in CH$_2$Cl$_2$ (15 mL) was added dropwise to the reaction mixture and stirred at room temperature for 16 h. The completion of the reaction was monitored on TLC using EtOAc: Hexanes (8:2) as a mobile phase. Saturated NaHCO$_3$ solution (30 mL) was added to the reaction mixture and aq. was extracted with EtOAc. The combined organic layer was dried over Na$_2$SO$_4$ and evaporated to get the pure product to yield 0.9 g of tert-butyl 4-(2-(nicotinamido)-1H-benzo[d]imidazol-1-yl)piperidine-1-carboxylate.

Step 2

To a 25 mL round bottomed flask, tert-butyl 4-(2-(nicotinamido)-1H-benzo[d]imidazol-1-yl)piperidine-1-carboxylate (0.5 g, 0.0012 mole) was added in 1,4 dioxane (5 mL) and the solution was cooled to 10° C. under N$_2$ atmosphere. To this, 20% HCl in 1,4-dioxane (5 mL) was added dropwise at 10° C. and the reaction mixture was stirred for 16 h at room temperature. After completion of the reaction, solvent was evaporated under reduced pressure to get crude compound which was triturated with acetone (10 mL) to yield 0.32 g of N-(1-(piperidin-4-yl)-1H-benzo[d]imidazol-2-yl)nicotinamide hydrochloride.

Intermediate 5

Synthesis of N-(1-(1-(2-cyanoacetyl)piperidin-4-yl)-1H-benzo[d]imidazol-2-yl)nicotinamide

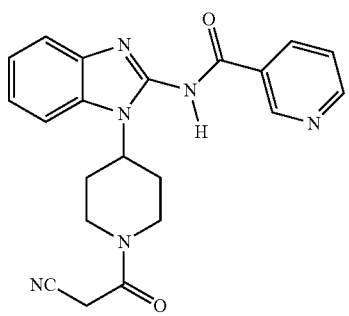 [SMILES: N#CCC(=O)N1CCC(n2c(NC(=O)c3cccnc3)nc3ccccc32)CC1]

To a 25 mL round bottomed flask, 2-cyanoacetic acid (0.095 g, 0.0011 mole) was added in CH$_2$Cl$_2$ (10 mL) and the solution was cooled to 0° C. under N$_2$ atmosphere. TBTU (0.313 g, 0.0009 mole) in DMF (1 mL) was added drop wise at 0° C. After addition, the reaction mixture was allowed to attain the room temperature. Then, N-(1-(piperidin-4-yl)-1H-benzo[d]imidazol-2-yl)nicotinamide hydrochloride (0.3 g, 0.00084 mole) and DIPEA (0.36 g, 0.0027 mole) were added to the reaction mixture and stirred at room temperature for 16 h. After completion of the reaction, water was added to the reaction mixture and product was extracted with CH$_2$Cl$_2$. The combined organic layer was dried over Na$_2$SO$_4$ and evaporated to get the crude product which was subjected for the column purification using 100-200 mesh size neutral silica by eluting the compound with 3% methanol in CH$_2$Cl$_2$ to yield 0.150 g of N-(1-(1-(2-cyanoacetyl)piperidin-4-yl)-1H-benzo[d]imidazol-2-yl)nicotinamide.

Example 3

Synthesis of N-(1-(1-(2-cyano-4-methylpent-2-enoyl)piperidin-4-yl)-1H-benzo[d]imidazol-2-yl)nicotinamide

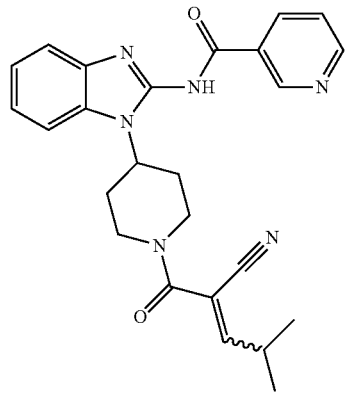 [SMILES: CC(C)C=C(C#N)C(=O)N1CCC(n2c(NC(=O)c3cccnc3)nc3ccccc32)CC1]

To a 25 mL 1N RBF, N-(1-(1-(2-cyanoacetyl)piperidin-4-yl)-1H-benzo[d]imidazol-2-yl)nicotinamide (0.14 g, 0.36 mmole) was added in dry methanol (15 mL) under N$_2$ atmosphere. Piperidine (1 drop) and isobutyraldehyde (0.026 g, 0.00036 mole) were added at room temperature and the reaction mixture was heated to reflux for 2 h. After completion of the reaction, methanol was evaporated to get the crude product which was subjected for the column purification. The crude compound was purified using column purification using 60-120 mesh size neutral silica by eluting the compound with 2% Methanol in CH$_2$Cl$_2$ to yield 0.038 g of N-(1-(1-(2-cyano-4-methylpent-2-enoyl)piperidin-4-yl)-1H-benzo[d]imidazol-2-yl) nicotinamide. LC-MS (ES, m/z): 443 [M+H].

Example 4

Synthesis of N-(1-(1-acryloylpiperidin-4-yl)-1H-benzo[d]imidazol-2-yl)nicotinamide

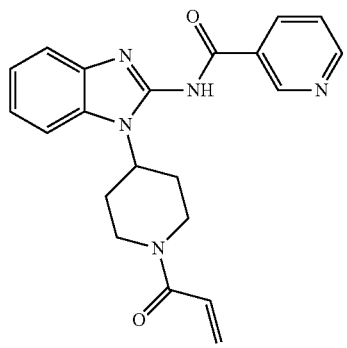 [SMILES: C=CC(=O)N1CCC(n2c(NC(=O)c3cccnc3)nc3ccccc32)CC1]

To a 10 mL vial, N-(1-(piperidin-4-yl)-1H-benzo[d]imidazol-2-yl)nicotinamide hydrochloride (0.1 g, 0.00028 mole) was taken in THF (5 mL) and cooled to −30° C. under $N_2$ atmosphere. Acryloyl chloride (50% solution in toluene) (0.025 g, 0.00028 mole) was added drop wise at −30° C. and the reaction mixture was stirred for 20 minutes at −30° C. After completion of the reaction, raise temperature to RT & solvent was evaporated under reduced pressure. To this, saturated $NaHCO_3$ solution was added dropwise to make pH basic, extracted with EtOAc. The combined organic layer was dried over $Na_2SO_4$ and evaporated to get the crude product which was subjected for the column purification. The crude compound was purified by column purification using 60-120 mesh size neutral silica by eluting the compound with 1.2% MeOH in $CH_2Cl_2$ to yield 0.026 g of N-(1-(1-acryloylpiperidin-4-yl)-1H-benzo[d]imidazol-2-yl)nicotinamide. LC-MS (ES, m/z): 376.3 [M+H].

Intermediate 6

Synthesis of tert-butyl 3-(2-imino-2,3-dihydro-1H-benzo[d]imidazol-1-yl)piperidine-1-carboxylate

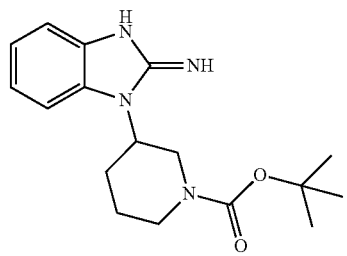 [SMILES: CC(C)(C)OC(=O)N1CCCC(n2c(=N)[nH]c3ccccc32)C1]

Step 1

To a 250 mL 3 neck RBF, 1-fluoro-2-nitrobenzene (3.52 g, 0.02496 mole) was taken in acetonitrile (50 mL) under $N_2$ atmosphere. DIPEA (13 mL, 0.075 mole) was added followed by slow addition of tert-butyl 3-aminopiperidine-1-carboxylate (5.0 g, 0.02496 mole) at room temperature and the reaction mixture was stirred at room temperature for 16 h. The reaction was monitored on TLC using EtOAc: hexanes (4:6) as a mobile phase. After 32 h, water was added to the reaction mixture and product was extracted with EtOAc. The combined organic layer was dried over $Na_2SO_4$ and evaporated to get the crude product which was subjected for the column purification. The crude compound was purified by column chromatography using 60-120 mesh size neutral silica by eluting the crude product with 3-5% EtOAc in hexanes to yield 1.7 g of tert-butyl 3-(2-nitrophenylamino)-piperidine-1-carboxylate.

Step 2

In a 100 mL 3 neck RBF, to a suspension of 10% Pd/C (0.180 g, 10% w/w) in methanol (15 mL), tert-butyl 3-(2-nitrophenylamino)piperidine-1-carboxylate (1.7 g, 0.00528 mole) in methanol (15 mL) was added under $N_2$ atmosphere. $H_2$ gas was purged to the reaction mixture for 2 h at room temperature. After completion of the reaction, the reaction mixture was filtered through celite and washed with methanol and filtrate was concentrated to yield 1.4 g of tert-butyl 3-(2-aminophenyl-amino)piperidine-1-carboxylate.

Step 3:

To a 100 mL RBF, tert-butyl 3-(2-aminophenylamino) piperidine-1-carboxylate (1.4 g, 0.00481 mole) was taken in ethanol (30 mL). Cyanogen bromide (0.61 g, 0.00577 mole) was added at room temperature and stirred for 2 h. After completion of the reaction, the pH of the reaction mass was adjusted to basic by drop wise addition of saturated $NaHCO_3$ solution and product was extracted with $CH_2Cl_2$. The organic layer was dried over $Na_2SO_4$ and evaporated to get crude which was purified by column purification using 60-120 mesh size neutral silica by eluting the compound with 3-4% methanol in $CH_2Cl_2$ to yield 1.3 g of tert-butyl 3-(2-imino-2,3-dihydro-1H-benzo[d]imidazol-1-yl)piperidine-1-carboxylate. LC-MS (ES, m/z): 317.3 [M+H].

Example 5

Synthesis of 4-chloro-N-(1-(1-(2-cyano-4-methylpent-2-enoyl)piperidin-3-yl)-1H-benzo[d]imidazol-2-yl)benzamide

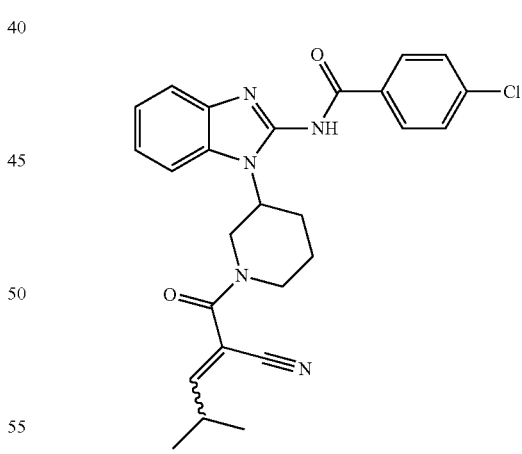

Step 1

To a 50 mL single neck RBF, 4-chlorobenzoic acid (0.192 g, 0.00123 mole) was taken in $CH_2Cl_2$ (15 mL) under $N_2$ atmosphere. EDC-HCl (0.295 g, 0.00154 mole), HOBt (0.208 g, 0.00154 mole) and TEA (0.4 mL, 0.003 mole) were added to the reaction mixture at room temperature and stirred for 20 min 3-(2-Imino-2,3-dihydro-1H-benzo[d]imidazol-1-yl)piperidine-1-carboxylate (0.325 g, 0.00102 mole) in $CH_2Cl_2$ (15 mL) was added dropwise to the reaction mixture and stirred at room temperature for 16 h.

The completion of the reaction was monitored on TLC using EtOAc: hexanes (4:6) as a mobile phase. Water was added to the reaction mixture and extracted with EtOAc. The combined organic layer was dried over Na₂SO₄ and evaporated to get the crude product which was purified by column purification using 60-120 mesh size neutral silica by eluting the compound with 20-25% EtOAc in hexanes to yield 0.3 g of tert-butyl 3-(2-(4-chlorobenzamido)-1H-benzo[d]imidazol-1-yl)piperidine-1-carboxylate.

Step 2

To a 25 mL RBF, tert-butyl 3-(2-(4-chlorobenzamido)-1H-benzo[d]imidazol-1-yl)piperidine-1-carboxylate (0.3 g, 0.00065 mole) was taken in 1,4-dioxane (5 mL) and cooled to 10° C. under N₂ atmosphere. HCl in 1,4 dioxane (20% solution) (6 mL) was added dropwise at 10° C. and the reaction mixture was stirred for 16 h at room temperature. After completion of the reaction, solvent was evaporated under reduced pressure to get crude compound. Crude compound was triturated with CH₂Cl₂ to yield 0.27 g of 4-chloro-N-(1-(piperidin-3-yl)-1H-benzo[d]imidazol-2-yl) benzamide hydrochloride.

Step 3

To a 25 mL RBF, 2-cyanoacetic acid (0.039 g, 0.00046 mole) was taken in CH₂Cl₂ (10 mL) and DIPEA (0.02 mL) and cooled to 0° C. under N₂ atmosphere. TBTU (0.129 g, 0.00040 mole) in DMF (0.5 mL) was added dropwise at 0° C. After addition, the reaction mixture was allowed warm to room temperature. 4-Chloro-N-(1-(piperidin-3-yl)-1H-benzo[d]imidazol-2-yl)benzamide hydrochloride (0.15 g, 0.00038 mole) and DIPEA (0.19 mL, 0.0011 mole) were added and trhe reaction mixture was stirred at room temperature for 16 h. After completion of the reaction, water was added to the reaction mixture and extracted with CH₂Cl₂. The combined organic layer was dried over Na₂SO₄ and evaporated to get the crude product which was subjected for the column purification. The crude compound was purified by column purification using 60-120 mesh size neutral silica by eluting the compound with 0.6% methanol in CH₂Cl₂ to yield 0.135 g of 4-chloro-N-(1-(1-(2-cyanoacetyl)piperidin-3-yl)-1H-benzo[d]imidazol-2-yl)benzamide.

Step 4

To a 10 mL vial, 4-chloro-N-(1-(1-(2-cyanoacetyl)piperidin-3-yl)-1H-benzo[d]imidazol-2-yl) benzamide (0.1 g, 0.00023 mole) was taken in ethanol (5 mL) under N₂ atmosphere. Piperidine acetate (3.3M solution in water) (0.02 mL) and isobutyraldehyde (0.02 mL, 0.00023 mole) were added at room temperature and the reaction mixture was heated to reflux for 2 h. Water was added to the reaction mixture and extracted with CH₂Cl₂. The combined organic layer was dried over Na₂SO₄ and evaporated to get the crude which was subjected for the column purification. The crude compound was purified by column purification using 60-120 mesh size neutral silica by eluting the compound with 75% CH₂Cl₂ in hexanes to yield 0.035 g of 4-chloro-N-(1-(1-(2-cyano-4-methylpent-2-enoyl)piperidin-3-yl)-1H-benzo[d]imidazol-2-yl)benzamide. LC-MS (ES, m/z): 476.3 [M+H].

Example 6

Synthesis of N-(1-(1-acryloylpiperidin-3-yl)-1H-benzo[d]imidazol-2-yl)-4-chlorobenzamide

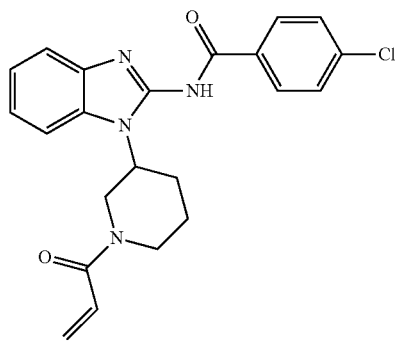 [SMILES: C=CC(=O)N1CCCC(n2c(NC(=O)c3ccc(Cl)cc3)nc3ccccc32)C1]

To a 10 mL vial, 4-chloro-N-(1-(piperidin-3-yl)-1H-benzo[d]imidazol-2-yl)benzamide hydrochloride (0.07 g, 0.00017 mole) was taken in THF (3 mL) and cooled to −30° C. under N₂ atmosphere. Acryloyl chloride (50% solution in toluene) (0.029 g, 0.00016 mole) was added drop wise at −30° C. and the reaction mixture was stirred for 20 minutes at −30° C. After completion of the reaction, saturated NaHCO₃ solution was added drop wise to make pH basic at −30° C. and the reaction mixture was allowed to warm up to room temperature and extracted with EtOAc. The combined organic layer was dried over Na₂SO₄ and evaporated to get the crude product which was subjected for the column purification. The crude compound was purified by column purification using 60-120 mesh size neutral silica by eluting the compound with 2-3% MeOH in CH₂Cl₂ to yield 0.037 g of N-(1-(1-acryloylpiperidin-3-yl)-1H-benzo[d]imidazol-2-yl)-4-chlorobenzamide. LC-MS (ES, m/z): 409.2 [M+H].

Example 7

Synthesis of N-(1-(1-(2-cyano-4-methylpent-2-enoyl)piperidin-3-yl)-1H-benzo[d]imidazol-2-yl) nicotinamide

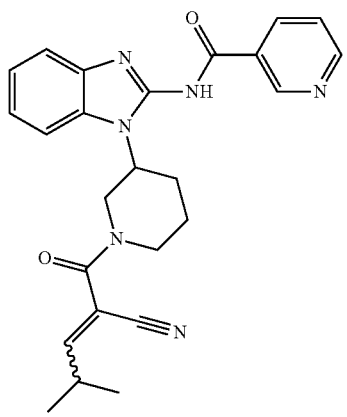 [SMILES: CC(C)C=C(C#N)C(=O)N1CCCC(n2c(NC(=O)c3cccnc3)nc3ccccc32)C1]

Step 1

To a 50 mL single neck RBF, nicotinic acid (0.280 g, 0.00227 mole) was taken in CH₂Cl₂ (15 mL) under N₂ atmosphere. EDC-HCl (0.545 g, 0.00284 mole), HOBt (0.436 g, 0.00154 mole) and TEA (0.79 mL, 0.0030 mole) were added to the reaction mixture at room temperature and stirred for 20 min. tert-Butyl 3-(2-Imino-2,3-dihydro-1H-benzo[d]imidazol-1-yl)piperidine-1-carboxylate (0.600 g, 0.00182 mole) in CH₂Cl₂ (15 mL) was added drop wise to the reaction mixture and stirred at room temperature for 16 h. After 16 h, water was added to the reaction mixture and extracted with CH₂Cl₂. The combined organic layer was dried over Na₂SO₄ and evaporated to get the crude product which was purified by column purification using 60-120 mesh size neutral silica by eluting the compound with 0.9% MeOH in CH₂Cl₂ to yield 0.3 g of tert-butyl 3-(2-(nicotinamido)-1H-benzo[d]imidazol-1-yl)piperidine-1-carboxylate.

Step 2

To a 25 mL RBF, tert-butyl 3-(2-(nicotinamido)-1H-benzo[d]imidazol-1-yl)piperidine-1-carboxylate (0.27 g, 0.00064 mole) was taken in 1,4-dioxane (20 mL) and cooled to 10° C. under N₂ atmosphere. HCl in 1,4-dioxane (20% solution) (10 mL) was added drop wise at 10° C. and the reaction mixture was stirred for 16 h at room temperature. After completion of the reaction, solvent was evaporated under reduced pressure to get crude compound. Crude compound was triturated with CH₂Cl₂ to yield 0.24 g of N-(1-(piperidin-3-yl)-1H-benzo[d]imidazol-2-yl)nicotinamide hydrochloride.

Step 3

To a 25 mL RBF, 2-cyanoacetic acid (0.039 g, 0.000469 mole) was taken in CH₂Cl₂ (10 mL) and DIPEA (0.02 mL) and cooled to 0° C. under N₂ atmosphere. TBTU (0.131 g, 0.00041 mole) in DMF (0.5 mL) was added drop wise at 0° C. After addition was complete, the reaction mixture was allowed to attain the room temperature. N-(1-(Piperidin-3-yl)-1H-benzo[d]imidazol-2-yl)nicotinamide hydrochloride (0.14 g, 0.000391 mole) and DIPEA (0.21 mL, 0.00117 mole) were added to the reaction mixture and the reaction mixture stirred at room temperature for 16 h. After completion of the reaction, water was added to the reaction mixture and the reaction mixture was extracted with CH₂Cl₂. The combined organic layer was dried over Na₂SO₄ and evaporated to get the crude product which was subjected for the column purification. The crude compound was purified using column purification using 60-120 mesh size neutral silica by eluting the compound with 2-3% methanol in CH₂Cl₂ to yield 0.1 g of N-(1-(1-(2-cyanoacetyl)piperidin-3-yl)-1H-benzo[d]imidazol-2-yl)nicotinamide.

Step 4

To a 10 mL vial, N-(1-(1-(2-cyanoacetyl)piperidin-3-yl)-1H-benzo[d]imidazol-2-yl) nicotinamide (0.09 g, 0.00023 mole) was taken in ethanol (5 mL) under N₂ atmosphere. Piperidine acetate (3.3M solution in water) (0.02 mL) and isobutyraldehyde (0.06 mL, 0.00069 mole) were added at room temperature and the reaction mixture was heated to reflux for 2 h. The completion of the reaction was monitored on TLC using CH₂Cl₂: MeOH (9:1) as a mobile phase. Water was added to the reaction mixture and the reaction mixture was extracted with CH₂Cl₂ The combined organic layer was dried over Na₂SO₄ and evaporated to get the crude which was subjected for the column purification. The crude compound was purified by column purification using 60-120 mesh size neutral silica by eluting the compound with 2.5-3% MeOH in CH₂Cl₂ to yield 0.035 g of N-(1-(1-(2-cyano-4-methylpent-2-enoyl)piperidin-3-yl)-1H-benzo[d]imidazol-2-yl)nicotinamide (LC-MS (ES, m/z): 443[M+H].

Example 8

Synthesis of N-(1-(1-acryloylpiperidin-3-yl)-1H-benzo[d]imidazol-2-yl)nicotinamide

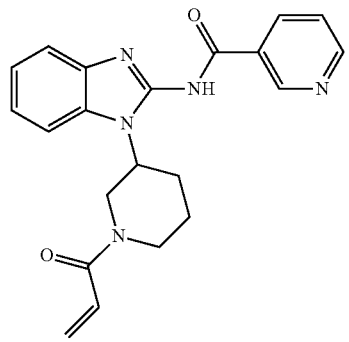 [SMILES: C=CC(=O)N1CCCC(n2c(NC(=O)c3cccnc3)nc3ccccc32)C1]

To a 10 mL vial, N-(1-(piperidin-3-yl)-1H-benzo[d]imidazol-2-yl)nicotinamide hydrochloride (0.07 g, 0.00019 mole) was taken in THF (3 mL) and cooled to −30° C. under N₂ atmosphere. Acryloyl chloride (50% solution in toluene) (0.015 g, 0.00017 mole) was added drop wise at −30° C. and the reaction mixture was stirred for 20 minutes at −30° C. After 30 min, saturated NaHCO₃ solution was added drop wise to make pH basic and extracted the reaction mixture was with EtOAc. The combined organic layer was dried over Na₂SO₄ and evaporated to get the crude product. The crude product was thus obtained was taken in THF (3 mL) followed by addition of DBU (0.1 ml) and the reaction mixture was stirred at room temperature for 9 h. The reaction mixture was diluted with water and extracted with EtOAc, the combined organic layer was dried, concentrated and subjected for the column purification. The crude compound was purified by column purification using 60-120 mesh size neutral silica by eluting the compound with 2-3% MeOH in CH₂Cl₂ to yield 0.020 g of N-(1-(1-acryloylpiperidin-3-yl)-1H-benzo[d]imidazol-2-yl)nicotinamide. LC-MS (ES, m/z): 376[M+H].

Example 9

Synthesis of N-(1-((1-acryloylpyrrolidin-2-yl)methyl)-1H-benzo[d]imidazol-2-yl)-4-chlorobenzamide

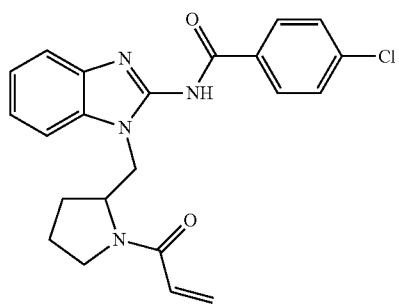 [SMILES: C=CC(=O)N1CCCC1Cn1c(NC(=O)c2ccc(Cl)cc2)nc2ccccc21]

Step 1

To a 50 mL single-neck RBF, 1-fluoro-2-nitrobenzene (2 g, 0.0141 mole) was taken in acetonitrile (20 mL) under N₂ atmosphere. DIEA (7.39 mL, 0.0425 mole) was added followed by addition of tert-butyl 2-(aminomethyl)pyrrolidine-1-carboxylate (3.4 g, 0.0170 mole) at room temperature and the reaction mixture was stirred at room temperature for 16 h. After 32 h, water was added to the reaction mixture and product was extracted with EtOAc. The combined organic layer was dried over $Na_2SO_4$ and evaporated to get the crude product which was purified by column chromatography using 60-120 mesh size neutral silica by eluting the compound with 3-5% EtOAc in hexanes to yield 2.8 g of tert-butyl 2-(2-nitrophenylamino)methyl)pyrrolidine-1-carboxylate.

Step 2

In a 100 mL 3 neck RBF, to a suspension of 10% Pd/C (0.33 g, 10% w/w) in methanol (30 mL), tert-butyl 2((2-nitrophenylamino)methyl)pyrrolidine-1-carboxylate (3.3 g, 0.0102 mole) in methanol (30 mL) was added under $N_2$ atmosphere. The $H_2$ gas was purged to the reaction mixture for 1.5 h at room temperature. After completion of the reaction, the reaction mixture was filtered through celite and washed with methanol and filtrate was concentrated to yield 2.8 g of tert-butyl 2((2-aminophenylamino)methyl)pyrrolidine-1-carboxylate.

Step 3

To a 100 mL RBF, tert-butyl 2((2-aminophenylamino) methyl)pyrrolidine-1-carboxylate (2.2 g, 0.00755 mole) was taken in ethanol (50 mL). Cyanogen bromide (0.959 g, 0.00906 mole) was added at room temperature and stirred for 4 h. After completion of the reaction, solvent was evaporated under reduced pressure to get crude compound & water added to this crude, then the pH of the reaction mass was adjusted to basic by addition of 40% NaOH solution and product was extracted with EtOAc. The organic layer was washed with water, dried over $Na_2SO_4$ and evaporated to yield 2.2 g of tert-butyl 2-((2-imino-2,3-dihydro-1H-benzo [d]imidazol-1-yl)methyl)pyrrolidine-1-carboxylate.

Step 4

To a 35 mL seal-tube, 4-chlorobenzoic acid (0.5 g, 0.0031 mole) was taken in $CH_2Cl_2$ (10 mL), EDC-HCl (0.71 g, 0.00372 mole), HOBt.$H_2O$ (0.571 g, 0.00372 mole), tert-butyl 2-(((2-imino-2,3-dihydro-1H-benzo[d]imidazol-1-yl) methyl)pyrrolidine-1-carboxylate (1.11 g, 0.0035 mole) and TEA (1.29 mL, 0.0093 mole) were added to the reaction mixture at room temperature & the reaction mixture was stirred for 3 h. Water was added to the reaction mixture and the reaction mixture was extracted with $CH_2Cl_2$. The combined organic layer was dried over $Na_2SO_4$ and evaporated to get the crude product which was purified by column purification using 60-120 mesh size neutral silica by eluting the compound with 20-25% EtOAc in hexanes to yield 0.434 g of tert-butyl 2-((2-(4-chlorobenzamido)-1H-benzo[d]imidazol-1-yl)methyl)pyrrolidine-1-carboxylate.

Step 5

To a 25 mL RBF, tert-butyl 2-((2-(4-chlorobenzamido)-1H-benzo[d]imidazol-1-yl)methyl)pyrrolidine-1-carboxylate (0.41 g, 0.00090 mole) was taken in $CH_2Cl_2$ (20 mL) and cooled to 0-5° C. TFA (8.2 mL) was added drop wise and after addition, the reaction mixture was stirred for 12 h at room temperature. After completion of the reaction, dilute the reaction mixture with $CH_2Cl_2$, neutralized with saturated $NaHCO_3$ solution and the combined organic layer washed with water and finally dried over $Na_2SO_4$ and evaporated under reduced pressure to yield 0.3 g of 4-chloro-N-(1-(pyrrolidin-2-ylmethyl)-1H-benzo[d]imidazol-2-yl)benzamide.

Step 6

To a 10 mL vial, 4-chloro-N-(1-(pyrrolidin-2-ylmethyl)-1H-benzo[d]imidazol-2-yl)benzamide (0.3 g, 0.00028 mole) was taken in THF (5 mL) and cooled to −50° C. under $N_2$ atmosphere. Acryloyl chloride (50% solution in toluene) (0.06 mL, 0.00031 mole) was added drop wise at −50° C. and the reaction mixture was stirred for 15 minutes at −50° C., followed by RT for 1 h. After completion of the reaction, to this, 40% NaOH solution was added drop wise to make pH basic and the reaction mixture was extracted with EtOAc. The combined organic layer was dried over $Na_2SO_4$ and evaporated to get the crude product which was purified by Prep TLC in 50% EtOAc in hexanes to yield 0.030 g of N-(1-(((1-acryloylpyrrolidin-2-yl)methyl)-1H-benzo[d]imidazol-2-yl)-4-chlorobenzamide. LC-MS (ES, m/z): 409 [M+H].

Example 10

Synthesis of 4-chloro-N-(1-((1-(2-cyano-4-methylpent-2-enoyl)pyrrolidin-2-yl)methyl)-1H-benzo[d]imidazol-2-yl)benzamide

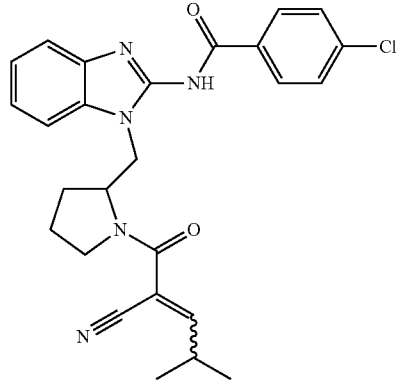 [SMILES: CC(C)C=C(C#N)C(=O)N1CCCC1Cn1c(NC(=O)c2ccc(Cl)cc2)nc2ccccc21]

Step 1

To a 35 mL seal-tube, 2-cyanoacetic acid (0.052 g, 0.0062 mole) was taken in $CH_2Cl_2$ (5 mL), EDC-HCl (0.127 g, 0.00067 mole), HOBt.$H_2O$ (0.127 g, 0.00067 mole), 4-chloro-N-(1-(pyrrolidin-2-ylmethyl)-1H-benzo[d]imidazol-2-yl)benzamide (0.2 g, 0.0005 6 mole) and TEA (0.23 mL, 0.00168 mole) were added to the reaction mixture at room temperature and stirred at room temperature for 3 h. After completion of the reaction, water was added to the reaction mixture and extracted with $CH_2Cl_2$. The combined organic layer was dried over $Na_2SO_4$ and evaporated to get the crude product which was purified by column purification using column-chromatography by eluting with 20-25% EtOAc in hexanes to yield 0.14 g of 4-chloro-N-(1-((1-(2-cyanoacetyl)pyrrolidin-2-yl)methyl)-1H-benzo[d]imidazol-2-yl)benzamide.

Step 2

To a 10 mL vial, 4-chloro-N-(1-((1-(2-cyanoacetyl)pyrrolidin-2-yl)methyl)-1H-benzo[d]imidazol-2-yl)benzamide (0.14 g, 0.00033 mole) was taken in ethanol (5 mL). Piperidine acetate (3.3M solution in water) (1 mL) and isobutyraldehyde (0.074 mL, 0.00082 mole) were added at room temperature and the reaction mixture was heated to reflux for 6 h. After completion of the reaction, water was added to the reaction mixture and extracted with EtOAc. The combined organic layer washed with water, brine, dried over $Na_2SO_4$ and evaporated to get the crude product. The crude compound was purified by Prep TLC in 50% EtOAc in hexanes to yield 0.016 g of 4-chloro-N-(1-((1-(2-cyano-4-methylpent-2-enoyl)pyrrolidin-2-yl)methyl)-1H-benzo[d]imidazol-2-yl)benzamide. LC-MS (ES, m/z): 376 [M+H].

Example 11

Synthesis of N-(1-((1-acryloylpyrro lidin-2-yl)methyl)-1H-benzo[d]imidazol-2-yl)nicotinamide

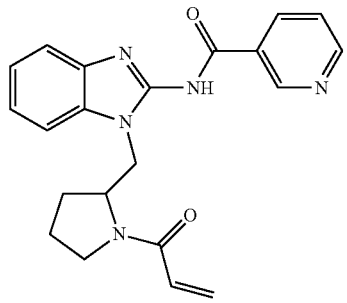 [SMILES: C=CC(=O)N1CCCC1Cn1c(NC(=O)c2cccnc2)nc2ccccc21]

Step 1
To a 35 ml seal-tube, nicotinic acid (0.4 g, 0.0032 mole) was taken in CH$_2$Cl$_2$ (5 mL), EDC-HCl (0.72 g, 0.0038 mole), HOBt.H$_2$O (0.58 g, 0.0038 mole), tert-butyl 2-((2-imino-2,3-dihydro-1H-benzo[d]imidazol-1-yl)methyl)pyrrolidine-1-carboxylate (1.012 g, 0.0032 mole) and TEA (1.3 ml, 0.0096 mole) were added to the reaction mixture at room temperature stirred at room temperature for 5 h. The completion of the reaction was monitored on TLC using EtOAc: hexanes (7:3) as a mobile phase. After completion of the reaction, water was added to the reaction mixture and extracted with CH$_2$Cl$_2$. The combined organic layer washed with brine, finally dried over Na$_2$SO$_4$ and evaporated to get the crude product which was subjected for the column purification. The crude compound was purified by column purification using 60-120 mesh size neutral silica by eluting the compound with 5-10% EtOAc in hexanes to yield 0.4 g of tert-butyl 2-((2-(nicotinamido)-1H-benzo[d]imidazol-1-yl)methyl)pyrrolidine-1-carboxylate.

Step 2
To a 25 mL RBF, tert-butyl 2-((2-(nicotinamido)-1H-benzo[d]imidazol-1-yl)methyl)-pyrrolidine-1-carboxylate (0.4 g, 0.00094 mole) was taken in CH$_2$Cl$_2$ (15 mL) and cooled to 0-5° C. TFA (8 mL) was added drop wise at 0-5° C. and the reaction mixture was stirred for 12 h at room temperature. After completion of the reaction, the reaction mixture was diluted with CH$_2$Cl$_2$, neutralized with saturated NaHCO$_3$ solution and the combined organic layer washed with water and dried over Na$_2$SO$_4$ and evaporated under reduced pressure to yield 0.22 g of N-(1-(pyrrolidin-2-ylmethyl)-1H-benzo[d]imidazol-2-yl)nicotinamide.

Step 3
To a 10 mL vial, N-(1-(pyrrolidin-2-ylmethyl)-1H-benzo[d]imidazol-2-yl)nicotinamide (0.1 g, 0.00031 mole) was taken in THF (3 mL) and cooled to −50° C. under N$_2$ atmosphere. Acryloyl chloride (50% solution in toluene) (0.06 mL, 0.00034 mole) was added drop wise at −50° C. and the reaction mixture was stirred for 15 minutes at −50° C., followed by RT for 1 h. After completion of the reaction, 40% NaOH solution was added drop wise to make pH basic and extracted with EtOAc. The combined organic layer washed with water, brine, dried over Na$_2$SO$_4$ and evaporated to get the crude product. The crude compound was purified by Prep TLC in 3% MeOH in CH$_2$Cl$_2$ to yield 0.023 g of N-(1-(1-acryloylpyrrolidin-2-yl)methyl)-1H-benzo[d]imidazol-2-yl)nicotinamide. LC-MS (ES, m/z): 376.2 [M+H].

Example 12

Synthesis of N-(1-((1-(2-cyano-4-methylpent-2-enoyl)pyrrolidin-2-yl)methyl)-1H-benzo[d]imidazol-2-yl)nicotinamide

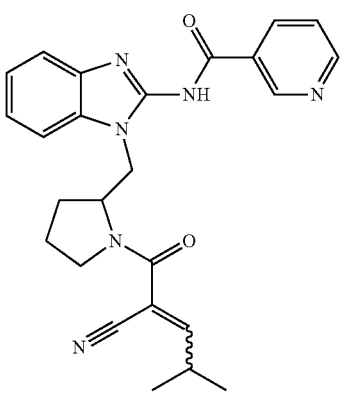 [SMILES: CC(C)C=C(C#N)C(=O)N1CCCC1Cn1c(NC(=O)c2cccnc2)nc2ccccc21]

Step 1
To a 35 mL seal-tube, 2-cyanoacetic acid (0.058 g, 0.0068 mole) was taken in CH$_2$Cl$_2$ (5 mL), EDC-HCl (0.14 g, 0.00074 mole), HOBt.H$_2$O (0.113 g, 0.00074 mole), N-(1-(pyrrolidin-2-ylmethyl)-1H-benzo[d]imidazol-2-yl)nicotinamide (0.2 g, 0.00062 mole) and TEA (0.25 mL, 0.00186 mole) were added to the reaction mixture at room temperature stirred at room temperature for 16 h. After completion of the reaction, water was added to the reaction mixture and the reaction mixture was extracted with CH$_2$Cl$_2$. The combined organic layer washed with saturated NaHCO$_3$ solution, water and brine. The organic layer was dried over Na$_2$SO$_4$ and evaporated to get the crude product which was purified by column purification by eluting the compound with 3% MeOH in CH$_2$Cl$_2$ to yield 0.08 g of N-(1-((1-(2-cyanoacetyl)pyrrolidin-2-yl)methyl)-1H-benzo[d]imidazol-2-yl)nicotinamide.

Step 2
To a 10 ml vial, N-(1-((1-(2-cyanoacetyl)pyrrolidin-2-yl)methyl)-1H-benzo[d]imidazol-2-yl)nicotinamide (0.075 g, 0.00019 mole) was taken in ethanol (2 mL). Piperidine acetate (3.3M solution in water) (0.2 mL) and isobutyraldehyde (0.043 mL, 0.00048 mole) were added at room temperature and the reaction mixture was heated to reflux for 2 h. After completion of the reaction, water was added to the reaction mixture and extracted with EtOAc. The combined organic layer washed with water, brine, dried over Na$_2$SO$_4$ and evaporated to get the crude which was purified by Prep TLC in 3% MeOH in CH$_2$Cl$_2$ to yield 0.03 g of N-(1-((1-(2-cyano-4-methylpent-2-enoyl)pyrrolidin-2-yl)methyl)-1H-benzo[d]imidazol-2-yl)nicotinamide. LC-MS (ES, m/z): 443.3 [M+H].

Example 13

Synthesis of (S)-N-(1-(1-acryloylpiperidin-4-yl)-5-(3,3-dimethylbutan-2-ylamino)methyl)-1H-benzo[d]imidazol-2-yl)-4-chlorobenzamide

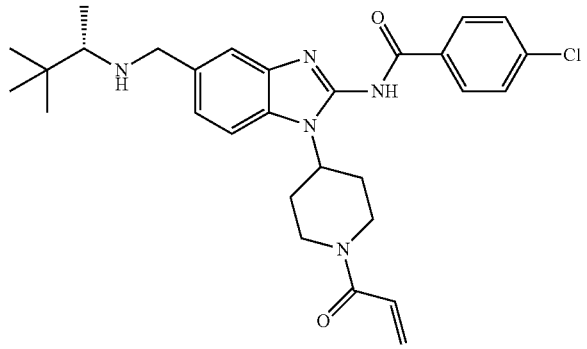 [SMILES: C=CC(=O)N1CCC(n2c(NC(=O)c3ccc(Cl)cc3)nc3cc(CN[C@@H](C)C(C)(C)C)ccc32)CC1]

Step 1

To a 100 mL three necked round bottom flask, 4-fluoro-3-nitrobenzaldehyde (2.0 g, 0.0118 mole) was taken in acetonitrile (25 mL) and DIPEA (6.1 mL, 0.0354 mole) was added drop wise at room temperature. After completion of addition, the reaction mass was stirred for 15 min at same temperature followed by slow addition of tert-butyl 4-aminopiperidine-1-carboxylate (3.5 g, 0.0177 mole) over 15 min After completion of the addition, the reaction mixture was stirred for 16 h. After completion of the reaction, acetonitrile was distilled out and water was added to residue, aq. was extracted by ethyl acetate. The combined organic layer was dried over $Na_2SO_4$, filtered and concentrated to afford crude product was purified using column purification by eluting the compound with 20% ethyl acetate in hexanes to yield 2.62 g of tert-butyl 4-(4-formyl-2-nitrophenylamino)piperidine-1-carboxylate.

Step 2

In a 100 mL 3-neck RBF, tert-butyl 4-(4-formyl-2-nitrophenylamino)piperidine-1-carboxylate (3.25 g, 0.00932 mole), (S)-3,3-dimethylbutan-2-amine (1.27 mL, 0.00932 mole) was added in 1,2-dichloroethane (50 mL) under $N_2$ atmosphere followed by addition of 5 drops of glacial acetic acid. The reaction mixture was stirred for 15 min at same temperature, followed by slow addition of sodium triacetoxyborohydride (2.96 g, 0.01398 mole). The reaction mixture was stirred for 6 h. After completion of the reaction, the reaction was quenched with 2M $Na_2CO_3$ solution and extracted by ethyl acetate. The combined organic layers were dried over $Na_2SO_4$, filtered and concentrated to afford yield 4.0 g of (S)-tert-butyl 4-(4-(3,3-dimethylbutan-2-ylamino)methyl)-2-nitrophenylamino)piperidine-1-carboxylate.

Step 3

In a 100 mL 3-neck RBF, (S)-tert-butyl 4-(4-(3,3-dimethylbutan-2-ylamino)methyl)-2-nitrophenylamino)piperidine-1-carboxylate (4.0 g, 0.00932 mole) was added in $CH_2Cl_2$ (20 mL) followed by pyridine (0.9 mL, 0.01118 mole) and cooled the reaction mixture to 0° C. Trifluroacetic anhydride (1.95 mL, 0.01397 mole) was added drop wise to the reaction mixture at 0° C. After completion of the addition, the reaction mixture was stirred for 1 h at room temperature. After completion of the reaction, the reaction mixture was quenched with 2M $NaHCO_3$ solution and extracted by $CH_2Cl_2$. The combined organic layer was dried over $Na_2SO_4$, filtered and concentrated to afford yield 4.0 g of (S)-tert-butyl4-(4-((N-(3,3-dimethylbutan-2-yl)-2,2,2-trifluoroacetamido)methyl)-2-nitrophenylamino)piperidine-1-carboxylate.

Step 4

In a 100 mL hydrogenator autoclave, to a suspension of 10% dry Pd/C (0.4 g, 10% w/w) in methanol (50 mL), (S)-tert-butyl4-(4-((N-(3,3-dimethylbutan-2-yl)-2,2,2-trifluoroacetamido)methyl)-2-nitrophenylamino)piperidine-1-carboxylate (3.0 g, 0.00282 mole) was added and the autoclave was screwed air tight. The reaction mixture was flushed twice under nitrogen atmosphere. The $H_2$ gas was pressurized into the autoclave at 50 psi pressure and the reaction mixture was stirred at room temperature for 4 h. After completion of the reaction, the reaction mixture was filtered through celite and washed with methanol and filtrate was concentrated to afford 3.0 g of (S)-tert-butyl 4-(2-amino-44N-(3,3-dimethylbutan-2-yl)-2,2,2-trifluoroacetamido)methyl)phenylamino)piperidine-1-carboxylate which was used in the next step without further purification.

Step 5

To a 100 mL RBF, (S)-tert-butyl 4-(2-amino-44N-(3,3-dimethylbutan-2-yl)-2,2,2-trifluoro-acetamido)-methyl)phenylamino)piperidine-1-carboxylate (3.0 g, 0.00599 mole) was taken in ethanol (25 mL). Cyanogen bromide (0.76 g, 0.00719 mole) was added at room temperature and stirred reaction mass for 3 h. After completion of the reaction, ethanol was distilled out and saturated $NaHCO_3$ solution was added to adjust pH basic and the reaction mixture was stirred for 1 h ande filtered. The filtrate was washed by water and dried to yield 3.05 g of (S)-tert-butyl 4-(5-((N-(3,3-dimethylbutan-2-yl)-2,2,2-trifluoroacetamido)methyl)-2-imino-2,3-dihydro-1H-benzo[d]imidazol-1-yl)piperidine-1-carboxylate which was used in next step without further purification.

Step 6

To a 50 mL single neck RBF, 4-chlorobenzoic acid (1.25 g, 0.00799 mole) was taken in $CH_2Cl_2$ (50 mL) under $N_2$ atmosphere. EDC.HCl (1.91 g, 0.00998 mole), HOBt (1.52 g, 0.010 mole) and TEA (2.8 mL, 0.01997 mole) were added to the reaction mixture at room temperature and stirred for 20 min (S)-tert-Butyl 4-(5-((N-(3,3-dimethylbutan-2-yl)-2,2,2-trifluoroacetamido)methyl)-2-imino-2,3-dihydro-1H-benzo[d]imidazol-1-yl)piperidine-1-carboxylate (3.5 g, 0.0066 mole) in $CH_2Cl_2$ (50 mL) was added drop wise to the reaction mixture and the reaction mixture was stirred at room temperature for 9 h. After completion of the reaction, saturated $NaHCO_3$ solution was added to the reaction mixture and aq. layer was extracted with EtOAc. The combined organic layer was dried over $Na_2SO_4$ and evaporated to get the crude product was purified using column purification by eluting the compound with 10% ethyl acetate in hexanes to yield 3.0 g of (S)-tert-butyl 4-(2-(4-chlorobenzamido)-5-(N-(3,3-dimethylbutan-2-yl)-2,2,2-trifluoroacetamido)methyl)-1H-benzo[d]imidazol-1-yl)piperidine-1-carboxylate.

Step 7

To a 25 mL RBF, (S)-tert-butyl4-(2-(4-chlorobenzamido)-5-(N-(3,3-dimethylbutan-2-yl)-2,2,2-trifluoroacetamido)methyl)-1H-benzo[d]imidazol-1-yl)piperidine-1-carboxylate (2.0 g, 0.00301 mole) was cooled to 10° C. under $N_2$ atmosphere. 20% HCl in 1,4-dioxane (10 mL) was added drop wise and the reaction mixture was stirred for 6 h at room temperature. After completion of the reaction, solvent was evaporated under reduced pressure to get crude compound. Crude compound was triturated with acetone to yield 1.5 g of (S)-4-chloro-N-(5((N-(3,3-dimethylbutan-2-yl)-2,2,2-trifluoroacetamido)methyl)-1-(piperidine-4-yl)-1H-benzo[d]imidazol-2-yl)benzamide.

Step 8

In a 50 mL single neck RBF, (S)-4-chloro-N-(5-((N-(3,3-dimethylbutan-2-yl)-2,2,2-trifluoroacetamido)methyl)-1-(piperidine-4-yl)-1H-benzo[d]imidazol-2-yl)benzamide (0.5 g, 0.00088 mole) was added in THF (5 mL), and the reaction mixture was cooled to –30° C. Acroloyl chloride (50% in toluene) (0.144 g, 0.00079 mole) was added drop wise to the reaction mixture at –30° C. After completion of addition, the reaction mixture was stirred for 30 minutes at room temperature. After completion of the reaction, the reaction mixture was quenched with 2M NaHCO₃ solution and extracted by EtOAc. The combined organic layers were dried over Na₂SO₄, filtered and concentrated to afford yield crude product. The crude product was taken in THF (2 mL) and DBU (0.3 mL) was added to it and the reaction mixture was stirred at room temperature for 16 h. After completion of the reaction, water was added and the aq. layer was extracted with EtOAc. The combined organic layers were dried over Na₂SO₄ and evaporated to get 0.5 g of (S)-N-(1-(1-acryloylpiperidin-4-yl)-5-(N-(3,3-dimethylbutan-2-yl)-2,2,2-trifluoroacetamido)methyl)-1H-benzo[d]imidazol-2-yl)-4-chlorobenzamide.

Step 9

To a 25 mL RBF, (S)-N-(1-(1-acryloylpiperidin-4-yl)-5-(N-(3,3-dimethylbutan-2-yl)-2,2,2-trifluoroacetamido)methyl)-1H-benzo[d]imidazol-2-yl)-4-chlorobenzamide (0.325 g, 0.00052 mole) was added in ethanol (4 mL) and cooled to 0° C. under N₂ atmosphere. NaBH₄ (0.079 g, 0.00210 mole) was added at 0° C. and the reaction mixture was stirred for 6 h at room temperature. After completion of the reaction, solvent was evaporated under reduced pressure to get crude compound. Crude compound was triturated with n-pentane (10 ml) to yield 400 mg of crude product, which was submitted to prep HPLC for further purification to get 15 mg of (S)-N-(1-(1-acryloylpiperidin-4-yl)-5-(3,3-dimethylbutan-2-ylamino)methyl)-1H-benzo[d]imidazol-2-yl)-4-chlorobenzamide. LC-MS (ES, m/z): 522 [M+H].

Intermediate 7

Synthesis of 4-chloro-N-(5-((N-((S)-3,3-dimethylbutan-2-yl)-2,2,2-trifluoroacetamido)methyl)-1-(piperidin-3-yl)-1H-benzo[d]imidazol-2-yl)benzamide

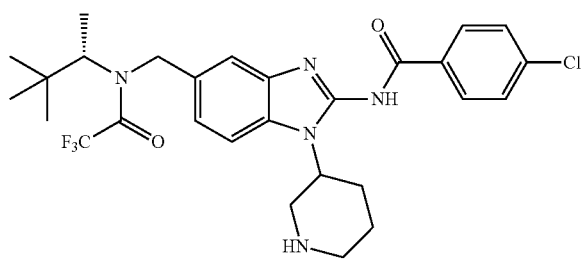 [SMILES: C[C@H](N(Cc1ccc2c(c1)nc(NC(=O)c1ccc(Cl)cc1)n2C1CCCNC1)C(=O)C(F)(F)F)C(C)(C)C]

Intermediate 7 was prepared by following the steps 1-7 in example 13 but replacing tert-butyl 4-aminopiperidine-1-carboxylate with tert-butyl 3-aminopiperidine-1-carboxylate.

Example 14

Synthesis of 4-chloro-N-(1-(1-(2-cyano-4-methylpent-2-enoyl)piperidin-3-yl)-5-((N-((S)-3,3-dimethylbutan-2-yl)-2,2,2-trifluoroacetamido)methyl)-1H-benzo[d]imidazol-2-yl)benzamide

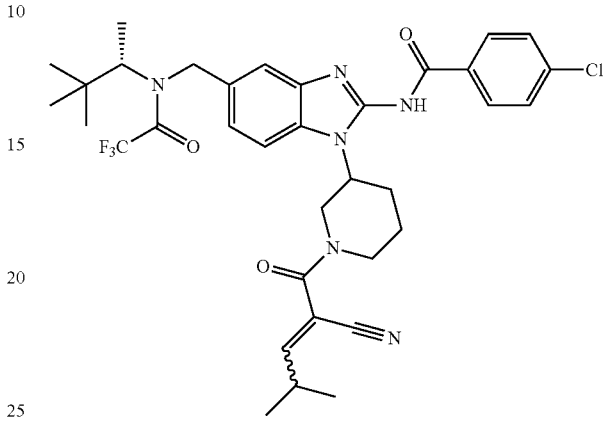

Step 1

To a 10 mL seal tube, 4-chloro-N-(5-((N-((S)-3,3-dimethylbutan-2-yl)-2,2,2-trifluoro-acetamido)methyl)-1-(piperidin-3-yl)-1H-benzo[d]imidazol-2-yl)benzamide (0.05 g, 0.0886 mmol) and 2-cynoaceticacid (0.011 g, 0.132 mmol) were taken in DCM (1.0 mL). EDC.HCl (0.02 g, 0.106 mmol), HOBt (0.014 g, 0.106 mmol) and TEA (0.026 g, 0.265 mmol) were added at room temperature under nitrogen atmosphere. The reaction mixture was stirred for overnight at room temperature. After completion of the reaction, water was poured into reaction mixture and extracted with ethyl acetate. The combined organic layers were dried over sodium sulphate and concentrated to give the crude product which was purified using column purification by eluting with 10-20% ethyl acetate in hexanes to yield 30 mg of 4-chloro-N-(1-(1-(2-cyanoacetyl)piperidin-3-yl)-5-((N-((S)-3,3-dimethylbutan-2-yl)-2,2,2-trifluoroacetamido)methyl)-1H-benzo[d]imidazol-2-yl)benzamide.

Step 2

To a 10 mL seal tube were added 4-chloro-N-(1-(1-(2-cyanoacetyl)piperidin-3-yl)-5-((N-((S)-3,3-dimethyl butan-2-yl)-2,2,2-trifluoroacetamido)methyl)-1H-benzo[d]imidazol-2-yl)benzamide (180 mg, 0.285 mmole), isobutaraldehyde (61.7 mg, 0.855 mmole), 3.3M solution of piperidine acetate in water (0.259 mL, 0.855 mmole) and ethanol (5 mL). The reaction mixture was heated in a seal tube at 80° C. for 2 h. After completion of the reaction, the reaction mixture was poured in water and extracted with ethyl acetate. The combined organic layers were washed with brine, dried over sodium sulphate, concentrated, and purified using column purification by eluting the compound with 0.5-1.0% methanol in chloroform to yield 30 mg 4-chloro-N-(1-(1-(2-cyano-4-methylpent-2-enoyl)piperidin-3-yl)-5-((N-((S)-3,3-dimethylbutan-2-yl)-2,2,2-trifluoroacetamido)-methyl)-1H-benzo[d]imidazol-2-yl)benzamide. LC-MS (ES, m/z): 685 [M+H].

Example 15

Synthesis of N-(1-(1-acryloylpiperidin-3-yl)-5-((N-((S)-3,3-dimethylbutan-2-yl)-2,2,2-trifluoroacetamido)methyl)-1H-benzo[d]imidazol-2-yl)-4-chlorobenzamide

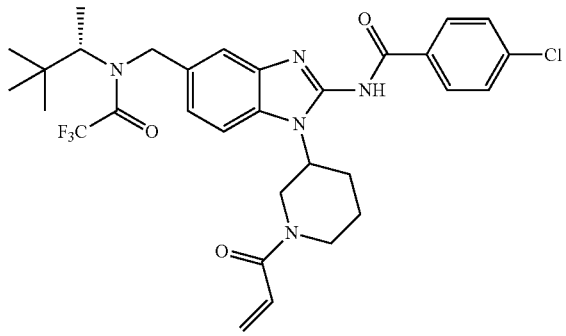 [SMILES: C=CC(=O)N1CCCC(n2c(NC(=O)c3ccc(Cl)cc3)nc3cc(CN(C(=O)C(F)(F)F)[C@@H](C)C(C)(C)C)ccc32)C1]

To a 25 mL one necked round bottom flask, 4-chloro-N-(5-((N-((S)-3,3-dimethylbutan-2-yl)-2,2,2-trifluoroacetamido)methyl)-1-(piperidin-3-yl)-1H-benzo[d]imidazol-2-yl)benzamide (0.250 g, 0.000443 mol) was taken in THF (2 mL) followed by drop wise addition of acryloyl chloride (50% sol. in toluene) (0.060 g, 0.000664 mol) at −30° C. and the reaction mixture was allowed to stir at same temperature for 30 min and 1.5 h at 0° C. After completion of the reaction, the reaction mass quenched with saturated sodium bicarbonate solution and extracted with CH$_2$Cl$_2$ and the combined organic layer was dried over sodium sulphate, concentrated to afford crude product which was purified using column purification by eluting the compound with 25-35% ethyl acetate in hexanes to yield 130 mg of N-(1-(1-acryloylpiperidin-3-yl)-5-((N-((S)-3,3-dimethylbutan-2-yl)-2,2,2-trifluoroacetamido)-methyl)-1H-benzo[d]imidazol-2-yl)-4-chlorobenzamide. LC-MS (ES, m/z): 685 [M+H].

Intermediate 8

Synthesis of tert-butyl 3-(5-(((benzyloxycarbonyl)((S)-3,3-dimethylbutan-2-yl)amino)methyl)-2-imino-2,3-dihydro-1H-benzo[d]imidazol-1-yl)piperidine-1-carboxylate

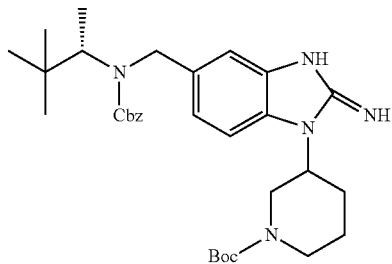 [SMILES: C[C@H](N(Cc1ccc2c(c1)[nH]c(=N)n2C1CCCN(C(=O)OC(C)(C)C)C1)C(=O)OCc1ccccc1)C(C)(C)C]

Step 1

To a single necked round bottom flask were added 4-fluoro-3-nitrobenzaldehyde (8.5 g, 0.0502 mole) and DIPEA (25.8 mL, 0.1507 mole) in acetonitrile (85 mL) followed by addition of tert-butyl 3-aminopiperidine-1-carboxylate (15 g, 0.0753 mole) at room temperature and the reaction mixture was stirred at room temperature for 20 h. The reaction mixture was diluted with water and extracted with ethyl acetate. The combined organic layer was dried over sodium sulfate and concentrated under vacuum to give crude product, which was purified using column purification by eluting the crude product with 25% ethyl acetate in hexanes to yield 13.5 g of tert-butyl 3-(4-formyl-2-nitrophenylamino)piperidine-1-carboxylate.

Step 2

To a 500 mL three necked round bottom flask were added tert-butyl 3-(4-formyl-2-nitrophenylamino)piperidine-1-carboxylate (13.5 g, 0.0386 mole) and (S)-3,3-dimethylbutan-2-amine (3.9 g, 0.0386 mole) in ethylene dichloride (208 mL) under nitrogen atmosphere at room temperature. After 10 min, the reaction mixture was stirred at room temperature and glacial acetic acid (0.1 ml) and NaBH(OAc)$_3$ (0.0579 mole) were added to reaction mixture and stirred at room temperature for 6 h. After completion of the reaction; the reaction mixture was diluted with water and extracted with CH$_2$Cl$_2$. The combined organic layer was dried over sodium sulfate and concentrated under vacuum to yield 18 g of 3-(4-(((S)-3,3-dimethylbutan-2-ylamino)methyl)-2-nitrophenyl-amino)piperidine-1-carboxylate.

Step 3

To a 250 mL three necked round bottom flask were added tert-butyl 3-(4-(((S)-3,3-dimethylbutan-2-ylamino)methyl)-2-nitrophenylamino)piperidine-1-carboxylate (3.8 g, 0.0087 mole), NaOH (0.77 g, 0.0192 mole) in water (38 mL) and cooled to 0° C.-5° C. Benzyl chloroformate (1.88 mL, 0.0131 mole) was added dropwise to reaction mixture at same temperature and then allowedt to warm up to room temperature. Dioxane (15 mL) was added to reaction mixture and stirred it at room temperature for 4 h. After completion of reaction, the reaction mixture was acidified with dilute HCl up to the pH=3-4, then extracted with ethyl acetate. Combined organic layer was dried over sodium sulfate, concentrated to give crude product which was purified using column purification by eluting compound with 5-10% ethyl acetate in hexanes to yield 4.0 g of tert-butyl 3-(4-(((benzyloxycarbonyl) ((S)-3,3-dimethylbutan-2-yl)amino)methyl)-2-nitrophenylamino)-piperidine-1-carboxylate.

Step 4

To a 250 mL single necked round bottom flask were added tert-butyl 3-(4-(((benzyloxy-carbonyl)((S)-3,3-dimethylbutan-2-yl)amino)methyl)-2-nitrophenylamino)piperidine-1-carboxylate (4 g, 0.0070 mole) in methanol (80 mL) and saturated NH$_4$Cl solution (80 mL) at room temperature; followed by portionwise addition of Zn powder (4 g). The reaction mixture was heated at 60° C. for 2 h. After completion of the reaction, methanol was evaporated under vacuum and the reaction mixture was filtered to remove the Zn. The filtrate was diluted with ethyl acetate and washed with water. The organic layer was dried over sodium sulfate and concentrated to yield 2.8 g of tert-butyl 3-(2-amino-4-(((benzyloxycarbonyl) ((S)-3,3-dimethylbutan-2-yl)amino)methyl)-phenylamino)-piperidine-1-carboxylate.

Step 5

To a 250 mL three necked round bottom flask were added tert-butyl 3-(2-amino-4-(((benzyloxycarbonyl)((S)-3,3-dimethylbutan-2-yl)amino)methyl)phenylamino)piperidine-1-carboxylate (2.8 g, 0.0052 mole) and ethanol (56 mL) followed by portion wise addition of cyanogen bromide (0.66 g, 0.0062 mole) at room temperature and stirred for 2 h. After completion of the reaction, the reaction mixture was concentrated under vacuum and diluted with saturated NaHCO₃ solution, then extracted with ethyl acetate. The combined organic layer was dried over sodium sulfate and concentrated to yield 2.5 g of tert-butyl 3-(5-(((benzyloxy-carbonyl)((S)-3,3-dimethylbutan-2-yl)amino)methyl)-2-imino-2,3-dihydro-1H-benzo[d]imidazol-1-yl)piperidine-1-carboxylate. LC-MS (ES, m/z): 564.6 [M+H].

Intermediate 9

Synthesis of benzyl(2-(4-chlorobenzamido)-1-(piperidin-3-yl)-1H-benzo[d]imidazol-5-yl)methyl-((S)-3,3-dimethylbutan-2-yl)carbamate

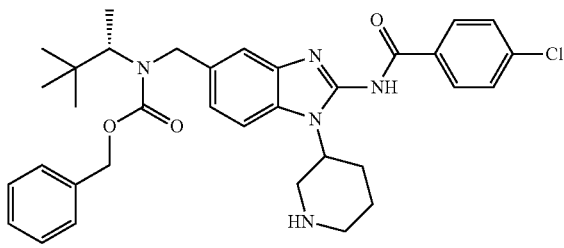 [SMILES: C[C@H](N(Cc1ccc2c(c1)nc(NC(=O)c1ccc(Cl)cc1)n2C1CCCNC1)C(=O)OCc1ccccc1)C(C)(C)C]

Step 1

To a 100 mL three necked round bottom flask were added 4-chlorobenzoic acid (0.832 g, 0.0053 mole), EDCI (1.275 g, 0.0066 mole), HOBt-H₂O (1.018 g, 0.0066 mole) and TEA (1.34 mL, 0.0133 mole) in CH₂Cl₂ (50 mL) at room temperature and stirred for 10 min. tert-Butyl 3-(5-(((benzyloxycarbonyl)((S)-3,3-dimethylbutan-2-yl)amino)methyl)-2-imino-2,3-dihydro-1H-benzo[d]imidazol-1-yl)piperidine-1-carboxylate (2.5 g, 0.0044 mole) was added and the reaction mixture was stirred at room temperature for 16 h. After completion of the reaction, the reaction mixture was diluted with saturated NaHCO₃ solution and the compound was extracted with CH₂Cl₂. The combined organic layer was dried over sodium sulfate, concentrated under vacuum to give crude product which was purified using column purification by eluting compound with 10-15% ethyl acetate in hexanes to yield 2.0 g of tert-butyl 3-(5-(((benzyloxycarbonyl)-(S)-3,3-dimethylbutan-2-yl)amino)methyl)-2-(4-chlorobenzamido)-1H-benzo[d]imidazol-1-yl)piperidine-1-carboxylate.

Step 2

To a 100 mL three necked round bottom flask were added tert-butyl 3-(5-(((benzyloxy-carbonyl)-((S)-3,3-dimethylbutan-2-yl)amino)methyl)-2-(4-chlorobenzamido)-1H-benzo[d]-imidazol-1-yl)piperidine-1-carboxylate (2 g, 0.0028 mole) and CH₂Cl₂ (20 mL) followed by dropwise addition of TFA (5 mL) at 0° C. The reaction mixture was allowed to warm up to room temperature and stirred for 2 h. The completion of reaction was monitored by TLC using chloroform: methanol (9:1) as a mobile phase. After completion, the reaction mixture was concentrated under vacuum, azeotroped with toluene and triturated with pentane to give solid product, which was dried under vacuum to yield 2.0 g of benzyl(2-(4-chlorobenzamido)-1-(piperidin-3-yl)-1H-benzo[d]imidazol-5-yl)methyl((S)-3,3-dimethylbutan-2-yl)carbamate as a TFA salt. LC-MS (ES, m/z): 602.7 [M+H].

Intermediate 10

Synthesis of 2-ethoxy-2-methylpropanal

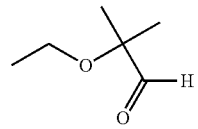

Step 1

In a 500 mL 3 neck round bottomed flask was dissolved 2-bromo-2-methylpropanoic acid (40 g, 239.5 mmole) in ethanol (320 mL) and cooled to 0 to 5° C. followed by dropwise addition of DIPEA (87.4 mL, 502.9 mmole) at 0 to 5° C. and the reaction mixture was stirred at 0° C. for 30 min. The reaction mixture was warmed to 40° C. for 16 h. After 16 h, the reaction mixture was cooled to room temperature, ethanol was removed in vacuo, leaving a thick white slurry. Diethyl ether and water was added to the slurry and cooled to 0° C. The mixture was acidified with 10% HCl (50 mL) and the organic layer was separated and washed with brine. To the organic phase was added 10% aq NaHSO₃ and the mixture was stirred at room temperature for 6 h. The biphasic mixture was acidified with 10% HCl (50 mL) to the pH 1.0±0.5. The organic phase was washed with brine (100 mL), dried over sodium sulfate, filtered and concentrated to give 30 g of 2-ethoxy-2-methylpropanoic acid. The product, 2-ethoxy-2-methylpropanoic acid, was carried forwarded to the next step without further purification.

Step 2

In a 500 mL three neck round bottomed flask was dissolved 2-ethoxy-2-methylpropanoic acid (30 g, 227.2 mmole) in ethanol (300 mL) and cooled to 0° C. followed by dropwise addition of thionyl chloride (49.7 mL, 681.8 mmole) at 0° C. The reaction mixture was refluxed at 80° C. for 3 h. After completion of the reaction, thionyl chloride and ethanol were evaporated in vacuo and the residue was cooled to 0° C. and basified with saturated NaHCO₃ solution and extracted with CH₂Cl₂, dried over sodium sulfate, filtered and concentrated to give 32 g of ethyl 2-ethoxy-2-methylpropanoate.

Step 3

In a 500 mL three neck round bottomed flask was dissolved ethyl 2-ethoxy-2-methylpropanoate (16 g, 100 mmole) in dry THF (133 mL) and cooled to 0 to −10° C. followed by dropwise addition of 1M solution of LiAlH₄ in THF (100 mL, 100 mmole) at 0 to −10° C. and the reaction mixture was stirred at 0° C. for 3 h. After completion of the reaction, the reaction mixture was quenched with sat. NH₄Cl solution and filtered through Buchner funnel to remove colloidal precipitates. The filtrate was extracted with ethyl acetate. The combined organics was dried over sodium sulfate and evaporated to afford 9 g of 2-ethoxy-2-methyl-propan-1-ol.

Step 4

In a 100 mL single neck round bottomed flask was dissolved 2-ethoxy-2-methylpropan-1-ol (9 g, 76.2 mmole) in dry CH₂Cl₂ (20 mL) and cooled to 10° C. Pyridinium chlorochromate was added to the reaction mixture portion wise at 10° C. and the reaction mixture was stirred at room temperature for 16 h. The completion of the reaction was monitored by TLC using neat CH₂Cl₂ as a mobile phase. After completion of the reaction, the reaction mixture was Intermediate 11

Synthesis of 2-(dimethylamino)-2-methylpropanal

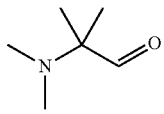

To a 250 mL three neck round bottomed flask, DMSO (10.27 mL, 143.3 mmole) and CH$_2$Cl$_2$ (15 mL) were cooled to −78° C. Oxalyl chloride (8.77 mL, 102.2 mmole) in CH$_2$Cl$_2$ (35 mL) was added dropwise at −78° C. The reaction mixture was stirred for 30 min at same temperature and 2-(dimethylamino)-2-methylpropan-1-ol (4 g, 34.1 mmole) in CH$_2$Cl$_2$ (25 mL) was added dropwise by maintaining the temperature at −78° C. and further stirred for 20 min at same temperature. TEA (32.6 mL, 232.6 mmole) was added dropwise at −78° C. and stiffed for 40 min at same temperature, followed by stirring at room temperature for 10 min After completion of the reaction, the reaction mixture was diluted with CH$_2$Cl$_2$ and neutralized with saturated NaHCO$_3$ solution. Organic layer was washed with brine solution, dried over Na$_2$SO$_4$ and distilled out excess of the solvent using downward distillation at 30° C. to yield crude product. The crude compound was purified using column purification by eluting compound with CH$_2$Cl$_2$ to yield 1 g of 2-(dimethylamino)-2-methylpropanal.

Example 16

Synthesis of 4-chloro-N-(1-(1-(2-cyano-4-methyl-pent-2-enoyl)piperidin-3-yl)-5-(((S)-3,3-dimethylbutan-2-ylamino)methyl)-1H-benzo[d]imidazol-2-yl)benzamide

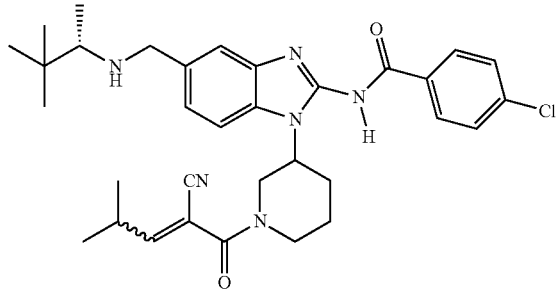 [SMILES: CC(C)C=C(C#N)C(=O)N1CCCC(n2c(NC(=O)c3ccc(Cl)cc3)nc3cc(CN[C@@H](C)C(C)(C)C)ccc32)C1]

Step 1

To a 50 mL one necked round bottom flask were added benzyl(2-(4-chlorobenzamido)-1-(piperidin-3-yl)-1H-benzo[d]imidazol-5-yl)methyl-((S)-3,3-dimethylbutan-2-yl)carbamate TFA salt (0.5 g, 0.7150 mmole), 2-cyano-4-methyl-pent-2-enoic acid (0.298 g, 2.1450 mmole) and CH$_2$Cl$_2$ (10 mL); followed by addition of PyBrOP (0.366 g, 0.7860 mmole) and TEA (0.3 mL) at 0° C. under nitrogen atmosphere and stirred for 15 min at the same temperature. After completion of the reaction, the reaction mixture was purified using column purification by eluting compound with 20% ethyl acetate in hexanes to yield 0.19 g of benzyl(2-(4-chlorobenzamido)-1-(1-(2-cyano-4-methylpent-2-enoyl)piperidin-3-yl)-1H-benzo[d]imidazol-5-yl)methyl((S)-3,3-dimethylbutan-2-yl)carbamate.

Step 2

To a 50 mL one necked round bottom flask were added benzyl(2-(4-chlorobenzamido)-1-(1-(2-cyano-4-methyl-pent-2-enoyl)piperidin-3-yl)-1H-benzo[d]imidazol-5-yl)methyl((S)-3,3-dimethylbutan-2-yl)carbamate (0.19 g, 0.2626 mmole) and acetic acid (1.9 mL) and cooled to 0° C.; followed by drop wise addition of 30% HBr in acetic acid (7.6 mL). After completion of addition the reaction mixture was allowed to warm up to room temperature and stirred for 1 h. After completion of the reaction; the reaction mixture was slowly diluted with saturated NaHCO$_3$ solution at 5° C. (pH ~7-8) and extracted with ethyl acetate. The combined organic layer was dried over sodium sulfate and concentrated under vacuum to give the crude product, which was purified by prep HPLC to yield 16 mg of 4-chloro-N-(1-(1-(2-cyano-4-methylpent-2-enoyl)piperidin-3-yl)-5-(((S)-3,3-dimethylbutan-2-ylamino)methyl)-1H-benzo[d]imidazol-2-yl)benzamide. LC-MS (ES, m/z): 589.4 [M+H].

Example 17

Synthesis of N-(1-(1-(4-amino-2-cyano-4-methyl-pent-2-enoyl)piperidin-3-yl)-5-(((S)-3,3-dimethylbutan-2-ylamino)methyl)-1H-benzo[d]imidazol-2-yl)-4-chlorobenzamide

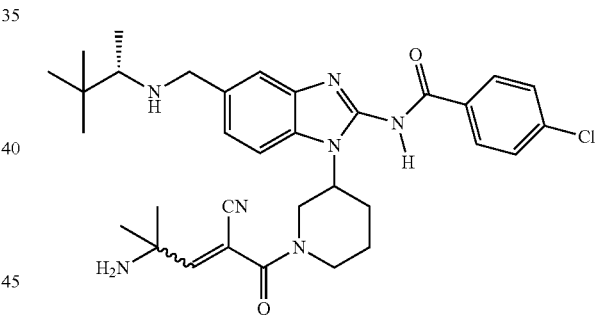

Step 1

To a 50 mL three necked round bottom flask were added 2-cyanoacetic acid (0.08 g, 0.9439 mmole) and HATU (0.45 g, 1.1799 mmole) in DMF (5 mL) under nitrogen atmosphere and stirred at room temperature for 10 min. A solution of benzyl(2-(4-chlorobenzamido)-1-(piperidin-3-yl)-1H-benzo[d]imidazol-5-yl)methyl((S)-3,3-dimethylbutan-2-yl)carbamate TFA salt (0.55 g, 0.7866 mmole) in DMF (5 mL) was dropwise added, followed by addition of DIPEA (0.54 mL, 3.1464 mmole) at room temperature. The reaction mixture was stirred at room temperature for 1 h. After completion of the reaction, the reaction mixture was poured in to water and extracted with ethyl acetate. The combined organic layer was washed with saturated NaHCO$_3$ solution, brine solution and dried over sodium sulfate and concentrated under vacuum to give 0.33 g of benzyl(2-(4-chlorobenzamido)-1-(1-(2-cyanoacetyl)piperidine-3-yl)-1H-benzo[d]imidazol-5-yl)methyl((S)-3,3-dimethylbutan-2-yl)carbamate.

Step 2

To a 20 mL sealed tube were added benzyl(2-(4-chlorobenzamido)-1-(1-(2-cyanoacetyl)piperidin-3-yl)-1H-benzo[d]imidazol-5-yl)methyl((S)-3,3-dimethylbutan-2-yl)carbamate (0.33 g, 0.4931 mmole), tert-butyl 2-methyl-1-oxopropan-2-ylcarbamate (0.28 g, 1.4739 mmole) and piperidine (0.1 mL) in 1,4 dioxane (8 mL). The reaction mixture was heated at 100° C. for 4 h. After completion of the reaction; the reaction mixture was concentrated under vacuum and the crude compound was purified using column purification by eluting the compound with 25% ethyl acetate in hexanes to yield 0.25 g benzyl N-[[1-[1-[4-(tert-butoxycarbonylamino)-2-cyano-4-methyl-pent-2-enoyl]-3-piperidyl]-2-[(4-chlorobenzoy)amino]benzimidazol-5-yl]methyl]-N-[(1S)-1,2,2-trimethylpropyl]carbamate.

Step 3

To a 50 mL one necked round bottom flask was added N-Boc protected benzyl(1-(1-(4-amino-2-cyano-4-methyl-pent-2-enoyl)piperidine-3-yl)-2-(4-chlorobenzamido)-1H-benzo[d]-imidazol-5-yl)methyl((S)-3,3-dimethylbutan-2-yl)carbamate (0.25 g, 0.2982 mmole) in acetic acid (2.5 mL) and the mixture cooled to 0° C. A solution of 30% HBr in acetic acid (10 mL) was added dropweise and after completion of addition the reaction mixture was allowed to warm up to room temperature and stirred for 1 h. After completion of the reaction, the reaction mixture was slowly diluted with saturated NaHCO₃ solution at 5° C. (pH ~7-8) and the product was extracted with ethyl acetate. The combined organic layer was dried over sodium sulfate and concentrated under vacuum to give crude product, which was purified by prep HPLC to yield 19 mg of N-(1-(1-(4-amino-2-cyano-4-methylpent-2-enoyl)piperidin-3-yl)-5-(((S)-3,3-dimethylbutan-2-ylamino)methyl)-1H-benzo[d]imidazol-2-yl)-4-chlorobenzamide as the formic acid salt. LC-MS (ES, m/z): 604.6 [M+H].

Example 18

Synthesis of N-(1-(1-(4-methylamino-2-cyano-4-methylpent-2-enoyl)piperidin-3-yl)-5-((((S)-3,3-dimethylbutan-2-yl)amino)methyl)-1H-benzo[d]imidazol-2-yl)-4-chlorobenzamide

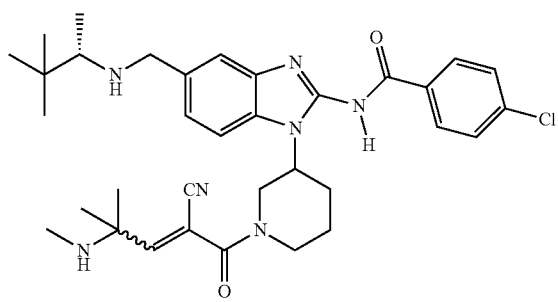 [SMILES: CNC(C)(C)C=C(C#N)C(=O)N1CCCC(n2c(NC(=O)c3ccc(Cl)cc3)nc3cc(CN[C@@H](C)C(C)(C)C)ccc32)C1]

Step 1

To a 20 mL seal tube were added benzyl(2-(4-chlorobenzamido)-1-(1-(2-cyanoacetyl)-piperidin-3-yl)-1H-benzo[d]imidazol-5-yl)methyl-((S)-3,3-dimethylbutan-2-yl)carbamate (0.6 g, 0.8965 mmole), tert-butyl methyl (2-methyl-1-oxopropan-2-yl)carbamate (0.54 g, 2.6895 mmole) and piperidine (0.17 mL) in 1,4 dioxane (12 mL). The reaction mixture was heated at 100° C. for 20 h. After completion of the reaction; the reaction mixture was concentrated under vacuum and purified using column purification eluting compound with 25% ethyl acetate in hexanes to yield 0.2 g tert-butyl N-[4-[3-[5-[[benzyloxycarbonyl-[(1S)-1,2,2-trimethylpropyl]amino]methyl]-2-[(4-chlorobenzoyl)amino]benzimidazol-1-yl]-1-piperidyl]-3-cyano-1,1-dimethyl-4-oxo-but-2-enyl]-N-methyl-carbamate.

Step 2

To a 50 mL one necked round bottom flask were added tert-butyl N-[4-[3-[5-[[benzyloxycarbonyl-[(1S)-1,2,2-trimethylpropyl]amino]methyl]-2-[(4-chlorobenzoyl)amino]-benzimidazol-1-yl]-1-piperidyl]-3-cyano-1,1-dimethyl-4-oxo-but-2-enyl]-N-methyl-carbamate (0.2 g, 0.2347 mmole) in acetic acid (2 mL) and cooled to 0° C. followed by drop wise addition of 30% HBr in acetic acid (8 mL). The reaction mixture was allowed to warm up to room temperature and stirred for 1 h. After completion of the reaction; the reaction mixture was slowly diluted with saturated NaHCO₃ solution at 5° C. (pH ~7-8) and compound was extracted with ethyl acetate. The combined organic layer was dried over sodium sulfate and concentrated under vacuum to give crude product, which was purified by prep HPLC to yield 25 mg of N-(1-(1-(4-methylamino-2-cyano-4-methylpent-2-enoyl)piperidin-3-yl)-5-((((S)-3,3-dimethylbutan-2-yl)amino)methyl)-1H-benzo[d]imidazol-2-yl)-4-chlorobenzamide as the formic acid salt. LC-MS (ES, m/z): 619 [M+H].

Example 19

Synthesis of 4-chloro-N-(1-(1-(2-cyano-4-(dimethylamino)-4-methylpent-2-enoyl)piperidin-yl)-5-(((S)-3,3-dimethylbutan-2-ylamino)methyl)-1H-benzo[d]imidazol-2-yl)benzamide

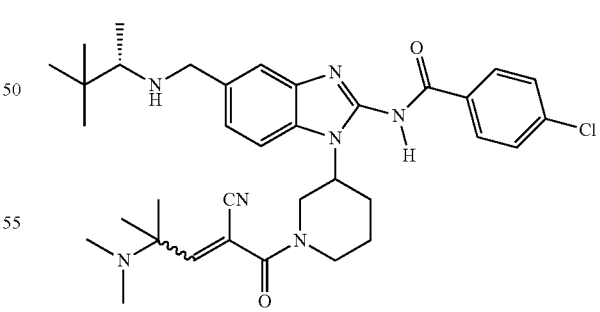

4-Chloro-N-(1-(1-(2-cyano-4-(dimethylamino)-4-methylpent-2-enoyl)piperidin-3-yl)-5-(((S)-3,3-dimethylbutan-2-ylamino)methyl)-1H-benzo[d]imidazol-2-yl)benzamide as the formic acid salt was prepared using the same procedure as example 18 but substituting 2-(dimethylamino)-2-methylpropanal for tert-butyl methyl (2-methyl-1-oxopropan-2-yl)carbamate. LC-MS (ES, m/z): 633 [M+H].

Example 20

Synthesis of N-(1-(1-acryloylpiperidin-3-yl)-5-(((S)-3,3-dimethylbutan-2-ylamino)methyl)-1H-benzo[d]imidazol-2-yl)-4-chlorobenzamide

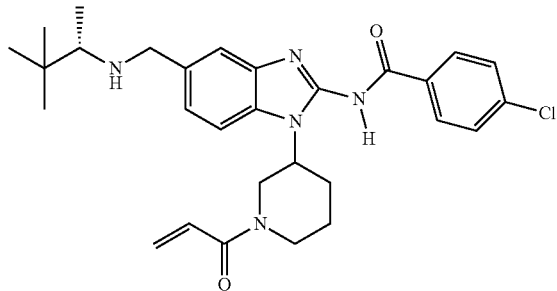 [SMILES: C=CC(=O)N1CCCC(n2c(NC(=O)c3ccc(Cl)cc3)nc3cc(CN[C@@H](C)C(C)(C)C)ccc32)C1]

Step 1

To a 50 mL one necked round bottom flask, a 50% solution of acrolyl chloride in toluene (0.3 mL, 0.858 mmole) was dropwise added to a solution of benzyl(2-(4-chlorobenzamido)-1-(piperidin-3-yl)-1H benzo[d]imidazol-5-yl)methyl((S)-3,3-dimethylbutan-2-yl)carbamate TFA salt (0.4 g, 0.5720 mmole) in THF (10 mL) at −30° C. under nitrogen atmosphere. The reaction mixture was allowed to warm up to room temperature and stirred for 1 h. After completion, the reaction mixture was poured in saturated NaHCO$_3$ solution and extracted with ethyl acetate. The combined organic layer was dried over sodium sulphate and concentrated under vacuum to give crude product To a 25 mL one necked round bottom flask were added the crude product (0.5 g) and cesium carbonate (0.56 g, 1.7162 mmole) in THF (5 mL) and heated at 60° C. for 15 min. The reaction mixture was cooled to room temperature; then water was added and the product was extracted with ethyl acetate. The combined organic layer was dried over sodium sulfate and concentrated under vacuum to yield 0.3 g of benzyl(1-(1-acryloylpiperidin-3-yl)-2-(4-chlorobenzamido)-1H-benzo[d]imidazol-5-yl)methyl((S)-3,3-dimethylbutan-2-yl)carbamate.

Step 2

To a 50 mL one necked round bottom flask were added benzyl(1-(1-acryloylpiperidin-3-yl)-2-(4-chlorobenzamido)-1H-benzo[d]imidazol-5-yl)methyl((S)-3,3-dimethylbutan-2-yl)carbamate (0.3 g, 0.4571 mmole) and acetic acid (3 mL) and the mixture was cooled to 0° C. A solution of 30% HBr in acetic acid (12 mL) was added dropwise and the mixture allowed to warm up to room temperature and stirred for 1 h. After completion of the reaction, the reaction mixture was slowly diluted with saturated NaHCO$_3$ solution at 5° C. (pH ~7-8) and the compound was extracted with ethyl acetate. The combined organic layer was dried over sodium sulfate and concentrated under vacuum to give crude product, which was purified by prep HPLC to yield 38 mg of N-(1-(1-acryloylpiperidin-3-yl)-5-(((S)-3,3-dimethylbutan-2-ylamino)methyl)-1H-benzo[d]imidazol-2-yl)-4-chlorobenzamide. LC-MS (ES, m/z): 522.5 [M+H].

Intermediate 12

Synthesis of tert-butyl 2-((5-(((benzyloxycarbonyl)-((S)-3,3-dimethylbutan-2-yl)amino)methyl)-2-imino-2,3-dihydro-1H-benzo[d]imidazol-1-yl)methyl)pyrrolidine-1-carboxylate

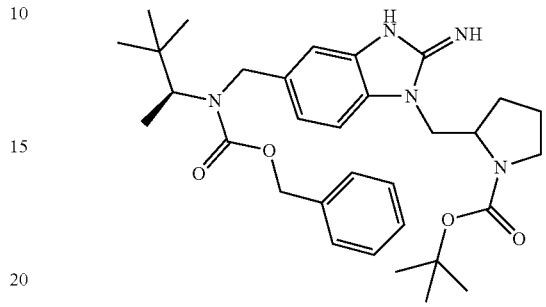

Step 1

To a 250 mL three necked round bottom flask, 4-fluoro-3-nitrobenzaldehyde (7.0 g, 0.0416 mole) was added in acetonitrile (100 mL) followed by addition of DIPEA (21.5 mL, 0.1248 mole) and the reaction mixture was stirred at room temperature for 10 min tert-Butyl 2-(aminomethyl)-pyrrolidine-1-carboxylate (12.5 g, 0.0624 mole) in acetonitrile (100 mL) was dropwise added to the reaction mixture and stirred at room temperature for 16 h. After 16 h, the reaction mixture was concentrated, diluted with water and extracted with CH$_2$Cl$_2$. The combined organic layers were dried over sodium sulphate and concentrated to give crude product which was purified using column purification eluting with 10% ethyl acetate in hexanes to yield 14 g of tert-butyl 2-((4-formyl-2-nitrophenylamino)methyl)pyrrolidine-1-carboxylate.

Step 2

To a 500 mL three necked round bottom flask under nitrogen atmosphere, tert-butyl 2-((4-formyl-2-nitrophenylamino)methyl)pyrrolidine-1-carboxylate (14 g, 0.0400 mole) and (S)-3,3-dimethylbutn-2-amine (4.04 g, 0.0400 mole) were added in 1,2 dichloroethane (300 mL) and the mixture stirred at room temperature for 10 min. Acetic acid (1.24 mL, catalytic amount) and NaBH(OAc)$_3$ (12.7 g, 0.0601 mole) were added respectively to the reaction mixture and the reaction mixture was stirred at room temperature for 6 h. After completion of the reaction, the reaction mixture was poured into saturated Na$_2$CO$_3$ solution followed by extraction with CH$_2$Cl$_2$. The combined organic layers were dried over sodium sulphate and concentrated to yield 17 g of tert-butyl 2-((4-(((S)-3,3-dimethylbutan-2-ylamino)methyl)-2-nitrophenylamino)methyl)pyrrolidine-1-carboxylate.

Step 3

To a 50 mL three necked round bottom flask, tert-butyl 2-((4-(((S)-3,3-dimethylbutan-2-ylamino)methyl)-2-nitrophenylamino)methyl)pyrrolidine-1-carboxylate (2.0 g, 0.0046 mole), NaOH (0.40 g, 0.0101 mole) were added in 1,4-dioxane (10 mL) and water (20 mL) and the reaction mixture was cooled it to 10° C. Benzyl chloroformate (0.98 mL, 0.0069 mole) was added dropwise to the cooled reaction mixture and the reaction mixture was allowed to warm to room temperature. Reaction mixture was stirred at room temperature for 3 h. After completion of the reaction, the reaction mixture was washed with 1N HCl and saturated NaHCO₃ solution. The organic layer was dried over sodium sulphate and concentrated to yield 1.7 g of tert-butyl 2-((4-(((benzyloxycarbonyl)((S)-3,3-dimethylbutan-2-yl)amino) methyl)-2-nitrophenylamino)-methyl)pyrrolidine-1-carboxylate.

Step 4

To a 50 mL three necked round bottom flask, tert-butyl 2-((4-(((benzyloxycarbonyl)((S)-3,3-dimethylbutan-2-yl) amino)methyl)-2-nitrophenylamino)methyl)pyrrolidine-1-carboxylate (1.7 g, 0.00298 mole) was added in methanol (17 mL) followed by zinc dust (0.5 g, 0.0149 mole) and saturated NH₄Cl solution (8.5 mL). The resultant mixture was heated at 50° C. for 2 h with stirring. After completion of the reaction, the reaction mixture was filtered through a celite bed, washed with methanol and the filtrate was concentrated to give the crude product. Water was added and the product was extracted with EtOAc. The combined organic layer was dried over sodium sulphate, concentrated to give the crude compound which was purified using column purification to yield 1.3 g of tert-butyl 2-((2-amino-4-(((benzyloxycarbonyl)((S)-3,3-dimethylbutan-2-yl)amino) methyl)-phenylamino)methyl)pyrrolidine-1-carboxylate.

Step 5

To a 50 mL three necked round bottom flask under nitrogen atmosphere, tert-butyl 2-((2-amino-4-(((benzyloxycarbonyl)((S)-3,3-dimethylbutan-2-yl)amino)methyl) phenylamino-methyl)pyrrolidine-1-carboxylate (1.3 g, 0.00241 mole) was added in ethanol (13 mL) followed by addition of cyanogen bromide (0.30 g, 0.00289 mole) at room temperature. The mixture was stirred at same temperature for 16 h and completion of the reaction was monitored on TLC using CH₂Cl₂: methanol (9:1) as a mobile phase. After completion of the reaction, the reaction mixture was concentrated under vacuum, diluted with saturated NaHCO₃ solution and extracted with ethyl acetate. The combined organic layer was dried over sodium sulphate and concentrated to give the crude product which was purified using column purification by eluting the compound with 1.5-2.0% methanol in chloroform to yield 1.2 g of tert-butyl 2-((5-(((benzyloxycarbonyl)((S)-3,3-dimethyl-butan-2-yl) amino)methyl)-2-imino-2,3-dihydro-1H-benzo[d]imidazol-1-yl)methyl)pyrrolidine-1-carboxylate. LC-MS (ES, m/z): 564.7 [M+H].

Example 21

Synthesis of 4-chloro-N-(1-((1-(2-cyano-4-methyl-pent-2-enoyl)pyrrolidin-2-yl)methyl)-5-(((S)-3,3-dimethylbutan-2-ylamino)methyl)-1H-benzo[d]imidazol-2-yl)benzamide

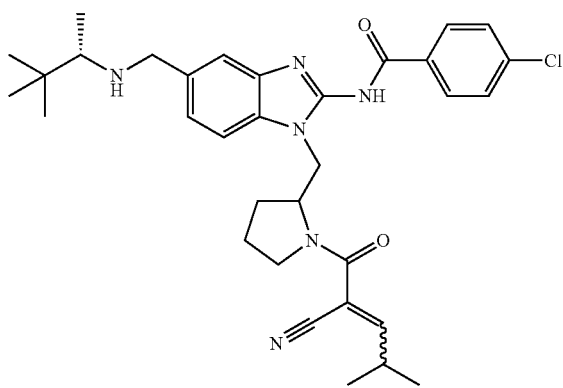 [SMILES: CC(C)C=C(C#N)C(=O)N1CCCC1Cn1c(NC(=O)c2ccc(Cl)cc2)nc2cc(CN[C@@H](C)C(C)(C)C)ccc21]

Step 1

To a 25 mL three necked round bottom flask under nitrogen atmosphere, 4-chlorobenzoic acid (0.366 g, 0.00234 mole) was added in CH₂Cl₂ (12 mL) followed by addition of EDC.HCl (0.485 g, 0.00254 mole), HOBt.H₂O (0.389 g, 0.00254 mole) and TEA (0.88 mL, 0.00636 mole) and the mixture was stirred at room temperature for 10 min tert-Butyl 24(5-(((benzyloxycarbonyl)((S)-3,3-dimethylbutan-2-yl)amino)methyl)-2-imino-2,3-dihydro-1H-benzo[d] imidazol-1-yl)methyl)-pyrrolidine-1-carboxylate (1.2 g, 0.00212 mole) was added to a reaction mixture and the reaction mixture was stirred it at room temperature for 4 h. After completion of the reaction, the reaction mixture was washed with saturated NaHCO₃ solution. The organic layer was dried over sodium sulphate, concentrated to give the crude product which purified using column purification by eluting the compound with 20% ethyl acetate in hexanes to yield 1 g of tert-butyl 2-((5-(((benzyloxy-carbonyl)((S)-3,3-dimethylbutan-2-yl)amino)methyl)-2-(4-chlorobenzamido)-1H-benzo[d]imidazol-1-yl)methyl)pyrrolidine-1-carboxylate.

Step 2

To a 50 mL RBF, tert-butyl 2-((5-(((benzyloxycarbonyl) ((S)-3,3-dimethylbutan-2-yl)amino)methyl)-2-(4-chlorobenzamido)-1H-benzo[d]imidazol-1-yl)methyl)pyrrolidine-1-carboxylate (1 g, 0.00142 mole) was added in CH₂Cl₂ and cooled to 0° C. TFA (11.1 mL) was slowly added at 0° C. and the reaction mixture was stirred for 16 h at RT. After completion of the reaction, CH₂Cl₂ was completely distilled out in vacuum followed by stripping with THF to get the crude residue which was triturated with diethyl ether and filtered to yield 1 g of benzyl(2-(4-chlorobenzamido)-1-(pyrrolidin-2-ylmethyl)-1H-benzo[d] imidazol-5-yl)methyl((S)-3,3-dimethylbutan-2-yl)carbamate as TFA salt.

Step 3

To a 25 mL one necked round bottom flask, benzyl(2-(4-chlorobenzamido)-1-(pyrrolidin-2-ylmethyl)-1H-benzo[d] imidazol-5-yl)methyl((S)-3,3-dimethylbutan-2-yl)carbamate TFA salt (0.55 g, 0.00091 mole), 2-cyano-4-methylpent-2-enoic acid (0.380 g, 0.00274 mole) were added in CH₂Cl₂ (3 mL), followed by addition of PyBrOP (0.466 g, 0.001 mole) and TEA (0.63 mL, 0.0045 mole) at 0° C. under nitrogen atmosphere and the reaction mixture was stirred for 15 min at same temperature. After the completion of the reaction, the reaction mixture was purified using column purification by eluting compound with 25% ethyl acetate in hexanes to yield 0.2 g of benzyl(2-(4-chloro-benzamido)-1-((1-(2-cyano-4-methylpent-2-enoyl)pyrrolidin-2-yl) methyl)-1H-benzo[d]imidazol-5-yl)methyl((S)-3,3-dimethylbutan-2-yl)carbamate.

Step 4

To a 50 mL round bottom flask, benzyl(2-(4-chlorobenzamido)-1-((1-(2-cyano-4-methylpent-2-enoyl)pyrrolidin-2-yl)methyl)-1H-benzo[d]imidazol-5-yl)methyl-((S)-3,3-dimethylbutan-2-yl)carbamate (0.17 g, 0.000013 mole) was added in acetic acid (3.4 mL) and cooled to 0° C. 30% HBr in acetic acid (8.5 ml) was added dropwise and after the completion of addition, the reaction mixture was allowed to warm up to room temperature and stirred for 30 min After completion of the reaction, the reaction mixture was slowly diluted with 6N NaOH solution at 5° C. (pH ~11-12) and the compound was extracted with ethyl acetate. The combined organic layer was dried over sodium sulfate and concentrated under vacuum to give crude product, which was purified by prep HPLC to yield 28 mg of 4-chloro-N-(1-((1-(2-cyano-4-methylpent-2-enoyl)pyrrolidin-2-yl)

methyl)-5-(((S)-3,3-dimethylbutan-2-ylamino)methyl)-1H-benzo[d]imidazol-2-yl)benzamide as the formic acid salt. LC-MS (ES, m/z): 589.7 [M+H].

Example 22

Synthesis of 4-chloro-N-(1-((1-(2-cyano-4-methyl-4-(methylamino)pent-2-enoyl)pyrrolidin-2-yl)methyl)-5-(((S)-3,3-dimethylbutan-2-ylamino)methyl)-1H-benzo[d]imidazol-2-yl)benzamide

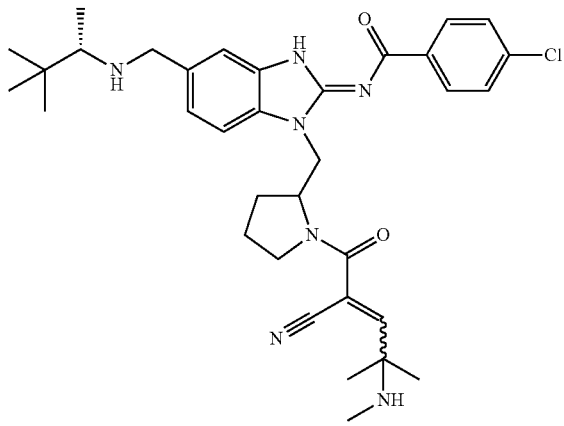 [SMILES: CNC(C)(C)C=C(C#N)C(=O)N1CCCC1Cn1/c(=N/C(=O)c2ccc(Cl)cc2)[nH]c2cc(CN[C@@H](C)C(C)(C)C)ccc21]

Step 1

To a 10 mL seal tube were added benzyl(2-(4-chlorobenzamido)-1-((1-(2-cyanoacetyl)-pyrrolidin-2-yl)methyl)-1H-benzo[d]imidazol-5-yl)methyl((S)-3,3-dimethylbutan-2-yl)carbamate (0.5 g, 0.000747 mole), tert-butyl methyl-(2-methyl-1-oxopropan-2-yl)carbamate (0.6 g, 0.002988 mole) and piperidine (0.36 mL) in 1,4 dioxane (5 mL). The reaction mixture was heated at 100° C. for 20 h. After completion of the reaction, the reaction mixture was concentrated under vacuum and purified using column purification eluting with 25% ethyl acetate in hexanes to yield 0.24 g tert-butyl N-[4-[2-[[5-[[benzyloxycarbonyl-[(1S)-1,2,2-trimethylpropyl]amino]methyl]-2-[(4-chlorobenzoyl)-amino]benzimidazo-1-yl]methyl]pyrrolidin-1-yl]-3-cyano-1,1-dimethyl-4-oxo-but-2-enyl]-N-methyl-carbamate.

Step 2

To a 25 mL one necked round bottom flask were added tert-butyl N-[4-[2-[[5-[[benzyloxy-carbonyl-[(1S)-1,2,2-trimethylpropyl]amino]methyl]-2-[(4-chlorobenzoy)amino]benzimidazo-1-yl]methyl]pyrrolidin-1-yl]-3-cyano-1,1-dimethyl-4-oxo-but-2-enyl]-N-methyl-carbamate (0.24 g, 0.00028 mole) in 1,4-dioxane (2.4 mL) and cooled to 0° C. followed by drop wise addition of HCl in dioxane (5 N) (2.4 mL) and then allowed it to warm up to room temperature and stirred for 2 h. After completion of the reaction, the reaction mixture was slowly diluted with saturated NaHCO₃ solution at 5° C. (pH ~7-8) and the compound was extracted with EtOAc. The combined organic layer was dried over sodium sulfate and concentrated under vacuum to yield 0.14 g of benzyl(2-(4-chlorobenzamido)-1-((1-(2-cyano-4-methyl-4-(methylamino)pent-2-enoyl)pyrrolidin-2-yl)methyl)-1H-benzo[d]imidazol-5-yl)methyl((S)-3,3-dimethylbutan-2-yl)carbamate.

Step 3

To a 25 mL one necked round bottom flask were added benzyl(1-((1-(4-amino-2-cyano-4-methylpent-2-enoyl)pyrrolidin-2-yl)methyl)-2-(4-chlorobenzamido)-1H-benzo[d]imidazol-5-yl)methyl((S)-3,3-dimethylbutan-2-yl)carbamate (0.14 g, 0.00018 mole) in acetic acid (1.4 mL) and cooled to 0° C. followed by drop wise addition of 30% HBr in acetic acid (5.6 mL). The reaction mixture was allowed it to warm up to room temperature and stirred for 1 h. After completion of the reaction, the reaction mixture was slowly diluted with saturated NaHCO₃ solution at 5° C. (pH ~7-8) and the compound was extracted with ethyl acetate. The combined organic layer was dried over sodium sulfate and concentrated under vacuum to give crude product, which was purified by column purification using 8% methanol in CH₂Cl₂ followed by trituration with diethyl ether to yield 0.028 g of 4-chloro-N-(1-((1-(2-cyano-4-methyl-4-(methylamino)pent-2-enoyl)pyrrolidin-2-yl)methyl)-5-(((S)-3,3-dimethylbutan-2-ylamino)methyl)-1H-benzo[d]imidazol-2-yl)benzamide. LC-MS (ES, m/z):619 [M+H].

Example 23

Synthesis of 4-chloro-N-(1-((1-(2-cyano-4,4-dimethylpent-2-enoyl)pyrrolidin-2-yl)methyl)-5-((((S)-3,3-dimethylbutan-2-yl)amino)methyl)-1H-benzo[d]imidazol-2-yl)benzamide

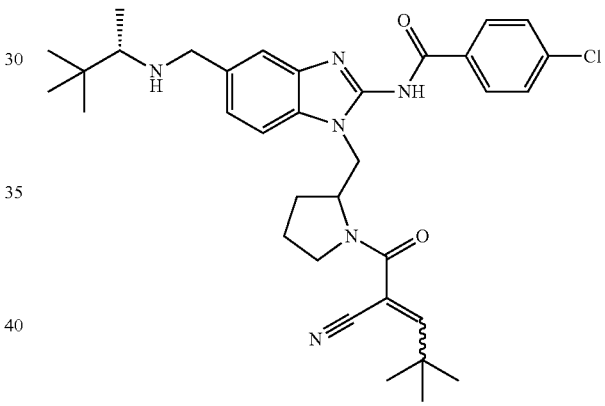

Step 1

To a 10 mL seal tube were added pyrrolidine (0.223 g, 0.003138 mole) and TMS-Cl (0.227 g, 0.002092 mole) in acetonitrile (10 mL) followed by pivaldehyde (0.135 g, 0.001569 mole) and the reaction mixture was stirred at RT for 10 min Benzyl (2-(4-chlorobenzamido)-1-((1-(2-cyanoacetyl)pyrrolidin-2-yl)methyl)-1H-benzo[d]imidazol-5-yl)methyl((S)-3,3-dimethylbutan-2-yl)-carbamate (0.35 g, 0.000523 mole) was added and stirred the mixture for 1 hr at RT. After the completion of the reaction, the reaction mixture was diluted with water and extracted with EtOAc and the combined organic layer was concentrated under vacuum. The crude compound was purified using column chromatography by eluting with 25% ethyl acetate in hexanes to yield 0.2 g benzyl(2-(4-chlorobenzamido)-1-((1-(2-cyano-4,4-dimethylpent-2-enoyl)pyrrolidin-2-yl)methyl)-1H-benzo[d]imidazol-5-yl)methyl((S)-3,3-dimethylbutan-2-yl)carbamate.

Step 2

To a 50 mL one necked round bottom flask were added benzyl(2-(4-chlorobenzamido)-1-((1-(2-cyano-4,4-dimethylpent-2-enoyl)pyrrolidin-2-yl)methyl)-1H-benzo[d]imidazol-5-yl)methyl-((S)-3,3-dimethylbutan-2-yl)carbamate (0.19 g, 0.000257 mole) in acetic acid (1.9 mL) and cooled to 0° C.; followed by drop wise addition of 30% HBr in acetic acid (7.6 mL). After completion of addition, the reaction mixture was allowed to warm up to room temperature and stirred for 1 h. After completion of the reaction, the reaction mixture was slowly diluted with saturated NaHCO$_3$ solution at 5° C. (pH ~7-8) and compound was extracted with ethyl acetate. The combined organic layer was dried over sodium sulfate and concentrated under vacuum to give crude product, which was purified by column chromatography by using 3-5% methanol in DCM to yield 0.033 g of 4-chloro-N-(1-((1-(2-cyano-4,4-dimethylpent-2-enoyl)pyrrolidin-2-yl)methyl)-5-((((S)-3,3-dimethylbutan-2-yl)amino)methyl)-1H-benzo[d]imidazol-2-yl)benzamide. LC-MS (ES, m/z):603.5 [M+H].

Example 24

Synthesis of N-(1-((1-acryloylpyrrolidin-2-yl)methyl)-5-(((S)-3,3-dimethylbutan-2-ylamino)methyl)-1H-benzo[d]imidazol-2-yl)-4-chlorobenzamide

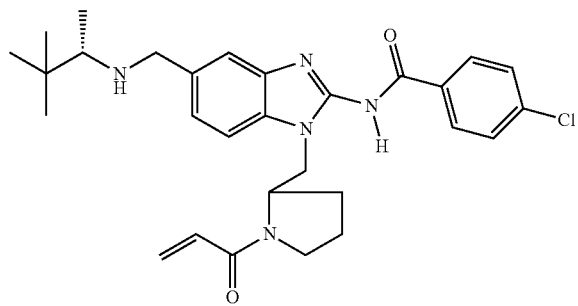 [SMILES: C=CC(=O)N1CCCC1Cn1c(NC(=O)c2ccc(Cl)cc2)nc2cc(CN[C@@H](C)C(C)(C)C)ccc21]

Step 1

To a 25 mL three necked round bottom flask under nitrogen atmosphere, benzyl(2-(4-chlorobenzamido)-1-(pyrrolidin-2-ylmethyl)-1H-benzo[d]imidazol-5-yl)methyl ((S)-3,3-dimethylbutan-2-yl)carbamate TFA salt (0.4 g, 0.000747 mole) as prepared above, was added in THF (8 mL) and the mixture was cooled to −30° C. A 50% solution of acryloyl chloride in toluene (0.13 mL, 0.000822 mole) was added and then the mixture was warmed to room temperature and stirred for 2 h. After completion of the reaction, the reaction mixture was diluted with saturated NaHCO$_3$ solution and extracted with ethyl acetate. The combined organic layer was dried over sodium sulphate, concentrated to give a solid which was dissolved in DMF (2 mL) followed by addition of Cs$_2$CO$_3$ (1.11 g, 0.00343 mole) and stirred at 55° C. overnight. Column purification afforded 0.35 g benzyl(1-((1-acryloylpyrrolidin-2-yl)methyl)-2-(4-chlorobenzamido)-1H-benzo[d]imidazol-5-yl)methyl((S)-3,3-dimethylbutan-2-yl)carbamate.

Step 2

Deprotection as in Step 4, Example 21, with HBr afforded N-(1-(1-acryloylpyrrolidin-2-yl)methyl)-5-(((S)-3,3-dimethylbutan-2-ylamino)methyl)-1H-benzo[d]imidazol-2-yl)-4-chlorobenzamide as the formic acid salt. LC-MS (ES, m/z): 523 [M+H].

Example 25

Synthesis of N-(1-((1-(4-amino-2-cyano-4-methylpent-2-enoyl)pyrrolidin-2-yl)methyl)-5-((((S)-3,3-dimethylbutan-2-yl)amino)methyl)-1H-benzo[d]imidazol-2-yl)-4-chlorobenzamide

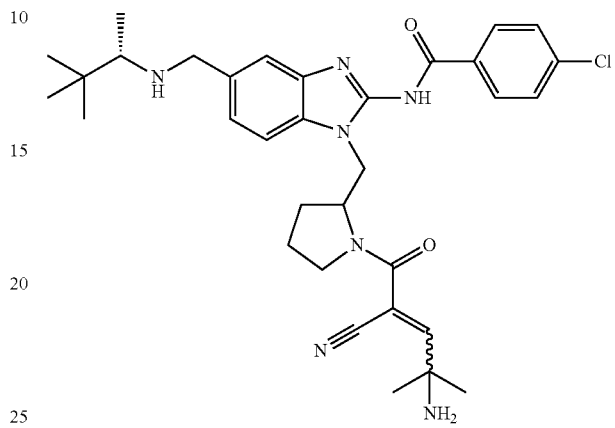

Step 1

To a 100 mL RBF, tert-butyl 2-((4-formyl-2-nitrophenylamino)methyl)pyrrolidine-1-carboxylate (7.5 g, 0.02146 mole) was added in CH$_2$Cl$_2$ (30 mL) and cooled to 0° C. TFA (12 mL) was slowly added at 0° C. and the reaction mixture was stirred for 1.5 h at RT. After the completion of the reaction, CH$_2$Cl$_2$ was completely distilled out in vacuum followed by stripping with THF to get the crude residue which was triturated with diethyl ether and filtered to yield 7.5 g of 3-nitro-4-(pyrrolidin-2-ylmethylamino)benzaldehyde as TFA salt, which was used in the next step.

Step 2

To a 100 mL three necked round bottom flask under nitrogen atmosphere were added 3-nitro-4-(pyrrolidin-2-ylmethylamino)benzaldehyde as TFA salt (7.5 g, 0.02066 mole), pyridine (4.89 g, 0.00309 mole) in CH$_2$Cl$_2$ (50 mL) and cooled it to 0° C. Trifluoroacetic anhydride (6.5 g, 0.0619 mole) was added drop wise to the cooled reaction mixture and then allowed it to warm up to room temperature and stirred at room temperature for 12 h. After completion of the reaction, the solvent is concentrated to give the crude product in which water was added and the solid obtained was filtered, washed with water and hexanes and dried in vacuum to yield 6 g of 3-nitro-4-((1-(2,2,2-trifluoroacetyl)pyrrolidin-2-yl)methylamino)benzaldehyde.

Step 3

To a 50 mL three necked round bottom flask under nitrogen atmosphere, 3-nitro-4-((1-(2,2,2-trifluoroacetyl)pyrrolidin-2-yl)methylamino)benzaldehyde (6 g, 0.0173 mole) and (S)-3,3-dimethyl butyl-2-amine (2.44 mL, 0.0173 mole) were added in 1,2 dichloroethane (30 mL) and stirred at room temperature for 10 min. Acetic acid (0.52 mL, catalytic amount) and NaBH(OAc)$_3$ (5.53 g, 0.0260 mole) were added respectively to the reaction mixture and stirred at room temperature for 6 h. After completion of the reaction, the reaction mixture was poured in to saturated Na$_2$CO$_3$ solution, followed by extraction with CH$_2$Cl$_2$. The combined organic layers were dried over sodium sulphate, concentrated to yield 4.6 g of 1-(2-((4-(((S)-3,3-dimethylbutan-2-ylamino)methyl)-2-nitrophenylamino)methyl)pyrrolidin-1-yl)-2,2,2-trifluoroethanone.

Step 4

To a 100 mL round bottom flask, 1-(2-((4-(((S)-3,3-dimethylbutan-2-ylamino)methyl)-2-nitrophenylamino)methyl)pyrrolidin-1-yl)-2,2,2-trifluoroethanone (4.6 g, 0.01069 mole) and TEA (4.3 mL) were taken in CH$_2$Cl$_2$ (40 mL). (Boc)$_2$O (3.49 g, 0.01604 mole) at 0° C. was added and the reaction mixture was stirred at room temperature for 16 hr. After completion of the reaction, the reaction mixture was poured in to water followed by extraction with EtOAc. The combined organic layers were dried over sodium sulphate and concentrated to give crude product which was purified using column purification by eluting the compound with 5% EtOAc in hexanes to yield 1.8 g tert-butyl(S)-3,3-dimethylbutan-2-yl (3-nitro-4-((1-(2,2,2-trifluoroacetyl)pyrrolidin-2-yl)methyl-amino)benzyl)-carbamate.

Step 5

To a 50 mL three necked round bottom flask, tert-butyl (S)-3,3-dimethylbutan-2-yl (3-nitro-4-((1-(2,2,2-trifluoroacetyl)pyrrolidin-2-yl)methylamino)benzyl)carbamate (1.8 g, 0.0033 mole) were added in methanol (20 mL) followed by moist 10% Pd/C (0.36 g). The reaction mixture was stirred under a balloon of H$_2$ gas for 4 h with stirring. After completion of the reaction, the reaction mixture was filtered through celite bed; washed with methanol and filtrate was concentrated to yield 1.5 g of tert-butyl 3-amino-4-((1-(2,2,2-trifluoroacetyl)pyrrolidin-2-yl)methylamino)benzyl((S)-3,3-dimethylbutan-2-yl)-carbamate.

Step 6

To a 50 mL three necked round bottom flask under nitrogen atmosphere, tert-butyl 3-amino-4-((1-(2,2,2-trifluoroacetyl)pyrrolidin-2-yl)methylamino)benzyl((S)-3,3-dimethylbutan-2-yl)carbamate (1.5 g, 0.0030 mole) was added in ethanol (15 mL) followed by addition of cyanogen bromide (0.38 g, 0.0036 mole) at room temperature and stirred at same temperature for 4 h. After completion of the reaction, the reaction mixture was concentrated under vacuum and diluted with saturated NaHCO$_3$ solution and extracted with EtOAc. The combined organic layer was dried over sodium sulphate, concentrated to give the crude product which was purified using column purification by eluting the compound with 1.5-2.0% methanol in chloroform to yield 1.6 g (crude) of tert-butyl (S)-3,3-dimethylbutan-2-yl((2-imino-1-((1-(2,2,2-trifluoroacetyl)pyrrolidin-2-yl)methyl)-2,3-dihydro-1H-benzo[d]imidazol-5-yl)methyl)carbamate.

Step 7

To a 100 mL three necked round bottom flask under nitrogen atmosphere, 4-chlorobenzoic acid (0.571 g, 0.00365 mole) was added in CH$_2$Cl$_2$ (30 mL) followed by addition of EDC.HCl (0.875 g, 0.00456 mole), HOBt (0.616 g, 0.00456 mole) and TEA (1.28 mL, 0.00914 mole) and stirred at room temperature for 10 min. tert-Butyl (S)-3,3-dimethylbutan-2-yl((2-imino-1-((1-(2,2,2-trifluoroacetyl)pyrrolidin-2-yl)methyl)-2,3-dihydro-1H-benzo[d]imidazol-5-yl)methyl)carbamate (1.6 g, 0.00304 mole) was added to the reaction mixture and stirred it at room temperature for 4 h. After completion of the reaction, the reaction mixture was washed with saturated NaHCO$_3$ solution. The organic layer was dried over sodium sulphate, concentrated to give the crude product which was purified using column purification by eluting with 20% EtOAc in hexanes to yield 1.28 g of tert-butyl (2-(4-chlorobenzamido)-1-((1-(2,2,2-trifluoroacetyl)pyrrolidin-2-yl)methyl)-1H-benzo[d]imidazol-5-yl)methyl((S)-3,3-dimethylbutan-2-yl)carbamate.

Step 8

To a 50 mL one necked round bottom flask were added tert-butyl (2-(4-chlorobenzamido)-1-((1-(2,2,2-trifluoroacetyl)pyrrolidin-2-yl)methyl)-1H-benzo[d]imidazol-5-yl)methyl((S)-3,3-dimethylbutan-2-yl)carbamate (1.08 g, 0.00162 mole) in ethanol (10 mL), followed by addition of NaBH$_4$ (0.247 g, 0.00650 mole) and stirred at room temperature for 1 h. After completion of the reaction, the reaction mixture was slowly diluted with saturated NH$_4$Cl solution and the product was extracted with EtOAc. The combined organic layer was dried over sodium sulfate and concentrated under vacuum to give crude product, which was purified by trituration with diethyl ether to yield 0.7 g of tert-butyl (2-(4-chlorobenzamido)-1-(pyrrolidin-2-ylmethyl)-1H-benzo[d]imidazol-5-yl)methyl((S)-3,3-dimethylbutan-2-yl)carbamate.

Step 9

To a 100 mL three necked round bottom flask were added 2-cyanoacetic acid (0.143 g, 0.00169 mole) and HATU (0.802 g, 0.00211 mole) in DMF (8 mL) under nitrogen atmosphere and stirred at room temperature for 10 min A solution of tert-butyl (2-(4-chlorobenzamido)-1-(pyrrolidin-2-ylmethyl)-1H-benzo[d]imidazol-5-yl)methyl((S)-3,3-dimethylbutan-2-yl)carbamate (0.8 g, 0.00140 mole) in DMF (7 mL) was drop wise added, followed by addition of DIPEA (0.71 mL, 0.00422 mole) at rt. The reaction mixture was stirred at room temperature for 2.5 h. The reaction mixture was poured into water and extracted with ethyl acetate. The combined organic layer was washed with saturated NaHCO$_3$ solution, brine solution, and dried over sodium sulfate and concentrated under vacuum to yield crude compound, which was subjected for the column purification using 2% MeOH in CH$_2$Cl$_2$ to give 0.85 g of tert-butyl (2-(4-chlorobenzamido)-1-((1-(2-cyanoacetyl)pyrrolidin-2-yl)methyl)-1H-benzo[d]imidazol-5-yl)methyl ((S)-3,3-dimethylbutan-2-yl)carbamate.

Step 10

To a 10 mL seal tube were added tert-butyl (2-(4-chlorobenzamido)-1-((1-(2-cyanoacetyl)pyrrolidin-2-yl)methyl)-1H-benzo[d]imidazol-5-yl)methyl((S)-3,3-dimethylbutan-2-yl)carbamate (0.225 g, 0.00035 mole), tert-butyl 2-methyl-1-oxopropan-2-ylcarbamate (0.198 g, 0.00106 mole) and piperidine (0.06 g) in 1,4 dioxane (2 mL). The reaction mixture was heated at 110° C. for 1 h. After completion of the reaction; the reaction mixture was concentrated under vacuum and the crude product was purified using column purification by eluting with 2% MeOH in CH$_2$Cl$_2$ to yield 0.125 g of tert-butyl N-[[1-[[1-[4-(tert-butoxycarbonylamino)-2-cyano-4-methyl-pent-2-enoyl]pyrrolidin-2-yl]methyl]-2-[(4-chlorobenzoy)amino]benzimidazol-5-yl]methyl]-N-[(1S)-1,2,2-trimethylpropyl]carbamate.

Step 11

To a 50 mL one necked round bottom flask were added tert-butyl N-[[1-[[1-[4-(tert-butoxycarbonylamino)-2-cyano-4-methyl-pent-2-enoyl]pyrrolidin-2-yl]methyl]-2-[(4-chlorobenzoy)amino]benzimidazol-5-yl]methyl]-N-[(1S)-1,2,2-trimethylpropyl]carbamate (0.125 g, 0.00015 mole) in CH$_2$Cl$_2$ (4.5 mL) and cooled to 0° C. followed by drop wise addition of TFA (0.5 mL). After completion of addition, the reaction mixture was allowed to warm up to room temperature and stirred for 2.5 h. After completion of the reaction; the reaction mixture was slowly diluted with saturated NaHCO$_3$ at 5° C. (pH ~7-8) and the product was extracted with EtOAc. The combined organic layer was dried over sodium sulfate and concentrated under vacuum to give crude product, which was purified by trituration with diethyl ether followed by again trituration with water and dried in vacuum to yield 0.030 g of N-(1-((1-(4-amino-2-cyano-4-methylpent-2-enoyl)pyrrolidin-2-yl)methyl)-5-(((S)-3,3-dimethylbutan-2-ylamino)methyl)-1H-benzo[d]imidazol-2-yl)-4-chlorobenzamide. LC-MS (ES, m/z): 605 [M+H].

Example 26

Synthesis of 4-chloro-N-(1-((1-(2-cyano-4-ethoxy-4-methylpent-2-enoyl)pyrrolidin-2-yl)methyl)-5-(((S)-3,3-dimethylbutan-2-ylamino)methyl)-1H-benzo[d]imidazol-2-yl)benzamide

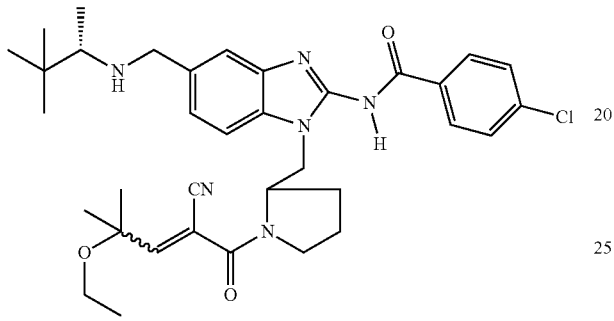

Step 1

To a 10 mL seal tube were added pyrrolidine (0.39 mL, 0.0000472 mole) and TMS-Cl (0.4 mL, 0.00314 mole) in acetonitrile (5 mL) followed by 2-ethoxy-2-methylpropanal (0.274 g, 0.000236 mole) and the reaction mixture was stirred at RT for 10 min. tert-Butyl (2-(4-chlorobenzamido)-1-((1-(2-cyanoacetyl)pyrrolidin-2-yl)methyl)-1H-benzo[d]imidazol-5-yl)methyl((S)-3,3-dimethylbutan-2-yl)carbamate (0.5 g, 0.000787 mole) was added and the reaction mixture was stirred for 1 h at RT. After completion of the reaction; the reaction mixture was diluted with water and extracted with EtOAc. The combined organic layer was concentrated under vacuum. The crude product was purified using column purification by eluting with 25% EtOAc in hexanes to yield 0.209 g of tert-butyl (2-(4-chlorobenzamido)-1-((1-(2-cyano-4-ethoxy-4-methylpent-2-enoyl)pyrrolidin-2-yl)methyl)-1H-benzo[d]imidazol-5-yl)methyl((S)-3,3-dimethylbutan-2-yl)carbamate.

Step 2

To a 10 mL one necked round bottom flask were added tert-butyl (2-(4-chlorobenzamido)-1-((1-(2-cyano-4-ethoxy-4-methylpent-2-enoyl)pyrrolidin-2-yl)methyl)-1H-benzo[d]imidazol-5-yl)methyl((S)-3,3-dimethylbutan-2-yl)carbamate (0.209 g, 0.00028 mole) in CH$_2$Cl$_2$ (1 mL) and cooled to 0° C. followed by drop wise addition of TFA (1 mL). After completion of addition, the reaction mixture was allowed to warm up to room temperature and stirred for 1 h. The reaction mixture was slowly diluted with saturated NaHCO$_3$ solution at 5° C. (pH ~7-8) and the product was extracted with EtOAc. The combined organic layer was dried over sodium sulfate and concentrated under vacuum to give crude product, which was purified by column purification by using 3-5% methanol in CH$_2$Cl$_2$ to yield 0.070 g of 4-chloro-N-(1-((1-(2-cyano-4-ethoxy-4-methylpent-2-enoyl)pyrrolidin-2-yl)methyl)-5-(((S)-3,3-dimethylbutan-2-ylamino)methyl)-1H-benzo[d]imidazol-2-yl)benzamide (39.1% yield). LC-MS (ES, m/z): 633 [M+H].

Example 27

Synthesis of 4-chloro-N-(1-((1-(2-cyano-4-(dimethylamino)-4-methylpent-2-enoyl)pyrrolidin-2-yl)methyl)-5-(((S)-3,3-dimethylbutan-2-ylamino)methyl)-1H-benzo[d]imidazol-2-yl)benzamide

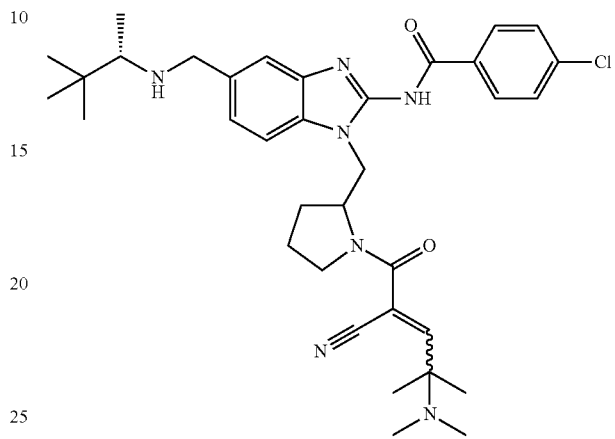

Step 1

To a 100 mL three necked round bottom flask, tert-butyl 2-((4-(((S)-3,3-dimethylbutan-2-ylamino)methyl)-2-nitrophenylamino)methyl)pyrrolidine-1-carboxylate (3.0 g, 0.0069 mole) was taken in water (15 mL) and dioxane (25 mL) followed by addition of Na$_2$CO$_3$ (1.98 g, 0.0186 mole). The reaction mixture was cooled to 0° C. and allyl chloroformate was added drop wise at 0° C. The reaction mixture was allowed to warm up to room temperature and stirred at RT for 24 h. Dioxane was evaporated under vacuum and the reaction mixture was diluted with EtOAc and washed with water. The organic was dried and concentrated to give the crude product which was purified using column purification by eluting the compound with 30% EtOAc in hexanes to yield 1.9 g of tert-butyl 2-((4-(((allyloxycarbonyl)((S)-3,3-dimethylbutan-2-yl)amino)methyl)-2-nitrophenylamino)methyl)-pyrrolidine-1-carboxylate.

Step 2

To a 250 mL three necked round bottom flask, tert-butyl 2-((4-(((allyloxycarbonyl)((S)-3,3-dimethylbutan-2-yl)amino)methyl)-2-nitrophenylamino)methyl)pyrrolidine-1-carboxylate (1.9 g, 0.00366 mole), Zn powder (1.9 g, ww) were taken in methanol (40 mL) and sat. ammonium chloride solution (40 mL) and heated at 50° C. for 1 h. After completion of the reaction, the reaction mixture was filtered through cotton; concentrated under vacuum to give the crude product which was diluted with EtOAc and washed with water and dried and concentrated to get 1.7 g (impure, used as such in next step without purification) of tert-butyl 2-((4-(((allyloxycarbonyl) ((S)-3,3-dimethylbutan-2-yl)amino)methyl)-2-aminophenylamino)methyl)pyrrolidine-1-carboxylate.

Step 3

To a 50 mL three necked round bottom flask, tert-butyl 2-((4-(((allyloxycarbonyl) ((S)-3,3-dimethylbutan-2-yl)amino)methyl)-2-aminophenylamino)methyl)pyrrolidine-1-carboxylate (1.7 g, 0.00348 mole) was taken in ethanol (17 mL) under nitrogen atmosphere followed by addition of cyanogen bromide (0.445 g, 0.00418 mole) at room temperature and stirred at same temperature for 3 h. After completion of the reaction, the reaction mixture was concentrated under vacuum and diluted with water and extracted with ethyl acetate. The combined organic layer was washed with saturated NaHCO$_3$ solution, dried over sodium sulphate and concentrated to get 2 g (impure, used as such in next step without purification) of tert-butyl 2-((5-(((allyloxycarbonyl)-((S)-3,3-dimethyl-butan-2-yl)amino)methyl)-2-imino-2,3-dihydro-1H-benzo[d]imidazol-1-yl)methyl)pyrrolidine-1-carboxylate.

Step 4

To a 100 mL three necked round bottom flask, 4-chlorobenzoic acid (0.732 g, 0.00467 mole) was take in DCM (80 mL) under nitrogen atmosphere followed by addition of EDC.HCl (1.12 g, 0.00585 mole), HOBt. H$_2$O (0.895 g, 0.00585 mole) and TEA (1.64 mL, 0.0117 mole) and stirred at room temperature for 15 min tert-Butyl 2-((5-(((allyloxycarbonyl)-((S)-3,3-dimethylbutan-2-yl)amino)methyl)-2-imino-2,3-dihydro-1H-benzo[d]imidazol-1-yl)methyl)pyrrolidine-1-carboxylate (2 g, 0.00389 mole) was added to reaction mixture and stirred it at room temperature for 12 h. After completion of the reaction, the reaction mixture was diluted with water and extracted with CH$_2$Cl$_2$. The organic layers were combined, dried over sodium sulphate and concentrated to give the crude product which was purified using column purification by eluting the compound with 10% EtOAc in hexanes to give 1.9 g of tert-butyl 2-((5-(((allyloxycarbonyl)((S)-3,3-dimethylbutan-2-yl)amino)methyl)-2-(4-chlorobenzamido)-1H-benzo[d]imidazol-1-yl)methyl)pyrrolidine-1-carboxylate.

Step 5

To a 50 mL single necked round bottom flask, tert-butyl 2-((5-(((allyloxycarbonyl)-((S)-3,3-dimethylbutan-2-yl)amino)methyl)-2-(4-chlorobenzamido)-1H-benzo[d]imidazol-1-yl)methyl)-pyrrolidine-1-carboxylate (1.9 g, 0.0052 mole) was taken in CH$_2$Cl$_2$ (10 ml) and cooled to 0° C. followed by drop wise addition of TFA (8 mL). After completion of addition, the reaction mixture was allowed to warm up to RT and stirred at rt for 7 h. After completion of the reaction, the reaction mixture was concentrated to dryness with the stripping of THF. The crude thus obtained was dissolved in diethyl ether, hexanes was added to it and the reaction mixture was stirred for 30 min. The white solid thus precipitated out was filtered and dried under vacuum to give 1.4 g of allyl (2-(4-chlorobenzamido)-1-(pyrrolidin-2-ylmethyl)-1H-benzo[d]imidazol-5-yl)methyl-((S)-3,3-dimethylbutan-2-yl)carbamate TFA salt.

Step 6

To a 50 mL single necked round bottom flask, 2-cyanoacetic acid (0.2 g, 0.002359 mole) was taken in DMF (26 mL) under N$_2$ atmosphere, followed by addition of HATU (1.35 g, 0.003538 mole) and stirred at room temperature for 30 min Allyl (2-(4-chlorobenzamido)-1-(pyrrolidin-2-ylmethyl)-1H-benzo[d]imidazol-5-yl)methyl-((S)-3,3-dimethylbutan-2-yl)carbamate as TFA salt (1.3 g, 0.002359 mole) and DIPEA (1.65 mL, 0.004718 mole) were added to reaction mixture and the reaction mixture was stirred at room temperature for 16 h. After completion of reaction, the reaction mixture was diluted with ice cold water at 0-5° C. and solid thus obtained was filtered and dried under vacuum to get solid which was further triturated with pentane to give 1.2 g of allyl (2-(4-chlorobenzamido)-1-((1-(2-cyanoacetyl)pyrrolidin-2-yl)methyl)-1H-benzo[d]imidazol-5-yl)methyl-((S)-3,3-dimethylbutan-2-yl)carbamate.

Step 7

To a 35 mL sealed tube, allyl (2-(4-chlorobenzamido)-1-((1-(2-cyanoacetyl)pyrrolidin-2-yl)methyl)-1H-benzo[d]imidazol-5-yl)methyl-((S)-3,3-dimethylbutan-2-yl)carbamate (0.35 g, 0.00056 mole), 2-(dimethylamino)-2-methylpropanal (0.195 g, 0.001696 mole) and piperidine (0.112 mL, 0.00113 mole) were taken in dioxane (8 mL). The reaction mixture was heated at 90° C. for 12 h. Dioxane was evaporated and the crude product was purified using column purification by eluting with 0.7-2% methanol in CH$_2$Cl$_2$ to yield 0.19 g of allyl (2-(4-chlorobenzamido)-1-((1-(2-cyano-4-(dimethylamino)-4-methylpent-2-enoyl)pyrrolidin-2-yl)methyl)-1H-benzo[d]imidazol-5-yl)methyl-((S)-3,3-dimethylbutan-2-yl)carbamate.

Step 8

To a 25 mL singled necked round bottom flask under, allyl (2-(4-chlorobenzamido)-1-((1-(2-cyano-4-(dimethylamino)-4-methylpent-2-enoyl)pyrrolidin-2-yl)methyl)-1H-benzo[d]imidazol-5-yl)methyl-((S)-3,3-dimethylbutan-2-yl)carbamate (180 mg, 0.00025 mole) in THF (4 mL) followed by addition of dimedone (211 mg, 0.0015 mole) and tetrakis-triphenylphosphine (6 mg, 0.000005 mole) and the reaction mixture was stirred for 6 h at rt. After completion of the reaction, THF was evaporated, reaction mixture was diluted with DCM, washed with excess of water to remove the dimedone. The organic layer was dried and concentrated to get the crude which was subjected to prep HPLC purification to afford 37 mg of 4-chloro-N-(1-((1-(2-cyano-4-(dimethylamino)-4-methylpent-2-enoyl)pyrrolidin-2-yl)methyl)-5-(((S)-3,3-dimethylbutan-2-ylamino)methyl)-1H-benzo[d]imidazol-2-yl)benzamide. LC-MS (ES, m/z): 632.5 [M+H].

Example 28

Synthesis of N-(1-((1-acryloylpyrrolidin-2-yl)methyl)-5-((((S)-3,3-dimethylbutan-2-yl)amino)methyl)-1H-benzo[d]imidazol-2-yl)-4-(difluoromethyl)benzamide

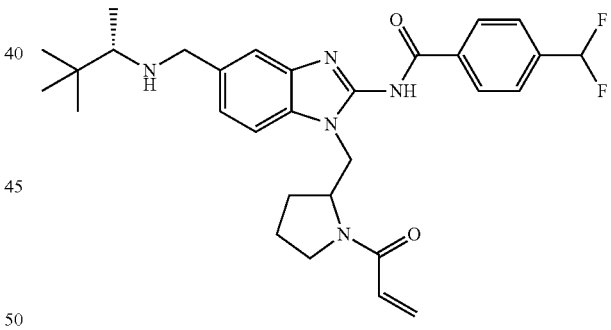

Step 1

To a 100 mL three necked round bottom flask were added 4-(difluoromethyl)benzoic acid (0.91 g, 0.0053 mole) and HATU (2.53 g, 0.0066 mole) in DMF (10 mL) under nitrogen atmosphere at 0° C. and stirred it for 15 min. tert-Butyl 2-((5-(((benzyloxycarbonyl)((S)-3,3-dimethylbutan-2-yl)amino)methyl)-2-imino-2,3-dihydro-1H-benzo[d]imidazol-1-yl)methyl)pyrrolidine-1-carboxylate (2.5 g, 0.0044 mole) in DMF (15 mL) and DIPEA (2.3 mL, 0.0133 mole) were drop wise added to it. The reaction mixture was allowed to warm up to room temperature and stirred for 12 h. After completion of the reaction, the reaction mixture was diluted with cold water and product was extracted with ethyl acetate. The combined organic layer was washed with brine solution, dried over sodium sulphate, concentrated under vacuum and resultant crude product was purified using column purification eluting compound with 20-30% ethyl acetate in hexanes to yield 2.0 g of tert-butyl 2-((5-(((benzyloxycarbonyl)((S)-3,3-dimethylbutan-2-yl)amino)methyl)-2-(4-(difluoromethyl)-benzamido)-1H-benzo[d]imidazol-1-yl)methyl)pyrrolidine-1-carboxylate.

Step 2

To a 100 mL single necked round bottom flask were added tert-butyl 2-((5-(((benzyloxy-carbonyl)((S)-3,3-dimethylbutan-2-yl)amino)methyl)-2-(4-(difluoromethyl)benzamide)-1H-benzo[d]imidazol-1-yl)methyl)pyrrolidine-1-carboxylate (2 g, 0.0027 mole) in CH$_2$Cl$_2$ (20 mL) under nitrogen atmosphere at 0° C. TFA (8 mL) was drop wise added at same temperature and then the reaction mixture was allowed it to warm up to room temperature and stirred at room temperature for 16 h. After completion of the reaction, the reaction mixture was concentrated under vacuum, azeotroped with toluene, triturated with pentane and dried under vacuum to yield 2.0 g of benzyl(2-(4-(difluoromethyl)benzamido)-1-(pyrrolidin-2-ylmethyl)-1H-benzo[d]imidazol-5-yl)methyl((S)-3,3-dimethylbutan-2-yl)carbamate TFA salt.

Step 3

To a 50 mL one necked round bottom flask 50% solution of acrolyl chloride in toluene (0.4 mL, 1.0249 mmole) was drop wise added to a solution of benzyl(2-(4-(difluoromethyl)benzamido)-1-(pyrrolidin-2-ylmethyl)-1H-benzo[d]imidazol-5-yl)methyl((S)-3,3-dimethylbutan-2-yl)carbamate TFA salt (0.5 g, 0.6833 mmole) in THF (10 mL) at −30° C. under nitrogen atmosphere. The reaction mixture was allowed to warm up to room temperature and stirred it for 1 h. After completion of the reaction; the reaction mixture was poured in saturated NaHCO$_3$ solution and extracted with ethyl acetate. The combined organic layer was dried over sodium sulphate and concentrated under vacuum to give crude product. To a 25 ml one necked round bottom flask were added crude product (0.55 g), cesium carbonate (0.667 g, 2.0499 mmole) in THF (5 mL) and heated at 60° C. for 15 min. The reaction mixture was cooled to room temperature; then water was added to it and extracted with ethyl acetate. The combined organic layer was dried over sodium sulfate and concentrated under vacuum to yield 0.4 g of benzyl(1-((1-acryloylpyrrolidin-2-yl)methyl)-2-(4-(difluoromethyl)-benzamido)-1H-benzo[d]imidazol-5-yl)methyl ((S)-3,3-dimethylbutan-2-yl)carbamate.

Step 4

To a 50 mL one necked round bottom flask were added benzyl(1-(1-acryloylpyrrolidin-2-yl)methyl)-2-(4-(difluoromethyl)benzamido)-1H-benzo[d]imidazol-5-yl)methyl ((S)-3,3-dimethylbutan-2-yl)carbamate (0.4 g, 0.5954 mmole) in acetic acid (4 mL) and cooled to 0° C. 30% HBr in acetic acid (16 mL) was added dropwise and the reaction mixture was allowed it to warm up to room temperature and stirred for 1 h. After completion of the reaction; reaction mixture was slowly diluted with saturated NaHCO$_3$ solution at 5° C. (pH ~7-8) and the product was extracted with ethyl acetate. The combined organic layer was dried over sodium sulfate and concentrated under vacuum to give crude product, which was purified by prep HPLC to yield 78 mg of N-(1-((1-acryloylpyrrolidin-2-yl)methyl)-5-((((S)-3,3-dimethylbutan-2-ylamino)methyl-1H-benzo[d]imidazol-2-yl)-4-(difluoromethyl)benzamide formic salt. LC-MS (ES, m/z): 538 [M+H].

Example 29

Synthesis of N-(1-((1-acryloylpyrrolidin-2-yl)methyl)-5-((((S)-3,3-dimethylbutan-2-yl)amino)-methyl)-1H-benzo[d]imidazol-2-yl)-5-(difluoromethyl)thiophene-2-carboxamide

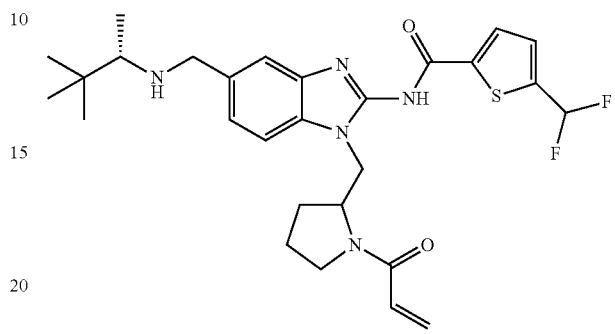

N-(1-((1-acryloylpyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide was prepared according to the procedure described in example 28 but substituting 5-(difluoromethyl)thiophene-2-carboxylic acid for 4-(difluoromethyl)benzoic acid and repeating steps 2-4. LC-MS (ES, m/z):544.2 [M+H].

Example 30

Synthesis of N-(1-((1-(2-cyano-4-methylpent-2-enoyl)pyrrolidin-2-yl)methyl)-5-((((S)-3,3-dimethylbutan-2-yl)amino)methyl)-1H-benzo[d]imidazol-2-yl)-4-(difluoromethyl)benzamide

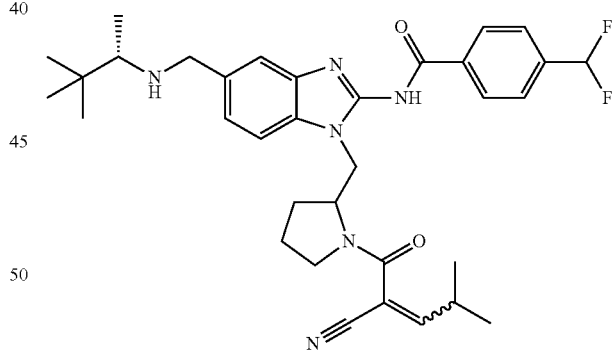

Step 1

To a 25 mL sealed tube under nitrogen atmosphere, benzyl(2-(4-(difluoromethyl)-benzamido)-1-(pyrrolidin-2-ylmethyl)-1H-benzo[d]imidazol-5-yl)methyl((S)-3,3-dimethylbutan-2-yl)carbamate as TFA salt (0.5 g, 0.000683 mole), 2-cyano-4-methylpent-2-enoic acid (0.284 g, 0.002049 mole) and PyBrOP (0.350 g, 0.000751 mole) were taken in CH$_2$Cl$_2$ (5 mL) and cooled to 0° C. TEA (0.47 mL, 0.003415 mole) was added drop wise to a reaction mixture and to stir at 0° C. for 30 min After completion of the reaction, water was added to reaction mixture and product was extracted with EtOAc. The combined organic layer was dried over Na$_2$SO$_4$ and evaporated to get crude. The crude compound was purified by column purification using 60-120 mesh size neutral silica by eluting with 20% EtOAc in hexanes to yield 0.27 g of benzyl(14(1-(2-cyano-4-methylpent-2-enoyl)pyrrolidin-2-yl)methyl)-2-(4-(difluoromethyl) benzamido)-1H-benzo[d]imidazol-5-yl)methyl((S)-3,3-dimethylbutan-2-yl)carbamate.

Step 2

To a 25 mL single neck round bottom flask under nitrogen atmosphere were taken benzyl (1-((1-(2-cyano-4-methylpent-2-enoyl)pyrrolidin-2-yl)methyl)-2-(4-(difluoromethyl) benzamido)-1H-benzo[d]imidazol-5-yl)methyl((S)-3,3-dimethylbutan-2-yl)carbamate (0.3 g, 0.000406 mole) was taken in acetic acid (3 mL) and cooled to 0° C. HBr in acetic acid (33% solution) (12 mL) was added drop wise to the reaction mixture to a reaction mixture and allowed it to stir at room temperature for 30 min. The reaction was monitored on TLC using $CH_2Cl_2$: methanol (9.5:0.5) as a mobile phase. After completion of reaction, saturated $NaHCO_3$ solution was added to it and product was extracted with EtOAc. The combined organic layer was dried over $Na_2SO_4$ and evaporated to get crude. The crude compound was purified using Prep HPLC to yield 0.105 g N-(1-((1-(2-cyano-4-methylpent-2-enoyl)pyrrolidin-2-yl)methyl)-5-(((S)-3,3-dimethylbutan-2-ylamino)-methyl)-1H-benzo[d]imidazol-2-yl)-4-(difluoromethyl)benzamide as formic salt. LC-MS (ES, m/z): 605 [M+H].

Example 31

Synthesis of N-(1-((1-(2-cyano-4-methylpent-2-enoyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide

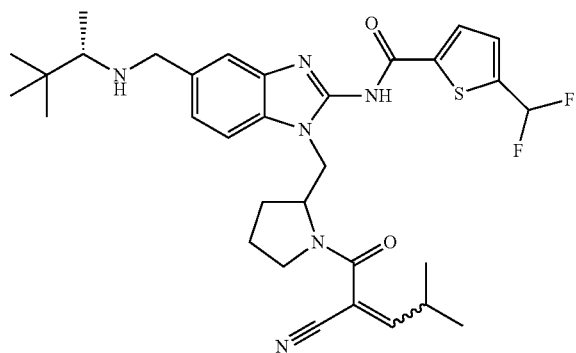 [SMILES: CC(C)C=C(C#N)C(=O)N1CCCC1Cn1c(NC(=O)c2ccc(C(F)F)s2)nc2cc(CN[C@@H](C)C(C)(C)C)ccc21]

N-(1-((1-(2-Cyano-4-methylpent-2-enoyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide was prepared as decribed in Example 30 but substituting 5-(difluoromethyl)-thiophene-2-carboxylic acid for 4-(difluoromethyl)benzoic acid. LC-MS (ES, m/z): 611.3 [M+H].

Example 32

Synthesis of (S)-N-(1-(1-acryloylpiperidin-4-yl)-5-((3,3-dimethylbutan-2-ylamino)methyl)-1H-benzo[d]imidazol-2-yl)-4-chlorobenzamide

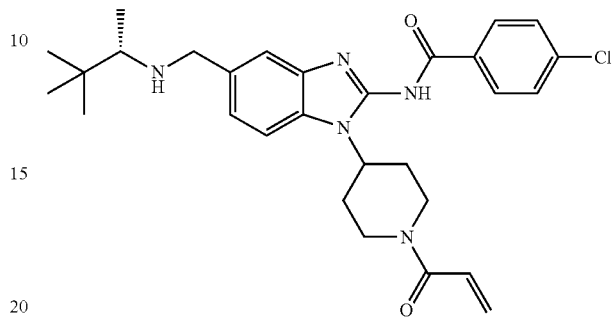

Step 1

To a 100 mL three necked round bottom flask, 4-fluoro-3-nitrobenzaldehyde (2.0 g, 0.0118 mole) was taken in acetonitrile (25 mL) and DIPEA (6.1 mL, 0.0354 mole) was added drop wise at room temperature. After completion of addition, the reaction mass was stirred for 15 min at same temperature followed by slow addition of tert-butyl 4-aminopiperidine-1-carboxylate (3.5 g, 0.0177 mole) over 15 min After completion of the addition, the reaction mixture was stirred for 16 h. Acetonitrile was distilled out and water was added to the residue. The product was extracted by ethyl acetate and the combined organic layer was dried over $Na_2SO_4$, filtered and concentrated to afford crude product which was purified using column purification by eluting the compound with 20% ethyl acetate in hexanes to yield 2.62 g of tert-butyl 4-(4-formyl-2-nitrophenylamino)-piperidine-1-carboxylate.

Step 2

In a 100 mL 3 neck flask, tert-butyl 4-(4-formyl-2-nitrophenylamino)piperidine-1-carboxylate (3.25 g, 0.00932 mole), (S)-3,3-dimethylbutan-2-amine (1.27 mL, 0.00932 mole) was added in 1,2-dichloroethane (50 mL) under $N_2$ atmosphere followed by addition of 5 drops of glacial acetic acid. The reaction mass was stirred for 15 min followed by slow addition of sodium triacetoxyborohydride (2.96 g, 0.01398 mole). After completion of the addition, the reaction mixture was stirred for 6 h. The reaction mixture was quenched with 2M $Na_2CO_3$ solution and extracted by ethyl acetate and the combined organic layers were dried over $Na_2SO_4$, filtered and concentrated to afford yield 4.0 g of (S)-tert-butyl 4-(4-(3,3-dimethylbutan-2-ylamino) methyl)-2-nitrophenylamino)piperidine-1-carboxylate. The product was carried forward to the next step without further purification.

Step 3

In a 100 mL 3 neck RBF, (S)-tert-butyl 4-(4-((3,3-dimethylbutan-2-ylamino)methyl)-2-nitrophenylamino)piperidine-1-carboxylate (4.0 g, 0.00932 mole) was added in $CH_2Cl_2$ (20 mL) followed by pyridine (0.9 mL, 0.01118 mole) and cooled the reaction mixture to 0° C. Trifluoroacetic anhydride (1.95 mL, 0.01397 mole) was added drop wise to the reaction mixture at 0° C. After completion of addition, the reaction mixture was stirred for 1 h at room temperature. The reaction mixture was quenched with 2M $NaHCO_3$ solution and extracted by $CH_2Cl_2$ and the combined organic layer was dried over Na₂SO₄, filtered and concentrated to afford yield 4.0 g of (S)-tert-butyl4-(4-((N-(3,3-dimethylbutan-2-yl)-2,2,2-trifluoroacetamido)methyl)-2-nitrophenylamino)-piperidine-1-carboxylate. The product was carried forward to the next step without further purification.
Step 4

In a 100 mL hydrogenator autoclave, to a suspension of 10% dry Pd/C (0.4 g, 10% w/w) in methanol (50 mL), (S)-tert-butyl4-(4-((N-(3,3-dimethylbutan-2-yl)-2,2,2-trifluoroacetamido)-methyl)-2-nitrophenylamino)piperidine-1-carboxylate (3.0 g, 2.82 mmole) was added and the autoclave was sealed. The reaction mixture was flushed twice under nitrogen atmosphere. The H₂ gas was pressurized into the autoclave at 50 psi pressure and the reaction mixture was stirred at room temperature for 4 h. The reaction mixture was filtered through celite and washed with methanol and filtrate was concentrated to afford 3.0 g of (S)-tert-butyl 4-(2-amino-4-((N-(3,3-dimethylbutan-2-yl)-2,2,2-trifluoroacetamido)methyl)phenylamino)piperidine-1-carboxylate. The product was carried forward to the next step without further purification.
Step 5

To a 100 mL RBF, (S)-tert-butyl 4-(2-amino-4-((N-(3,3-dimethylbutan-2-yl)-2,2,2-trifluoroacetamido)methyl)phenylamino)piperidine-1-carboxylate (3.0 g, 0.00599 mole) was taken in ethanol (25 mL). Cyanogen bromide (0.76 g, 0.00719 mole) was added at room temperature and stirred reaction mass for 3 h. Ethanol was distilled out and saturated NaHCO₃ solution was added to adjust pH basic and stirred it for 1 h then filtered it and washed by water followed by drying the product to yield 3.05 g of (S)-tert-butyl 4-(5-((N-(3,3-dimethylbutan-2-yl)-2,2,2-trifluoroacetamido)-methyl)-2-imino-2,3-dihydro-1H-benzo[d]imidazol-1-yl)piperidine-1-carboxylate (96.82% yield; crude). The product was carried forward to the next step without further purification.
Step 6

To a 50 mL single neck RBF, 4-chlorobenzoic acid (1.25 g, 0.00799 mole) was taken in CH₂Cl₂ (50 mL) under N₂ atmosphere. EDC.HCl (1.91 g, 0.00998 mole), HOBt (1.52 g, 0.00998 mole) and TEA (2.8 mL, 0.01997 mole) were added to the reaction mixture at room temperature and stirred for 20 min (S)-tert-Butyl 4-(5-((N-(3,3-dimethylbutan-2-yl)-2,2,2-trifluoroacetamido)-methyl)-2-imino-2,3-dihydro-1H-benzo[d]imidazol-1-yl)piperidine-1-carboxylate (3.5 g, 0.00665 mole) in CH₂Cl₂ (50 mL) was added drop wise to the reaction mixture and stirred at room temperature for 9 h. Saturated NaHCO₃ solution was added to the reaction mixture and aq. layer was extracted with EtOAc. The combined organic layer was dried over Na₂SO₄ and evaporated to get the crude product which was purified using column purification by eluting the compound with 10% ethyl acetate in hexanes to yield 3.0 g of (S)-tert-butyl 4-(2-(4-chlorobenzamido)-5-((N-(3,3-dimethylbutan-2-yl)-2,2,2-trifluoro-acetamido)-methyl)-1H-benzo[d]imidazol-1-yl)piperidine-1-carboxylate.
Step 7

To a 25 mL RBF, (S)-tert-butyl 4-(2-(4-chlorobenzamido)-5-((N-(3,3-dimethylbutan-2-yl)-2,2,2-trifluoroacetamido)methyl)-1H-benzo[d]imidazol-1-yl)piperidine-1-carboxylate (2.0 g, 0.00301 mole) was cooled to 10° C. under N₂ atmosphere. 20% HCl in 1,4-dioxane (10 mL) was added drop wise at 10° C. and the reaction mixture was stirred for 6 h at room temperature. The solvent was evaporated under reduced pressure to get crude compound which was triturated with acetone to yield 1.5 g of (S)-4-chloro-N-(5-((N-(3,3-dimethylbutan-2-yl)-2,2,2-trifluoroacetamido)methyl)-1-(piperidine-4-yl)-1H-benzo[d]imidazol-2-yl)benzamide.
Step 8

In a 50 mL single neck flask, (S)-4-chloro-N-(5-((N-(3,3-dimethylbutan-2-yl)-2,2,2-trifluoroacetamido)methyl)-1-(piperidine-4-yl)-1H-benzo[d]imidazol-2-yl)benzamide (0.5 g, 0.00088 mole) was added in THF (5 mL), and the reaction mixture was cooled to −30° C. Acryloyl chloride (50% in toluene) (0.144 g, 0.00079 mole) was added dropwise to the reaction mixture at −30° C. The reaction mixture was stirred for 30 minutes at room temperature and then quenched with 2M NaHCO₃ solution and extracted by EtOAc and the combined organic layer was dried over Na₂SO₄, filtered and concentrated to afford yield crude product. The crude product was taken in THF (2 mL) and DBU (0.3 mL) was added to it and the reaction mixture was stirred at room temperature for 16 h. The combined organic layer was dried over Na₂SO₄ and evaporated to get 0.5 g of (S)-N-(1-(1-acryloylpiperidin-4-yl)-5-((N-(3,3-dimethylbutan-2-yl)-2,2,2-trifluoroacetamido)-methyl)-1H-benzo[d]imidazol-2-yl)-4-chlorobenzamide.
Step 9

To a 25 mL RBF, (S)-N-(1-(1-acryloylpiperidin-4-yl)-5-((N-(3,3-dimethylbutan-2-yl)-2,2,2-trifluoroacetamido)methyl)-1H-benzo[d]imidazol-2-yl)-4-chlorobenzamide (0.325 g, 0.00052 mole) was added in ethanol (4 mL) and cooled to 0° C. under N₂ atmosphere. NaBH₄ (0.079 g, 0.00210 mole) was added at 0° C. and the reaction mixture was stirred for 6 h at room temperature. The solvent was evaporated under reduced pressure to get crude compound. Crude compound was triturated with n-pentane to yield 400 mg of crude product, which was purified by prep HPLC to get 15 mg pure (S)-N-(1-(1-acryloylpiperidin-4-yl)-5-((3,3-dimethylbutan-2-ylamino)methyl)-1H-benzo[d]imidazol-2-yl)-4-chlorobenzamide. LC-MS (ES, m/z): 522.4 [M+H].

Example 33

Synthesis of 4-chloro-N-(1-(1-(2-cyano-4-methylpent-2-enoyl)piperidin-3-yl)-5-((N-((S)-3,3-dimethylbutan-2-yl)-2,2,2-trifluoroacetamido)methyl)-1H-benzo[d]imidazol-2-yl)benzamide

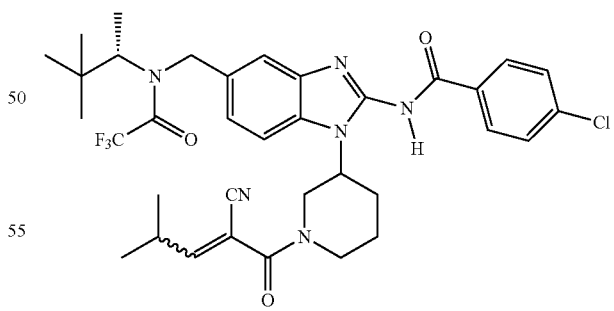

Step 1

To a 10 mL seal tube, 4-chloro-N-(5-((N-((S)-3,3-dimethylbutan-2-yl)-2,2,2-trifluoroacetamido)methyl)-1-(piperidin-3-yl)-1H-benzo[d]imidazol-2-yl)benzamide (0.05 g, 0.0000886 mol) and 2-cynoacetic acid (0.011 g, 0.000132 mol) were taken in DCM (1.0 mL). EDC.HCl (0.02 g, 0.000106 mol), HOBt (0.014 g, 0.000106 mol) and TEA (0.026 g, 0.000265 mol) were added at room temperature under nitrogen atmosphere. The reaction mass was stirred for overnight at room temperature. After completion of the reaction, water was poured into reaction mixture and extracted with ethyl acetate. The combined organic layers were dried over sodium sulphate and concentrated to give the crude product which was purified using column purification by eluting the compound with 10-20% ethyl acetate in hexanes to yield 30 mg of 4-chloro-N-(1-(1-(2-cyanoacetyl)piperidin-3-yl)-5-((N-((S)-3,3-dimethylbutan-2-yl)-2,2,2-trifluoroacetamido)methyl)-1H-benzo[d]imidazol-2-yl)benzamide.

Step 2

To a 10 mL seal tube were added 4-chloro-N-(1-(1-(2-cyanoacetyl)piperidin-3-yl)-5-((N-((S)-3,3-dimethyl butan-2-yl)-2,2,2-trifluoroacetamido)methyl)-1H-benzo[d]imidazol-2-yl)benzamide (180 mg, 0.000285 mole), isobutyraldehyde (61.7 mg, 0.000855 mole), 3.3M solution of piperidine acetate in water (0.259 mL, 0.000855 mole) and ethanol (5 mL). The reaction mixture was heated in a seal tube at 80° C. for 2 h. After completion of the reaction, the reaction mixture was poured in water and extracted with ethyl acetate. The combined organic layer was washed with brine solution. The organic layer was dried over sodium sulphate, concentrated to give the crude product which was purified using column purification by with 0.5-1.0% methanol in chloroform to yield 30 mg 4-chloro-N-(1-(1-(2-cyano-4-methylpent-2-enoyl)piperidin-3-yl)-5-((N-((S)-3,3-dimethylbutan-2-yl)-2,2,2-trifluoroacetamido)methyl)-1H-benzo[d]imidazol-2-yl)benzamide. LC-MS (ES, m/z): 683.4 [M–H].

Example 34

Synthesis of N-(1-(1-acryloylpiperidin-3-yl)-5-((N-((S)-3,3-dimethylbutan-2-yl)-2,2,2-trifluoroacetamido)methyl)-1H-benzo[d]imidazol-2-yl)-4-chlorobenzamide

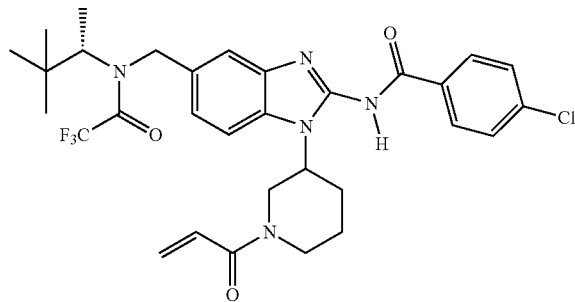 [SMILES: C=CC(=O)N1CCCC(n2c(NC(=O)c3ccc(Cl)cc3)nc3cc(CN(C(=O)C(F)(F)F)[C@@H](C)C(C)(C)C)ccc32)C1]

To a 25 mL one necked round bottom flask, 4-chloro-N-(5-((N-((S)-3,3-dimethylbutan-2-yl)-2,2,2-trifluoroacetamido)methyl)-1-(piperidin-3-yl)-1H-benzo[d]imidazol-2-yl)benzamide (0.250 g, 0.000443 mol) was taken in THF (2 mL) followed by drop wise addition of acryloyl chloride (50% sol. in toluene) (0.060 g, 0.000664 mol) at −30° C. and the reaction mixture was allowed to stir at same temperature for 30 min and 1.5 h at 0° C. After completion of the reaction, the reaction mass quenched with saturated sodium bicarbonate solution and extracted with $CH_2C_2$ and the combined organic layer was dried over sodium sulphate, concentrated to afford crude product which was purified using column purification by eluting the compound with 25-35% ethyl acetate in hexanes to yield 130 mg of N-(1-(1-acryloylpiperidin-3-yl)-5-((N-((S)-3,3-dimethylbutan-2-yl)-2,2,2-trifluoroacetamido)-methyl)-1H-benzo[d]imidazol-2-yl)-4-chlorobenzamide. LC-MS (ES, m/z): 618.4 [M+H].

Example 35

Synthesis of 4-chloro-N-(1-((1-(2-cyano-4-methylpent-2-enoyl)pyrrolidin-2-yl)methyl)-5-((N-((S)-3,3-dimethylbutan-2-yl)-2,2,2-trifluoroacetamido)methyl)-1H-benzo[d]imidazol-2-yl)benzamide

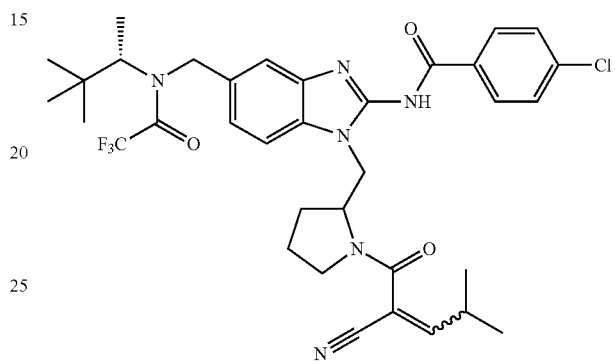

Step 1

To a 100 mL three necked round bottom flask under nitrogen atmosphere were added tert-butyl2-((4-(((S)-3,3-dimethylbutan-2-ylamino)methyl)-2-nitrophenylamino) methyl)pyrrolidine-1-carboxylate (5.0 g, 0.0023 mole), pyridine (1.11 mL, 0.0027 mole) in DCM (50 mL) and cooled it to 0° C. Trifluoroacetic anhydride (2.41 mL, 0.0034 mmole) was added dropwise to the cooled reaction mixture and then allowed it to warm up to room temperature. The reaction mixture was stirred at room temperature for 1 h. After completion of the reaction, the reaction mixture was washed with 10% HCl solution followed by saturated $NaHCO_3$ solution). The organic layer was dried over sodium sulphate, concentrated to give the crude product which was purified using column purification by eluting the compound with 5% ethyl acetate in hexanes to yield 4.9 g of tert-butyl 2-((4-((N-((S)-3,3-dimethylbutan-2-yl)-2,2,2-trifluoroacetamido)methyl)-2-nitrophenylamino)-methyl)pyrrolidine-1-carboxylate.

Step 2

To a 100 mL three necked round bottom flask were added tert-butyl 2-((4-((N-((S)-3,3-dimethylbutan-2-yl)-2,2,2-trifluoroacetamido)methyl)-2-nitrophenylamino)methyl)pyrrolidine-1-carboxylate (4.9 g, 0.0097 mole), 10% Pd/C (0.5 g, 0.1 times) in methanol (50 mL) followed by $H_2$ purging at room temperature for 2 h with stirring. The reaction mixture was stirred at room temperature for 1 h. After completion of the reaction, the reaction mixture was filtered through celite bed; washed with methanol and filtrate was concentrated to give the crude product which was purified using column purification by eluting the compound with 5% ethyl acetate in hexanes to yield 4.1 g of tert-butyl2-((2-amino-44((N-((S)-3,3-dimethylbutan-2-yl)-2,2,2-trifluoroacetamido)-methyl)phenylamino)methyl)pyrrolidine-1-carboxylate.

Step 3

To a 250 mL three necked round bottom flask under nitrogen atmosphere were added tert-butyl 2-((2-amino-4-((N-((S)-3,3-dimethylbutan-2-yl)-2,2,2-trifluoroacetamido)

methyl)phenyl-amino)methyl)-pyrrolidine-1-carboxylate (4.1 g, 0.0081 mole) in ethanol (80 mL) followed by addition of cyanogen bromide (1.04 g, 0.0098 mole) at room temperature and stirred at same temperature for 1 hr. After completion of the reaction, the reaction mixture was concentrated under vacuum and diluted with saturated NaHCO$_3$ solution and extracted with ethyl acetate. The combined organic layer was dried over sodium sulphate, concentrated to give the crude product which was purified using column purification by eluting the compound with 1.5-2.0% methanol in chloroform to yield 3.7 g of tert-butyl 2-((5-((N-((S)-3,3-dimethylbutan-2-yl)-2,2,2-trifluoroacetamido)methyl)-2-imino-2,3-dihydro-1H-benzo[d]imidazol-1-yl)methyl) pyrrolidine-1-carboxylate.

Step 4

To a 250 mL three necked round bottom flask under nitrogen atmosphere were added 4-chlorobenzoic acid (1.32 g, 0.0084 mole) in DCM (80 mL) followed by addition of EDC.HCl (2.02 g, 0.0105 mole), HOBt (1.62 g, 0.0105 mole) and TEA (2.94 mL, 0.0211 mole) and stirred at room temperature for 10 min. tert-Butyl 2-((5-((N-((S)-3,3-dimethylbutan-2-yl)-2,2,2-trifluoro-acetamido)methyl)-2-imino-2,3-dihydro-1H-benzo[d]imidazol-1-yl)methyl)-pyrrolidine-1-carboxylate (3.70 g, 0.0070 mole) was added to a reaction mixture and stirred it at room temperature for 12 h. After completion of the reaction, the reaction mixture was washed with saturated NaHCO$_3$ solution. The organic layer was dried over sodium sulphate, concentrated to give the crude product which was purified using column purification by eluting the compound with 20% ethyl acetate in hexanes to yield 3.6 g of tert-butyl 2-((2-(4-chlorobenzamido)-5-((N-((S)-3,3-dimethylbutan-2-yl)-2,2,2-trifluoroacetamido) methyl)-1H-benzo[d]imidazol-1-yl)methyl)pyrrolidine-1-carboxylate.

Step 5

To a 250 mL three necked round bottom flask under nitrogen atmosphere were added tert-butyl 2-((2-(4-chlorobenzamido)-5-((N-((S)-3,3-dimethylbutan-2-yl)-2,2,2-trifluoroacetamido)-methyl)-1H-benzo[d]imidazol-1-yl) methyl)pyrrolidine-1-carboxylate (3.40 g, 0.0052 mole) and 20% HCl in dioxane (70 mL) and stirred at room temperature for 2 h. After completion of the reaction, the reaction mixture was concentrated to dryness; ethyl acetate was added the reaction mixture was stirred it at 40° C. for 15 min and then filtered the solid under vacuum. The resultant solid was washed with diethyl ether and dried under vacuum to yield 2.8 g of 4-chloro-N-(5-((N-((S)-3,3-dimethylbutan-2-yl)-2,2,2-trifluoroacetamido)methyl)-1-(pyrrolidin-2-ylmethyl)-1H-benzo[d]-imidazol-2-yl)benzamide hydrochloride.

Step 6

To a 50 mL three necked round bottom flask under nitrogen atmosphere were added 2-cyanoacetic acid (77 mg, 0.0009158 mole) in DMF (11 mL) followed by addition of HATU (552 mg, 0.0013737 mole) and stirred at room temperature for 30 min. 4-Chloro-N-(5-((N-((S)-3,3-dimethylbutan-2-yl)-2,2,2-trifluoroacetamido)methyl)-1-(pyrrolidin-2-ylmethyl)-1H-benzo[d]imidazol-2-yl)benzamide hydrochloride (550 mg, 0.0009158 mole) and DIEA (0.63 mL, 0.0036633 mole) were added to a reaction mixture and the reaction mixture was stirred at room temperature for 12 h. The reaction mixture was diluted with saturated NaHCO$_3$ solution and extracted with ethyl acetate. The combined organic layer was washed with cold water and brine. The organic layer was dried over sodium sulphate, concentrated to give the crude product which was purified using column purification by eluting with 60-70% ethyl acetate in hexanes to yield 400 mg 4-chloro-N-(1-((1-(2-cyanoacetyl)pyrrolidin-2-yl)methyl)-5-((N-((S)-3,3-dimethylbutan-2-yl)-2,2,2-trifluoroacetamido)methyl)-1H-benzo[d]imidazol-2-yl)benzamide.

Step 7

To a 10 mL sealed tube were added 4-chloro-N-(1-((1-(2-cyanoacetyl)pyrrolidin-2-yl)methyl)-5-((N-((S)-3,3-dimethylbutan-2-yl)-2,2,2-trifluoroacetamido)methyl)-1H-benzo[d]imidazol-2-yl)benzamide (150 mg, 0.000237 mole), isobutaraldehyde (0.07 mL, 0.000713 mole), 3.3M solution of piperidine acetate in water (0.21 mL, 0.000713 mole) and ethanol (5 mL). The reaction mixture was heated in a seal tube at 80° C. for 2 h. After completion of the reaction, the reaction mixture was poured in water and extracted with ethyl acetate. The combined organic layer was washed with brine. The organic layer was dried over sodium sulphate, concentrated to give the crude product which was purified using column purification by eluting with 0.5-1.0% methanol in chloroform to yield 24 mg 4-chloro-N-(1-((1-(2-cyano-4-methylpent-2-enoyl)pyrrolidin-2-yl)methyl)-5-((N-((S)-3,3-dimethylbutan-2-yl)-2,2,2-trifluoroacetamido)methyl)-1H-benzo[d]-imidazol-2-yl) benzamide. LC-MS (ES, m/z): 685 [M+H].

Example 36

Synthesis of N-(1-((1-acryloylpyrrolidin-2-yl) methyl)-5-((N-((S)-3,3-dimethylbutan-2-yl)-2,2,2-trifluoroacetamido)methyl)-1H-benzo[d]imidazol-2-yl)-4-chlorobenzamide

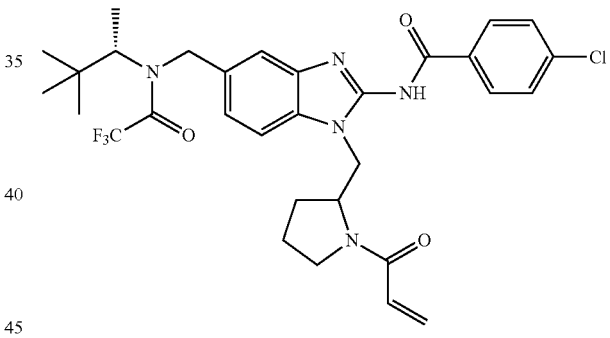

To a 25 mL three necked round bottom flask under nitrogen atmosphere were added 4-chloro-N-(5-((N-((S)-3,3-dimethylbutan-2-yl)-2,2,2-trifluoroacetamido)methyl)-1-(pyrrolidin-2-ylmethyl)-1H-benzo[d]imidazol-2-yl)benzamide (200 mg, 0.000333 mole) in THF (5 mL) and cooled to −30° C. 50% Solution of acryloyl chloride in toluene (0.1 mL, 0.000299 mole) was added and the reaction mixture was allowed it to warm up to room temperature and stirred for 2 h. After completion of the reaction, the reaction mixture was diluted with saturated NaHCO$_3$ solution and extracted with ethyl acetate. The combined organic layer was dried over sodium sulphate, concentrated to give the crude product which was dissolved in THF (2 mL) followed by addition of DBU (151 mg, 0.000999 mole) and the reaction mixture stirred it at room temperature overnight and then purified using column purification by eluting with 30% ethyl acetate in hexanes to yield 110 mg N-(1-((1-acryloylpyrrolidin-2-yl)methyl)-5-((N-((S)-3,3-dimethylbutan-2-yl)-2,2,2-trifluoroacetamido)methyl)-1H-benzo[d]imidazol-2-yl)-4-chlorobenzamide. LC-MS (ES, m/z): 618.3 [M+H].

Example 37

Synthesis of 4-chloro-N-(1-((1-(2-cyano-4-methyl-pent-2-enoyl)pyrrolidin-2-yl)methyl)-5-((((S)-3,3-dimethylbutan-2-yl)(methyl)amino)methyl)-1H-benzo[d]imidazol-2-yl)benzamide

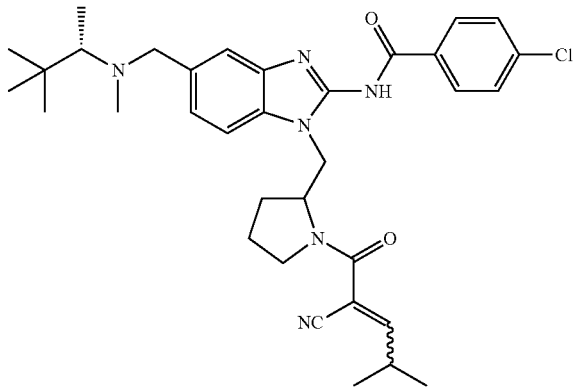 [SMILES: CC(C)C=C(C#N)C(=O)N1CCCC1Cn1c(NC(=O)c2ccc(Cl)cc2)nc2cc(CN(C)[C@@H](C)C(C)(C)C)ccc21]

Step 1

To a 50 mL three necked round bottom flask under nitrogen atmosphere were added NaBH$_4$ (683 mg, 0.0212 mole) in ethanol (10 mL) at room temperature followed by addition of tert-butyl 2-((2-(4-chlorobenzamido)-5-((N-((S)-3,3-dimethylbutan-2-yl)-2,2,2-trifluoroacetamido)methyl)-1H-benzo[d]imidazol-1-yl)methyl)pyrrolidine-1-carboxylate (800 mg, 0.0014 mole) in ethanol (5 mL) at room temperature. The reaction mixture was stirred at room temperature for 4 h. After completion of the reaction, the reaction mixture was concentrated and diluted with water and extracted with ethyl acetate. The combined organic layer was washed with brine. The organic layer was dried over sodium sulphate, concentrated to give the crude product which was purified using column purification by eluting with 1-3% methanol in chloroform to yield 500 mg of tert-butyl 2-((2-(4-chlorobenzamido)-5-(((S)-3,3-dimethylbutan-2-ylamino)methyl)-1H-benzo[d]Imidazol-1-yl)methyl)pyrrolidine-1-carboxylate.

Step 2

To a 35 mL seal tube under nitrogen atmosphere were added tert-butyl 2-((2-(4-chlorobenzamido)-5-(((S)-3,3-dimethylbutan-2-ylamino)methyl)-1H-benzo[d]imidazol-1-yl)methyl)pyrrolidine-1-carboxylate (350 mg, 0.0006 mole), paraformaldehyde (37 mg, 0.0012 mole), acetic acid (0.1 mL) and THF at room temperature. The reaction mixture was heated at 80° C. for 2 h in a sealed tube, and then NaBH(OAc)$_3$ (391 mg, 0.0018 mole) was added to reaction mixture and heating continued at 80° C. for 30 min After completion of the reaction, the reaction mixture was poured in water and extracted with ethyl acetate. The combined organic layer was washed with brine. The organic layer was dried over sodium sulphate, concentrated to give the crude product which was purified using column purification by eluting the compound with 40% ethyl acetate in hexanes to yield 140 mg of tert-butyl 2-((2-(4-chlorobenzamido)-5-((((S)-3,3-dimethylbutan-2-yl)(methyl)amino)methyl)-1H-benzo[d]imidazol-1-yl)methyl)pyrrolidine-1-carboxylate.

Step 3

To a 10 mL one necked round bottom flask under nitrogen atmosphere were added tert-butyl 2-((2-(4-chlorobenzamido)-5-((((S)-3,3-dimethylbutan-2-yl)(methyl)amino)methyl)-1H-benzo[d]imidazol-1-yl)methyl)pyrrolidine-1-carboxylate (140 mg, 0.000240 mole) in 20% HCl in dioxane (3 mL) and stirred at room temperature for 16 h. After completion of the reaction, the reaction mixture was concentrated to dryness, the resultant solid was triturated with ethyl acetate and pentane and then dried under vacuum to yield 95 mg of 4-chloro-N-(5((((S)-3,3-dimethylbutan-2-yl)(methyl)amino)methyl)-1-(pyrrolidin-2-ylmethyl)-1H-benzo[d]imidazol-2-yl)benzamide hydrochloride.

Step 4

To a 10 mL one necked round bottom flask under nitrogen atmosphere were added 2-cyanoacetic acid (25 mg, 0.000183 mole) in DMF (2 mL) followed by addition of HATU (112 mg, 0.000274 mole) and stirred at room temperature for 30 min. 4-Chloro-N-(5((((S)-3,3-dimethylbutan-2-yl)(methyl)amino)methyl)-1-(pyrrolidin-2-ylmethyl)-1H-benzo[d]imidazol-2-yl)benzamide hydrochloride (95 mg, 0.000183 mole) and DIEA (0.13 mL, 0.000732 mole) were added to a reaction mixture and the reaction mixture was stirred at room temperature for 16 h. The reaction mixture was diluted with saturated NaHCO$_3$ solution and extracted with ethyl acetate. The combined organic layer was washed with cold water and brine solution. The organic layer was dried over sodium sulphate, concentrated to give the crude product which was purified using column purification by eluting with 0.5% methanol in chloroform to yield 60 mg 4-chloro-N-(1-((1-(2-cyanoacetyl)pyrrolidin-2-yl)methyl)-5-((((S)-3,3-dimethylbutan-2-yl)(methyl)amino)methyl)-1H-benzo[d]imidazol-2-yl)benzamide.

Step 5

To a 10 mL seal tube were 4-chloro-N-(1-((1-(2-cyano-acetyl)pyrrolidin-2-yl)methyl)-5-((((S)-3,3-dimethylbutan-2-yl)(methyl)amino)methyl)-1H-benzo[d]imidazol-2-yl)benzamide (60 mg, 0.109 mmole), isobutaraldehyde (0.03 mL, 0.3278 mmole), 3.3 M solution of piperidine acetate in water (0.1 mL, 0.0003278 mole) and ethanol (2 mL). The reaction mixture was heated in a sealed tube at 80° C. for 2 h. After completion of the reaction, the reaction mixture was poured in to water and extracted with ethyl acetate. The combined organic layer was washed with brine. The organic layer was dried over sodium sulphate, concentrated to give the desired crude product which was purified using column purification by eluting the compound with 0.5-1.0% methanol in chloroform to yield 13 mg 4-chloro-N-(1-((1-(2-cyano-4-methylpent-2-enoyl)pyrrolidin-2-yl)methyl)-5-((((S)-3,3-dimethylbutan-2-yl)(methyl)amino)methyl)-1H-benzo[d]imidazol-2-yl)benzamide. LC-MS (ES, m/z): 504.3 [M+H].

Example 38

Synthesis of 4-chloro-N-(1-(1-(2-cyano-4-methyl-pent-2-enoyl)piperidin-3-yl)-5-((((S)-3,3-dimethylbutan-2-yl)(methyl)amino)methyl)-1H-benzo[d]imidazol-2-yl)benzamide

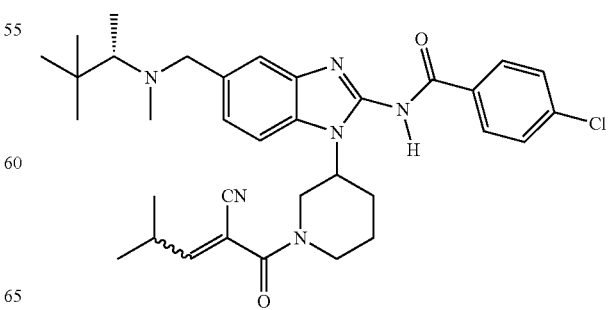

The title compound was prepared using the procedure in example 27 but substituting tert-butyl 3-(2-(4-chlorobenzamido)-5-((N-((S)-3,3-dimethylbutan-2-yl)-2,2,2-trifluoroacetamido)-methyl)-1H-benzo[d]imidazol-1-yl)piperidine-1-carboxylate for tert-butyl 2-((2-(4-chlorobenzamido)-5-((N-((S)-3,3-dimethylbutan-2-yl)-2,2,2-trifluoroacetamido)methyl)-1H-benzo[d]imidazol-1-yl)methyl)pyrrolidine-1-carboxylate. Similarly, 4-chloro-N-(1-(1-(2-cyanoacetyl)piperidin-3-yl)-5-((((S)-3,3-dimethylbutan-2-yl)(methyl)amino)methyl)-1H-benzo[d]imidazol-2-yl)benzamide was prepared. LC-MS (ES, m/z): 603.2 [M+H].

Example 39

Synthesis of N-(1-(1-(2-cyano-4-(dimethylamino)-4-methylpent-2-enoyl)piperidin-3-yl)-1H-benzo[d]imidazol-2-yl)-5-(1H-pyrazol-4-yl)thiophene-2-carboxamide

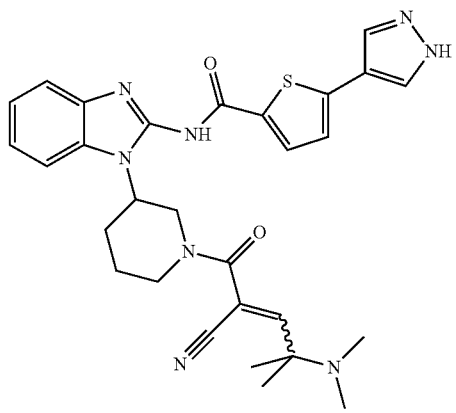 [SMILES: CN(C)C(C)(C)C=C(C#N)C(=O)N1CCCC(n2c(NC(=O)c3ccc(-c4cn[nH]c4)s3)nc3ccccc32)C1]

Step 1

To a 35 mL seal-tube, 5-bromothiophene-2-carboxylic acid (1.7 g, 0.0082 mole) was taken in CH$_2$Cl$_2$ (20 mL), and tert-butyl 3-(2-imino-2,3-dihydro-1H-benzo[d]imidazol-1-yl)piperidine-1-carboxylate (2.85 g, 0.0090 mole), DIPEA (4.28 mL, 0.0246 mole) and DMAP (0.097 g, 0.0008 mole) were added to it followed by drop-wise addition of T3P (7.8 mL, 0.0123 mole) to reaction mixture at RT and stirred for 1 h. The completion of the reaction was monitored on TLC using EtOAc: hexanes (4:6) as a mobile phase. Water was added to the reaction mixture and extracted with CH$_2$Cl$_2$. The combined organic layer was dried over Na$_2$SO$_4$ and evaporated to get the crude product which was subjected for the column purification. The crude compound was purified by column purification using 60-120 mesh size neutral silica by eluting the compound with 20-25% EtOAc in hexanes to yield 1.2 g of tert-butyl 3-(2-(5-bromothiophene-2-carboxamido)-1H-benzo[d]imidazol-1-yl)piperidine-1-carboxylate.

Step 2

In a 150 mL seal tube, to a solution of tert-butyl 3-(2-(5-bromothiophene-2-carboxamido)-1H-benzo[d]imidazol-1-yl)piperidine-1-carboxylate (1 g, 0.00198 mole), tert-butyl 4-(4,4,5,5-tetramethyl-1,3,2-dioxaborolan-2-yl)-1H-pyrazole-1-carboxylate (0.641 g, 0.00218 mole) in 1,4-dioxane (40 mL) and water (10 mL), Cs$_2$CO$_3$ (0.71 g, 0.00218 mole) was added and degassed for 15 min using N$_2$. Bis(tri-t-butylphophine)Pd(0) (0.101 g, 0.000198 mole) was added and the reaction was carried out under N$_2$ atmosphere at 80° C. for 2 h. After completion of the reaction, the reaction mixture was diluted with water and extracted with EtOAc. The organic layers were combined washed with brine, dried and concentrated to get the crude product which was purified by column chromatography using 60-120 mesh size neutral silica by eluting with 14-15% EtOAc in hexanes to yields a mixture of tert-butyl 3-(2-(5-(1H-pyrazol-4-yl)thiophene-2-carboxamido)-1H-benzo[d]imidazol-1-yl)piperidine-1-carboxylate and tert-butyl 3-(2-(5-(1-(tert-butoxycarbonyl)-1H-pyrazol-4-yl)thiophene-2-carboxamido)-1H-benzo[d]imidazol-1-yl)piperidine-1-carboxylate.

Step 3

Tert-butyl 3-(2-(5-(1H-pyrazol-4-yl)thiophene-2-carboxamido)-1H-benzo[d]imidazol-1-yl)piperidine-1-carboxylate (1.5 g, 0.00304 mole) was taken in CH$_2$Cl$_2$ (25 mL) and cooled to 0-5° C. TFA (14 mL) was added drop wise at 0-5° C. and the reaction mixture was stirred for 4 h at room temperature. After completion of the reaction, the reaction mixture was poured in to NaHCO$_3$ solution and extracted with EtOAc. The combined organics were washed with water. The organic layer was separated and dried over sodium sulphate, concentrated to yield 0.95 g of N-(1-(piperidin-3-yl)-1H-benzo[d]imidazol-2-yl)-5-(1H-pyrazol-4-yl)thiophene-2-carboxamide.

Step 4

To a 25 mL RBF, 2-cyanoacetic acid (0.095 g, 0.00112 mole) was taken in CH$_2$Cl$_2$ (8 mL) and cooled to 0° C. under N$_2$ atmosphere. TBTU (0.359 g, 0.00112 mole) and DMF (0.04 mL) was added at 0° C. After addition was complete the reaction mixture was allowed to warm to room temperature. N-(1-(piperidin-3-yl)-1H-benzo[d]imidazol-2-yl)-5-(1H-pyrazol-4-yl)thiophene-2-carboxamide (0.4 g, 0.00101 mole) and DIPEA (0.52 mL, 0.00243 mole) were added to the reaction mixture and stirred at room temperature for 16 h. After completion of the reaction, water was added to the reaction mixture and extracted with CH$_2$Cl$_2$. The combined organic layer was dried over Na$_2$SO$_4$ and evaporated to get the crude product which was purified using column purification using 60-120 mesh size neutral silica by eluting the compound with 2-3% methanol in CH$_2$Cl$_2$ to yield 0.13 g of N-(1-(1-(2-cyanoacetyl)piperidin-3-yl)-1H-benzo[d]imidazol-2-yl)-5-(1H-pyrazol-4-yl)thiophene-2-carboxamide.

Step 5

To a 10 mL sealed tube, N-(1-(1-(2-cyanoacetyl) piperidin-3-yl)-1H-benzo[d]imidazol-2-yl)-5-(1H-pyrazol-4-yl)thiophene-2-carboxamide (0.105 g, 0.00023 mole) was taken in ethanol (0.6 mL). Piperidine (0.07 mL, 0.00069 mole) and 2-(dimethylamino)-2-methylpropanal (0.065 g, 0.00057 mole) were added at room temperature and the reaction mixture was heated to reflux for 8 h. After completion of the reaction, ethanol was evaporated and water was added to the reaction mixture and extracted with EtOAc. The combined organic layer was washed with water, brine, dried over Na$_2$SO$_4$ and evaporated to get the crude which was purified by prep HPLC to yield 0.022 g of N-(1-(1-(2-cyano-4-(dimethylamino)-4-methylpent-2-enoyl)piperidin-3-yl)-1H-benzo[d]imidazol-2-yl)-5-(1H-pyrazol-4-yl)thiophene-2-carboxamide. LC-MS (ES, m/z): 557.6 [M+H].

Example 40

Synthesis of N-(1-(1-(2-cyano-4-methylpent-2-enoyl)piperidin-3-yl)-1H-benzo[d]imidazol-2-yl)-5-(1H-pyrazol-4-yl)thiophene-2-carboxamide

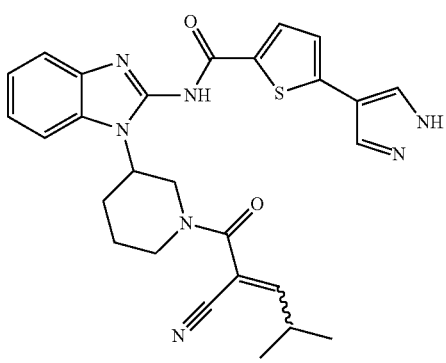 [SMILES: CC(C)C=C(C#N)C(=O)N1CCCC(n2c(NC(=O)c3ccc(/C(C=N)=C/N)s3)nc3ccccc32)C1]

To a 10 mL vial, N-(1-(1-(2-cyanoacetyl)piperidin-3-yl)-1H-benzo[d]imidazol-2-yl)-5-(1H-pyrazol-4-yl)thiophene-2-carboxamide (0.12 g, 0.00026 1 mole) was taken in ethanol (3 mL). Piperidine acetate (3.3M solution in water) (0.236 mL, 0.000783 mole) and isobutyraldehyde (0.026 mL, 0.000287 mole) were added at room temperature and the reaction mixture was heated to reflux for 1 h. After completion of the reaction, ethanol was evaporated and water was added to the reaction mixture and extracted with EtOAc. The combined organic layer was washed with water brine, dried over Na$_2$SO$_4$ and evaporated to get the crude which was purified by prep HPLC to yield 0.026 g of N-(1-(1-(2-cyano-4-methylpent-2-enoyl) piperidin-3-yl)-1H-benzo[d]imidazol-2-yl)-5-(1H-pyrazol-4-yl)thiophene-2-carboxamide. LC-MS (ES, m/z): 514.2 [M+H].

Example 41

Synthesis of N-(1-(1-acryloylpiperidin-3-yl)-1H-benzo[d]imidazol-2-yl)-5-(1H-pyrazol-4-yl)thiophene-2-carboxamide

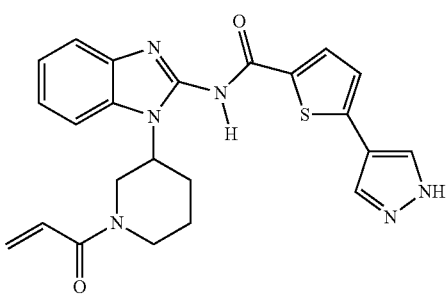 [SMILES: C=CC(=O)N1CCCC(n2c(NC(=O)c3ccc(-c4cn[nH]c4)s3)nc3ccccc32)C1]

To a 10 mL vial, N-(1-(piperidin-3-yl)-1H-benzo[d]imidazol-2-yl)-5-(1H-pyrazol-4-yl)thiophene-2-carboxamide (0.1 g, 0.00025 mole) was taken in THF (3 mL) and cooled to −50° C. under N$_2$ atmosphere. Acryloyl chloride (50% solution in toluene) (0.049 mL, 0.00027 mole) was added dropwise at −50° C. and the reaction mixture was stirred for 15 minutes at −50° C., and at RT for 30 min After completion of the reaction, 40% NaOH solution was added drop wise to make pH basic and extracted with EtOAc. The combined organic layer was dried over Na$_2$SO$_4$ and evaporated to get the crude which purified by Prep TLC in 50% EtOAc in hexanes to yield 0.030 g of N-(1-(1-acryloylpiperidin-3-yl)-1H-benzo[d]imidazol-2-yl)-5-(1H-pyrazol-4-yl)thiophene-2-carboxamide. LC-MS (ES, m/z): 447.3 [M+H].

Example 42

Synthesis of N-(1-(1-(4-(dimethylamino)but-2-enoyl)piperidin-3-yl)-1H-benzo[d]imidazol-2-yl)-5-(1H-pyrazol-4-yl)thiophene-2-carboxamide

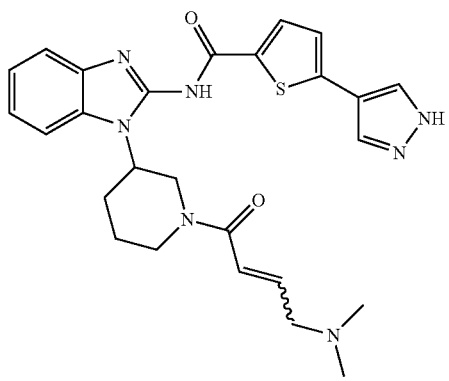 [SMILES: CN(C)CC=CC(=O)N1CCCC(n2c(NC(=O)c3ccc(-c4cn[nH]c4)s3)nc3ccccc32)C1]

To a 10 mL seal tube under nitrogen atmosphere were added 4-(dimethylamino)but-2-enoic acid (0.032 g, 0.00025 mole) in DMF (3 mL) followed by addition of HATU (0.131 g, 0.00034 mole) and the reaction mixture stirred at room temperature for 15 min. N-(1-(Piperidin-3-yl)-1H-benzo[d]imidazol-2-yl)-5-(1H-pyrazol-4-yl)thiophene-2-carboxamide (0.09 g, 0.00023 mole) and DIPEA (0.11 mL, 0.00069 mole) were added to the reaction mixture and stirred at room temperature for 2 h. The reaction was monitored on TLC using MeOH: CH$_2$Cl$_2$ (0.5:9.5) as a mobile phase. After 2 h, the reaction mixture was diluted with saturated NaHCO$_3$ solution and extracted with EtOAc. The combined organic layer was washed with cold water and brine solution. The organic layer was dried over sodium sulphate and concentrated to give the crude product which was purified using column purification by eluting with 0.5% methanol in CH$_2$Cl$_2$ to yield 0.020 g N-(1-(1-(4-(dimethylamino)but-2-enoyl)piperidin-3-yl)-1H-benzo[d]imidazol-2-yl)-5-(1H-pyrazol-4-yl)-thiophene-2-carboxamide. LC-MS (ES, m/z): 504.3 [M+H].

Example 43

Synthesis of N-(1-((1-(2-cyano-4-methylpent-2-enoyl)azetidin-3-yl)methyl)-1H-benzo[d]imidazol-2-yl)-5-(1H-pyrazol-4-yl)thiophene-2-carboxamide

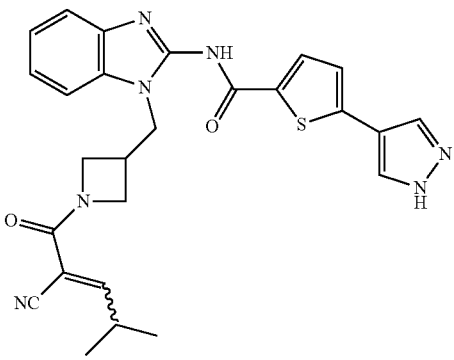 [SMILES: CC(C)C=C(C#N)C(=O)N1CC(Cn2c(NC(=O)c3ccc(-c4cn[nH]c4)s3)nc3ccccc32)C1]

Step 1

Into a 20-mL round-bottom flask, was placed 1-fluoro-2-nitrobenzene (197.4 mg, 1.40 mmol, 1.00 equiv), tert-butyl 3-(aminomethyl)azetidine-1-carboxylate (260.4 mg, 1.40 mmol, 1.00 equiv), potassium carbonate (386.4 mg, 2.80 mmol, 2.00 equiv) and MeCN (10 mL). The resulting solution was stirred overnight at 80° C. The resulting mixture was concentrated under vacuum and then diluted with 10 mL of water. The resulting solution was extracted with ethyl acetate and the organic layers combined, washed with brine and then dried over anhydrous sodium sulfate and concentrated under vacuum. The residue was applied onto a silica gel column with ethyl acetatepetroleum ether (30:1 to 5:1). This resulted in 400 mg (93%) of tert-butyl 3-[[(2-nitrophenyl)amino]methyl]-azetidine-1-carboxylate as a yellow solid.

Step 2

Into a 250-mL round-bottom flask, was placed tert-butyl 3-[[(2-nitrophenyl)amino]methyl]-azetidine-1-carboxylate (5.8 g, 18.87 mmol, 1.00 equiv), palladium on carbon (2.9 g) and ethanol (150 mL). $H_2$ (gas) was introduced into the reaction vessel and the resulting solution was stirred overnight at 25° C. The solids were then filtered out and the resulting mixture was concentrated under vacuum. The resulting residue was diluted with sodium carbonate (sat.) and extracted with dichloromethane. The organic layers were combined, washed with brine and then dried with anhydrous sodium sulfate. After filtration and concentrated under vacuum, this resulted in 5.18 g (crude) of tert-butyl 3-[[(2-aminophenyl)amino]methyl]azetidine-1-carboxylate as a brown oil.

Step 3

Into a 250-mL round-bottom flask, was placed tert-butyl 3-[[(2-aminophenyl)amino]methyl]-azetidine-1-carboxylate (5.18 g, 18.68 mmol, 1.00 equiv), cyanogen bromide (2.08 g, 19.64 mmol, 1.05 equiv) and ethanol (100 mL). The resulting solution was stirred overnight at 25° C. and then concentrated under vacuum. The resulting residue was diluted with 100 mL of a sat.$Na_2CO_3$ solution and extracted with ethyl acetate. The organic layers were combined, washed with brine and then dried with anhydrous sodium sulfate, filtrated and concentrated under vacuum, to give 4.5 g of tert-butyl 3-[(2-amino-1H-1,3-benzodiazol-1-yl)methyl]azetidine-1-carboxylate as a light yellow solid.

Step 4

Into a 250-mL round-bottom flask, was placed tert-butyl 3-[(2-amino-1H-1,3-benzodiazol-1-yl)methyl]azetidine-1-carboxylate (3.5 g, 11.58 mmol, 1.00 equiv), 5-bromothiophene-2-carboxylic acid (4.6 g, 22.22 mmol, 1.92 equiv), PyBop (11.6 g, 22.35 mmol, 1.93 equiv), N,N-dimethylformamide (150 mL) and triethylamine (7.524 g, 74.50 mmol, 6.44 equiv). The resulting solution was stirred overnight at 25° C. and then quenched with water. This was extracted with dichloromethane and the organic layers were combined, washed with brine and dried over anhydrous sodium sulfate. Filtration and concentration of the organics under vacuum, resulted in 4.7 g of tert-butyl 3-[[2-(5-bromothiophene-2-amido)-1H-1,3-benzodiazol-1-yl]methyl]azetidine-1-carboxylate as a light yellow solid.

Step 5

Into a 50-mL round-bottom flask, was placed tert-butyl 3-[[2-(5-bromothiophene-2-amido)-1H-1,3-benzodiazol-1-yl]methyl]azetidine-1-carboxylate (4.7 g, 9.56 mmol, 1.00 equiv), tert-butyl 4-(tetramethyl-1,3,2-dioxaborolan-2-yl)-1H-pyrazole-1-carboxylate (3.67 g, 12.48 mmol, 1.30 equiv), potassium carbonate (3.974 g, 28.80 mmol, 3.01 equiv), 1,4-dioxane (120 mL), water (30 mL) and Pd(dppf)$Cl_2$ (784 mg, 0.96 mmol, 0.10 equiv). The resulting solution was stirred overnight at 100° C. and then the solids were filtered out. The resulting solution was diluted with water and extracted with ethyl acetate. The organic layers were combined, washed with brine and then dried over anhydrous sodium sulfate. After filtration and concentrated under vacuum, the residue was applied onto a silica gel column and eluted with ethyl acetatepetroleum ether (1:30 to 1:1) to give 1.68 g of tert-butyl 3-([2-[5-(1H-pyrazol-4-yl)thiophene-2-amido]-1H-1,3-benzodiazol-1-yl]methyl)-azetidine-1-carboxylate as a light yellow solid.

Step 6

Into a 50-mL round-bottom flask, was placed tert-butyl 3-([2-[5-(1H-pyrazol-4-yl)thiophene-2-amido]-1H-1,3-benzodiazol-1-yl]methyl)azetidine-1-carboxylate (250 mg, 0.52 mmol, 1.00 equiv), dichloromethane (15 mL) and trifluoroacetic acid (3 mL). The resulting solution was stirred for 4 h at 25° C. and then concentrated under vacuum to give 250 mg (crude) of N-[1-(azetidin-3-ylmethyl)-1H-1,3-benzodiazol-2-yl]-5-(1H-pyrazol-4-yl)thiophene-2-carboxamide as a brown oil.

Step 7

Into a 250-mL round-bottom flask, was placed N-[1-(azetidin-3-ylmethyl)-1H-1,3-benzodiazol-2-yl]-5-(1H-pyrazol-4-yl)thiophene-2-carboxamide (89 mg, 0.24 mmol, 1.00 equiv), 2-cyanoacetic acid (26.8 mg, 0.32 mmol, 1.34 equiv), HATU (119 mg), N,N-dimethylformamide (5 mL) and TEA (106 mg). The resulting solution was stirred overnight at room temperature and then diluted with $H_2O$. The resulting solution was extracted with ethyl acetate and the organic layers combined, dried over anhydrous sodium sulfate, filtered and concentrated under vacuum to give 30 mg of N-(1-[[1-(2-cyanoacetyl)azetidin-3-yl]methyl]-1H-1,3-benzodiazol-2-yl)-5-(1H-pyrazol-4-yl)thiophene-2-carboxamide as a light green solid.

Step 8

Into a 50-mL round-bottom flask purged and maintained with an inert atmosphere of nitrogen, was placed N-(1-[[1-(2-cyanoacetyl)azetidin-3-yl]methyl]-1H-1,3-benzodiazol-2-yl)-5-(1H-pyrazol-4-yl)thiophene-2-carboxamide (110 mg, 0.25 mmol, 1.00 equiv), dichloromethane (10 mL), methanol (10 mL), piperidine (63 mg) and 2-methylpropanal (89 mg, 1.23 mmol, 5.00 equiv). The resulting solution was stirred overnight at room temperature and then concentrated under vacuum. The crude product (55 mg) was purified by Prep-HPLC with the following conditions (1#-Pre-HPLC-005(Waters)): Column, SunFire Prep C18 19*150 mm 5 um; mobile phase, water with 0.05% TFA and CH$_3$CN (10% CH$_3$CN up to 40% in 10 min); Detector, 254 nm. This resulted in 15.1 mg (12%) of N-[1-([1-[(2E)-2-cyano-2-(2-methylpropylidene)acetyl]azetidin-3-yl]methyl)-1H-1,3-benzodiazol-2-yl]-5-(1H-pyrazol-4-yl)thiophene-2-carboxamide as a white solid. LC-MS m/z: 500 (M+1).

Example 44

Synthesis of N-(1-[[(2R)-1-[2-cyano-2-[2-methyl-2-(morpholin-4-yl) propylidene]acetyl]-pyrrolidin-2-yl]methyl]-1H-1,3-benzodiazol-2-yl)-5-(1H-pyrazol-4-yl)thiophene-2-carboxamide

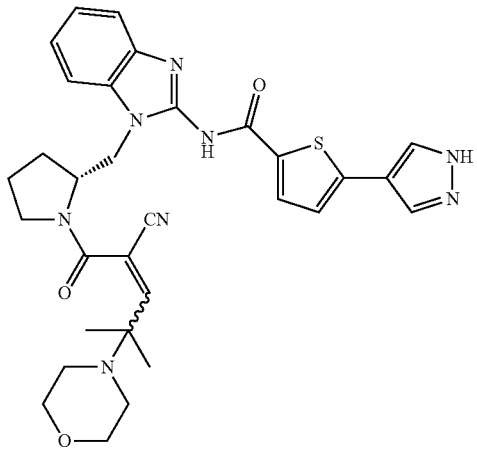 [SMILES: CC(C)(C=C(C#N)C(=O)N1CCC[C@@H]1Cn1c(NC(=O)c2ccc(-c3cn[nH]c3)s2)nc2ccccc21)N1CCOCC1]

Step 1

Into a 1-L round-bottom flask, was placed a solution of 1-fluoro-2-nitrobenzene (8.1 g, 57.41 mmol, 1.10 equiv), CH$_3$CN (500 mL), potassium carbonate (14.4 g, 104.19 mmol, 2.00 equiv) and tert-butyl (2R)-2-(aminomethyl)pyrrolidine-1-carboxylate (10 g, 49.93 mmol, 1.00 equiv). The resulting solution was stirred overnight at 80° C. in an oil bath. The reaction mixture was then quenched by the addition of water. The resulting solution was extracted with ethyl acetate and the organic layers combined and concentrated under vacuum. The residue was applied onto a silica gel column with ethyl acetatepetroleum ether (1:10) to give 6 g of tert-butyl (2R)-2-[[(2-nitrophenyl)amino]methyl]-pyrrolidine-1-carboxylate as a yellow oil.

Step 2

Into a 1-L round-bottom flask, was placed methanol (300 mL), palladium on carbon (1 g) and tert-butyl (2R)-2-[[(2-nitrophenyl)amino]methyl]pyrrolidine-1-carboxylate (6 g, 18.67 mmol, 1.00 equiv). The flask was evacuated and flushed three times with nitrogen, followed by flushing with H$_2$ (gas) and then stirred at 25° C. overnight. The solids were filtered out and the resulting mixture was concentrated under vacuum to give 4.9 g of tert-butyl (2R)-2-[[(2-aminophenyl)-amino]-methyl]-pyrrolidine-1-carboxylate as a red solid.

Step 3

Into a 1-L round-bottom flask, was placed a solution of tert-butyl (2R)-2-[[(2-aminophenyl)amino]-methyl]pyrrolidine-1-carboxylate (4.9 g, 16.82 mmol, 1.00 equiv), ethanol (500 mL) and cyanogen bromide (2 g, 18.88 mmol, 1.12 equiv). The resulting solution was stirred overnight at room temperature and then concentrated under vacuum. The residue was applied onto a silica gel column with dichloromethanemethanol (10:1). This resulted in 3 g of (R)-tert-butyl 2-((2-amino-1H-benzo[d]imidazol-1-yl)methyl)pyrrolidine-1-carboxylate as a red solid.

Step 4

Into a 1-L round-bottom flask, was placed a solution (R)-tert-butyl 2-((2-amino-1H-benzo[d]imidazol-1-yl) methyl)pyrrolidine-1-carboxylate (6.3 g, 21.62 mmol, 1.00 equiv), 5-bromothiophene-2-carboxylic acid (2.29 g, 21.62 mmol, 1.00 equiv), PyBop (6.6 g, 1.50 equiv), N,N-dimethylformamide (300 mL) and TEA (4.3 g, 42.49 mmol, 5.00 equiv). The resulting solution was stirred overnight at room temperature and then concentrated under vacuum. The residue was applied onto a silica gel column with dichloromethanemethanol (10:1). This resulted in 6.3 g of of (R)-tert-butyl 2-((2-(5-bromothiophene-2-carboxamido)-1H-benzo[d]imidazol-1-yl)methyl)pyrrolidine-1-carboxylate as a red solid.

Step 5

Into a 1-L round-bottom flask, was placed a solution of of (R)-tert-butyl 2-((2-(5-bromothiophene-2-carboxamido)-1H-benzo[d]imidazol-1-yl)methyl)pyrrolidine-1-carboxylate (4.3 g, 8.52 mmol, 1.00 equiv), 1,4-dioxane (400 mL), 4-(tetramethyl-1,3,2-dioxaborolan-2-yl)-1H-pyrazole (3 g, 15.46 mmol, 1.20 equiv), potassium carbonate (3.5 g, 25.36 mmol, 3.00 equiv) and Pd(dppf)Cl$_2$ (1.4 g, 1.72 mmol). The resulting solution was stirred overnight at 80° C. in an oil bath. The reaction mixture was then quenched by the addition of water and extracted with ethyl acetate. The organic layers were combined and dried over anhydrous sodium sulfate. The solids were filtered out and the resulting mixture was concentrated under vacuum. The residue was applied onto a silica gel column with ethyl acetatepetroleum ether (1:10). This resulted in 1 g of (R)-tert-butyl 2-((2-(5-(1H-pyrazol-4-yl)thiophene-2-carboxamido)-1H-benzo[d]imidazol-1-yl)methyl)pyrrolidine-1-carboxylate as a white solid.

Step 6

Into a 250-mL round-bottom flask, was placed a solution of (R)-tert-butyl 2-((2-(5-(1H-pyrazol-4-yl)thiophene-2-carboxamido)-1H-benzo[d]imidazol-1-yl)methyl)pyrrolidine-1-carboxylate (1 g, 2.03 mmol, 1.00 equiv), dichloromethane (100 mL) and trifluoroacetic acid (25 mL). The resulting solution was stirred for 4 h at room temperature. The resulting mixture was concentrated under vacuum. This resulted in 800 mg (crude) of (R)-5-(1H-pyrazol-4-yl)-N-(1-(pyrrolidin-2-ylmethyl)-1H-benzo[d]imidazol-2-yl)thiophene-2-carboxamideas an off-white solid.

Step 7

Into a 250-mL round-bottom flask, was placed 2-cyanoacetic acid (300 mg, 3.53 mmol, 2.00 equiv), HATU (1.36 g, 3.58 mmol, 2.00 equiv), triethylamine (900 mg, 8.91 mmol, 5.00 equiv), and a solution of (R)-5-(1H-pyrazol-4-yl)-N-(1-(pyrrolidin-2-ylmethyl)-1H-benzo[d]imidazol-2-yl)thiophene-2-carboxamide (700 mg, 1.78 mmol, 1.00 equiv) in N,N-dimethylformamide (100 mL). The resulting solution was stirred overnight at room temperature and then quenched by the addition of water. The solid was collected by filtration. This resulted in 0.65 g (crude) of N-(1-[[(2R)-1-(2-cyanoacetyl)pyrrolidin-2-yl]methyl]-1H-1,3-benzodiazol-2-yl)-5-(1H-pyrazol-4-yl)thiophene-2-carboxamide as an off-white solid.

Step 8

Into a 100-mL round-bottom flask, was placed a solution of N-(1-[[(2R)-1-(2-cyanoacetyl)pyrrolidin-2-yl]methyl]-

1H-1,3-benzodiazol-2-yl)-5-(1H-pyrazol-4-yl)thiophene-2-carboxamide (200 mg, 0.44 mmol, 1.00 equiv), DCM:MeOH (1:1) (50 mL), piperidine (111 mg, 1.30 mmol, 3.00 equiv) and 2-methyl-2-(morpholin-4-yl)propanal (341 mg, 2.17 mmol, 4.98 equiv). The resulting solution was stirred overnight at room temperature. The resulting mixture was concentrated under vacuum. The crude product (90 mg) was purified by Prep-HPLC with the following conditions (1#-Pre-HPLC-005(Waters)): Column, SunFire Prep C18 19*150 mm 5 um; mobile phase, WATER WITH 0.05% TFA and CH3CN (10% CH3CN up to 40% in 10 min); Detector, 254 nm. This resulted in 34 mg (13%) of N-(1-[[(2R)-1-[2-cyano-2-[2-methyl-2-(morpholin-4-yl) propylidene]acetyl]-pyrrolidin-2-yl]methyl]-1H-1,3-benzodiazol-2-yl)-5-(1H-pyrazol-4-yl)thiophene-2-carboxamide as a white solid. LC-MS: mz 599 (M+H+).

Example 45

Synthesis of (S)-N-(1-((1-(2-cyano-4-methylpent-2-enoyl)pyrrolidin-2-yl)methyl)-1H-benzo[d]-imidazol-2-yl)-5-(1H-pyrazol-4-yl)thiophene-2-carboxamide

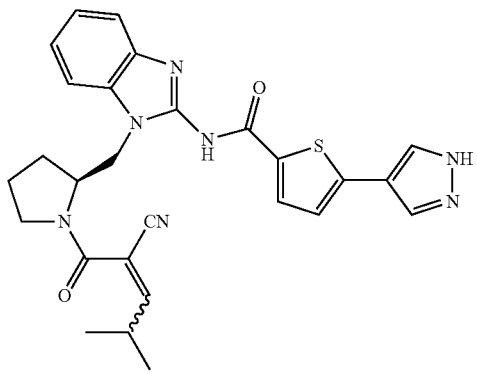 [SMILES: CC(C)C=C(C#N)C(=O)N1CCC[C@H]1Cn1c(NC(=O)c2ccc(-c3cn[nH]c3)s2)nc2ccccc21]

Step 1
Into a 500-mL round-bottom flask purged and maintained with an inert atmosphere of nitrogen, was placed a solution of 1-fluoro-2-nitrobenzene (1.41 g, 9.99 mmol, 1.00 equiv) in N,N-dimethylformamide (120 mL), tert-butyl (2S)-2-(aminomethyl)pyrrolidine-1-carboxylate (2.00 g, 9.99 mmol, 1.00 equiv) and potassium carbonate (2.21 g, 16.01 mmol, 1.60 equiv). The resulting solution was stirred overnight at 75° C. and then diluted with H$_2$O. The resulting solution was extracted with ethyl acetate and the organic layers combined and dried over anhydrous sodium sulfate, filtered and concentrated under vacuum. This resulted in 3 g (crude) of tert-butyl (2S)-2-[(2-nitrophenyl)amino]pyrrolidine-1-carboxylate as a yellow solid.

Step 2
Into a 1000-mL round-bottom flask, was placed a solution of tert-butyl (2S)-2-[(2-nitrophenyl)amino]pyrrolidine-1-carboxylate (6.42 g, 20.89 mmol, 1.00 equiv) in ethanol (500 mL) and palladium on carbon (3 g, 0.50 equiv). To the reaction vessel, was introduced H$_2$(gas). The resulting solution was stirred overnight at room temperature. The solids were filtered out. The resulting mixture was concentrated under vacuum. This resulted in 5 g (crude) of tert-butyl (2S)-2-[(2-aminophenyl)amino]pyrrolidine-1-carboxylate as a yellow oil.

Step 3
Into a 250-mL round-bottom flask purged and maintained with an inert atmosphere of nitrogen, was placed a solution of tert-butyl (2S)-2-[(2-aminophenyl)amino]pyrrolidine-1-carboxylate (2.83 g, 9.71 mmol, 1.00 equiv) in ethanol (100 mL) and BrCN (1.08 g, 10.19 mmol, 1.00 equiv). The resulting solution was stirred overnight at room temperature. The resulting mixture was concentrated under vacuum and then diluted with H$_2$O. The pH value of the solution was adjusted to 9-10 with K$_2$CO$_3$ (sat., aq.). The resulting solution was extracted with ethyl acetate and the organic layers combined. The resulting mixture was washed with brine, dried and concentrated under vacuum. This resulted in 2 g of (S)-tert-butyl 2-((2-amino-1H-benzo[d]imidazol-1-yl)methyl)pyrrolidine-1-carboxylate as a yellow solid.

Step 4
Into a 100-mL round-bottom flask, was placed (S)-tert-butyl 2-((2-amino-1H-benzo[d]-imidazol-1-yl)methyl)pyrrolidine-1-carboxylate (2.5 g, 7.90 mmol, 1.00 equiv), 5-bromothiophene-2-carboxylic acid (2.1 g, 11.11 mmol, 1.20 equiv), PyBop (6.6 g, 1.50 equiv), N,N-dimethylformamide (30 mL) and TEA (4.3 g, 42.49 mmol, 5.00 equiv). The resulting solution was stirred overnight at r.t. The resulting mixture was concentrated under vacuum and then applied onto a silica gel column with ethyl acetatepetroleum ether (1:3). This resulted in 2.1 g of tert-butyl (2S)-2-[[2-(5-bromothiophene-2-amido)-1H-1,3-benzodiazol-1-yl]methyl]pyrrolidine-1-carboxylate as a red solid.

Step 5
Into a 500-mL round-bottom flask, was placed tert-butyl (2S)-2-[[2-(5-bromothiophene-2-amido)-1H-1,3-benzodiazol-1-yl]methyl]pyrrolidine-1-carboxylate (2.5 g, 4.96 mmol, 1.00 equiv), 4-(tetramethyl-1,3,2-dioxaborolan-2-yl)-1H-pyrazole (1.2 g, 6.18 mmol, 1.20 equiv), Pd(pddf)Cl$_2$ (0.8 g, 0.20 equiv), water (50 mL), 1,4-dioxane (200 mL) and potassium carbonate (2.1 g, 3.00 equiv) was stirred overnight at 95° C. in an oil bath. The resulting mixture was concentrated under vacuum and the residue was applied onto a silica gel column with dichloromethane/ethyl acetate (3:1). This resulted in 0.7 g of tert-butyl (2S)-2-([2-[5-(1H-pyrazol-4-yl)thiophene-2-amido]-1H-1,3-benzodiazol-1-yl]methyl)pyrrolidine-1-carboxylate as a light yellow solid.

Step 6
Into a 50-mL round-bottom flask, was placed tert-butyl (2S)-2-([2-[5-(1H-pyrazol-4-yl)thiophene-2-amido]-1H-1,3-benzodiazol-1-yl]methyl)pyrrolidine-1-carboxylate (300 mg, 0.61 mmol, 1.00 equiv), trifluoroacetic acid (2 mL) and dichloromethane (10 mL). The resulting solution was stirred overnight at room temperature and then concentrated under vacuum. This resulted in 200 mg of 5-(1H-pyrazol-4-yl)-N-[3-[(2S)-pyrrolidin-2-ylmethyl]-1H-1,3-benzodiazol-2-yl]thiophene-2-carboxamide as a yellow green solid.

Step 7
Into a 50-mL round-bottom flask, was placed a solution of 5-(1H-pyrazol-4-yl)-N-[1-[(2S)-pyrrolidin-2-ylmethyl]-1H-1,3-benzodiazol-2-yl]thiophene-2-carboxamide (50 mg, 0.13 mmol, 1.00 equiv), N,N-dimethylformamide (10 mL), 2-cyanoacetic acid (22 mg, 0.26 mmol, 2.00 equiv), TEA (129 mg, 1.28 mmol, 10.00 equiv) and HATU (97 mg, 0.26 mmol, 2.00 equiv). The resulting solution was stirred overnight at room temperature and then quenched by the addition of water. The solids were collected by filtration. This resulted in 9.4 mg of N-(1-[[(2S)-1-(2-cyanoacetyl)-pyrrolidin-2-yl]methyl]-1H-1,3-benzodiazol-2-yl)-5-(1H-pyrazol-4-yl)thiophene-2-carboxamide as a white solid.

Step 8

Into a 25-mL round-bottom flask purged and maintained with an inert atmosphere of nitrogen, was placed a solution of (S)-N-(1-((1-(2-cyanoacetyl)pyrrolidin-2-yl)methyl)-1H-benzo[d]imidazol-2-yl)-5-(1H-pyrazol-4-yl)thiophene-2-carboxamide (225 mg, 0.49 mmol, 1.00 equiv), dioxane (12.4 mL), isobutyraldehyde (177 mg, 2.45 mmol, 5.00 equiv) and piperidine (83.6 mg, 0.98 mmol, 2.00 equiv). The resulting solution was stirred overnight at 40° C. and then concentrated under vacuum. The crude product (100 mL) was purified by Prep-HPLC with the following conditions: Column, SunFire Prep C18, 19*150 mm 5 um; mobile phase, water and CH₃CN (10% CH₃CN up to 60% in 20 min); Detector, 254 nm. The resulting solution was concentrated under vacuum and lyophilized. This resulted in 50 mg of (S)-N-(1-((1-(2-cyano-4-methylpent-2-enoyl)pyrrolidin-2-yl)methyl)-1H-benzo[d]imidazol-2-yl)-5-(1H-pyrazol-4-yl)thiophene-2-carboxamide as a white solid. LC-MS: mz 514 (M+H+).

Example 46

Synthesis of N-(1-((1-(4-amino-2-cyano-4-methylpent-2-enoyl)azetidin-3-yl)methyl)-1H-benzo[d]imidazol-2-yl)-5-(1H-pyrazol-4-yl)thiophene-2-carboxamide trifluoroacetic acid salt

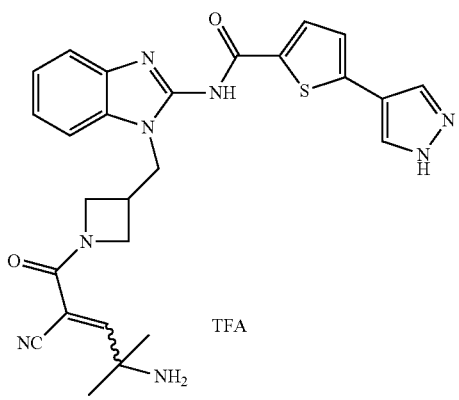 [SMILES: CC(C)(N)C=C(C#N)C(=O)N1CC(Cn2c(NC(=O)c3ccc(-c4cn[nH]c4)s3)nc3ccccc32)C1]

Step 1

Into a 100-mL round-bottom flask purged and maintained with an inert atmosphere of nitrogen, was placed N-(1-[[1-(2-cyanoacetyl)azetidin-3-yl]methyl]-1H-1,3-benzodiazol-2-yl)-5-(1H-pyrazol-4-yl)thiophene-2-carboxamide (250 mg, 0.56 mmol, 1.00 equiv), DCM/MeOH (1:1) (40 mL), piperidine (143.1 mg, 1.68 mmol, 2.99 equiv), 4A molecular sieves (250 mg) and tert-butyl N-(2-methyl-1-oxopropan-2-yl)carbamate (524.7 mg, 2.80 mmol, 4.99 equiv). The resulting solution was stirred overnight at 40° C. and then the solids were filtered out. The resulting mixture was concentrated under vacuum to provide tert-butyl (5-(3-((2-(5-(1H-pyrazol-4-yl)thiophene-2-carboxamido)-1H-benzo[d]imidazol-1-yl)methyl)azetidin-1-yl)-4-cyano-2-methyl-5-oxopent-3-en-2-yl)carbamate.

Step 2

Into a 50-mL round-bottom flask purged and maintained with an inert atmosphere of nitrogen, was placed tert-butyl (5-(3-((2-(5-(1H-pyrazol-4-yl)thiophene-2-carboxamido)-1H-benzo[d]imidazol-1-yl)methyl)azetidin-1-yl)-4-cyano-2-methyl-5-oxopent-3-en-2-yl)carbamate (300 mg, 0.49 mmol, 1.00 equiv), dichloromethane (10 mL) and trifluoroacetic acid (2 mL). The resulting solution was stirred overnight at room temperature and then concentrated under vacuum. The resulting solution was diluted with 10 mL of DMSO and the solids were filtered out to collect 75 mg of N-(1-((1-(4-amino-2-cyano-4-methylpent-2-enoyl)azetidin-3-yl)methyl)-1H-benzo[d]imidazol-2-yl)-5-(1H-pyrazol-4-yl)thiophene-2-carboxamide as a trifluoroacetic acid salt.

Example 47

Synthesis of (S)-N-(1-((1-(2-cyano-4-methyl-4-morpholinopent-2-enoyl)pyrrolidin-2-yl)methyl)-1H-benzo[d]imidazol-2-yl)-5-(1H-pyrazol-4-yl)thiophene-2-carboxamide

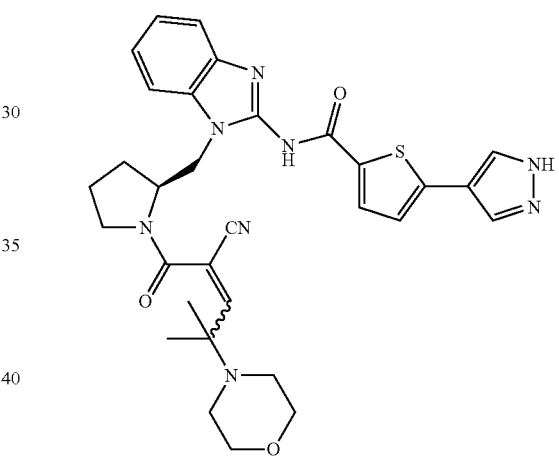

Into a 100 mL round-bottom flask, was placed a solution of N-(1-[[(2S)-1-(2-cyanoacetyl)-pyrrolidin-2-yl]methyl]-1H-1,3-benzodiazol-2-yl)-5-(1H-pyrazol-4-yl)thiophene-2-carboxamide (230 mg, 0.50 mmol, 1.00 equiv), NMP (10 mL), 2-methyl-2-(morpholin-4-yl)propanal (393 mg, 2.50 mmol, 5.00 equiv), piperidine (85 mg, 1.00 mmol, 2.00 equiv), AcOH (6 mg, 0.10 mmol, 0.20 equiv) and 4A molecular sieves (230 mg). The resulting solution was stirred overnight at 40° C. and then the solids were filtered out. The resulting mixture was concentrated under vacuum. The crude product (150 mg) was purified by Prep-HPLC with the following conditions (1#-Pre-HPLC-005(Waters)): Column, SunFire Prep C18 19*150 mm 5 um; mobile phase, water with 0.05% TFA and CH3CN (10% CH₃CN up to 33% in 10 min); Detector, 254 nm. This resulted in 100 mg of N-(1-[[(2S)-1-[2-cyano-2-[2-methyl-2-(morpholin-4-yl) propylidene]acetyl]pyrrolidin-2-yl]methyl]-1H-1,3-benzodiazol-2-yl)-5-(1H-pyrazol-4-yl)thiophene-2-carboxamide as a white solid. LC-MS: mz 599 (M+H+).

Example 48

Synthesis of N-(1-(2-(2-cyano-4-methylpent-2-enamido)ethyl)-1H-benzo[d]imidazol-2-yl)-5-(1H-pyrazol-4-yl)thiophene-2-carboxamide

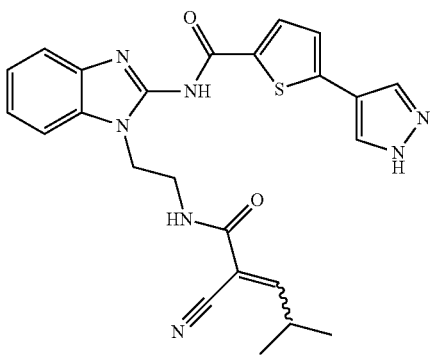 [SMILES: CC(C)C=C(C#N)C(=O)NCCn1c(NC(=O)c2ccc(-c3cn[nH]c3)s2)nc2ccccc21]

Step 1

Into a 1 L mL round-bottom flask purged and maintained with an inert atmosphere of nitrogen, was placed a solution of 1-fluoro-2-nitrobenzene (20 g, 141.74 mmol, 1.00 equiv), N,N-dimethylformamide (400 mL), tert-butyl N-(2-aminoethyl)carbamate (22.7 g, 141.69 mmol, 1.00 equiv) and potassium carbonate (31.4 g, 227.54 mmol, 1.60 equiv). The resulting solution was stirred overnight at 75° C. and then diluted with H₂O. The resulting solution was extracted with ethyl acetate and the organic layers combined, washed with brine and then dried over anhydrous sodium sulfate. After filtration and concentrated under vacuum, this resulted in 35 g of tert-butyl N-[2-[(2-nitrophenyl)amino]ethyl]carbamate as a solid.

Step 2

Into a 2000-mL round-bottom flask, was placed methanol (1000 mL), palladium on carbon (8 g) and tert-butyl N-[2-[(2-nitrophenyl)amino]ethyl]carbamate (20 g, 71.10 mmol, 1.00 equiv). To the reaction vessel was introduced H₂(gas) and the resulting mixture was stirred overnight at 25° C. The solids were then filtered out and the solvent was concentrated under vacuum. This resulted in 17 g (crude) of tert-butyl N-[2-[(2-aminophenyl)amino]ethyl]carbamate as a red solid.

Step 3

Into a 250-mL round-bottom flask, was placed a solution of tert-butyl N-[2-[(2-aminophenyl)amino]ethyl]carbamate (500 mg, 1.99 mmol, 1.00 equiv), ethanol (50 mL), and cyanogen bromide (230 mg, 2.17 mmol, 1.09 equiv). The resulting solution was stirred for 2 h at room temperature and then concentrated under vacuum. The residue was applied onto a silica gel column with ethyl acetatepetroleum ether (1:20 to 1:5). This resulted in 0.5 g of tert-butyl N-[2-(2-amino-1H-1,3-benzodiazol-1-yl)ethyl]carbamate as a red solid.

Step 4

Into a 250-mL round-bottom flask, was placed a solution of N-[2-(2-amino-1H-1,3-benzodiazol-1-yl)ethyl]carbamate (5 g, 18.09 mmol, 1.00 equiv), 5-bromothiophene-2-carboxylic acid (4.5 g, 21.73 mmol, 1.20 equiv), TEA (4.5 g, 44.55 mmol, 2.46 equiv), N,N-dimethylformamide (100 mL) and PyBop (9.3 g, 17.92 mmol, 0.99 equiv). The resulting solution was stirred at 25° C. and then quenched by the addition of water. The solids were collected by filtration. The filter cake washed with ethyl acetate: petroleum ether (1:1). This resulted in 4.6 g of tert-butyl N-[2-[2-(5-bromothiophene-2-amido)-1H-1,3-benzodiazol-1-yl]ethyl]carbamate as a yellow solid.

Step 5

Into a 1000-mL round-bottom flask, was placed tert-butyl N-[2-[2-(5-bromothiophene-2-amido)-1H-1,3-benzodiazol-1-yl]ethyl]carbamate (1.89 g, 4.06 mmol, 1.00 equiv), tert-butyl 4-(tetramethyl-1,3,2-dioxaborolan-2-yl)-1H-pyrazole-1-carboxylate (2.864 g, 9.74 mmol, 2.40 equiv), Pd(dppf)Cl₂ (1.334 g, 1.82 mmol, 0.45 equiv), potassium carbonate (2.224 g, 16.12 mmol, 4.00 equiv), 1,4-dioxane (380 mL) and water (95 mL). The resulting solution was stirred for 45 h at 100° C. and then cooled to room temperature. The reaction mixture was then quenched by the addition of 100 mL of water and extracted with dichloromethane. The organic layers were combined, dried over anhydrous sodium sulfate, filtered and then concentrated under vacuum. This resulted in 0.7 g of tert-butyl N-(2-[2-[5-(1H-pyrazol-4-yl)thiophene-2-amido]-1H-1,3-benzodiazol-1-yl]ethyl)-carbamate as a light yellow solid.

Step 6

Into a 100-mL round-bottom flask, was placed dichloromethane (60 mL), tert-butyl N-(2-[2-[5-(1H-pyrazol-4-yl)thiophene-2-amido]-1H-1,3-benzodiazol-1-yl]ethyl)carbamate (1.6 g, 3.54 mmol, 1.00 equiv) and trifluoroacetic acid (15 mL). The resulting solution was stirred overnight at 25° C. and then concentrated under vacuum. This resulted in 1.2 g (crude) of N-[1-(2-aminoethyl)-1H-1,3-benzodiazol-2-yl]-5-(1H-pyrazol-4-yl)thiophene-2-carboxamide as a yellow solid.

Step 7

Into a 50-mL round-bottom flask purged and maintained with an inert atmosphere of nitrogen, was placed N-[1-(2-aminoethyl)-1H-1,3-benzodiazol-2-yl]-5-(1H-pyrazol-4-yl)thiophene-2-carboxamide (1.2 g, 3.41 mmol, 1.00 equiv), N,N-dimethylformamide (20 mL), TEA (3.44 g, 34.00 mmol, 9.98 equiv), HATU (2.6 g) and 2-cyanoacetic acid (580 mg, 6.82 mmol, 2.00 equiv). The resulting solution was stirred overnight at room temperature and then quenched by the addition of water/ice. The solids were collected by filtration and then dried in an oven under reduced pressure. This resulted in 1.107 g of N-[1-[2-(2-cyanoacetamido)ethyl]-1H-1,3-benzodiazol-2-yl]-5-(1H-pyrazol-4-yl)thiophene-2-carboxamide as a tan solid.

Step 8

Into a 50-mL round-bottom flask purged and maintained with an inert atmosphere of nitrogen, was placed N-[1-[2-(2-cyanoacetamido)ethyl]-1H-1,3-benzodiazol-2-yl]-5-(1H-pyrazol-4-yl)thiophene-2-carboxamide (200 mg, 0.48 mmol, 1.00 equiv), dichloromethane (10 mL), methanol (10 mL), piperidine (121.7 mg, 1.43 mmol, 3.00 equiv) and 2-methylpropanal (171.8 mg, 2.38 mmol, 5.00 equiv). The resulting solution was stirred overnight at room temperature and then concentrated under vacuum. The crude product was purified by Flash-Prep-HPLC with the following conditions (IntelFlash-1): Column, silica gel; mobile phase; Detector, UV 254 nm. This resulted in 17.5 mg (8%) of N-(1-(2-(2-cyano-4-methylpent-2-enamido)ethyl)-1H-benzo[d]imidazol-2-yl)-5-(1H-pyrazol-4-yl)thiophene-2-carboxamide as a white solid. LC-MS m/z: 473+1(M+1).

Example 49

Synthesis of N-(1-(2-(4-amino-2-cyano-4-methyl-pent-2-enamido)ethyl)-1H-benzo[d]imidazol-2-yl)-5-(1H-pyrazol-4-yl)thiophene-2-carboxamide trifluoroacetic acid salt

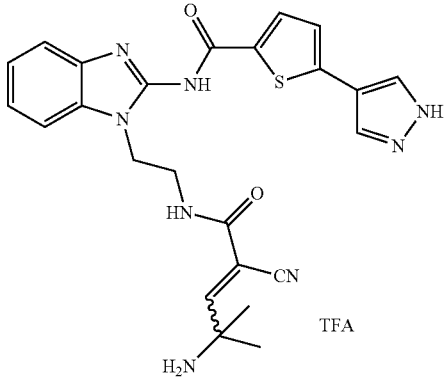 [SMILES: CC(C)(N)C=C(C#N)C(=O)NCCn1c(NC(=O)c2ccc(-c3cn[nH]c3)s2)nc2ccccc21]

Step 1

Into a 50-mL round-bottom flask purged and maintained with an inert atmosphere of nitrogen, was placed N-[1-[2-(2-cyanoacetamido)ethyl]-1H-1,3-benzodiazol-2-yl]-5-(1H-pyrazol-4-yl)thiophene-2-carboxamide (300 mg, 0.72 mmol, 1.00 equiv), DCM/MeOH (1:1) (20 mL), piperidine (182.6 mg, 2.14 mmol, 3.00 equiv), 4A molecular sieves (300 mg) and tert-butyl N-(2-methyl-1-oxopropan-2-yl)carbamate (669.5 mg, 3.58 mmol, 5.00 equiv). The resulting solution was stirred overnight at 40° C. and then the solids were filtered out and the resulting mixture was concentrated under vacuum.

Step 2

Into a 50-mL round-bottom flask purged and maintained with an inert atmosphere of nitrogen, was placed tert-butyl N-[4-cyano-2-methyl-4-[(2-[2-[5-(1H-pyrazol-4-yl)thiophene-2-amido]-1H-1,3-benzodiazol-1-yl]ethyl)carbamoyl]but-3-en-2-yl]carbamate (400 mg, 0.68 mmol, 1.00 equiv), dichloromethane (10 mL) and trifluoroacetic acid (2 mL). The resulting solution was stirred for 4 h at room temperature and then the solids were collected by filtration. The resulting solution was diluted with DMSO and the solids were filtered out to collect 80 mg of N-(1-(2-(4-amino-2-cyano-4-methylpent-2-enamido)ethyl)-1H-benzo[d]imidazol-2-yl)-5-(1H-pyrazol-4-yl)thiophene-2-carboxamide as a trifluoroacetic acid salt. LC-MS m/z: 488+1 (M+1).

Example 50

Synthesis of (R)-N-(1-((1-(2-cyano-4-methylpent-2-enoyl)pyrrolidin-2-yl)methyl)-1H-benzo[d]imidazol-2-yl)-5-(difluoromethyl)thiophene-2-carboxamide trifluoroacetic acid salt

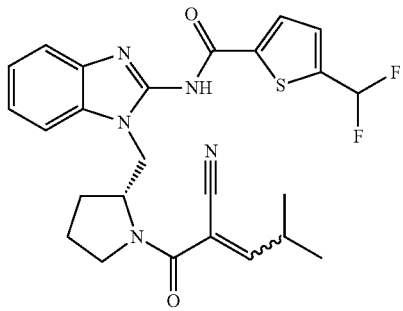 [SMILES: CC(C)C=C(C#N)C(=O)N1CCC[C@@H]1Cn1c(NC(=O)c2ccc(C(F)F)s2)nc2ccccc21]

Step 1

Into a 100 mL round-bottom flask, was placed 5-(difluoromethyl)thiophene-2-carboxylic acid (100 mg, 0.56 mmol, 1.00 equiv), PyBop (490 mg), tert-butyl (2R)-2-[(2-amino-1H-1,3-benzodiazol-1-yl)methyl]pyrrolidine-1-carboxylate (198 mg, 0.63 mmol, 1.11 equiv), TEA (0.5 mL) and N,N-dimethylformamide (5 mL). The resulting solution was stirred overnight at 25° C. and then diluted with $H_2O$. The resulting solution was extracted with ethyl acetate and the organic layers were combined and concentrated under vacuum. This resulted in 280 mg (crude) of tert-butyl (2R)-2-([2-[5-(difluoromethyl)thiophene-2-amido]-1H-1,3-benzodiazol-1-yl]methyl)pyrrolidine-1-carboxylate as brown oil.

Step 2

Into a 100-mL round-bottom flask, was placed tert-butyl (2R)-2-([2-[5-(difluoromethyl)-thiophene-2-amido]-1H-1,3-benzodiazol-1-yl]methyl)pyrrolidine-1-carboxylate (280 mg, 0.59 mmol, 1.00 equiv), dichloromethane (10 mL) and trifluoroacetic acid (2 mL). The resulting solution was stirred overnight at 25° C. and then concentrated under vacuum. This resulted in 200 mg (crude) of 5-(difluoromethyl)-N-[1-[(2R)-pyrrolidin-2-ylmethyl]-1H-1,3-benzodiazol-2-yl]thiophene-2-carboxamide as a brown oil.

Step 3

Into a 100-mL round-bottom flask, was placed 5-(difluoromethyl)-N-[1-[(2R)-pyrrolidin-2-ylmethyl]-1H-1,3-benzodiazol-2-yl]thiophene-2-carboxamide (100 mg, 0.27 mmol, 1.00 equiv), HATU (152 mg, 0.40 mmol, 1.50 equiv), 2-cyanoacetic acid (34 mg, 0.40 mmol, 1.50 equiv), TEA (80.5 mg, 0.80 mmol, 3.00 equiv) and N,N-dimethylformamide (50 mL). The resulting solution was stirred for 12 h at room temperature and then quenched by the addition of water. The solids were collected by filtration to isolate N-(1-[[(2R)-1-(2-cyanoacetyl)pyrrolidin-2-yl]methyl]-1H-1,3-benzodiazol-2-yl)-5-(difluoromethyl)thiophene-2-carboxamide.

Step 4

Into a 50-mL round-bottom flask, was placed N-(1-[[(2R)-1-(2-cyanoacetyl)pyrrolidin-2-yl]methyl]-1H-1,3-benzodiazol-2-yl)-5-(difluoromethyl)thiophene-2-carboxamide (211 mg, 0.48 mmol, 1.00 equiv), 2-methylpropanal (0.2 mL, 5.00 equiv), piperidine (117.2 mg, 3.00 equiv), 4A molecular sieves (10 mg) and DCM/MeOH1:1 (20 mL). The resulting solution was stirred overnight at room temperature and then the solids were filtered out. The filtrate was concentrated under vacuum and the crude product was purified by Prep-HPLC with the following conditions: ACN/$H_2O$ (0.05% TFA)30%-80%; Detector, 254 nm. This resulted in 50 mg of (R)-N-(1-((1-(2-cyano-4-methylpent-2-enoyl)pyrrolidin-2-yl)methyl)-1H-benzo[d]imidazol-2-yl)-5-(difluoromethyl)thiophene-2-carboxamide trifluoroacetate as an off-white solid. LC-MS m/z: 498 (M+1).

Example 51

Synthesis (S)-N-(1-((1-(2-cyano-4-methylpent-2-enoyl)pyrrolidin-2-yl)methyl)-1H-benzo[d]imidazol-2-yl)-5-(difluoromethyl)thiophene-2-carboxamide

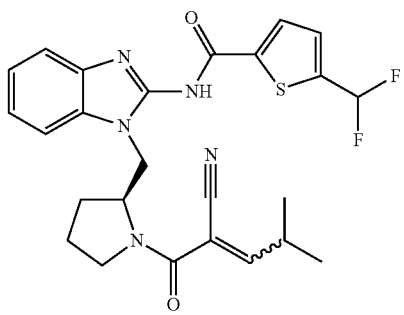 [SMILES: CC(C)C=C(C#N)C(=O)N1CCC[C@H]1Cn1c(NC(=O)c2ccc(C(F)F)s2)nc2ccccc21]

Step 1

Into a 100-mL round-bottom flask, was placed 5-(difluoromethyl)thiophene-2-carboxylic acid (100 mg, 0.56 mmol, 1.00 equiv), tert-butyl (2S)-2-[(2-amino-1H-1,3-benzodiazol-1-yl)methyl]pyrrolidine-1-carboxylate (198 mg, 0.63 mmol, 1.00 equiv), PyBop (490 mg, 0.94 mmol, 1.50 equiv), N,N-dimethylformamide (5 mL) and TEA (0.5 mL). The resulting solution was stirred overnight at 25° C. and then diluted with H₂O. The resulting solution was extracted with ethyl acetate and the organic layers were combined and concentrated under vacuum. This resulted in 280 mg (crude) of tert-butyl (2S)-2-([2-[5-(difluoromethyl)thiophene-2-amido]-1H-1,3-benzodiazol-1-yl]methyl)pyrrolidine-1-carboxylate as a brown oil.

Step 2

Into a 50-mL round-bottom flask, was placed a solution of tert-butyl (2S)-2-([2-[5-(difluoromethyl)thiophene-2-amido]-1H-1,3-benzodiazol-1-yl]methyl)pyrrolidine-1-carboxylate (300 mg, 0.63 mmol, 1.00 equiv) in dichloromethane (50 mL) and trifluoroacetic acid (15 mL). The resulting solution was stirred overnight at room temperature and then concentrated under vacuum. This resulted in 250 mg (crude) of 5-(difluoromethyl)-N-[1-[(2S)-pyrrolidin-2-ylmethyl]-1H-1,3-benzodiazol-2-yl]thiophene-2-carboxamide as a red oil.

Step 3

Into a 100-mL round-bottom flask, was placed 5-(difluoromethyl)-N-[1-[(2S)-pyrrolidin-2-ylmethyl]-1H-1,3-benzodiazol-2-yl]thiophene-2-carboxamide (200 mg, 0.53 mmol, 1.00 equiv), HATU (404 mg, 1.06 mmol, 2.00 equiv), TEA (268.8 mg, 2.66 mmol, 5.00 equiv), 2-cyanoacetic acid (90.4 mg, 1.06 mmol, 2.00 equiv) and N,N-dimethylformamide (50 mL). The resulting solution was stirred for 12 h at room temperature and then quenched by the addition of water. The solids were collected by filtration which resulted in 120 mg of N-(1-[[(2S)-1-(2-cyanoacetyl)pyrrolidin-2-yl]methyl]-1H-1,3-benzodiazol-2-yl)-5-(difluoromethyl)thiophene-2-carboxamide as an off-white solid.

Step 4

Into a 50-mL round-bottom flask, was placed N-(1-[[(2S)-1-(2-cyanoacetyl)pyrrolidin-2-yl]methyl]-1H-1,3-benzodiazol-2-yl)-5-(difluoromethyl)thiophene-2-carboxamide (140 mg, 0.32 mmol, 1.00 equiv), 2-methylpropanal (0.14 mL, 5.00 equiv), piperidine (77.8 mg, 3.00 equiv), 4A molecular sieves (10 mg) and DCM/MeOH1:1 (20 mL). The resulting solution was stirred overnight at room temperature and then the solids were filtered out. The filtrate was concentrated under vacuum and the crude product was purified by Prep-HPLC with the following conditions: ACN/H₂O(0.05% TFA) 30%-80%; Detector, 254 nm. This resulted in 40 mg of (S)-N-(1-((1-(2-cyano-4-methylpent-2-enoyl)pyrrolidin-2-yl)methyl)-1H-benzo[d]imidazol-2-yl)-5-(difluoromethyl)thiophene-2-carboxamide trifluoroacetate as an off-white solid.

Intermediate 13

Synthesis of tert-butyl (2R)-2-[[2-[[5-(difluoromethyl)thiophene-2-carbonyl]amino]-5-(hydroxymethyl)benzimidazol-1-yl]methyl]pyrrolidine-1-carboxylate

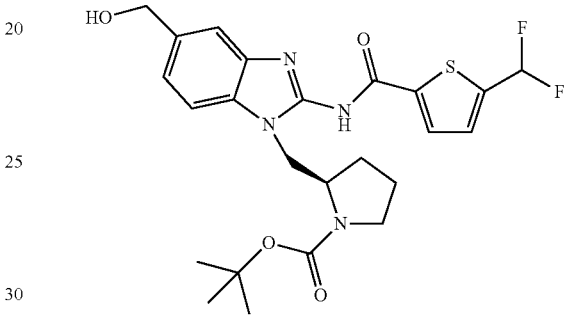

Step 1

To the mixture of methyl 4-fluoro-3-nitro-benzoate (20.0 g, 100 mmol), N-ethyl-N-isopropyl-propan-2-amine (35.5 mL, 200 mmol) and MeCN (150 mL) was stirred in a 3-neck flask and flushed with argon for 15 minutes. tert-Butyl (2R)-2-(aminomethyl)pyrrolidine-1-carboxylate (25.0 g, 124.86 mmol) was diluted with CH₃CN (130 mL) and was added dropwise over 50 min. The reaction mixture was allowed to stir at room temp for 3.5 h. The orange mixture was concentrated to dryness and partitioned between DCM and HCl (1N). Organic layers were washed with brine, dried over MgSO₄, and concentrated to obtain 37.5 g of tert-butyl (2R)-2-[(4-methoxycarbonyl-2-nitro-anilino)methyl]pyrrolidine-1-carboxylate as a yellow oil.

Step 2

A mixture of tert-butyl (2R)-2-[(4-methoxycarbonyl-2-nitro-anilino)methyl]pyrrolidine-1-carboxylate (37.5 g, 98.8 mmol) and methanol (1200 mL) was cooled to 0° C. Saturated ammonium chloride (200 mL) was added to solution. Zinc dust (32.74 g, 500.78 mmol) was added to resultant slurry and the resultant mixture was stirred at rt for 35 min. The reaction mixture was filtered through a thin pad of celite and washed with MeOH. The filtrated solution was concentrated and worked up with EtOAc and water). The organic was pushed through a short silica plug and washed with EtOAc. The collected solution was concentrated to obtain 32.1 grams (93%) brown solid of tert-butyl (2R)-2-[(2-amino-4-methoxycarbonyl-anilino)methyl]pyrrolidine-1-carboxylate.

Step 3

A mixture of tert-butyl (2R)-2-[(2-amino-4-methoxycarbonyl-anilino)methyl]pyrrolidine-1-carboxylate (32.1 g, 91.87 mmol) and ethanol (380 mL) was stirred at room temperature under Argon for 10 minutes cyanogen bromide (10.7 g, 101 mmol) was added. The resultant mixture was stirred at rt for 3 h. The reaction mixture was evaporated to dryness and worked up with NaHCO₃ and DCM. The layers were separated. The organic layers were dried (MgSO4), filtered and concentrated to obtain 34.5 grams (100%) gray solid of methyl 1-[[(2R)-1-tert-butoxycarbonylpyrrolidin-2-yl]methyl]-2-imino-3H-benzimidazole-5-carboxylate.
Step 4

To a solution of 5-(difluoromethyl)thiophene-2-carboxylic acid (40.4 mg, 22.7 mmol) in DMF (25 mL) at 0° C. for 15 minutes was added methyl 1-[[(2R)-1-tert-butoxycarbonylpyrrolidin-2-yl]methyl]-2-imino-3H-benzimidazole-5-carboxylate (8.50 mg, 22.7 mmol) in DMF (12 mL) and DIPEA (7.82 mL, 45.4 mmol). After stirring 4 h at rt, the solution was evaporated. The crude mixture was diluted with DCM and was washed with NaHCO₃ (sat). The organic layers were separated and dried with MgSO₄, filtered and concentrated to black crude oil. The crude oil was purified by column chromatography to obtain 7.35 grams of methyl 1-[[(2R)-1-tert-butoxycarbonylpyrrolidin-2-yl]methyl]-2-[[5-(difluoromethyl)thiophene-2-carbonyl]amino]-benzimidazole-5-carboxylate as off white solid.
Step 5

To a solution of methyl 1-[[(2R)-1-tert-butoxycarbonylpyrrolidin-2-yl]methyl]-2-[[5-(difluoromethyl)thiophene-2-carbonyl]amino]benzimidazole-5-carboxylate (5.89 g, 11.01 mmol) in THF (40 mL) at −78° C. for 5 minutes was added 2M LiAlH₄ in THF (6.6 mL, 13.21 mmol). The reaction mixture was stirred for 10 minutes at −78° C. and then was allowed to warm to room temp. After 30-45 minutes, the reaction mixture was quenched with NaHCO₃ (sat) and worked up with DCM. The organic layers were separated, brined and dried (MgSO₄). The crude was concentrated and purified by column chromatography to obtain 3.05 grams (55%) of tert-butyl (2R)-2-[[2-[[5-(difluoromethyl)thiophene-2-carbonyl]amino]-5-(hydroxymethyl)benzimidazol-1-yl]methyl]pyrrolidine-1-carboxylate as yellow solid. MS (pos. ion) m/z: 507 (M+1).

Example 52

Synthesis of (R)-N-(1-((1-(2-cyano-4-methylpent-2-enoyl)pyrrolidin-2-yl)methyl)-5-((neopentylamino)methyl)-1H-benzo[d]imidazol-2-yl)-5-(difluoromethyl)thiophene-2-carboxamide

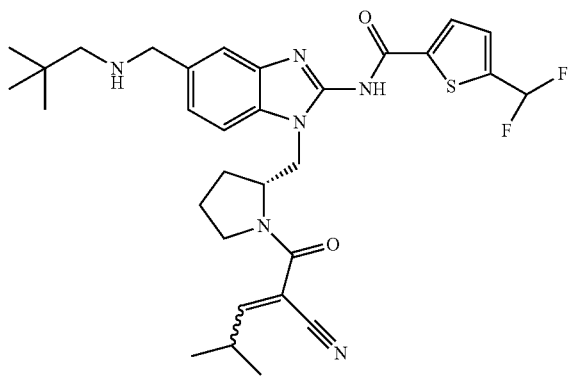 [SMILES: CC(C)C=C(C#N)C(=O)N1CCC[C@@H]1Cn1c(NC(=O)c2ccc(C(F)F)s2)nc2cc(CNCC(C)(C)C)ccc21]

Step 1

To a solution of tert-butyl (2R)-2-[[2-[[5-(difluoromethyl)thiophene-2-carbonyl]amino]-5-(hydroxymethyl)benzimidazol-1-yl]methyl]pyrrolidine-1-carboxylate (547 mg, 1.08 mmol) in DCM (8 mL) was added 4N HCl in dioxane (5 mL). The reaction mixture was stirred at rt for 2 h. The reaction mixture was concentrated and dried under reduced pressure to obtain 545 mgs of 5-(difluoromethyl)-N-[5-(hydroxymethyl)-1-[[(2R)-pyrrolidin-2-yl]methyl]benzimidazol-2-yl]-thiophene-2-carboxamide.
Step 2

To a solution of 5-(difluoromethyl)-N-[5-(hydroxymethyl)-1-[[(2R)-pyrrolidin-2-yl]methyl]-benzimidazol-2-yl]thiophene-2-carboxamide (600 mg, 1.48 mmol) and 2-cyanoacetic acid (376.7 mg, 4.43 mmol) in DMF (20 mL) was added DIPEA (1.27 mL, 7.38 mmol). The solution was stirred at rt for 7 minutes and then HATU (1.68 g, 4.43 mmol) was added. The resultant mixture was stirred at rt for 4.5 h. The reaction mixture was evaporated to an oil which was purified by chromatography to obtain 650 mg (93%) of N-[1-[[(2R)-1-(2-cyanoacetyl)pyrrolidin-2-yl]methyl]-5-(hydroxymethyl)benzimidazol-2-yl]-5-(difluoromethyl)thiophene-2-carboxamide as white solid.
Step 3

To a solution of N-[1-[[(2R)-1-(2-cyanoacetyl)pyrrolidin-2-yl]methyl]-5-(hydroxymethyl)-benzimidazol-2-yl]-5-(difluoromethyl)thiophene-2-carboxamide (680 mg, 1.44 mmol) in DCM (15 mL) was added Dess-Martin Periodinane (1.22 g, 2.87 mmol). The reaction mixture was stirred at room temperature for 20 min. The reaction mixture was concentrated and purified by chromatography to obtain 430 mg (64%) of N-[1-[[(2R)-1-(2-cyanoacetyl)pyrrolidin-2-yl]methyl]-5-formyl-benzimidazol-2-yl]-5-(difluoromethyl)thiophene-2-carboxamide as brown solid.
Step 4

To a solution of N-[1-[[(2R)-1-(2-cyanoacetyl)pyrrolidin-2-yl]methyl]-5-formyl-benzimidazol-2-yl]-5-(difluoromethyl)thiophene-2-carboxamide (82 mg, 0.17 mmol), 2,2-dimethylpropan-1-amine (30.32 mg, 0.35 mmol) in DCM (7 mL) was added NaBH₃CN (16.39 mg, 0.26 mmol). The reaction mixture was stirred at rt for 2 h. The reaction mixture was concentrated and purified by chromatography to obtain 40 mg (42%) of N-[1-[[(2R)-1-(2-cyanoacetyl)pyrrolidin-2-yl]methyl]-5-[(2,2-dimethylpropylamino)methyl]benzimidazol-2-yl]-5-(difluoromethyl)thiophene-2-carboxamide as oil.
Step 5

A solution of N-[1-[[(2R)-1-(2-cyanoacetyl)pyrrolidin-2-yl]methyl]-5-[(2,2-dimethyl-propylamino)methyl]benzimidazol-2-yl]-5-(difluoromethyl)thiophene-2-carboxamide (40 mg, 0.07 mmol), pyrrolidine (0.02 mL, 0.22 mmol), and 2-methylpropanal (26.58 mg, 0.37 mmol in DCM (7 mL) was stirred at room temperature for 10 minutes and then chloro(trimethyl)silane (0.04 mL, 0.29 mmol) was added dropwise. The resultant mixture was stirred at room temperature for 1 h. The crude mixture was concentrated and purified by chromatography to obtain 18 mg (41%) of (R)-N-(1-((1-(2-cyano-4-methylpent-2-enoyl)pyrrolidin-2-yl)methyl)-5-((neopentylamino)methyl)-1H-benzo[d]imidazol-2-yl)-5-(difluoromethyl)thiophene-2-carboxamide as white solid. MS (pos. ion) m/z: 597 (M+1).

Example 53

Synthesis of (R)-N-(1-((1-(2-cyano-4-methylpent-2-enoyl)pyrrolidin-2-yl)methyl)-5-(((2,2,2-trifluoroethyl)amino)methyl)-1H-benzo[d]imidazol-2-yl)-5-(difluoromethyl)thiophene-2-carboxamide

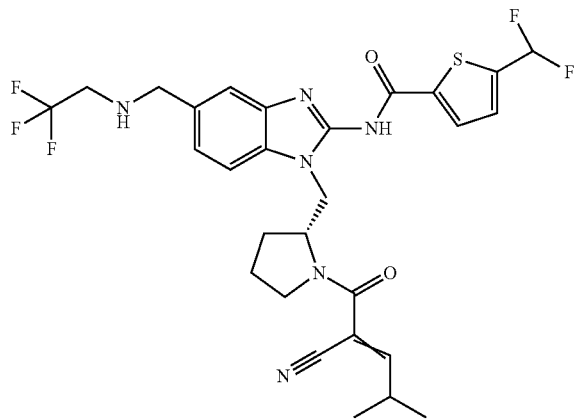 [SMILES: CC(C)C=C(C#N)C(=O)N1CCC[C@@H]1Cn1c(NC(=O)c2ccc(C(F)F)s2)nc2cc(CNCC(F)(F)F)ccc21]

Substituting trifluoroethylamine for 2,2-dimethylpropan-1-amine in step 4, Ex 52 above and continuing as in step 5 affords (R)-N-(1-((1-(2-cyano-4-methylpent-2-enoyl)pyrrolidin-2-yl)methyl)-5-(((2,2,2-trifluoroethyl)amino)methyl)-1H-benzo[d]imidazol-2-yl)-5-(difluoromethyl)thiophene-2-carboxamide. MS (pos. ion) m/z: 609 (M+1).

Example 54

Synthesis of N-(1-(((R)-1-(2-cyano-4-methylpent-2-enoyl)pyrrolidin-2-yl)methyl)-5-((2,6-dimethylmorpholino)methyl)-1H-benzo[d]imidazol-2-yl)-5-(difluoromethyl)thiophene-2-carboxamide

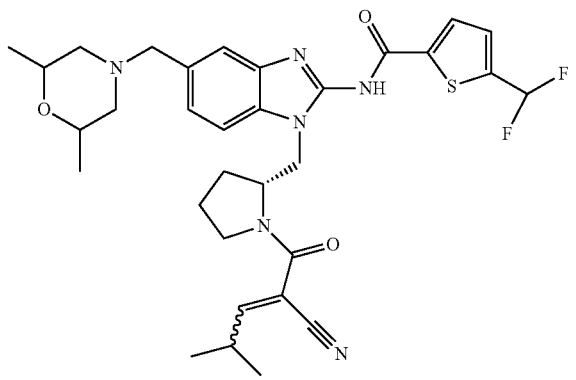 [SMILES: CC(C)C=C(C#N)C(=O)N1CCC[C@@H]1Cn1c(NC(=O)c2ccc(C(F)F)s2)nc2cc(CN3CC(C)OC(C)C3)ccc21]

Step 1

To solution of tert-butyl (2R)-2-[[2-[[5-(difluoromethyl)thiophene-2-carbonyl]amino]-5-(hydroxymethyl)benzimidazol-1-yl]methyl]pyrrolidine-1-carboxylate (452 mg, 0.89 mmol) and DCM (15 mL) was added Dess Martin Periodinane. The result was stirred at room temp for 18 h. The reaction mixture was worked up with water and DCM and the organic layer was dried (MgSO$_4$) and concentrated to oil. The crude was purified by column chromatography to obtain 445 mg (98%) of tert-butyl (2R)-2-[[2-[[5-(difluoromethyl)thiophene-2-carbonyl]amino]-5-formyl-benzimidazol-1-yl]methyl]pyrrolidine-1-carboxylate as gray solid.

Step 2

To solution of tert-butyl (2R)-2-[[2-[[5-(difluoromethyl)thiophene-2-carbonyl]amino]-5-formyl-benzimidazol-1-yl]methyl]pyrrolidine-1-carboxylate (100 mg, 0.20 mmol), 2,6-dimethylmorpholine (0.06 mL, 0.40 mmol) in DCM (5 mL) was added NaBH$_3$CN (24.9 mg, 0.40 mmol). The reaction mixture was stirred at room temp for 2 h. The reaction mixture was purified by chromatography to obtain 100 mg (84%) of tert-butyl (2R)-2-[[2-[[5-(difluoromethyl)thiophene-2-carbonyl]amino]-5-[(2,6-dimethylmorpholin-4-yl)methyl]-benzimidazol-1-yl]methyl]pyrrolidine-1-carboxylate.

Step 3

To solution mixture of (2R)-tert-butyl 2-((2-(5-(difluoromethyl)thiophene-2-carboxamido)-5-((2,6-dimethylmorpholino)methyl)-1H-benzo[d]imidazol-1-yl)methyl)pyrrolidine-1-carboxylate (100 mg, 0.17 mmol) and 4M HCl in dioxane (4 mL, 0.17 mmol) was dissolved in DCM (3 mL) and stirred at room temp. After 2 h, the reaction mixture was worked up with water and DCM. Then the aqueous layer was basified with KOH to pH~11 and extracted with DCM and dried (MgSO$_4$) to obtain 65 mg (78%) of 5-(difluoromethyl)-N-(5-((2,6-dimethylmorpholino)methyl)-1-((R)-pyrrolidin-2-ylmethyl)-1H-benzo[d]imidazol-2-yl)thiophene-2-carboxamide.

Step 4

To the solution of 5-(difluoromethyl)-N-(5-((2,6-dimethylmorpholino)methyl)-1-((R)-pyrrolidin-2-ylmethyl)-1H-benzo[d]imidazol-2-yl)thiophene-2-carboxamide (65 mg, 0.13 mmol), DIPEA (0.07 mL, 0.39 mmol), 2-cyano-4-methyl-pent-2-enoic acid (53.88 mg, 0.39 mmol) and DMF (4 mL) was stirred for 10 minutes and then added HATU (98.09 mg, 0.26 mmol). The reaction mixture was stirred at room temperature. After 4 h, the crude mixture was concentrated and purified by chromatography to obtain 55 mg (68%) of N-(1-(((R)-1-(2-cyano-4-methylpent-2-enoyl)pyrrolidin-2-yl)methyl)-5-((2,6-dimethylmorpholino)methyl)-1H-benzo[d]imidazol-2-yl)-5-(difluoromethyl)thiophene-2-carboxamide as off white solid. MS (pos. ion) m/z: 625 (M+1).

Example 55

Synthesis of (R)-N-(1-((1-(2-cyano-4-methylpent-2-enoyl)pyrrolidin-2-yl)methyl)-5-(morpholinomethyl)-1H-benzo[d]imidazol-2-yl)-5-(difluoromethyl)thiophene-2-carboxamide

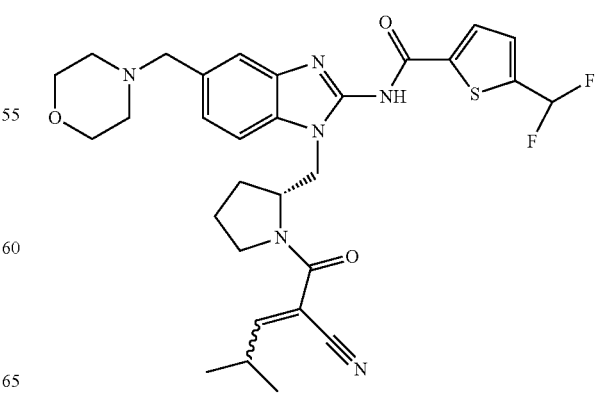

Substituting morpholine for 2,6-dimethylmorpholine in step 2 and followed by steps 3-5 as described in example 54 afforded (R)-N-(1-((1-(2-cyano-4-methylpent-2-enoyl)pyrrolidin-2-yl)methyl)-5-(morpholinomethyl)-1H-benzo[d]imidazol-2-yl)-5-(difluoro-methyl)thiophene-2-carboxamide. MS (pos. ion) m/z: 597 (M+1).

Example 56

Synthesis of (R)-N-(1-((1-(2-cyano-4-methylpent-2-enoyl)pyrrolidin-2-yl)methyl)-5-(4-methylpiperazin-1-yl)methyl)-1H-benzo[d]imidazol-2-yl)-5-(difluoromethyl)thiophene-2-carboxamide

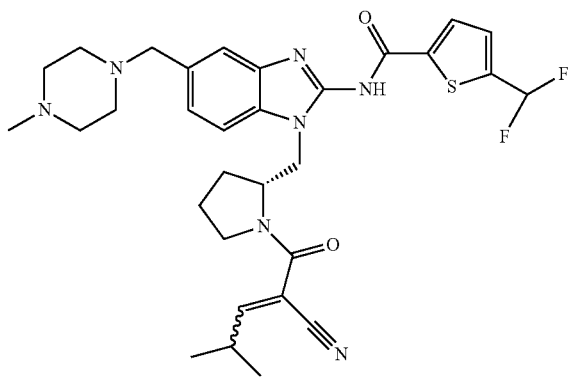 [SMILES: CC(C)C=C(C#N)C(=O)N1CCC[C@@H]1Cn1c(NC(=O)c2ccc(C(F)F)s2)nc2cc(CN3CCN(C)CC3)ccc21]

Substituting N-methyl piperazine for 2,6-dimethylmorpholine in step 2 and following steps 3-5 as described in example 54 afforded (R)-N-(1-((1-(2-cyano-4-methylpent-2-enoyl)pyrrolidin-2-yl)methyl)-5-((4-methylpiperazin-1-yl)methyl)-1H-benzo[d]imidazol-2-yl)-5-(difluoromethyl)thiophene-2-carboxamide. MS (pos. ion) m/z: 610 (M+1).

Intermediate 14

Synthesis of (R)-tert-butyl 2-((2-amino-5-((((benzyloxy)carbonyl)((S)-3,3-dimethylbutan-2-yl)amino)methyl)-1H-benzo[d]imidazol-1-yl)methyl)pyrrolidine-1-carboxylate

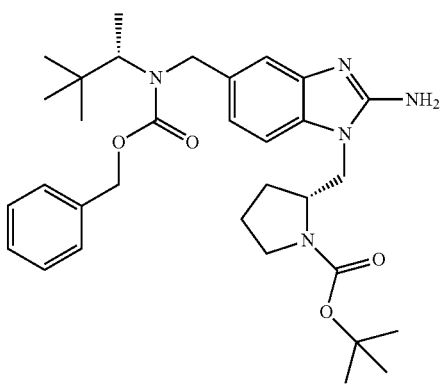 [SMILES: C[C@H](N(Cc1ccc2c(c1)nc(N)n2C[C@H]1CCCN1C(=O)OC(C)(C)C)C(=O)OCc1ccccc1)C(C)(C)C]

Step 1

To a 500 mL three neck round bottomed flask, 4-fluoro-3-nitrobenzaldehyde (10.0 g, 59 mmol) was dissolved in acetonitrile (100 mL) followed by addition of DIPEA (22.8 gm, 177 mmol). After stirring 10 min at rt, (S)-tert-butyl 2-(aminomethyl)pyrrolidine-1-carboxylate (14.2 g, 70 mmol) in acetonitrile (100 mL) was added dropwise and the reaction mixture was stirred at rt for 24 h. The reaction mixture was concentrated, diluted with water and extracted with $CH_2Cl_2$. The combined organic layer were dried over sodium sulfate and concentrated to give crude product which was purified using column purification by eluting the compound with 10% ethyl acetate in hexanes to yield 18.2 g of (S)-tert-butyl 2-((4-formyl-2-nitrophenylamino)-methyl)pyrrolidine-1-carboxylate.

Step 2

To a 1 L three neck round bottomed flask under nitrogen atmosphere, (S)-tert-butyl 2-((4-formyl-2-nitrophenylamino)methyl)pyrrolidine-1-carboxylate (18 g, 51 mmol) and (S)-3,3-dimethyl butn-2-amine (5.2 g, 51 mmol) were dissolved in 1,2 dichloroethane (400 mL) and stirred at rt for 10 min Acetic acid (1.6 mL, catalytic amount) and $NaBH(OAc)_3$ (16.37 g, 77 mmol) were added and the reaction mixture tined at room temperature for 16 h. The reaction mixture was poured in to saturated $Na_2CO_3$ solution (100 mL) followed by extraction with $CH_2Cl_2$. The combined organic layers were dried over sodium sulfate and concentrated to yield 22.4 g of (S)-tert-butyl 2-((4-(((S)-3,3-dimethylbutan-2-ylamino)methyl)-2-nitrophenylamino)methyl)pyrrolidine-1-carboxylate.

Step 3

To a 500 mL three neck round bottomed flask, (S)-tert-butyl 2-((4-(((S)-3,3-dimethylbutan-2-ylamino)methyl)-2-nitrophenylamino)methyl)pyrrolidine-1-carboxylate (22.3 g, 51 mmol) and NaOH (4.5 g, 112 mmol) were suspended in 1,4-dioxane (200 mL) & water (200 mL) and cooled to 10° C. Benzyl chloroformate (13.1 g, 77 mmol) was added dropwise to the cooled reaction mixture and then the reaction mixture was stirred at rt for 16 h. The reaction mixture was diluted with ethyl acetate and washed with 1N HCl solution followed by saturated $NaHCO_3$ solution. The organic layer was dried over sodium sulfate and concentrated to yield 22 g of (S)-tert-butyl 2-((4-(((benzyloxycarbonyl)((S)-3,3-dimethylbutan-2-yl)amino)methyl)-2-nitrophenyl-amino)-methyl)pyrrolidine-1-carboxylate.

Step 4

To a 500 mL three neck round bottomed flask, (S)-tert-butyl 2-((4-(((benzyloxycarbonyl) ((S)-3,3-dimethylbutan-2-yl)amino)methyl)-2-nitrophenylamino)methyl)pyrrolidine-1-carboxylate (21.9 g, 38 mmol) was dissolved in methanol (250 mL) followed by addition of zinc dust (12.5 g, 193 mmol) and saturated $NH_4Cl$ solution (10.3 g, 193 mmol). The mixture was heated at 50° C. for 2 h with stirring. The reaction mixture was filtered through a celite bed and washed with methanol and the filtrate was concentrated to give the crude product. Water was added & extracted with ethyl acetate. The combined organic layer was dried over sodium sulfate and concentrated to give the crude compound which was purified using column purification to yield 20.1 g of (S)-tert-butyl 2-((2-amino-4-(((benzyloxycarbonyl)((S)-3,3-dimethylbutan-2-yl)amino)methyl)phenylamino)-methyl)pyrrolidine-1-carboxylate.

Step 5

To a 500 mL three neck round bottomed flask under nitrogen atmosphere, (S)-tert-butyl 2-((2-amino-4-(((benzyloxycarbonyl)((S)-3,3-dimethylbutan-2-yl)amino)methyl)phenylamino)-methyl)-pyrrolidine-1-carboxylate (20 g, 37 mmol) was dissolved in ethanol (200 mL) followed by addition of cyanogen bromide (4.7 g, 45 mmol) at rt and the mixture was stirred for 4 h. The reaction mixture was concentrated under vacuum and diluted with saturated NaHCO₃ solution and extracted with ethyl acetate. The combined organic layer was dried over sodium sulfate and concentrated to give the crude product which was purified using diethyl ether trituration to yield 13.2 g of (S)-tert-butyl 2-((5-(((benzyloxycarbonyl)((S)-3,3-dimethylbutan-2-yl) amino)methyl)-2-imino-2,3-dihydro-1H-benzo[d]imidazol-1-yl)methyl)pyrrolidine-1-carboxylate.

Intermediate 15

Synthesis of 5-(difluoromethyl)thiophene-2-carboxylic acid

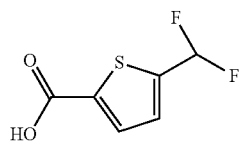

Step 1

To a 35 ml microwave vial, ethyl thiophene-2-carboxylate (1.5 g, 0.01019 mole) and hexamine (2.68 g, 0.02038 mole) were dissolved in TFA (12 mL). The reaction mixture was heated at 90° C. in microwave for 3 h. The reaction mass was diluted and basified with saturated Na₂CO₃ solution and extracted with EtOAc. The combined organic layer was washed with brine, dried over Na₂SO₄ and evaporated to get the crude compound which was purified by flash column chromatography to obtain 0.75 g of ethyl 5-formylthiophene-2-carboxylate.

Step 2

To a 250 mL 3 neck round bottomed flask, ethyl 5-formylthiophene-2-carboxylate (7 g, 37.83 mmole) was dissolved in dry CH₂Cl₂ (60 mL) and stirred at room temperature. To this solution, DAST (5 mL, 37.83 mmole) (in dry CH₂Cl₂ (20 mL)) was added dropwise at room temperature and the reaction mixture was stirred 1 h. DAST (5 mL, 0.37.83 mmole) was again added dropwise at room temperature and the reaction mixture was further stirred for 3 h. The reaction mixture was slowly diluted with sat. NaHCO₃ solution and kept overnight. Product was extracted with EtOAc. The combined organic layer was washed with brine, dried over Na₂SO₄ and evaporated to get crude. The crude compound was purified by flash column purification to yield 5.5 g of ethyl 5-(difluoromethyl)-thiophene-2-carboxylate.

Step 3

To a 250 mL 3-neck round bottomed flask, ethyl 5-(difluoromethyl)thiophene-2-carboxylate (5.5 g, 28.65 mmole) was dissolved in methanol (100 ml) at room temperature. To this, 1N NaOH solution (60 mL) was added slowly and stirred for 2 h at room temperature. Methanol was evaporated under reduced pressure, cooled to 5-10° C. and 1N HCl was added dropwise to make pH 5-6. The precipitate was filtered, washed with hexanes and dried to get pure 4.5 g of 5-(difluoromethyl)thiophene-2-carboxylic acid.

Intermediate 16

Synthesis of benzyl((2-(5-(difluoromethyl)thiophene-2-carboxamido)-14((R)-pyrrolidin-2-ylmethyl)-1H-benzo[d]imidazol-5-yl)methyl)((S)-3,3-dimethylbutan-2-yl)carbamate

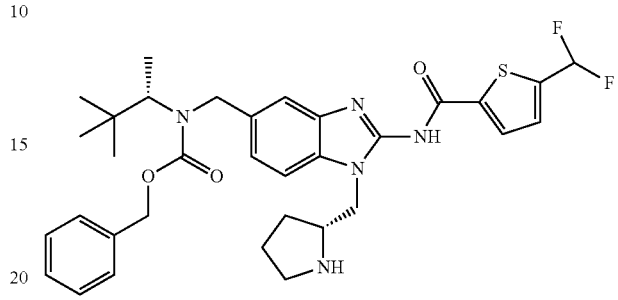

Step 1

To a 100 mL 3-neck round bottomed flask, 5-(difluoromethyl)thiophene-2-carboxylic acid (0.947 g, 0.00532 mole) was dissolved in DMF (25 mL) and cooled to 0° C. under N₂ atmosphere. To this, HATU (2.528 g, 6.653 mmole) was added at 0° C. and the reaction mixture was stirred for 30 minutes at same temperature. tert-Butyl-2-((5-(((benzyloxycarbonyl)((S)-3,3-dimethylbutan-2-yl)amino)methyl)-2-imino-2,3-dihydro-1H-benzo[d]imidazol-1-yl)methyl)pyrrolidine-1-carboxylate (2.5 g, 4.435 mmole) was added followed by DIPEA (2.25 mL, 3.30 mmole) and the reaction mixture was stirred at room temperature for 4 h. Water was added to the reaction mixture and product was extracted with EtOAc. The combined organic layer was washed with water and brine, dried over Na₂SO₄ and evaporated to afford a crude compound which was purified by column chromatography to yield 2.0 g of tert-butyl 2-((5-(((benzyloxycarbonyl)((S)-3,3-dimethylbutan-2-yl)amino)methyl)-2-(5-(difluoromethyl)thiophene-2-carboxamido)-1H-benzo[d]imidazol-1-yl)-methyl)pyrrolidine-1-carboxylate.

Step 2

To a 100 mL single neck round bottomed flask, tert-butyl 2-((5-(((benzyloxycarbonyl)((S)-3,3-dimethylbutan-2-yl) amino)methyl)-2-(5-(difluoromethyl)thiophene-2-carboxamido)-1H-benzo[d]imidazol-1-yl)methyl)pyrrolidine-1-carboxylate (2 g, 2.762 mmole) was dissolved in CH₂Cl₂ (20 mL) and cooled to 0° C. under N₂ atmosphere. To this solution, TFA (10 mL) was added dropwise and stirred for 6 h at room temperature. CH₂Cl₂ and TFA were evaporated under reduced pressure followed by stripping with THF. The crude thus obtained was dissolved in minimum diethyl ether and pure product was precipitated out with hexanes to afford 1.5 g of benzyl(2-(5-(difluoromethyl)thiophene-2-carboxamido)-1-(pyrrolidin-2-ylmethyl)-1H-benzo[d]imidazol-5-yl)-methyl((S)-3,3-dimethylbutan-2-yl)carbamate as TFA salt.

Example 57

Synthesis of N-(1-(((R)-1-(2-cyano-3-(3-methyloxetan-3-yl)acryloyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide

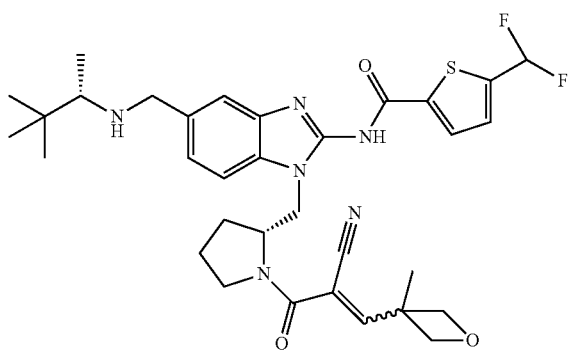 [SMILES: C[C@H](NCc1ccc2c(c1)nc(NC(=O)c1ccc(C(F)F)s1)n2C[C@H]1CCCN1C(=O)C(C#N)=CC1(C)COC1)C(C)(C)C]

Step 1

To a 100 mL three neck round bottomed flask, under nitrogen atmosphere, 2-cyanoacetic acid (0.613 g, 7.214 mmole) was dissolved in dry DMF (30 mL) and cooled to 0° C. To this, HATU (1.37 g, 3.607 mmole) dissolved in dry DMF (10 mL) was added dropwise and stirred at 0° C. for 30 minutes. Benzyl (2-(5-(difluoromethyl)thiophene 2-carboxamido)-1-((R)-pyrrolidin-2-ylmethyl)-1H-benzo[d]imidazol-5-yl)methyl ((S)-3,3-dimethylbutan-2-yl) carbamate as a TFA salt (1.5 g, 2.404 mmole) dissolved in dry DMF (10 mL) was added dropwise followed by addition of DIPEA (2.06 mL, 12.02 mmole) at same temperature and the reaction mass was stirred at room temperature for 2 h. The reaction mixture was diluted with water and extracted with EtOAc. The combined organic layer was dried over Na₂SO₄ and concentrated to give the crude compound which was subjected to column to yield 1.1 g of benzyl(1-(((R)-1-(2-cyanoacetyl)pyrrolidin-2-yl)methyl)-2-(5-(difluoromethyl)thiophene-2-carboxamido)-1H-benzo[d]imidazol-5-yl)methyl((S)-3,3-dimethyl-butan-2-yl)carbamate.

Step 2

To a 25 mL vial, benzyl(1-(((R)-1-(2-cyanoacetyl)pyrrolidin-2-yl)methyl)-2-(5-(difluoro-methyl)thiophene-2-carboxamido)-1H-benzo[d]imidazol-5-yl)methyl((S)-3,3-dimethylbutan-2-yl)carbamate (0.75 g, 1.085 mmole) was dissolved in acetonitrile (7.5 mL). TMSI (0.75 mL) diluted in CH₂Cl₂ (0.75 mL) was added dropwise at room temperature and the reaction mixture was heated at 60° C. for 30 minutes. The reaction mixture was concentrated to give crude compound which was subjected to column purification to yield 0.5 g of N-(1-(((R)-1-(2-cyanoacetyl)pyrrolidin-2-yl)methyl)-5-(((S)-3,3-dimethylbutan-2-ylamino)methyl)-1H-benzo[d]imidazol-2-yl)-5-(difluoro-methyl)thiophene-2-carboxamide.

Step 3

To a 25 mL sealed vial under nitrogen atmosphere N-(1-(((R)-1-(2-cyanoacetyl)pyrrolidin-2-yl)methyl)-5-(((S)-3,3-dimethylbutan-2-ylamino)methyl)-1H-benzo[d]imidazol-2-yl)-5-(difluoromethyl)thiophene-2-carboxamide (0.25 g, 0.449 mmole), 3-methyloxetane-3-carbaldehyde (0.135 g, 1.348 mmole) and piperidine (0.088 mL, 0.899 mmole) was taken in 1,4 dioxane (5 mL). The reaction mixture was heated at 80° C. for 5 h and then was diluted with water (30 mL) and extracted with EtOAc. The combined organic layer was dried over Na₂SO₄ and concentrated to give the crude compound which was purified using Prep HPLC to give 15 mg of N-(1-(((R)-1-(2-cyano-3-(3-methyloxetan-3-yl) acryloyl)pyrrolidin-2-yl)methyl)-5-(((S)-3,3-dimethylbutan-2-ylamino)methyl)-1H-benzo[d]imidazol-2-yl)-5-(difluoromethyl)thiophene-2-carboxamide as a formic acid salt. MS (pos. ion) m/z: 658 (M+1).

Example 58

Synthesis of N-(1-(((R)-1-(2-cyano-4-ethoxy-4-methylpent-2-enoyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide

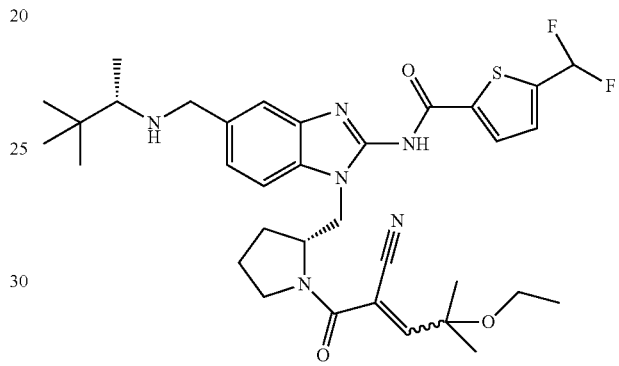

Using the procedure described for Example 57 but substituting 2-ethoxy-2-methylpropanal for 3-methyloxetane-3-carbaldehyde afforded N-(1-(((R)-1-(2-cyano-4-ethoxy-4-methylpent-2-enoyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide as a formic acid salt. MS (pos. ion) m/z: 658 (M+1).

Example 59

Synthesis of N-(1-(((R)-1-(2-cyano-4-methylpent-2-enoyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide

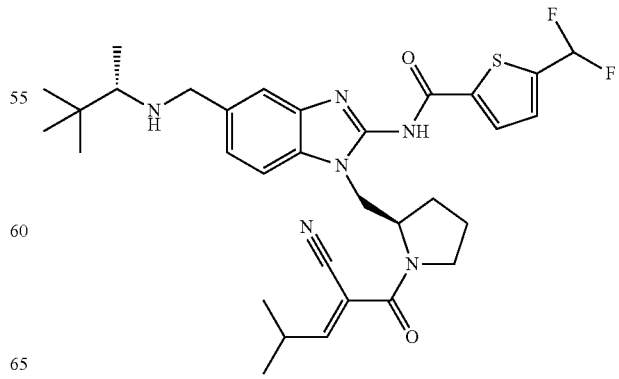

Using the protocol as in Ex. 31, but using benzyl((2-(5-(difluoromethyl)thiophene-2-carboxamido)-1-(((R)-pyrrolidin-2-ylmethyl)-1H-benzo[d]imidazol-5-yl)methyl)((S)-3,3-dimethylbutan-2-yl)carbamate in place of the racemate, N-(1-(((R)-1-(2-cyano-4-dimethylpent-2-enoyl)pyrrolidin-2-yl)methyl)-5-((((S)-3,3-dimethylbutan-2-yl)amino)methyl)-1H-benzo[d]-imidazol-2-yl)-5-(difluoromethyl)thiophene-2-carboxamide was prepared.

Example 60

Synthesis of N-(1-(((R)-1-(2-cyano-4,4-dimethyl-pent-2-enoyl)pyrrolidin-2-yl)methyl)-5-((((S)-3,3-dimethylbutan-2-yl)amino)methyl)-1H-benzo[d]imidazol-2-yl)-5-(difluoromethyl)thiophene

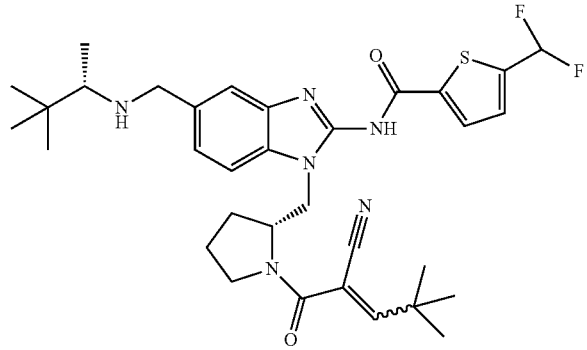 [SMILES: C[C@H](NCc1ccc2c(c1)nc(NC(=O)c1ccc(C(F)F)s1)n2C[C@H]1CCCN1C(=O)C(C#N)=CC(C)(C)C)C(C)(C)C]

Using the same protocol as in Ex. 59, but using 2-cyano-4,4-dimethylpent-2-enoic acid in place of 2-cyano-4-methylpent-2-enoic acid, N-(1-(((R)-1-(2-cyano-4,4-dimethylpent-2-enoyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide was prepared.

Example 61

Synthesis of (R)-N-(1-((1-(2-cyano-4-methylpent-2-enoyl)pyrrolidin-2-yl)methyl)-5-((isobutylamino)methyl)-1H-benzo[d]imidazol-2-yl)-5-(difluoromethyl)thiophene-2-carboxamide

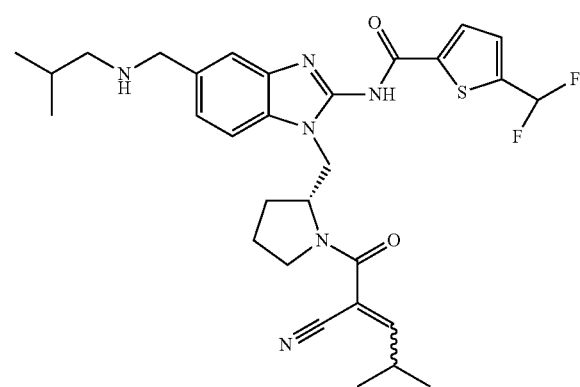 [SMILES: CC(C)C=C(C#N)C(=O)N1CCC[C@@H]1Cn1c(NC(=O)c2ccc(C(F)F)s2)nc2cc(CNCC(C)C)ccc21]

Substituting 2-methylpropan-1-amine for 2,2-dimethylpropan-1-amine in Step 4, Example 52 above and continuing as in Step 5 afford (R)-N-(1-((1-(2-cyano-4-methylpent-2-enoyl)-pyrrolidin-2-yl)methyl)-5-((isobutylamino)methyl)-1H-benzo[d]imidazol-2-yl)-5-(difluoromethyl)-thiophene-2-carboxamide. MS (pos. ion) m/z: 583 (M+1).

Example 62

Synthesis of (R)-N-(1-((1-(2-cyano-4-methylpent-2-enoyl)pyrrolidin-2-yl)methyl)-5-((((3-methyloxetan-3-yl)methyl)amino)methyl)-1H-benzo[d]imidazol-2-yl)-5-(difluoromethyl)thiophene-2-carboxamide

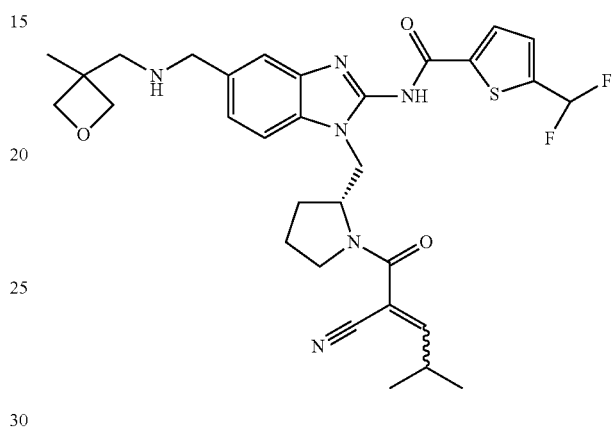

Substituting (3-methyloxetan-3-yl)methanamine for 2,2-dimethylpropan-1-amine in Step 4, Example 52 above and continuing as in Step 5 afforded (R)-N-(1-((1-(2-cyano-4-methylpent-2-enoyl)pyrrolidin-2-yl)methyl)-5-((((3-methyloxetan-3-yl)methyl)amino)methyl)-1H-benzo[d]-imidazol-2-yl)-5-(difluoromethyl)thiophene-2-carboxamide. MS (pos. ion) m/z: 611 (M+1).

Example 63

Synthesis of (R)-N-(5-(2-oxa-6-azaspiro[3.3]heptan-6-ylmethyl)-1-((1-(2-cyano-4-methylpent-2-enoyl)pyrrolidin-2-yl)methyl)-1H-benzo[d]imidazol-2-yl)-5-(difluoromethyl)thiophene-2-carboxamide

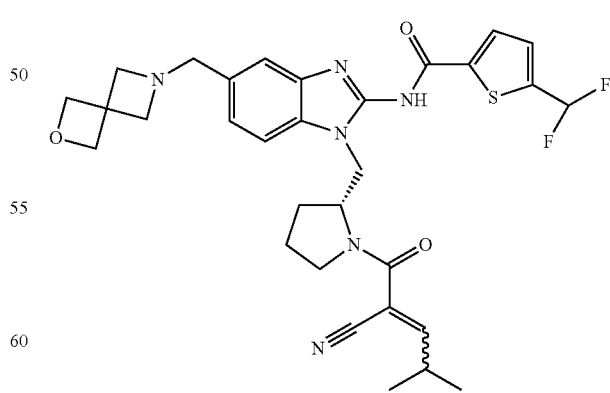

Substituting 2-oxa-6-azaspiro[3.3]heptane; oxalic acid for 2,2-dimethylpropan-1-amine in Step 4, Example 52 above and continuing as in Step 5 afforded (R)-N-(5-(2-oxa-6-azaspiro-[3.3]heptan-6-ylmethyl)-1-((1-(2-cyano-4-methylpent-2-enoyl)pyrrolidin-2-yl)methyl)-1H-benzo[d]imidazol-2-yl)-5-(difluoromethyl)thiophene-2-carboxamide. MS (pos. ion) m/z: 609 (M+1).

Example 64

Synthesis of (R)-N-(1-((1-(2-cyano-4-methylpent-2-enoyl)pyrrolidin-2-yl)methyl)-5-(((2-hydroxy-2-methylpropyl)amino)methyl)-1H-benzo[d]imidazol-2-yl)-5-(difluoromethyl)thiophene-2-carboxamide

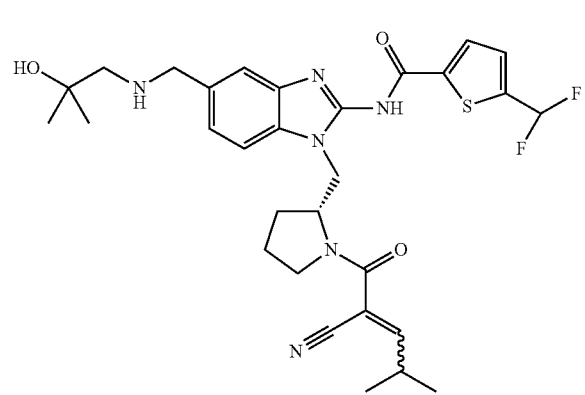 [SMILES: CC(C)C=C(C#N)C(=O)N1CCC[C@@H]1Cn1c(NC(=O)c2ccc(C(F)F)s2)nc2cc(CNCC(C)(C)O)ccc21]

Substituting 1-amino-2-methyl-propan-2-ol for 2,2-dimethylpropan-1-amine in Step 4, Example 52 above and continuing as in Step 5 afforded (R)-N-(1-((1-(2-cyano-4-methylpent-2-enoyl)pyrrolidin-2-yl)methyl)-5-(((2-hydroxy-2-methylpropyl)amino)methyl)-1H-benzo[d]imidazol-2-yl)-5-(difluoromethyl)thiophene-2-carboxamide. MS (pos. ion) m/z: 599 (M+1).

Example 65

Synthesis of (R)-N-(1-((1-(2-cyano-4-methylpent-2-enoyl)pyrrolidin-2-yl)methyl)-5-(((cyclopropylmethyl)amino)methyl)-1H-benzo[d]imidazol-2-yl)-5-(difluoromethyl)thiophene-2-carboxamide

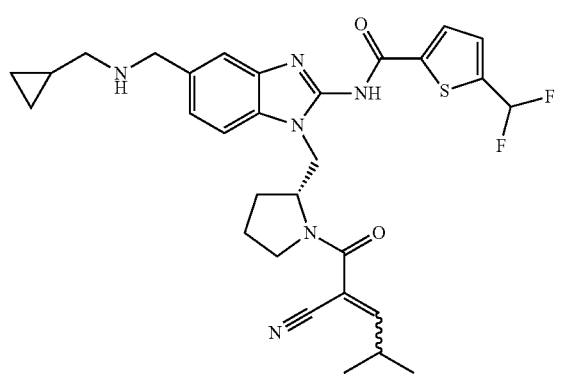 [SMILES: CC(C)C=C(C#N)C(=O)N1CCC[C@@H]1Cn1c(NC(=O)c2ccc(C(F)F)s2)nc2cc(CNCC3CC3)ccc21]

Substituting cyclopropylmethanamine for 2,2-dimethylpropan-1-amine in Step 4, Example 52 above and continuing as in Step 5 afforded (R)-N-(1-((1-(2-cyano-4-methylpent-2-enoyl)-pyrrolidin-2-yl)methyl)-5-(((cyclopropylmethyl)amino)methyl)-1H-benzo[d]imidazol-2-yl)-5-(difluoromethyl)-thiophene-2-carboxamide. MS (pos. ion) m/z: 581 (M+1).

Example 66

Synthesis of (R)-N-(1-((1-(2-cyano-4-methylpent-2-enoyl)pyrrolidin-2-yl)methyl)-5-((3-(2-hydroxypropan-2-yl) azetidin-1-yl)methyl)-1H-benzo[d]imidazol-2-yl)-5-(difluoromethyl)thiophene-2-carboxamide

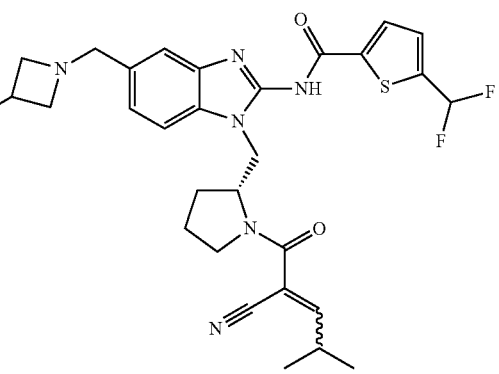

Substituting 2-(azetidin-3-yl)propan-2-ol hydrochloride for 2,2-dimethylpropan-1-amine in Step 4, Example 52 above and continuing as in Step 5 afforded (R)-N-(1-((1-(2-cyano-4-methylpent-2-enoyl)pyrrolidin-2-yl)methyl)-5-((3-(2-hydroxypropan-2-yl)azetidin-1-yl)methyl)-1H-benzo[d]imidazol-2-yl)-5-(difluoromethyl)thiophene-2-carboxamide. MS (pos. ion) m/z: 625 (M+1).

Example 67

Synthesis of (R)-N-(1-((1-(2-cyano-4-methylpent-2-enoyl)pyrrolidin-2-yl)methyl)-5-(3-hydroxy-azetidin-1-yl)methyl)-1H-benzo[d]imidazol-2-yl)-5-(difluoromethyl)thiophene-2-carboxamide

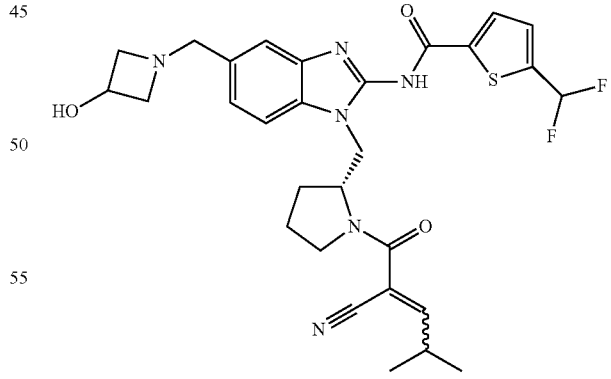

Substituting azetidin-3-ol hydrochloride for 2,2-dimethylpropan-1-amine in Step 4, Example 52 above and continuing as in Step 5 provided (R)-N-(1-((1-(2-cyano-4-methylpent-2-enoyl)pyrrolidin-2-yl)methyl)-5-(3-hydroxyazetidin-1-yl)methyl)-1H-benzo[d]imidazol-2-yl)-5-(difluoromethyl)-thiophene-2-carboxamide. MS (pos. ion) m/z: 583 (M+1).

Example 68

Synthesis of (R)-N-(1-((1-(2-cyano-4-methylpent-2-enoyl)pyrrolidin-2-yl)methyl)-5-((4-(2-hydroxypropan-2-yl)piperidin-1-yl)methyl)-1H-benzo[d]imidazol-2-yl)-5-(difluoromethyl)thiophene-2-carboxamide

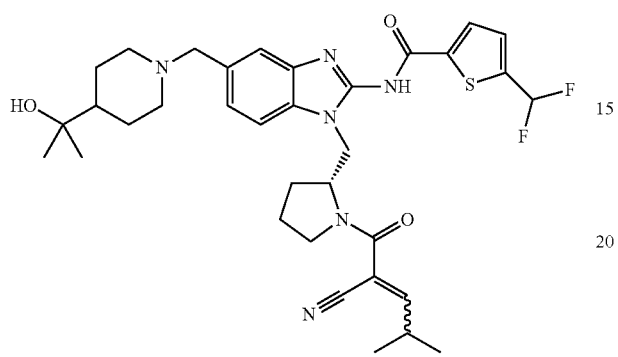

Substituting 2-(4-piperidyl)propan-2-ol for 2,2-dimethylpropan-1-amine in Step 4, Example 52 above and continuing as in Step 5 afforded (R)-N-(1-((1-(2-cyano-4-methylpent-2-enoyl)pyrrolidin-2-yl)methyl)-5-((4-(2-hydroxypropan-2-yl)piperidin-1-yl)methyl)-1H-benzo[d]-imidazol-2-yl)-5-(difluoromethyl)thiophene-2-carboxamide. MS (pos. ion) m/z: 653 (M+1).

Example 69

Synthesis of (R)-N-(1-((1-(2-cyano-3-(3-methyloxetan-3-yl)acryloyl)pyrrolidin-2-yl)methyl)-5-((neopentylamino)methyl)-1H-benzo[d]imidazol-2-yl)-5-(difluoromethyl)thiophene-2-carboxamide

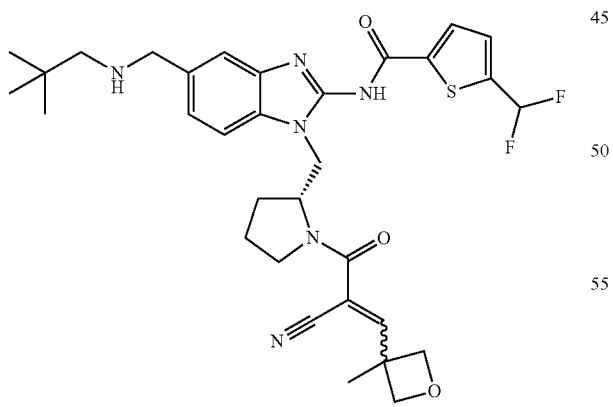

Substituting 3-methyloxetane-3-carbaldehyde for 2-methylpropanal in Step 5, Example 52 above afforded (R)-N-(1-((1-(2-cyano-3-(3-methyloxetan-3-yl)acryloyl)pyrrolidin-2-yl)methyl)-5-((neopentylamino)methyl)-1H-benzo[d]imidazol-2-yl)-5-(difluoromethyl)thiophene-2-carboxamide. MS (pos. ion) m/z: 625 (M+1).

Example 70

Synthesis of (R)-N-(1-((1-(2-cyano-4,4-dimethyl-5-morpholinopent-2-enoyl)pyrrolidin-2-yl)-methyl)-5-(hydroxymethyl)-1H-benzo[d]imidazol-2-yl)-5-(difluoromethyl)thiophene-2-carboxamide

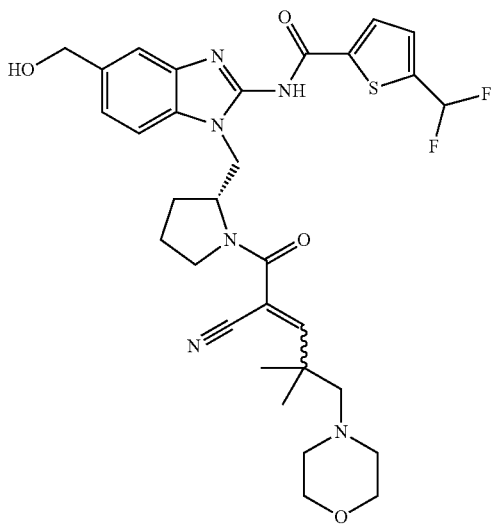 [SMILES: CC(C)(C=C(C#N)C(=O)N1CCC[C@@H]1Cn1c(NC(=O)c2ccc(C(F)F)s2)nc2cc(CO)ccc21)CN1CCOCC1]

To a mixture of (R)-N-(1-((1-(2-cyanoacetyl)pyrrolidin-2-yl)methyl)-5-(hydroxymethyl)-1H-benzo[d]imidazol-2-yl)-5-(difluoromethyl)thiophene-2-carboxamide (111 mg, 0.23 mmol) (from Example 52, Steps 1 and 2) 2,2-dimethyl-3-morpholino-propanal (0.1 mL, 0.47 mmol), pyrrolidine (0.06 mL, 0.70 mmol), and DCM (3 mL) were stirred at rt for 5 minutes and added chloro(trimethyl)silane (0.12 mL, 0.940 mmol). The resultant mixture was stirred at rt for 3 h, concentrated and purified by chromatography to obtain 12 mg of (R)-N-(1-((1-(2-cyano-4,4-dimethyl-5-morpholinopent-2-enoyl)pyrrolidin-2-yl)methyl)-5-(hydroxymethyl)-1H-benzo[d]imidazol-2-yl)-5-(difluoromethyl)-thiophene-2-carboxamide. MS (pos. ion) m/z: 627 (M+1).

Example 71

Synthesis of (R)-N-(1-((1-(2-cyano-4-methylpent-2-enoyl)pyrrolidin-2-yl)methyl)-5-(hydroxymethyl)-1H-benzo[d]imidazol-2-yl)-5-(difluoromethyl)thiophene-2-carboxamide

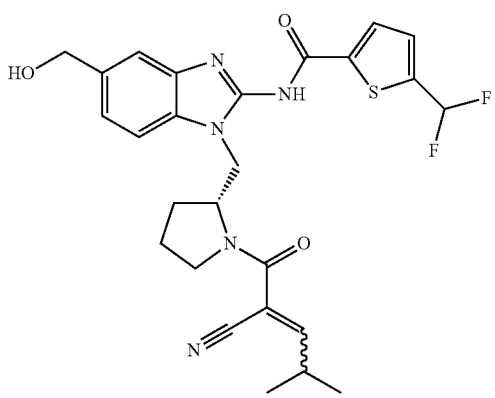 [SMILES: CC(C)C=C(C#N)C(=O)N1CCC[C@@H]1Cn1c(NC(=O)c2ccc(C(F)F)s2)nc2cc(CO)ccc21]

To a solution of (R)-5-(difluoromethyl)-N-(5-(hydroxymethyl)-1-(pyrrolidin-2-ylmethyl)-1H-benzo[d]imidazol-2-yl)thiophene-2-carboxamide (27 mg, 0.07 mmol), 2-cyano-4-methyl-pent-2-enoic acid (13.87 mg, 0.10 mmol), HATU (25.24 mg, 0.07 mmol), DIPEA (0.01 mL, 0.07 mmol) in DMF (10 mL) was stirred at rt for 100 minutes. The reaction mixture was evaporated to afford an oil which was worked up with DCM and water. The organic layers were dried (MgSO₄) and concentrated and the oil was purified by chromatography to obtain 10 mg of (R)-N-(1-((1-(2-cyano-4-methylpent-2-enoyl)pyrrolidin-2-yl)methyl)-5-(hydroxymethyl)-1H-benzo[d]-imidazol-2-yl)-5-(difluoromethyl)thiophene-2-carboxamide as white solid. MS (pos. ion) m/z: 528 (M+1).

Example 72

Synthesis of (R)-N-(1-((1-(2-cyano-4-methylpent-2-enoyl)pyrrolidin-2-yl)methyl)-5-(3-hydroxypentan-3-yl)-1H-benzo[d]imidazol-2-yl)-5-(difluoromethyl)thiophene-2-carboxamide

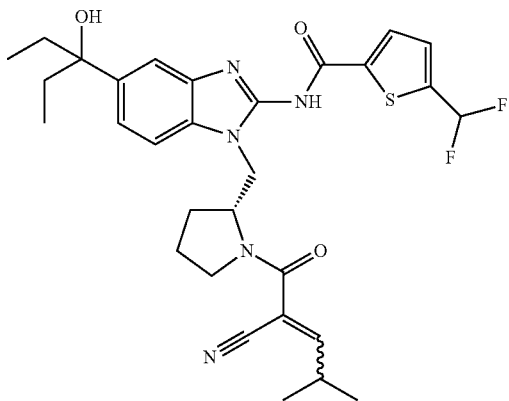 [SMILES: CCC(O)(CC)c1ccc2c(c1)nc(NC(=O)c1ccc(C(F)F)s1)n2C[C@H]1CCCN1C(=O)C(C#N)=CC(C)C]

A mixture of (R)-methyl 1-((1-(tert-butoxycarbonyl)pyrrolidin-2-yl)methyl)-2-(5-(difluoromethyl)thiophene-2-carboxamido)-1H-benzo[d]imidazole-5-carboxylate (482 mg, 0.90 mmol), and THF (20 mL) was cooled to 0° C. in an ice-bath and bromo(ethyl)magnesium in 3M diethyl ether (721 mg, 5.41 mmol) was added dropwise over 5 min. The resultant mixture was stirred at 0° C. for 15 min and then allowed to warm to rt and stirred 2 hours. The reaction mixture was quenched with saturated ammonium chloride and washed with DCM and the organic layers was dried with MgSO₄. The concentrated crude was purified by chromatography to obtain (R)-tert-butyl 2-((2-(5-(difluoromethyl)thiophene-2-carboxamido)-5-(3-hydroxypentan-3-yl)-1H-benzo[d]imidazol-1-yl)methyl)pyrrolidine-1-carboxylate, 180 mg as a yellow oil. Continuing as in Steps 1, 2, and 5, Example 52, afforded 48 mg of (R)-N-(1-((1-(2-cyano-4-methylpent-2-enoyl)-pyrrolidin-2-yl)methyl)-5-(3-hydroxypentan-3-yl)-1H-benzo[d]imidazol-2-yl)-5-(difluoromethyl)-thiophene-2-carboxamide as a white solid.

Example 73

Synthesis of (R)-N-(1-((1-(2-cyano-4-methylpent-2-enoyl)pyrrolidin-2-yl)methyl)-5-((neopentylamino)methyl)-1H-benzo[d]imidazol-2-yl)isoxazole-5-carboxamide

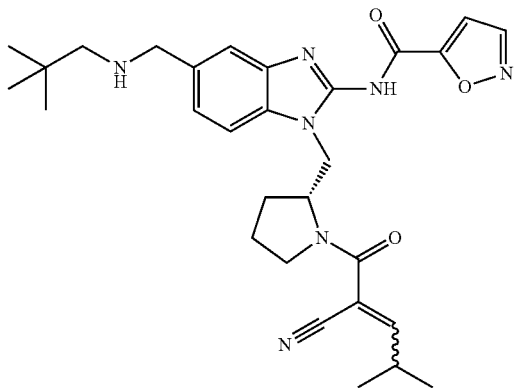 [SMILES: CC(C)C=C(C#N)C(=O)N1CCC[C@@H]1Cn1c(NC(=O)c2ccno2)nc2cc(CNCC(C)(C)C)ccc21]

Step 1
To a solution of (R)-methyl 1-((1-(tert-butoxycarbonyl)pyrrolidin-2-yl)methyl)-2-imino-2,3-dihydro-1H-benzo[d]imidazole-5-carboxylate (1120 mg, 2.99 mmol) (Intermediate 13, Step 3), isoxazole-5-carboxylic acid (507.3 mg, 4.49 mmol), and DIPEA (1.03 mL, 5.9 8 mmol) in DMF (6 mL)) was added HATU (1705 mg, 4.49 mmol). The resultant mixture was stirred at rt for 2 hours. The reaction mixture was evaporated, then the crude mixture was diluted with DCM and washed with brine. The organic layers were separated and dried with MgSO₄, filtered and concentrated to crude oil. This crude oil was purified by chromatography to obtain 1380 mg of (R)-methyl 1-((1-(tert-butoxycarbonyl)pyrrolidin-2-yl)methyl)-2-(isoxazole-5-carboxamido)-1H-benzo[d]imidazole-5-carboxylate.

Step 2
A mixture of (R)-methyl 1-((1-(tert-butoxycarbonyl)pyrrolidin-2-yl)methyl)-2-(isoxazole-5-carboxamido)-1H-benzo[d]imidazole-5-carboxylate (1027 mg, 2.19 mmol) in THF (20 mL) was stirred at 0° C. and then was added LAH (2M in THF) (3.3 mL, 6.56 mmol). The resultant mixture was then stirred at rt for 1 hour. The reaction mixture was quenched with NaHCO₃ (sat, 30 mL) and worked up with DCM. The organic layers were washed with brine and dried (MgSO₄). The crude was concentrated to an oil and purified by chromatography to obtain 600 mg of (R)-tert-butyl 2-((5-(hydroxymethyl)-2-(isoxazole-5-carboxamido)-1H-benzo[d]imidazol-1-yl)methyl)pyrrolidine-1-carboxylate.

Step 3
To the mixture of (R)-tert-butyl 2-((5-(hydroxymethyl)-2-(isoxazole-5-carboxamido)-1H-benzo[d]imidazol-1-yl)methyl)pyrrolidine-1-carboxylate (320 mg, 0.72 mmol) in DCM (2 mL) was added 4N HCl in dioxane (3 .mL). The resultant mixture was stirred at rt for 4 hours. The reaction mixture was concentrated and dried in hi-vac to obtain 309 mg of (R)-N-(5-(hydroxymethyl)-1-(pyrrolidin-2-ylmethyl)-1H-benzo[d]imidazol-2-yl)isoxazole-5-carboxamide as the HCl salt.

Step 4

To a solution of (R)-N-(5-(hydroxymethyl)-1-(pyrrolidin-2-ylmethyl)-1H-benzo[d]imidazol-2-yl)isoxazole-5-carboxamide, HCl salt (247 mg, 0.72 mmol), DIPEA (0.37 mL, 2.17 mmol), and 2-cyanoacetic acid (123 mg, 1.45 mmol) in DMF (4 mL) was stirred at rt for 10 minutes then added HATU (412.44 mg, 1.09 mmol). The resulting mixture was stirred at rt for 1 hour. The reaction mixture was concentrated and worked up with water and then the organic layers was dried (MgSO$_4$) and concentrated to oil. DCM was added and the resulting precipitate was filtered to collect the solid product which was purified by chromatography to obtain 280 mg of (R)-N-(1-((1-(2-cyanoacetyl)pyrrolidin-2-yl)methyl)-5-(hydroxymethyl)-1H-benzo[d]imidazol-2-yl)isoxazole-5-carboxamide.

Step 5

To the solution of (R)-N-(1-((1-(2-cyanoacetyl)pyrrolidin-2-yl)methyl)-5-(hydroxymethyl)-1H-benzo[d]imidazol-2-yl)isoxazole-5-carboxamide (280 mg, 0.69 mmol) was added Dess Martin periodinane (436.18 mg, 1.0 3 mmol). The resulting mixture was stirred at rt for 100 min. The reaction mixture was worked up with DCM and water and the organic layer was dried (MgSO$_4$) then concentrated to oil. The crude oil was purified by chromatography to afford 230 mg of (R)-N-(1-((1-(2-cyanoacetyl)pyrrolidin-2-yl)methyl)-5-formyl-1H-benzo[d]imidazol-2-yl)isoxazole-5-carboxamide.

Step 6

To a mixture of (R)-N-(1-((1-(2-cyanoacetyl)pyrrolidin-2-yl)methyl)-5-formyl-1H-benzo[d]imidazol-2-yl)isoxazole-5-carboxamide (278 mg, 0.68 mmol), 2,2-dimethylpropan-1-amine (0.19 mL, 1.71 mmol), and DCM (8 mL) was added NaBH$_3$CN (85.97 mg, 1.37 mmol).

The resultant mixture was stirred at rt for 1 hour. The reaction mixture was washed sequentially with water and brine. The organic layer was dried (MgSO$_4$) and concentrated to oil then purified by chromatography to obtain 230 mg of (R)-N-(1-((1-(2-cyanoacetyl)pyrrolidin-2-yl)methyl)-5-((neopentyl-amino)methyl)-1H-benzo[d]imidazol-2-yl)isoxazole-5-carboxamide.

Step 7

To a solution of (R)-N-(1-((1-(2-cyanoacetyl)pyrrolidin-2-yl)methyl)-5-((neopentylamino)-methyl)-1H-benzo[d]imidazol-2-yl)isoxazole-5-carboxamide (115 mg, 0.24 mmol), 2-methylpropanal (0.07 mL, 0.72 mmol), pyrrolidine (0.1 mL, 1.2 mmol), and DCM (3 mL) was added chloro(trimethyl)-silane (0.12 mL, 0.96 mmol). The resultant solution was stirred at rt for 1 hour. The reaction mixture was concentrated to dryness and then purified by chromatography to obtain (R)-N-(1-((1-(2-cyano-4-methylpent-2-enoyl)pyrrolidin-2-yl)methyl)-5-((neopentylamino)methyl)-1H-benzo[d]imidazol-2-yl)isoxazole-5-carboxamide, 48 mg. MS (pos. ion) m/z: 532 (M+1).

Example 74

Synthesis of (R)-N-(1-((1-(2-cyano-4,4-dimethylpent-2-enoyl)pyrrolidin-2-yl)methyl)-5-((neopentylamino)methyl)-1H-benzo[d]imidazol-2-yl)isoxazole-5-carboxamide

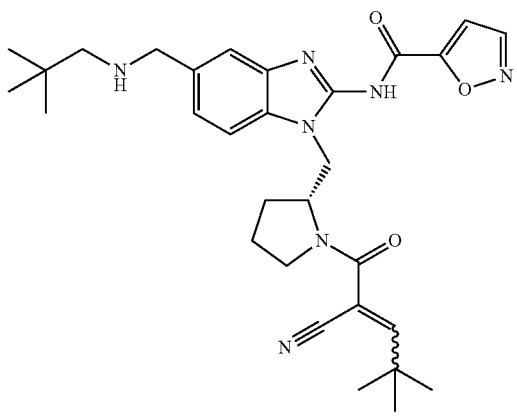 [SMILES: CC(C)(C)C=C(C#N)C(=O)N1CCC[C@@H]1Cn1c(NC(=O)c2ccno2)nc2cc(CNCC(C)(C)C)ccc21]

Substituting 2,2-dimethylpropanal for 2-methylpropanal in Step 7, Example 73 above afford (R)-N-(1-((1-(2-cyano-4,4-dimethylpent-2-enoyl)pyrrolidin-2-yl)methyl)-5-((neopentyl-amino)methyl)-1H-benzo[d]imidazol-2-yl)isoxazole-5-carboxamide. MS (pos. ion) m/z: 546 (M+1).

Example 75

Synthesis of (R)-N-(1-((1-(2-cyano-3-(3-methyloxetan-3-yl)acryloyl)pyrrolidin-2-yl)methyl)-5-((neopentylamino)methyl)-1H-benzo[d]imidazol-2-yl)isoxazole-5-carboxamide

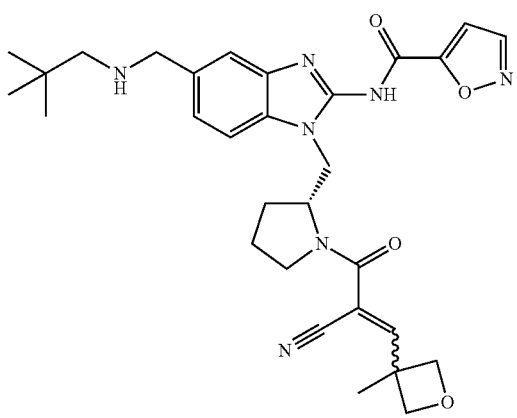 [SMILES: CC(C)(C)CNCc1ccc2c(c1)nc(NC(=O)c1ccno1)n2C[C@H]1CCCN1C(=O)C(C#N)=CC1(C)COC1]

Substituting 3-methyloxetane-3-carbaldehyde for 2-methylpropanal in Step 7, Example 73 above afforded (R)-N-(1-((1-(2-cyano-3-(3-methyloxetan-3-yl)acryloyl)pyrrolidin-2-yl)methyl)-5-((neopentylamino)methyl)-1H-benzo[d]imidazol-2-yl)isoxazole-5-carboxamide. MS (pos. ion) m/z: 560 (M+1).

Example 76

Synthesis of (R)-N-(1-((1-(2-cyano-4-methylpent-2-enoyl)pyrrolidin-2-yl)methyl)-5-((neopentylamino)methyl)-1H-benzo[d]imidazol-2-yl)nicotinamide

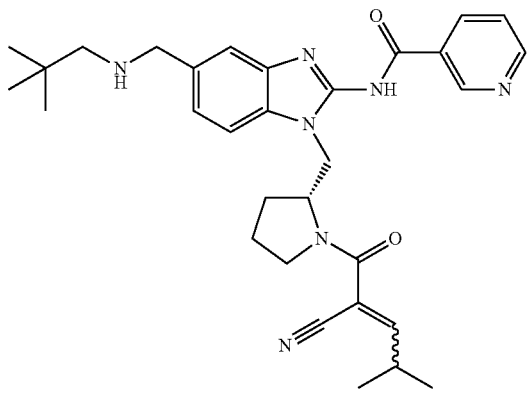 [SMILES: CC(C)C=C(C#N)C(=O)N1CCC[C@@H]1Cn1c(NC(=O)c2cccnc2)nc2cc(CNCC(C)(C)C)ccc21]

Substituting nicotinic acid for isoxazole-5-carboxylic acid in Step 1, Ex 73 above and continuing as in Steps 2-7 afforded (R)-N-(1-((1-(2-cyano-4-methylpent-2-enoyl)pyrrolidin-2-yl)methyl)-5-((neopentylamino)methyl)-1H-benzo[d]imidazol-2-yl)nicotinamide. MS (pos. ion) m/z: 542 (M+1).

Example 77

Synthesis of (R)-N-(1-((1-(2-cyano-4-methylpent-2-enoyl)pyrrolidin-2-yl)methyl)-5-((neopentyl-amino)methyl)-1H-benzo[d]imidazol-2-yl)-3-(difluoromethyl)benzamide

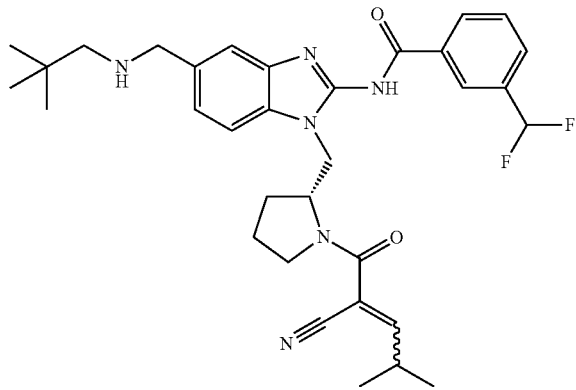 [SMILES: CC(C)C=C(C#N)C(=O)N1CCC[C@@H]1Cn1c(NC(=O)c2cccc(C(F)F)c2)nc2cc(CNCC(C)(C)C)ccc21]

Substituting 3-(difluoromethyl)benzoic acid for isoxazole-5-carboxylic acid in Step 1, Example 73 above and continuing as in Steps 2-7 afforded (R)-N-(1-((1-(2-cyano-4-methylpent-2-enoyl)pyrrolidin-2-yl)methyl)-5-((neopentylamino)methyl)-1H-benzo[d]imidazol-2-yl)-3-(difluoromethyl)benzamide. MS (pos. ion) m/z: 591 (M+1).

Example 78

Synthesis of (R)-N-(1-((1-(2-cyano-4-methylpent-2-enoyl)pyrrolidin-2-yl)methyl)-6-((neopentylamino)methyl)-1H-benzo[d]imidazol-2-yl)-5-(difluoromethyl)thiophene-2-carboxamide

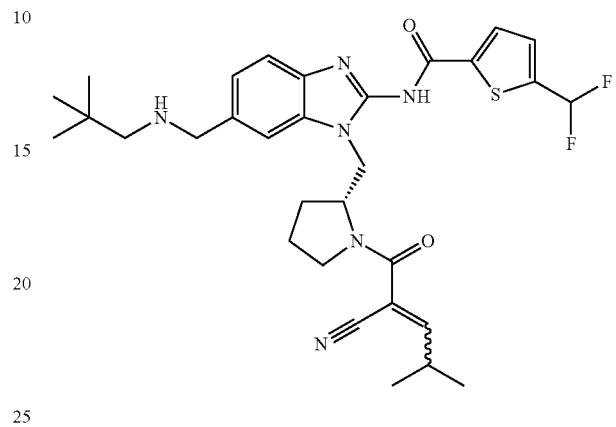

Step 1

To a solution (R)-N-(1-((1-(2-cyanoacetyl)pyrrolidin-2-yl)methyl)-6-(hydroxymethyl)-1H-benzo[d]imidazol-2-yl)-5-(difluoromethyl)thiophene-2-carboxamide (245 mg, 0.52 mmol), (prepared as (R)-N-(1-((1-(2-cyano acetyl)pyrrolidin-2-yl)methyl)-5-(hydroxymethyl)-1H-benzo[d]imidazol-2-yl)-5-(difluoromethyl)thiophene-2-carboxamide but using methyl 3-fluoro-4-nitrobenzoate) in 10 mL of DCM was added Dess-Martin periodinane. The reaction mixture was stirred 1 h, filtered and the solvent removed to afford 240 mg of (R)-N-(1-((1-(2-cyanoacetyl)pyrrolidin-2-yl)methyl)-6-formyl-1H-benzo[d]imidazol-2-yl)-5-(difluoromethyl)thiophene-2-carboxamide.

Step 2

To a mixture of (R)-N-(1-((1-(2-cyanoacetyl)pyrrolidin-2-yl)methyl)-6-formyl-1H-benzo[d]imidazol-2-yl)-5-(difluoromethyl)thiophene-2-carboxamide (240 mg) in 10 mL of DCM was added, 2-dimethylpropan-1-amine (0.06 mL) followed by NaBH$_3$CN (29 mg). The mixture was stirred for 2 h and then partitioned between DCM and saturated sodium chloride. The organic phase was dried over sodium sulfate, filtered, and concentrated to afford 184 mg of (R)-N-(1-((1-(2-cyanoacetyl)pyrrolidin-2-yl)methyl)-6-((neopentylamino)methyl)-1H-benzo[d]imidazol-2-yl)-5-(difluoromethyl)thiophene-2-carboxamide.

Step 3

To a solution of (R)-N-(1-((1-(2-cyanoacetyl)pyrrolidin-2-yl)methyl)-6-((neopentyl-amino)methyl)-1H-benzo[d]imidazol-2-yl)-5-(difluoromethyl)thiophene-2-carboxamide (85 mg) in 10 mL of DCM was added 2-methylpropanal (0.3 mL). The reaction mixture was cooled to 0° C. and pyrrolidine (0.08 mL, 0.93 mmol) was added followed by TMS-Cl (0.08 mL, 0.62 mmol).

The ice bath was removed and the reaction mixture was stirred at rt for 1 hour. After removal of solvent under vacuum, the residue was purified by chromatography to afford (R)-N-(1-((1-(2-cyano-4-methylpent-2-enoyl)pyrrolidin-2-yl)methyl)-6-((neopentylamino)methyl)-1H-benzo[d]imidazol-2-yl)-5-(difluoromethyl)thiophene-2-carboxamide (30 mg) as a white powder. LC-MS (ES, m/z): 597 [M+H].

Example 79

Synthesis of (R)-N-(1-((1-(2-cyano-3-(3-methyloxetan-3-yl)acryloyl)pyrrolidin-2-yl)methyl)-6-((neopentylamino)methyl)-1H-benzo[d]imidazol-2-yl)-5-(difluoromethyl)thiophene-2-carboxamide

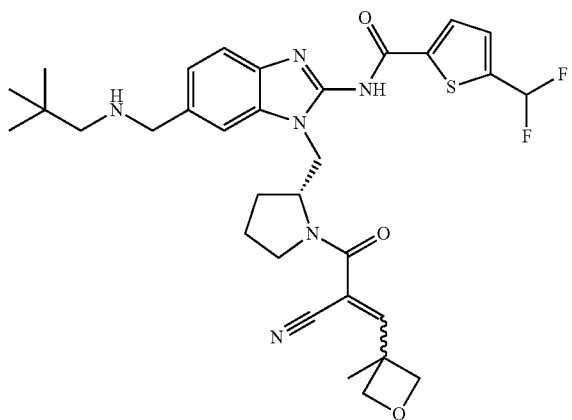 [SMILES: CC(C)(C)CNCc1ccc2nc(NC(=O)c3ccc(C(F)F)s3)n(C[C@H]3CCCN3C(=O)C(C#N)=CC3(C)COC3)c2c1]

Following the procedure in Step 3, Example 78, but replacing 2-methylpropanal with 3-methyloxetane-3-carbaldehyde afforded (R)-N-(1-((1-(2-cyano-3-(3-methyloxetan-3-yl)acryloyl)pyrrolidin-2-yl)methyl)-6-((neopentylamino)methyl)-1H-benzo[d]imidazol-2-yl)-5-(difluoromethyl)thiophene-2-carboxamide. LC-MS (ES, m/z): 625 [M+H].

Example 80

Synthesis of N-(1-((1-(2-cyano-4-(dimethylamino)-4-methylpent-2-enoyl)azetidin-3-yl)methyl)-1H-benzo[d]imidazol-2-yl)-5-(difluoromethyl)thiophene-2-carboxamide

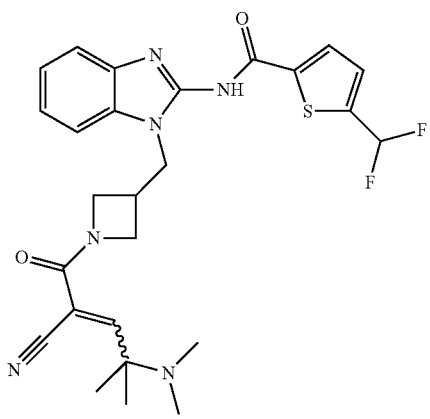 [SMILES: CN(C)C(C)(C)C=C(C#N)C(=O)N1CC(Cn2c(NC(=O)c3ccc(C(F)F)s3)nc3ccccc32)C1]

Step 1

Into a 100-mL round-bottom flask, was placed a solution of tert-butyl 3-[(2-amino-1H-1,3-benzodiazol-1-yl)methyl]azetidine-1-carboxylate (Example 43, Step 3) (1 g, 3.31 mmol) in 50 mL of DMF. 5-(Difluoromethyl)thiophene-2-carboxylic acid (650 mg, 3.65 mmol), PyBop (1.9 g, 3.66 mmol), and triethylamine (2.1 mL) were added to the reaction mixture. The resulting solution was stirred overnight at rt, and then it was diluted with H$_2$O. The solids were collected by filtration, and dried in an oven under reduced pressure to give 1.6 g of tert-butyl 3-([2-[5-(difluoromethyl)-thiophene-2-amido]-1H-1,3-benzodiazol-1-yl]methyl)azetidine-1-carboxylate as a pink solid.

Step 2

Into a 50-mL round-bottom flask, was placed a solution of tert-butyl 3-([2-[5-(difluoro-methyl)thiophene-2-amido]-1H-1,3-benzodiazol-1-yl]methyl)azetidine-1-carboxylate (300 mg, 0.65 mmol) in DCM (10 mL) and trifluoroacetic acid (2 mL). The resulting solution was stirred overnight at rt, and then it was diluted with DCM. The resulting mixture was washed with saturated sodium bicarbonate (aq.), and concentrated under vacuum to give 200 mg of N-[1-(azetidin-3-ylmethyl)-1H-1,3-benzodiazol-2-yl]-5-(difluoromethyl)thiophene-2-carboxamide as a yellow solid.

Step 3

Into a 100-mL round-bottom flask, was placed a solution of N-[1-(azetidin-3-ylmethyl)-1H-1,3-benzodiazol-2-yl]-5-(difluoromethyl)thiophene-2-carboxamide (270 mg, 0.75 mmol) in DMF (20 mL). 2-Cyanoacetic acid (70 mg, 0.82 mmol), triethylamine (380 mg, 3.76 mmol), and HATU (342 mg, 0.90 mmol) were added to the reaction mixture. The resulting solution was stirred overnight at rt, and then it was diluted with H$_2$O. The solids were collected by filtration, and dried in an oven under reduced pressure to give 200 mg of N-(1-[[1-(2-cyano-acetyl)azetidin-3-yl]methyl]-1H-1,3-benzodiazol-2-yl)-5-(difluoromethyl)thiophene-2-carboxamide as a brown solid.

Step 4

Into a 100-mL round-bottom flask, was placed a solution of N-(1-[[1-(2-cyanoacetyl)-azetidin-3-yl]methyl]-1H-1,3-benzodiazol-2-yl)-5-(difluoromethyl)thiophene-2-carboxamide (220 mg, 0.51 mmol), 2-(dimethylamino)-2-methylpropanal (300 mg, 2.60 mmol), and piperidine (130 mg, 1.53 mmol) in toluene (50 mL). The resulting solution was stirred overnight at 110° C. in an oil bath, and then concentrated under vacuum. The crude product (150 mg) was purified by Prep-HPLC to afford 18 mg of N-(1-((1-(2-cyano-4-(dimethylamino)-4-methylpent-2-enoyl)azetidin-3-yl)methyl)-1H-benzo[d]imidazol-2-yl)-5-(difluoromethyl)thiophene-2-carboxamide as an off-white solid. LC-MS (m/z): 527 [M+H].

Example 81

Synthesis of N-(1-((1-(2-cyano-4-methyl-4-morpholinopent-2-enoyl)azetidin-3-yl)methyl)-1H-benzo[d]imidazol-2-yl)-5-(difluoromethyl)thiophene-2-carboxamide

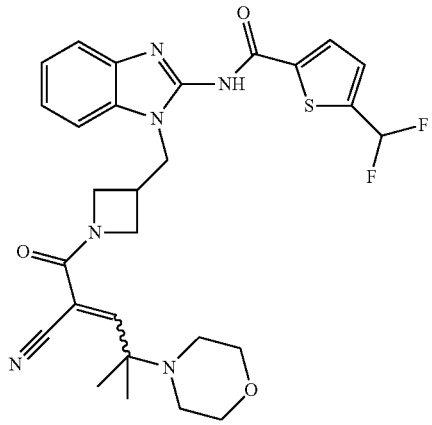 [SMILES: CC(C)(C=C(C#N)C(=O)N1CC(Cn2c(NC(=O)c3ccc(C(F)F)s3)nc3ccccc32)C1)N1CCOCC1]

Following the procedure in Step 4, Example 80, but substituting 2-methyl-2-morpholino-propanal in place of 2-(dimethylamino)-2-methylpropanal afforded N-(1-((1-(2-cyano-4-methyl-4-morpholino-pent-2-enoyl)azetidin-3-yl)methyl)-1H-benzo[d]imidazol-2-yl)-5-(difluoromethyl)-thiophene-2-carboxamide. LC-MS (m/z): 569 [M+H].

Example 82

Synthesis of N-(1-((1-(4-amino-2-cyano-4-methyl-pent-2-enoyl)azetidin-3-yl)methyl)-1H-benzo[d]imidazol-2-yl)-5-(difluoromethyl)thiophene-2-carboxamide

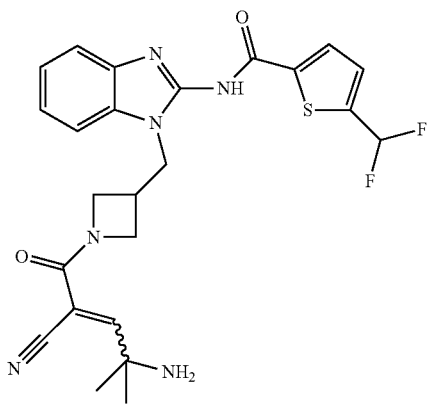 [SMILES: CC(C)(N)C=C(C#N)C(=O)N1CC(Cn2c(NC(=O)c3ccc(C(F)F)s3)nc3ccccc32)C1]

Step 1

Following the procedure in Step 4, Example 80, but substituting tert-butyl N-(2-methyl-1-oxopropan-2-yl)carbamate in place of 2-(dimethylamino)-2-methylpropanal afforded tert-butyl (4-cyano-5-(3-((2-(5-(difluoromethyl)thiophene-2-carboxamido)-1H-benzo[d]imidazol-1-yl)methyl)-azetidin-1-yl)-2-methyl-5-oxopent-3-en-2-yl)carbamate.

Step 2

Into a 50-mL round-bottom flask, was placed a solution of tert-butyl (4-cyano-5-(3-((2-(5-(difluoromethyl)thiophene-2-carboxamido)-1H-benzo[d]imidazol-1-yl)methyl)azetidin-1-yl)-2-methyl-5-oxopent-3-en-2-yl)carbamate (130 mg, 0.22 mmol) in DCM (10 mL) and trifluoroacetic acid (2 mL). The resulting solution was stirred overnight at rt, and then it was concentrated under vacuum. The crude product (90 mg) was purified by Prep-HPLC to afford 40 mg of N-(1-((1-(4-amino-2-cyano-4-methylpent-2-enoyl)azetidin-3-yl)methyl)-1H-benzo[d]imidazol-2-yl)-5-(difluoromethyl)thiophene-2-carboxamide as the formic acid salt as a white solid. LC-MS (m/z): 499 [M+H].

Example 83

Synthesis of (R)-N-(1-((1-(2-cyano-4,4-dimethyl-pent-2-enoyl)pyrrolidin-2-yl)methyl)-1H-benzo[d]imidazol-2-yl)-5-(difluoromethyl)thiophene-2-carboxamide

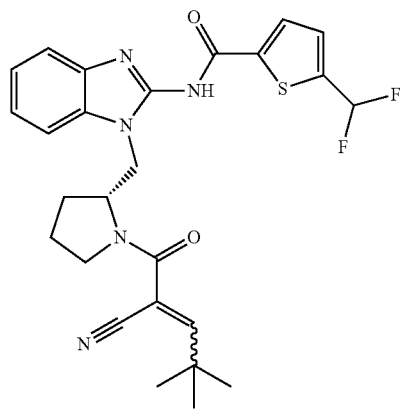 [SMILES: CC(C)(C)C=C(C#N)C(=O)N1CCC[C@@H]1Cn1c(NC(=O)c2ccc(C(F)F)s2)nc2ccccc21]

Into a 250-mL round-bottom flask, was placed a solution of 5-(difluoromethyl)-N-[1-[(2R)-pyrrolidin-2-ylmethyl]-1H-1,3-benzodiazol-2-yl]thiophene-2-carboxamide (150 mg, from Step 3, Example 50), 2-cyano-4,4-dimethylpent-2-enoic acid (70 mg, 0.46 mmol, 1.15 equiv), HATU (177 mg, 0.47 mmol, 1.17 equiv), and triethylamine (0.2 mL) in DMF (30 mL). The resulting solution was stirred overnight at rt, and then it was diluted with water. The solids were collected by filtration. The crude product (100 mg) was purified by Prep-HPLC to afford 29.2 mg of (R)-N-(1-((1-(2-cyano-4,4-dimethylpent-2-enoyl)pyrrolidin-2-yl)methyl)-1H-benzo[d]imidazol-2-yl)-5-(difluoromethyl)thiophene-2-carboxamide as an off-white solid. LC-MS (m/z): 512 [M+H].

Example 84

Synthesis of (R)-N-(1-((1-(2-cyano-4-methylpent-2-enoyl)pyrrolidin-2-yl)methyl)-1H-benzo[d]imidazol-2-yl)-3-methylbenzamide

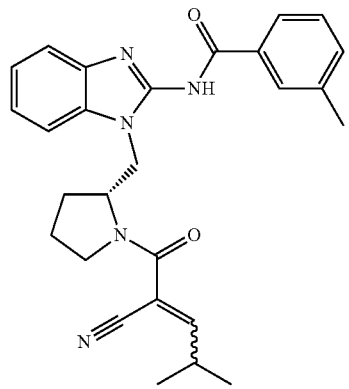 [SMILES: Cc1cccc(C(=O)Nc2nc3ccccc3n2C[C@H]2CCCN2C(=O)C(C#N)=CC(C)C)c1]

(R)-3-Methyl-N-(1-(pyrrolidin-2-ylmethyl)-1H-benzo[d]imidazol-2-yl)benzamide (prepared as in Example 50 but substituting 3-methylbenzoic acid for 5-(difluoromethyl) thiophene-2-carboxylic acid) was dissolved in N,N-dimethylformamide (10 mL). DIEA (231.9 mg, 1.79 mmol, 4.00 equiv), HATU (255.8 mg, 0.67 mmol, 1.50 equiv), and 2-cyano-4-methylpent-2-enoic acid (93.6 mg, 0.67 mmol, 1.50 equiv) were added to the reaction mixture and the resulting solution was stirred overnight at rt. The reaction was quenched with water and the resulting solution was extracted with dichloromethane, and the combined organic layers were concentrated under vacuum. The crude product (100 mg) was purified by Prep HPLC to afford 47.4 mg of (R)-N-(1-((1-(2-cyano-4-methylpent-2-enoyl)pyrrolidin-2-yl)methyl)-1H-benzo[d]imidazol-2-yl)-3-methylbenzamide as a white solid. LC-MS (m/z): 456.3 [M+1].

Example 85

Synthesis of (R)-N-(1-((1-(2-cyano-4-methylpent-2-enoyl)pyrrolidin-2-yl)methyl)-1H-benzo[d]imidazol-2-yl)-3-(difluoromethyl)benzamide

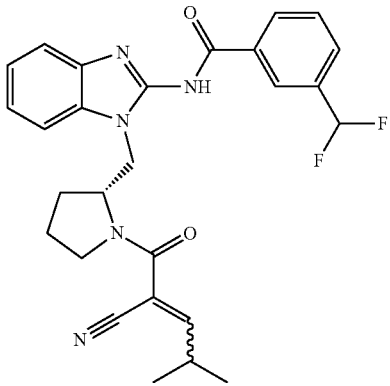 [SMILES: CC(C)C=C(C#N)C(=O)N1CCC[C@@H]1Cn1c(NC(=O)c2cccc(C(F)F)c2)nc2ccccc21]

(R)-3-(Difluoromethyl)-N-(1-(pyrrolidin-2-ylmethyl)-1H-benzo[d]imidazol-2-yl)-benzamide (prepared as in Example 50 but substituting 3-(difluoromethyl)benzoic acid for 5-(difluoromethyl)-thiophene-2-carboxylic acid) was reacted with 2-cyano-4-methylpent-2-enoic acid as in Example 84 to afford (R)-N-(1-((1-(2-cyano-4-methylpent-2-enoyl)pyrrolidin-2-yl)methyl)-1H-benzo[d]imidazol-2-yl)-3-(difluoromethyl)benzamide. LC-MS (m/z): 492.1 [M+H].

Example 86

Synthesis of (R)-N-(1-((1-(2-cyano-4-methylpent-2-enoyl)pyrrolidin-2-yl)methyl)-1H-benzo[d]imidazol-2-yl)isoxazole-5-carboxamide

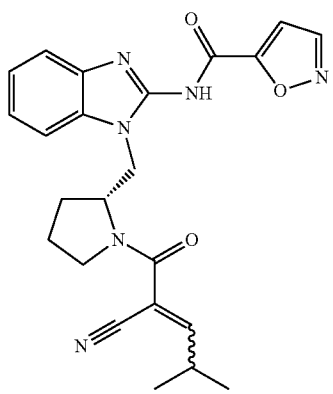 [SMILES: CC(C)C=C(C#N)C(=O)N1CCC[C@@H]1Cn1c(NC(=O)c2ccno2)nc2ccccc21]

(R)-N-(1-(Pyrrolidin-2-ylmethyl)-1H-benzo[d]imidazol-2-yl)isoxazole-5-carboxamide (prepared as in Example 50 but substituting isoxazole-5-carboxylic acid for 5-(difluoromethyl)-thiophene-2-carboxylic acid), was reacted with 2-cyano-4-methylpent-2-enoic acid as in Example 84 to afford (R)-N-(1-((1-(2-cyano-4-methylpent-2-enoyl)pyrrolidin-2-yl)methyl)-1H-benzo[d]imidazol-2-yl)isoxazole-5-carboxamide. LC-MS (m/z):433[M+H].

Example 87

Synthesis of N-(1-(2-(2-cyano-N,4,4-trimethylpent-2-enamido)ethyl)-1H-benzo[d]imidazol-2-yl)-5-(difluoromethyl)thiophene-2-carboxamide

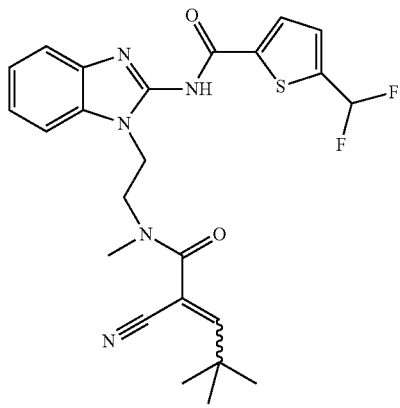 [SMILES: CN(CCn1c(NC(=O)c2ccc(C(F)F)s2)nc2ccccc21)C(=O)C(C#N)=CC(C)(C)C]

5-(Difluoromethyl)-N-(1-(2-(methylamino)ethyl)-1H-benzo[d]imidazol-2-yl)thiophene-2-carboxamide, (prepared as in Example 50 but substituting tert-butyl(2-aminoethyl)(methyl)-carbamate for tert-butyl 2-(aminomethyl)pyrrolidine-1-carboxylate) was reacted as in Example 83 to afford N-(1-(2-(2-cyano-N,4,4-trimethylpent-2-enamido)ethyl)-1H-benzo[d]imidazol-2-yl)-5-(difluoromethyl-)thiophene-2-carboxamide. LC-MS (m/z): 486 [M+H].

Example 88

Synthesis of (R)-N-(1-((1-(2-cyano-5-hydroxy-4,4-dimethylpent-2-enoyl)pyrrolidin-2-yl)methyl)-1H-benzo[d]imidazol-2-yl)-5-(difluoromethyl)thiophene-2-carboxamide

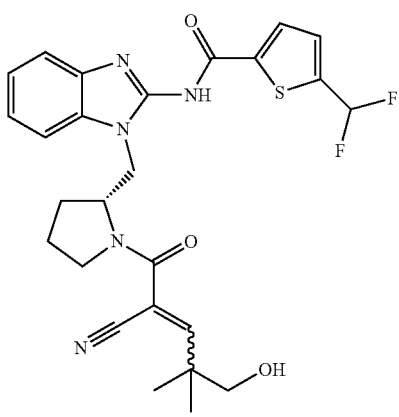 [SMILES: CC(C)(C=C(C#N)C(=O)N1CCC[C@@H]1Cn1c(NC(=O)c2ccc(C(F)F)s2)nc2ccccc21)CO]

Step 1

To a solution of 2,2-dimethylpropane-1,3-diol (10 g, 96.02 mmol, 1.00 equiv) and imidazole (9.8 g, 144.12 mmol, 1.50 equiv) in DCM (50 mL) was added a solution of TBSCl (15.9 g, 106 mmol, 1.10 equiv) in DCM (50 mL) dropwise. The resulting solution was stirred for 3 h at rt, and then diluted with water. The resulting solution was extracted with DCM, and the combined organic layers were washed with brine, dried over anhydrous sodium sulfate and concentrated under vacuum to give 18 g of 3-[(tert-butyldimethylsilyl)oxy]-2,2-dimethylpropan-1-ol as a light yellow oil.

Step 2

To a solution of 3-[(tert-butyldimethylsilyl)oxy]-2,2-dimethylpropan-1-ol (5 g, 22.89 mmol, 1.00 equiv) in dichloromethane (100 mL) was added Dess-Martin periodinane (10 g, 23.58 mmol, 1.03 equiv) and the resulting solution was stirred for 4 h at rt. The reaction mixture was diluted with 100 mL of DCM and the solids were filtered out. The filtrate was washed with saturated aqueous sodium bicarbonate solution and brine, dried over sodium sulfate and concentrated under vacuum to give 3.2 g of 3-[(tert-butyldimethylsilyl)oxy]-2,2-dimethylpropanal as a colorless oil.

Step 3

To a solution of 3-[(tert-butyldimethylsilyl)oxy]-2,2-dimethylpropanal (3.6 g, 16.64 mmol) in toluene, 2-cyanoacetic acid (1.5 g, 17.63 mmol) and ammonium acetate (200 mg, 2.59 mmol) were added. The resulting solution was stirred overnight at 140° C. in an oil bath. The resulting mixture was washed with water and brine, dried over anhydrous sodium sulfate and concentrated under vacuum to give 2.4 g of 5-((tert-butyldimethylsilyl)oxy)-2-cyano-4,4-dimethylpent-2-enoic acid as a yellow oil.

Step 4

Into a 100-mL round-bottom flask, was placed a solution of 5-(difluoromethyl)-N-[1-[(2R)-pyrrolidin-2-ylmethyl]-1H-1,3-benzodiazol-2-yl]thiophene-2-carboxamide (400 mg, 1.06 mmol) in 20 ml of DMF. 5-((tert-Butyldimethylsilyl)oxy)-2-cyano-4,4-dimethylpent-2-enoic acid (670 mg, 2.36 mmol), HATU (800 mg, 2.10 mmol), and triethylamine (0.5 mL) were added to the reaction mixture. The resulting solution was stirred overnight at rt, and then diluted with water. The resulting solution was extracted with dichloromethane, and the combined organic layers were washed with brine, dried over anhydrous sodium sulfate and concentrated under vacuum to give 300 mg of (R)-N-(1-((1-(5-((tert-butyldimethylsilyl)oxy)-2-cyano-4,4-dimethyl-pent-2-enoyl)pyrrolidin-2-yl)methyl)-1H-benzo[d]imidazol-2-yl)-5-(difluoromethyl)thiophene-2-carboxamide as a brown oil.

Step 5

To a solution of (R)-N-(1-((1-(5-((tert-butyldimethylsilyl)oxy)-2-cyano-4,4-dimethylpent-2-enoyl)pyrrolidin-2-yl)methyl)-1H-benzo[d]imidazol-2-yl)-5-(difluoromethyl)thiophene-2-carboxamide (400 mg, 0.62 mmol) in 5 mL of methanol was added 4N HCl in dioxane (5 mL). The resulting solution was stirred overnight at room temperature, and then it was concentrated under vacuum. The crude product (300 mg) was purified by Prep-HPLC to afford 166.0 mg of (R)-N-(1-((1-(2-cyano-5-hydroxy-4,4-dimethyl-pent-2-enoyl)pyrrolidin-2-yl)methyl)-1H-benzo[d]imidazol-2-yl)-5-(difluoromethyl)thiophene-2-carboxamide as a light yellow solid. LC-MS (m/z): 528 [M+H].

Example 89

Synthesis of (R)-N-(1-(1-(2-cyano-4-methylpent-2-enoyl)pyrrolidin-3-yl)-1H-benzo[d]imidazol-2-yl)-5-(difluoromethyl)thiophene-2-carboxamide

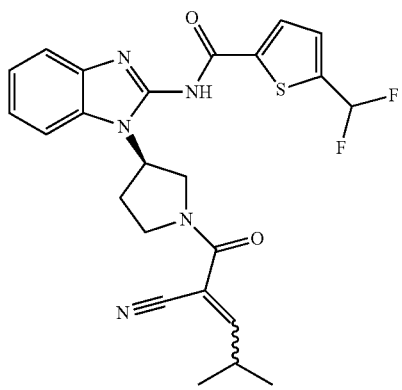 [SMILES: CC(C)C=C(C#N)C(=O)N1CC[C@@H](n2c(NC(=O)c3ccc(C(F)F)s3)nc3ccccc32)C1]

(R)-5-(Difluoromethyl)-N-(1-(pyrrolidin-3-yl)-1H-benzo[d]imidazol-2-yl)thiophene-2-carboxamide (prepared as in Example 50 but substituting (R)-tert-butyl 3-aminopyrrolidine-1-carboxylate for (R)-tert-butyl 2-(aminomethyl)pyrrolidine-1-carboxylate) was dissolved in 20 mL of DMF. TEA (335.1 mg, 3.31 mmol), 2-cyano-4-methylpent-2-enoic acid (153.6 mg, 1.10 mmol, and HATU (629.5 mg, 1.66 mmol) were added to the reaction mixture. The resulting solution was stirred overnight at rt and then concentrated under vacuum. The crude product was purified by Prep-HPLC to afford 173 mg of (R)-N-(1-(1-(2-cyano-4-methylpent-2-enoyl)pyrrolidin-3-yl)-1H-benzo[d]imidazol-2-yl)-5-(difluoromethyl)thiophene-2-carboxamide LC-MS m/z: 484.2 [M+1].

Example 90

Synthesis of (R)-1-((1-(2-cyano-4-methylpent-2-enoyl)pyrrolidin-2-yl)methyl)-2-(5-(difluoro-methyl)thiophene-2-carboxamido)-N-neopentyl-1H-benzo[d]imidazole-5-carboxamide

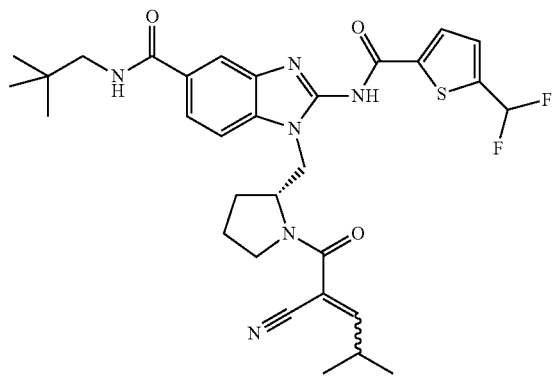 [SMILES: CC(C)C=C(C#N)C(=O)N1CCC[C@@H]1Cn1c(NC(=O)c2ccc(C(F)F)s2)nc2cc(C(=O)NCC(C)(C)C)ccc21]

Step 1

To a solution of (R)-methyl 1-((1-(tert-butoxycarbonyl)pyrrolidin-2-yl)methyl)-2-(5-(difluoromethyl)thiophene-2-carboxamido)-1H-benzo[d]imidazole-5-carboxylate (242 mg, 0.45 mmol) in THF (50 mL) was added KOH (50.79 mg, 0.91 mmol). The resulting mixture was heated at 45° C. for 3 days. The mixture was concentrated to an oil and purified by chromatography to obtain 169 mg of (R)-1-((1-(tert-butoxycarbonyl)pyrrolidin-2-yl)methyl)-2-(5-(difluoromethyl)-thiophene-2-carboxamido)-1H-benzo[d]imidazole-5-carboxylic acid.

Step 2

A mixture of (R)-1-((1-(tert-butoxycarbonyl)pyrrolidin-2-yl)methyl)-2-(5-(difluoro-methyl)thiophene-2-carboxamido)-1H-benzo[d]imidazole-5-carboxylic acid (169 mg, 0.32 mmol), 2,2-dimethylpropan-1-amine (0.08 mL, 0.65 mmol), DIPEA (0.28 mL, 1.62 mmol) and DMF (6 mL) was stirred at rt for 5 minutes and then HATU (246.74 mg, 0.65 mmol) was added. After stirring 1 h, the crude was concentrated in vacuo and then purified by chromatography to obtain 160 mg of (R)-tert-butyl 2-((2-(5-(difluoromethyl)thiophene-2-carboxamido)-5-(neopentylcarbamoyl)-1H-benzo[d]imidazol-1-yl)methyl)pyrrolidine-1-carboxylate.

Step 3

To a mixture of (R)-tert-butyl 2-((2-(5-(difluoromethyl)thiophene-2-carboxamido)-5-(neopentylcarbamoyl)-1H-benzo[d]imidazol-1-yl)methyl)pyrrolidine-1-carboxylate (160 mg, 0.27 mmol) and DCM (6 mL) was added 4N HCl in dioxane (6 .mL). The resulting mixture was stirred at room temp for 1 h, concentrated and dried in hi-vac to obtain 180 mg of (R)-2-(5-(difluoromethyl)-thiophene-2-carboxamido)-N-neopentyl-1-(pyrrolidin-2-ylmethyl)-1H-benzo[d]imidazole-5-carboxamide as the HCl salt.

Step 4

To a solution of (R)-2-(5-(difluoromethyl)thiophene-2-carboxamido)-N-neopentyl-1-(pyrrolidin-2-ylmethyl)-1H-benzo[d]imidazole-5-carboxamide (132 mg, 0.27 mmol), DIPEA (0.37 mL, 2.16 mmol), 2-cyanoacetic acid (91.74 mg, 1.08 mmol) in DMF (6 mL) was stirred at rt for 10 minutes then HATU (153.68 mg, 0.40 mmol) was added. After 20 h, the mixture was evaporated and worked up with brine and DCM and the organic phase was concentrated. Purification by chromatography afforded 140 mg of (R)-1-((1-(2-cyanoacetyl)pyrrolidin-2-yl)methyl)-2-(5-(difluoromethyl)thiophene-2-carboxamido)-N-neopentyl-1H-benzo[d]imidazole-5-carboxamide as a white solid.

Step 5

To a solution of (R)-1-((1-(2-cyanoacetyl)pyrrolidin-2-yl)methyl)-2-(5-(difluoromethyl)-thiophene-2-carboxamido)-N-neopentyl-1H-benzo[d]imidazole-5-carboxamide (70 mg, 0.13 mmol), pyrrolidine (0.03 mL, 0.38 mmol) and 2-methylpropanal (0.03 mL, 0.38 mmol) in DCM (8 mL) was added TMSCl (0.06 mL, 0.50 mmol). After stirring for 7 hours, the crude mixture was worked up with water and DCM and the organic layers were dried (MgSO$_4$) and concentrated to afford oil which was purified by chroamtography to obtain 1-((1-(2-cyano-4-methylpent-2-enoyl)pyrrolidin-2-yl)methyl)-2-(5-(difluoromethyl)thiophene-2-carboxamido)-N-neopentyl-1H-benzo[d]imidazole-5-carboxamide (11 mg) as white solid. MS (pos. ion) m/z: 611 (M+H).

Example 91

Synthesis of (R)-1-((1-(2-cyano-3-(3-methyloxetan-3-yl)acryloyl)pyrrolidin-2-yl)methyl)-2-(5-(difluoromethyl)thiophene-2-carboxamido)-N-neopentyl-1H-benzo[d]imidazole-5-carboxamide

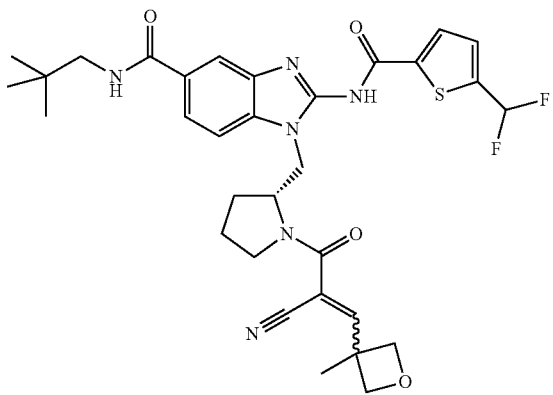 [SMILES: CC(C)(C)CNC(=O)c1ccc2c(c1)nc(NC(=O)c1ccc(C(F)F)s1)n2C[C@H]1CCCN1C(=O)C(C#N)=CC1(C)COC1]

Substituting 3-methyloxetane-3-carbaldehyde for 2-methylpropanal in Step 5, Example 90 above produced (R)-1-((1-(2-cyano-3-(3-methyloxetan-3-yl)acryloyl)pyrrolidin-2-yl)methyl)-2-(5-(difluoromethyl)thiophene-2-carboxamido)-N-neopentyl-1H-benzo[d]imidazole-5-carboxamide. MS (pos. ion) m/z: 639 (M+1).

Example 92

Synthesis of (R)-1-((1-acryloylpyrrolidin-2-yl)methyl)-2-(5-(difluoromethyl)thiophene-2-carboxamido)-N-neopentyl-1H-benzo[d]imidazole-5-carboxamide

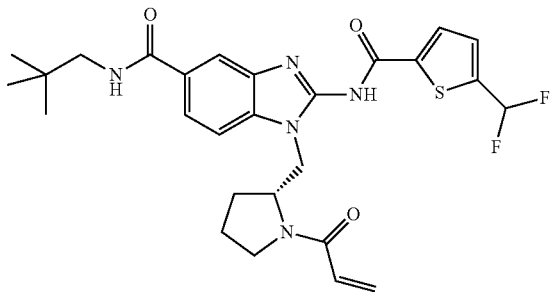 [SMILES: C=CC(=O)N1CCC[C@@H]1Cn1c(NC(=O)c2ccc(C(F)F)s2)nc2cc(C(=O)NCC(C)(C)C)ccc21]

To a solution of (R)-2-(5-(difluoromethyl)thiophene-2-carboxamido)-N-neopentyl-1-(pyrrolidin-2-ylmethyl)-1H-benzo[d]imidazole-5-carboxamide (82.35 mg, 0.17 mmol, Step 3 Example 89) in DCM (12 mL), was added TEA (0.09 mL, 0.67 mmol) followed by prop-2-enoyl chloride (0.02 mL, 0.25 mmol). After stirring 10 minutes, the reaction mixture was partitioned between water and DCM and the organic phase was dried (MgSO$_4$) and evaporated. The crude oil was purified by chromatography to provide (R)-1-((1-acryloylpyrrolidin-2-yl)methyl)-2-(5-(difluoromethyl)-thiophene-2-carboxamido)-N-neopentyl-1H-benzo[d]imidazole-5-carboxamide, 31 mg (33.9%). MS (pos. ion) m/z: 544 (M+1).

Example 93

Synthesis of 1-(((R)-1-(2-cyano-4,4-dimethylpent-2-enoyl)pyrrolidin-2-yl)methyl)-2-(5-(difluoromethyl)thiophene-2-carboxamido)-N-((S)-3,3-dimethylbutan-2-yl)-1H-benzo[d]imidazole-5-carboxamide

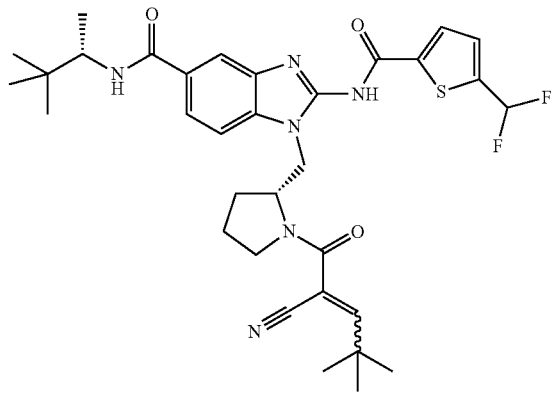 [SMILES: C[C@H](NC(=O)c1ccc2c(c1)nc(NC(=O)c1ccc(C(F)F)s1)n2C[C@H]1CCCN1C(=O)C(C#N)=CC(C)(C)C)C(C)(C)C]

Substituting (2S)-3,3-dimethylbutan-2-amine for 2,2-dimethylpropan-1-amine in Step 2, Example 89 above and continuing as in Steps 3-5, Example 90 but substituting 2,2-dimethylpropanal for 2-methylpropanal in Step 5, afforded 1(((R)-1-(2-cyano-4,4-dimethylpent-2-enoyl)pyrrolidin-2-yl)methyl)-2-(5-(difluoromethyl)thiophene-2-carboxamido)-N-((S)-3,3-dimethylbutan-2-yl)-1H-benzo[d]imidazole-5-carboxamide. MS (pos. ion) m/z: 639 (M+1).

Example 94

Synthesis of 1-(((R)-1-acryloylpyrrolidin-2-yl)methyl)-2-(5-(difluoromethyl)thiophene-2-carboxamido)-N-((S)-3,3-dimethylbutan-2-yl)-1H-benzo[d]imidazole-5-carboxamide

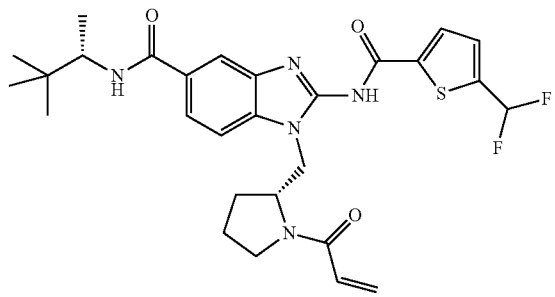 [SMILES: C=CC(=O)N1CCC[C@@H]1Cn1c(NC(=O)c2ccc(C(F)F)s2)nc2cc(C(=O)N[C@@H](C)C(C)(C)C)ccc21]

Substituting (2S)-3,3-dimethylbutan-2-amine for 2,2-dimethylpropan-1-amine in Step 2, Example 90 above and continuing as in Step 3, Example 89 produced 2-(5-(difluoromethyl)-thiophene-2-carboxamido)-N-((S)-3,3-dimethylbutan-2-yl)-1-((R)-pyrrolidin-2-ylmethyl)-1H-benzo[d]imidazole-5-carboxamide which was reacted as in Example 91 to obtain 1-(((R)-1-acryloylpyrrolidin-2-yl)methyl)-2-(5-(difluoromethyl)thiophene-2-carboxamido)-N-((S)-3,3-dimethylbutan-2-yl)-1H-benzo[d]imidazole-5-carboxamide, 31 mg. MS (pos. ion) m/z: 558 (M+H).

BIOLOGICAL EXAMPLES

Example 1

Inhibition of Itk Enzymatic Activity . . . in Vitro Assay

The ability of the compounds of the present disclosure to inhibit ITK was measured using the Caliper assay format, which is an electrophoretic separation of a phosphorylated peptide substrate from unphosphorylated peptide. The enzymatic reaction occurred in a buffer of 100 mM HEPES pH 7.5, 5 mM $MgCl_2$, 0.01% Triton-X 100, 0.1% Bovine Serum Albumin, and 1% DMSO. Three-fold dilutions of compounds were prepared in DMSO. Compounds were added to enzyme and pre-incubated for 15 minutes prior to reaction. The enzymatic reaction was initiated by addition of phospho-acceptor peptide FAM-GEEPLYWSFPAKKK-NH2 (also known as SRCtide) to 1 uM and ATP to its Km value (ITK: 10 uM). The reaction proceeded for 3 hours and was terminated by addition of EDTA. The assay employed an enzyme concentration of 1 nM. The top compound concentration was 5 uM. The amount of phosphorylated substrate was determined by the Caliper instrumentation, and dose-response curves were fit using standard methods to determine the $IC_{50}$ values. The $IC_{50}$ for a representative compound of the present disclosure is provided in Table 1 below.

| Cpd # (see Cpd Table 1 above) | ITK $IC_{50}$ um | Cpd # (see Cpd Table 1 above) | ITK $IC_{50}$ um | Cpd # (see Cpd Table 1 above) | ITK $IC_{50}$ um |
| --- | --- | --- | --- | --- | --- |
| 1 | .929 | 32 | 0.142 | 102 | 0.0076 |
| 2 | 1.78 | 33 | 0.0070 | 108 | 0.026 |
| 3 | 0.53 | 36 | 0.040 | 114 | 0.179 |
| 4 | >5 | 37 | 0.02 | 115 | 0.0145 |
| 5 | 0.67 | 40 | 0.0056 | 113 | 0.0023 |
| 7 | >5 | 42 | 0.01 | 116 | 0.0103 |
| 10 | 1.72 | 44 | 0.0199 | 117 | 0.0093 |
| 12 | 0.12 | 49 | 0.005 | 118 | 0.0118 |
| 13 | >4 | 50 | 0.037 | 119 | 0.92 |
| 14 | 0.32 | 51 | 0.013 | 121 | 0.035 |
| 17 | 0.13 | 53 | 0.12 | 122 | 0.052 |
| 18 | 0.028 | 54 | 1.89 | 124 | 0.17 |
| 19 | 0.01 | 58 | 0.0070 | 125 | 0.77 |
| 20 | 0.0006 | 59 | 0.0006 | 126 | 0.215 |
| 21 | 0.003 | 60 | 0.005 | 127 | 0.018 |
| 22 | 0.0018 | 61 | 0.0024 | 128 | 0.0137 |
| 23 | 0.023 | 62 | 0.0035 | 129 | 0.68 |
| 24 | 0.019 | 68 | 0.127 | 132 | 0.028 |
| 25 | 0.137 | 69 | 0.571 | 134 | 0.0026 |
| 26 | 0.012 | 72 | >5 | 135 | 0.019 |
| 30 | 0.312 | 73 | >5 | 136 | 0.006 |
| 80 | 0.959 | 79 | 1.01 | 138 | 0.068 |
| 88 | 0.743 | 89 | 0.049 | 63 | 0.0013 |
| 86 | 0.044 | 87 | 0.0248 | 64 | 0.0054 |
| 85 | 0.0075 | 84 | 0.973 | | |

Example 2

Determination of Drug-Kinase Residence Time

The following is a protocol to distinguish whether a compound displays a slow or non-existent dissociation rate from Itk, such as typically would occur if a covalent bond is formed between the compound and the target. The read-out for slow dissociation was the extent that the compound of interest can block binding of an excess amount of a high affinity fluorescent tracer molecule to the kinase active site, as detected using time-resolved fluorescence resonance energy transfer (TR-FRET).

The experiment was conducted in a buffer consisting of 50 mM Hepes pH 7.5, 10 mM $MgCl_2$, 0.01% Triton X-100, and 1 mM EGTA. 500 nM Itk (Invitrogen Cat. #PV3875) was incubated with 1.5 uM of test compound for 30 minutes in a volume of 10 uL. The mixture was then diluted 50-fold by addition of 4 uL sample to 196 uL of buffer. A 10 uL volume of the diluted kinasetest compound solution was then added to a well of a small volume 384 well plate (such as Greiner Cat. #784076). In order to probe for reversibility of the kinase-compound binding interaction, a competition solution containing both a high affinity fluorescent tracer and an antibody coupled to Europium was prepared. The competition solution contained 5 uM Tracer 236 (Invitrogen Cat. #PV5592), which is a proprietary high affinity ligand for Itk coupled to the fluorophore AlexaFluor 647. The competition solution also contained 12.5 nM of an Anti-His antibody coupled to Europium (Invitrogen Cat. #PV5594) which is designed to bind the His purification tag in Itk. After addition of 10 uL of the competition solution to the Greiner plate, the mixture was incubated for various times to allow time for dissociation of non-covalent inhibitors and binding of the high affinity tracer. It was expected that slow dissociating inhibitors will block binding of the tracer while rapidly dissociating inhibitors will not. Binding of the tracer to Itk was detected using TR-FRET between the Europium moiety of the Anti-His antibody and the AlexaFluor 647 group of Tracer 236. Binding was evaluated using a Perkin Elmer Envision instrument (Model 2101) equipped with filters and mirrors compatible with LANCE-type TR-FRET experiments. The excitation wavelength was 337 nm and the emission wavelengths were 620 nm and 665 nm. Data was acquired as the ratio of emission at 665 nm to 620 nm and was plotted as the percentage of signal obtained in the absence of competitor compound. The background signal was obtained by omission of kinase from the reaction.

When the compound is an irreversible covalent inhibitor, tracer was completely blocked from binding to the target throughout the entire course of the experiment. When the compound was a reversible covalent inhibitor, the tracer bound to the target as the compound dissociated from the target. The data were evaluated as occupancy of the target at 1, 6 and 24 hours after initiation of dissociation. The results for representative compounds are shown in Table 2 below.

TABLE 2

| Compound # (see Cpd Table 1 above) | Occupancy @ 1 hr (%) | Occupancy @ 6 hr (%) | Occupancy @ 24 hr (%) |
| --- | --- | --- | --- |
| 20 | 104 | 105 | 105 |
| 22 | 101 | 98 | 98 |
| 27 | 87 | 87 | 89 |
| 49 | 31 | 16 | 8 |
| 40 | 96 | 85 | 72 |
| 34 | 91 | 95 | 96 |

Example 3

Cellular Potency Measured T Cell Receptor (TCR)-Induced Activation of Jurkat Cells Cellular potencies of ITK inhibitory compounds were measured by blockade of activation of the transcription factor Nuclear Factor in Activated T cells (NFAT) following stimulation of the T cell receptor. Activation was measured using the Cell Sensor cell line NFAT-bla Jurkat from Invitrogen (Madison, Wis.) that utilizes a reporter construct for NFAT activation. Tripling dilutions of ITK inhibitors were pre-incubated with Jurkat T cells for 1 hour followed by activation with predetermined $IC_{80}$ concentrations of anti-CD3 and anti-CD28 for 5 hours. The NFAT reporter activity was then assessed by addition of the beta-lactamase substrate followed by incubation for an additional 2 hours. Substrate cleavage was then measured by monitoring the change in fluorescence resonance energy transfer using appropriate excitation and emission wavelength filters. The percent inhibition was then plotted as a function of the log of the compound concentration to calculate an $IC_{50}$ using standard curve-fitting software. Data for representative compounds are shown in Table 3 below.

TABLE 3

| Compound # (see Cpd Table 1 above) | TCR-induced NFAT (μM) |
| --- | --- |
| 20 | .0029 |
| 27 | .0015 |
| 40 | .286 |
| 34 | .027 |
| 60 | .043 |
| 61 | .046 |
| 62 | .240 |
| 63 | .02 |
| 64 | .03 |

Example 4

IL-2 Production in Anti-CD3 and Anti-CD28 Stimulated Human PBMCs

Peripheral blood mononuclear cells (PBMCs) isolated from human whole blood were preincubated with or without inhibitors in RPMI 1640+10% fetal bovine serum at 37° C. for 30 min PBMCs were stimulated with 2.5 ug/ml plate bound anti-CD3 and 1 ug/ml soluble anti-CD28 overnight and supernatant was collected for AlphaLISA IL2 assay. The IL-2 production was measured as AlphaLISA signal counts using Envision plate reader. Human Blood was obtained from healthy volunteer through Stanford Blood Center. Blood was collected by venipuncture into sodium heparin tubes. Blood was layered over Ficoll-Histopaque in 50 ml conical tube and centrifuged at 2000 rpm for 20 minutes at room temperature. Mononuclear cells were collected into 50 ml conical tubes, pooled and diluted with 1×PBS to make up final volume to 50 ml in each tube. Cells were pelleted at 1500 rpm for 5 minutes and cells are washed two times. The cells were counted in Vi-Cell using trypan blue to determine cell number and viability. PBMCs were then resuspended in RPMI 1640 with 10% fetal bovine serum at a concentration 1×106 cells/ml.

A 96-well polystyrene plate was coated with 2.5 ug/ml anti-CD3 in PBS overnight at 4° C. The wells in column one were coated with PBS only for unstimulated controls. Compounds of the disclosure were dissolved at 10 mM in 100% DMSO and 1:3 serial dilutions of compounds are prepared in DMSO. These compounds were further diluted in complete medium to make final DMSO 0.2% in 96-well polypropylene plate. To treat PBMC with compounds, 100 ul of 1×105 cells were cultured in 96-well polypropylene plate.

Then 8 ul of each diluted compound was added in the corresponding wells in duplicate and 8 ul of medium with 2.5% DMSO was added to control wells. The plates were incubated at 37° C. incubator for 30 min. The anti-CD3 coated plates were washed with PBS twice. 92 ul of media containing 1 ug/ml anti-CD28 were added to all wells except unstimulated controls. In unstimulated wells, 92 ul medium was added. Plates were incubated overnight at 37° C., 5% $CO_2$ incubator.

The next day, 150 ul of supernatant was removed from each well for AlphaLISA IL2 assay. According to manufacturer's protocol, 1× buffer, IL2 standards (10 conc), 2.5× acceptor plus biotinylated beads mixture, 2× streptavidin donor beads were prepared. To each well, 2.5 ul standards or samples are added and then 10 ul of 2.5× mixture beads were added to each well. The plate was sealed with aluminum plate sealer and incubated at room temp on shaker for 1 hr. 12.5 ul of streptavidin donor beads are added to each well in dark room. The plate was sealed with aluminum plate sealer and incubated at room temp on shaker for 30 min. The plate was read in an Envision plate reader.

The $IC_{50}$ for each compound was determined from a ten-point dose response curve for all compounds, each dose being tested in duplicate wells. The IC50 represents the concentration of a compound that shows 50% inhibition of IL-2 production in response to anti-CD3+anti-CD28 stimulated PBMCs with compound to 50% of that in control wells without compounds, and was calculated using curve fitting software.

Data for representative compounds are shown in Table 4 below.

TABLE 4

| Compound # (see Cpd Table 1 above) | CD 3/CD28-induced IL-2 (μM) |
|---|---|
| 20 | .018 |
| 27 | .049 |
| 40 | 1.07 |
| 34 | .13 |
| 60 | .15 |
| 61 | .24 |
| 62 | .42 |
| 63 | .21 |
| 64 | .24 |

Example 5

Delayed Type Hypersensitivity in Mice

Delayed type hypersensitivity is a standard model for measuring T cell mediated skin inflammation in vivo. Previous studies suggest that an inhibitor of ITK should be efficacious in such a model (see von Bonin et al. Inhibition of the IL-2-inducible tyrosine kinase (Itk) activity: a new concept for the therapy of inflammatory skin diseases, *Exp Dermatol*, 20:41-47, 2010). Starting on study day zero (0), mice were randomized by body weight (using MS Excel) in to treatment groups, sensitized with aliquots of 150 microliters of a 5% oxazolone (Sigma) solution (3 parts ethanol+1 part acetone) epicutaneously on their shaved abdomens. The right ears of the same (Isoflurane anesthetized) mice were challenged with 3% oxazolone solution 7 days later (Day 7), (i.e., 10 microliters on the front and another 10 microliters on the back of the right ears; whereas the left ears were painted on both ears with the ethanolacetone mixture. One hour prior to challenge, certain groups received an ITK inhibitor at a dose and route determined to be appropriate based on previous phmacodynamic studies. Twenty-four hours later, animals were terminated via cervical dislocation and then, a 7-mm disc of ear (by using a cork borer, from Fisher Scientific) was punched out and weighed since weight is proportional to edema. Compound of the disclosure were active in this model.

Example 6

Mass Spectral Analysis

A protein kinase that is inhibited by compound of Formula (IA) or (I) may be subjected to mass spectral analysis to assess whether the compounds of Formula (IA) or (I) form permanent, irreversible covalent adducts or reversible covalent bond. Suitable analytical methods to examine intact full protein or peptide fragments generated upon tryptic cleavage of the protein kinase are generally known in the art. Such methods identify permanent, irreversible covalent protein adducts by observing a mass peak that corresponds to the mass of a control sample plus the mass of an irreversible adduct. One such method is described below.

Mass spectral analysis of intact full kinase
Method:

A protein kinase (5 uM) is incubated with a compound of Formula (IA) or I (25 uM, 5 equiv) for 1 h at room temperature in buffer (20 mM Hepes [pH 8.0], 100 mM NaCl, 10 mM $MgCl_2$). A control sample is also prepared which does not have a compound of Formula (IA) and I. The reaction is stopped by adding an equal volume of 0.4% formic acid, and the samples are analyzed by liquid chromatography (Microtrap C18 Protein column [Michrom Bioresources], 5% MeCN, 0.2% formic acid, 0.25 mL/min; eluted with 95% MeCN, 0.2% formic acid) and in-line ESI mass spectrometry (LCT Premier, Waters). Molecular masses of the protein kinase and any adducts may be determined with MassLynx deconvolution software.

Results: High-resolution intact mass spectrometry analysis of a kinase that is inhibited by a compound of Formula (IA) or I where $R^b$ is other than hydrogen will reveal a spectrum similar to the kinase in the absence of inhibitor (e.g. control sample). There will be no formation of a new peak in the mass spectrum corresponding to the molecular mass of the kinase plus the molecular mass of the compound of Formula (IA) or I. On the basis of this experiment no permanent, irreversible protein adduct will be apparent to one skilled in the art. Compounds of Formula (IA) or (I) where $R^b$ is hydrogen will show a new peak in the mass spectrum corresponding to the molecular mass of the kinase plus the molecular mass of the compound of Formula (IA) or I respectively, indicating a permanent, irreversible covalent bond formation between the protein and the compound of Formula (IA) or (I) respectively.

Example 7

Recovery of Kinase Activity Upon Dialysis

Standard experimental methods to establish reversibility are known in the art. Protein dialysis is one such method. A solution containing a protein kinase that is inhibited by a compound of Formula (IA) or I may be subjected to extensive dialysis to establish if the kinase inhibitor is reversible. Partial or complete recovery of protein kinase activity over time during dialysis is indicative of reversibility.

Method:

A compound of Formula (IA) or I and/or pharmaceutically acceptable salt described herein (1 uM) is added to a solution of protein kinase (50 nM, pre-activated if necessary) in a buffer containing 20 mM Hepes [pH 8.0], 10 mM $MgCl_2$, 2.5 mM tris(2-carboxyethyl)phosphine (TCEP), 0.25 mg/mL BSA, and 100 uM ATP. After 60 min at rt, the reactions is transferred to a dialysis cassette (0.1-0.5 mL Slide-A-Lyzer, MWCO 10 kDa, Pierce) and dialyzed against 2 L of buffer (20 mM Hepes [pH 8.0], 10 mM $MgCl_2$, 1 mM DTT) at 4° C. The dialysis buffer is exchanged after 2 h, and then is exchanged every 24 h until the end of the experiment. Aliquots are removed from the dialysis cassettes every 24 h, flash frozen in liquid nitrogen, and subsequently analyzed for protein kinase activity in triplicate. Kinase activity for each sample is normalized to the DMSO control for that time point and expressed as the mean±SD.

Results: Kinase activity recovers from inhibition by reversible kinase inhibitors upon dialysis. Upon extensive dialysis at 4° C. or at room temperature, kinase activity partially or completely recovers in a time-dependent manner from inhibition by an excess (20 equiv, 1.0 uM) of reversible kinase inhibitor.

Example 8

Reversibility of Binding

The following approach can be used to differentiate compounds that form irreversible bonds with their targets, such as acrylamide compounds, from compound that bind reversibly such as a reversible covalent inhibitor. Reactions are prepared with the protein target at a higher concentration than the compounds of interest. Both irreversible and reversible compounds bind the target and became depleted from solution. The reactions are then treated with perturbations including both denaturation with 5 M guanidine hydrochloride and digestion with trypsin, disrupting proper folding of the target. It will be found that the perturbation returns reversible compounds to solution due to dissociation from the target while irreversible compounds remain bound to the target. The concentration of compound in solution is assessed both preceding and following perturbation using high performance liquid chromatography (HPLC) coupled to tandem mass spectrometry. Using this technique, it can be demonstrated that an acrylamide-containing compound i.e, compounds of Formula (IA) or (I) where $R^b$ is hydrogen is depleted from solution in both the native and perturbed state, while reversible compounds compounds of Formula (IA) or (I) where $R^b$ is other than hydrogen depletes in the folded state but returns to solution following perturbation of the target.

Pharmaceutical Compositions

Parenteral Composition

To prepare a parenteral pharmaceutical composition suitable for administration by injection, 100 mg of a water-soluble salt of a compound of Formula (IA) or I is dissolved in 2% HPMC, 1% Tween 80 in DI water, pH 2.2 with MSA, q.s. to at least 20 mg/mL. The mixture is incorporated into a dosage unit form suitable for administration by injection.

Oral Composition

To prepare a pharmaceutical composition for oral delivery, 400 mg of a compound of Formula (IA) or I and the following ingredients are mixed intimately and pressed into single scored tablets.

Tablet Formulation

| Ingredient | Quantity per tablet mg |
|---|---|
| compound | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound | 200 |
| lactose spray dried | 148 |
| magnesium stearate | 2 |

Sublingual (Hard Lozenge) Composition

To prepare a pharmaceutical composition for buccal delivery, such as a hard lozenge, mix 100 mg of a compound of Formula (IA) or I with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Fast-Disintegrating Sublingual Tablet

A fast-disintegrating sublingual tablet is prepared by mixing 48.5% by weigh of a compound of Formula (IA) or I, 44.5% by weight of microcrystalline cellulose (KG-802), 5% by weight of low-substituted hydroxypropyl cellulose (50 μm), and 2% by weight of magnesium stearate. Tablets are prepared by direct compression (AAPS PharmSciTech. 2006; 7(2):E41). The total weight of the compressed tablets is maintained at 150 mg. The formulation is prepared by mixing the amount of a compound of Formula (IA) or I with the total quantity of microcrystalline cellulose (MCC) and two-thirds of the quantity of low-substituted hydroxypropyl cellulose (L-HPC) by using a three dimensional manual mixer (Inversina®, Bioengineering AG, Switzerland) for 4.5 minutes. All of the magnesium stearate (MS) and the remaining one-third of the quantity of L-HPC are added 30 seconds before the end of mixing.

Inhalation Composition

To prepare a pharmaceutical composition for inhalation delivery, 20 mg of a compound of Formula (IA) or I is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of a compound of Formula (IA) or I is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical opthalmic solution composition, 100 mg of a compound of Formula (IA) or I is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound of Formula (IA) or I is mixed with 30 mL of a 0.05M phosphate buffer solution (pH 4.4). The solution is placed in a nasal administrator designed to deliver 100 μl of spray for each application.

What is claimed is:
1. A compound of Formula (IA):

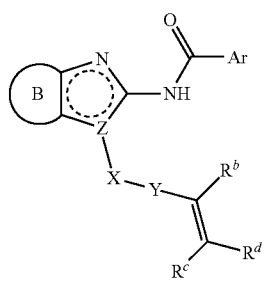

Formula (IA)

wherein:
(i) when Z is N, then ring B is:

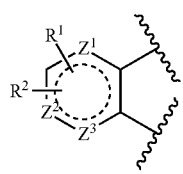

(a)

wherein:
$Z^1$, $Z^2$, and $Z^3$ are CH (or C if substituted with $R^1$ or $R^2$) or $Z^1$, $Z^2$, and $Z^3$ are independently N or CH (or C if substituted with $R^1$ or $R^2$) provided that only one of $Z^1$, $Z^2$, and $Z^3$ is N; and (ii) when Z is C, then ring B is:

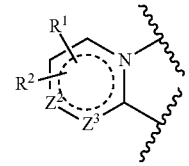

(b)

wherein:
$Z^2$ and $Z^3$ are CH (or C if substituted with $R^1$ or $R^2$) or $Z^2$ and $Z^3$ are independently N or CH (or C if substituted with $R^1$ or $R^2$) provided that only one of $Z^2$ and $Z^3$ is N;

$R^1$ is hydrogen, hydroxyalkyl, alkoxyalkyl, —$NR^3COR^4$, —$CONR^3R^5$, -(alkylene)-$NR^3R^5$ (where each $R^3$ is hydrogen, or alkyl, $R^4$ is alkyl, haloalkyl, cycloalkyl, optionally substituted aryl or optionally substituted heteroaryl, and each $R^5$ is hydrogen, alkyl, haloalkyl, hydroxyalkyl, alkoxyalkyl, acyl, cycloalkylalkyl, or heterocyclylalkyl optionally substituted with one, two, or three substituents independently selected from alkyl, halo, hydroxy, alkoxy, hydroxyalkyl, or alkoxyalkyl; or $R^3$ and $R^5$ together with the nitrogen atom to which they are attached form heterocycloamino or spiroheterocycloamino wherein the heterocycloamino ring is optionally substituted with one, two, or three substituents independently selected from alkyl, halo, hydroxyl, alkoxy, hydroxyalkyl, or alkoxyalkyl), —$NR^6R^7$ (where $R^6$ is hydrogen or alkyl and $R^7$ is hydrogen, alkyl, haloalkyl, hydroxyalkyl, alkoxyalkyl, or acyl, or $R^6$ and $R^7$ together with the nitrogen atom to which they are attached form heterocyclyl optionally substituted with one or two substituents independently selected from alkyl, halo, hydroxyl, hydroxyalkyl, or alkoxyalkyl), or —$OR^8$ (where $R^8$ is hydroxyalkyl, alkoxyalkyl, or heterocyclylalkyl optionally substituted with one, two, or three substituents independently selected from alkyl, halo, hydroxyalkyl, or alkoxyalkyl);

$R^2$ is hydrogen, alkyl, cycloalkyl, cyano, alkoxy, hydroxy, halo, haloalkyl, or haloalkoxy;

Ar is 5-$CHF_2$ thien-2-yl or a five membered heteroaryl ring substituted with optionally substituted heteroaryl;

X is alkylene, cycloalkylene,

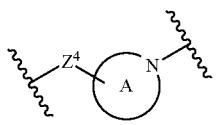

(where $Z^4$ is bond or alkylene, and ring A is heterocycloamino optionally substituted with one or two substituents independently selected from alkyl, hydroxy, or fluoro), -alkylene-O—, -cycloalkylene-$NR^a$—, or -(alkylene)-$NR^a$- (where each $R^a$ is hydrogen, alkyl or cycloalkyl);

Y is —CO— or —$SO_2$—;

$R^b$ is hydrogen, cyano, nitro, halo, haloalkyl, haloalkoxy, alkylthio, or alkylsulfonyl;

$R^c$ is hydrogen, alkyl, haloalkoxy, substituted alkyl, cycloalkyl, cycloalkylene$NR^{d1}R^e$ or cycloalkylene(alkylene)$NR^{d1}R^e$ (where each $R^{d1}$ and $R^e$ are independently hydrogen, alkyl, or cycloalkyl), alkoxyalkyloxyalkyl, or 3 to 6 membered saturated monocyclic heterocyclyl containing one or two heteroatoms selected from N, O, or S and optionally substituted with one or two substituents independently selected from hydroxy, alkyl or fluoro; and $R^d$ is hydrogen or alkyl, or $R^b$ and $R^d$ together form a bond; provided that when $R^b$ is other than hydrogen, then $R^c$ is not hydrogen and $R^d$ is hydrogen;

and/or a pharmaceutically acceptable salt thereof.

2. The compound of claim 1 having the structure (I):

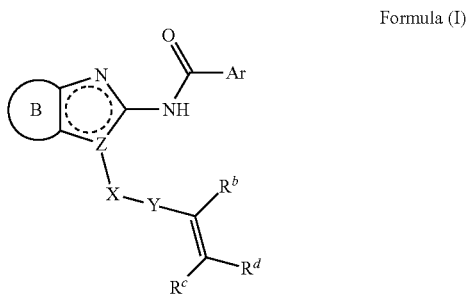

Formula (I)

wherein:
(i) when Z is N, then ring B is:

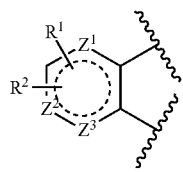

(a)

wherein:
$Z^1$, $Z^2$, and $Z^3$ are CH (or C if substituted with $R^1$ or $R^2$) or $Z^1$, $Z^2$, and $Z^3$ are independently N or CH (or C if substituted with $R^1$ or $R^2$) provided that only one of $Z^1$, $Z^2$, and $Z^3$ is N; and (ii) when Z is C, then ring B is:

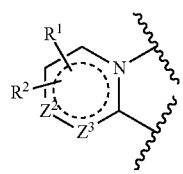

(b)

wherein:
$Z^2$ and $Z^3$ are CH (or C if substituted with $R^1$ or $R^2$) or $Z^2$ and $Z^3$ are independently N or CH (or C if substituted with $R^1$ or $R^2$) provided that only one of $Z^2$ and $Z^3$ is N;

$R^1$ is hydrogen, hydroxyalkyl, alkoxyalkyl, —$NR^3COR^4$, —$CONR^3R^5$, -(alkylene)-$NR^3R^5$ (where each $R^3$ is hydrogen, or alkyl, $R^4$ is cycloalkyl, optionally substituted aryl or optionally substituted heteroaryl, and each $R^5$ is hydrogen, alkyl, haloalkyl, hydroxyalkyl, alkoxyalkyl, acyl, or heterocyclylalkyl optionally substituted with one or two substituents independently selected from alkyl, halo, hydroxyalkyl, or alkoxyalkyl; or $R^3$ and $R^5$ together with the nitrogen atom to which they are attached form heterocycloamino or spiroheterocycloamino wherein the heterocycloamino ring is optionally substituted with one or two substituents independently selected from alkyl, halo, hydroxyalkyl, or alkoxyalkyl), —$NR^6R^7$ (where $R^6$ is hydrogen or alkyl and $R^7$ is hydrogen, alkyl, haloalkyl, hydroxyalkyl, alkoxyalkyl, or acyl, or $R^6$ and $R^7$ together with the nitrogen atom to which they are attached form heterocyclyl optionally substituted with one or two substituents independently selected from alkyl, halo, hydroxyl, hydroxyalkyl, or alkoxyalkyl), or —$OR^8$ (where $R^8$ is hydroxyalkyl, alkoxyalkyl, or heterocyclylalkyl optionally substituted with one or two substituents independently selected from alkyl, halo, hydroxyalkyl, or alkoxyalkyl);

$R^2$ is hydrogen, alkyl, cycloalkyl, cyano, alkoxy, hydroxy, halo, haloalkyl, or haloalkoxy;

X is alkylene, cycloalkylene, or

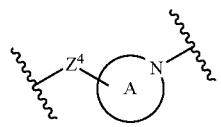

(where $Z^4$ is bond or alkylene, and ring A is heterocycloamino optionally substituted with one or two substituents independently selected from alkyl, hydroxy, or fluoro), -alkylene-O—, -cycloalkylene-$NR^a$—, or -(alkylene)-$NR^a$- (where each $R^a$ is hydrogen, alkyl or cycloalkyl);

Y is —CO— or —$SO_2$—;

$R^b$ is hydrogen, cyano, nitro, halo, haloalkyl, haloalkoxy, alkylthio, or alkylsulfonyl;

$R^c$ is hydrogen, alkyl, haloalkoxy, substituted alkyl, cycloalkyl, cycloalkylene$NR^{d1}R^e$ or cycloalkylene(alkylene)$NR^{d1}R^e$ (where each $R^{d1}$ and $R^e$ are independently hydrogen, alkyl, or cycloalkyl), or 3 to 6 membered saturated monocyclic heterocyclyl containing one or two heteroatoms selected from N, O or S and optionally substituted with one or two substituents independently selected from hydroxy, alkyl or fluoro; and $R^d$ is hydrogen, alkyl, or $R^b$ and $R^d$ together form a bond; provided that when $R^b$ is other than hydrogen, then $R^c$ is not hydrogen and $R^d$ is hydrogen;

or a pharmaceutically acceptable salt thereof.

3. The compound or a pharmaceutically acceptable salt thereof of claim 2 wherein the compound of Formula (I) has the structure (Ia):

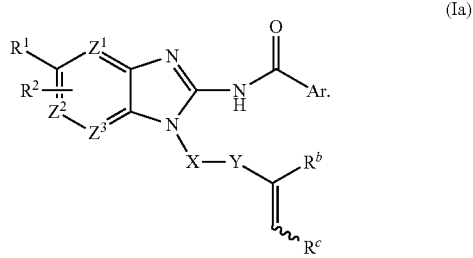

(Ia)

4. The compound or a pharmaceutically acceptable salt thereof of claim 3 wherein $Z^1$, $Z^2$, and $Z^3$ are CH (or C if substituted with $R^2$).

5. The compound or a pharmaceutically acceptable salt thereof of claim 2 wherein the compound of Formula (I) has the structure (Ib):

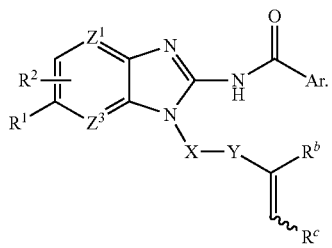

(Ib)

6. The compound or a pharmaceutically acceptable salt thereof of claim 5 wherein $Z^1$ and $Z^3$ are CH (or C if substituted with $R^2$).

7. The compound or a pharmaceutically acceptable salt thereof of claim 2 wherein $R^b$ and $R^c$ are hydrogen.

8. The compound or a pharmaceutically acceptable salt thereof of claim 2 wherein $R^b$ is cyano and $R^c$ is alkyl, substituted alkyl, cycloalkyl, or 3 to 6 membered saturated monocyclic heterocyclyl containing one or two heteroatoms selected from N, O, or S and optionally substituted with one or two substituents independently selected from hydroxy, alkyl or fluoro.

9. The compound or a pharmaceutically acceptable salt thereof of claim 8 wherein $R^c$ is alkyl.

10. The compound or a pharmaceutically acceptable salt thereof of claim 8 wherein $R^c$ is cycloalkyl.

11. The compound or a pharmaceutically acceptable salt thereof of claim 8 wherein $R^c$ is substituted alkyl.

12. The compound or a pharmaceutically acceptable salt thereof Of claim 8 wherein $R^c$ is alkyl substituted with hydroxy, alkoxy, —NRR' (where R is hydrogen, alkyl, hydroxyalkyl, or alkoxyalkyl and R' is hydrogen or alkyl) or heterocyclyl which is optionally substituted with one or two groups independently selected from alkyl or hydroxyl.

13. The compound or a pharmaceutically acceptable salt thereof of claim 8 wherein $R^c$ is 3 to 6 membered saturated monocyclic heterocyclyl containing one or two heteroatoms selected from N, O, or S and optionally substituted with one or two substituents independently selected from hydroxy, alkyl or fluoro.

14. The compound or a pharmaceutically acceptable salt thereof of claim 2 wherein —X—Y— is

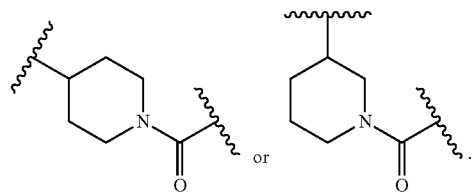 [SMILES: *C(=O)N1CCC(*)CC1 ; "or" ; *C(=O)N1CCCC(*)C1 ; "."]

15. The compound or a pharmaceutically acceptable salt thereof of claim 2 wherein —X—Y— is

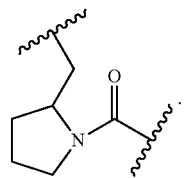 [SMILES: *CC1CCCN1C(*)=O ; "."]

16. The compound or a pharmaceutically acceptable salt thereof of claim 2 wherein —X—Y— is

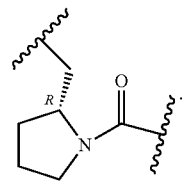

17. The compound or a pharmaceutically acceptable salt thereof of claim 2 wherein $R^1$ is hydrogen, —NR³COR⁴, or -(alkylene)-NR³R⁵ where $R^3$ is hydrogen or alkyl, $R^4$ is optionally substituted aryl or heteroaryl, and $R^5$ is hydrogen, alkyl, haloalkyl, or acyl or $R^3$ and $R^5$ together with the nitrogen atom to which they are attached form heterocycloamino optionally substituted with one or two substituents independently selected from alkyl, halo, hydroxyalkyl, or alkoxyalkyl.

18. The compound or a pharmaceutically acceptable salt thereof of claim 17 wherein $R^1$ is hydrogen.

19. The compound or a pharmaceutically acceptable salt thereof of claim 17 wherein $R^1$ is -(alkylene)-NR³R⁵ where $R^3$ is hydrogen or alkyl and $R^5$ is hydrogen, alkyl, haloalkyl, or acyl.

20. The compound or a pharmaceutically acceptable salt thereof of claim 17 wherein $R^1$ is (S)-CH₂N(COCF₃)CH(CH₃)C(CH₃)₃, (S)-CH₂NHCH(CH₃)C(CH₃)₃, or (S)-CH₂N(CH₃)CH(CH₃)C(CH₃)₃, preferably (S)-CH₂NHCH(CH₃)C(CH₃)₃.

21. The compound or a pharmaceutically acceptable salt thereof of claim 2 wherein $R^2$ is hydrogen.

22. A compound selected from:
N-(1-(1-acryloylpiperidin-4-yl)-1H-benzo[d]imidazol-2(3H)-ylidene)-4-chlorobenzamide;
N-(1-(1-acryloylpiperidin-4-yl)-1H-benzo[d]imidazol-2(3H)-ylidene)nicotinamide;
N-(1-(1-acryloylpiperidin-3-yl)-1H-benzo[d]imidazol-2(3H)-ylidene)-4-chlorobenzamide;
4-chloro-N-(1-(1-(2-cyano-4-methylpent-2-enoyl)piperidin-4-yl)-1H-benzo[d]imidazol-2(3H)-ylidene)benzamide;
N-(1-(1-(2-cyano-4-methylpent-2-enoyl)piperidin-3-yl)-1H-benzo[d]imidazol-2(3H)-ylidene)nicotinamide;
N-(1-(1-acryloylpiperidin-3-yl)-1H-benzo[d]imidazol-2(3H)-ylidene)nicotinamide;
4-chloro-N-(1-((1-(2-cyano-4-methylpent-2-enoyl)pyrrolidin-2-yl)methyl)-1H-benzo[d]imidazol-2(3H)-ylidene)benzamide;
N-(1-((1-acryloylpyrrolidin-2-yl)methyl)-1H-benzo[d]imidazol-2(3H)-ylidene)-4-chlorobenzamide;
N-(1-(1-(2-cyano-4-methylpent-2-enoyl)piperidin-4-yl)-1H-benzo[d]imidazol-2(3H)-ylidene)nicotinamide;

N-(1-((1-(2-cyano-4-methylpent-2-enoyl)pyrrolidin-2-yl) methyl)-1H-benzo[d]imidazol-2(3H)-ylidene)nicotinamide;

N-(1-((1-acryloylpyrrolidin-2-yl)methyl)-1H-benzo[d] imidazol-2(3H)-ylidene)nicotinamide;

(S)-N-(1-(1-acryloylpiperidin-4-yl)-5-(((3,3-dimethylbutan-2-yl)amino)methyl)-1H-benzo[d]imidazol-2(3H)-ylidene)-4-chlorobenzamide;

4-chloro-N-(1-(1-(2-cyano-4-methylpent-2-enoyl)piperidin-3-yl)-5-((N-((S)-3,3-dimethylbutan-2-yl)-2,2,2-trifluoroacetamido)methyl)-1H-benzo[d]imidazol-2(3H)-ylidene)benzamide;

N-(1-(1-acryloylpiperidin-3-yl)-5-((N-((S)-3,3-dimethylbutan-2-yl)-2,2,2-trifluoroacetamido)methyl)-1H-benzo[d]imidazol-2(3H)-ylidene)-4-chlorobenzamide;

4-chloro-N-(1-((1-(2-cyano-4-methylpent-2-enoyl)pyrrolidin-2-yl)methyl)-5-((N-((S)-3,3-dimethylbutan-2-yl)-2,2,2-trifluoroacetamido)methyl)-1H-benzo[d]imidazol-2(3H)-ylidene)benzamide;

N-(1-((1-acryloylpyrrolidin-2-yl)methyl)-5-((N-((S)-3,3-dimethylbutan-2-yl)-2,2,2-trifluoroacetamido)methyl)-1H-benzo[d]imidazol-2(3H)-ylidene)-4-chlorobenzamide;

4-chloro-N-(1-((1-(2-cyano-4-methylpent-2-enoyl)pyrrolidin-2-yl)methyl)-5-((((S)-3,3-dimethylbutan-2-yl)(methyl)amino)methyl)-1H-benzo[d]imidazol-2(3H)-ylidene)benzamide;

4-chloro-N-(1-(1-(2-cyano-4-methylpent-2-enoyl)piperidin-3-yl)-5-((((S)-3,3-dimethylbutan-2-yl)(methyl)amino)methyl)-1H-benzo[d]imidazol-2(3H)-ylidene)benzamide;

N-(1-(1-(2-cyano-4-methylpent-2-enoyl)piperidin-3-yl)-1H-benzo[d]imidazol-2(3H)-ylidene)-5-(1H-pyrazol-4-yl)thiophene-2-carboxamide N-(1-(1-acryloylpiperidin-3-yl)-1H-benzo[d]imidazol-2(3H)-ylidene)-5-(1H-pyrazol-4-yl)thiophene-2-carboxamide;

N-(1-(1-(2-cyano-4-(dimethylamino)-4-methylpent-2-enoyl)piperidin-3-yl)-1H-benzo[d]imidazol-2(3H)-ylidene)-5-(1H-pyrazol-4-yl)thiophene-2-carboxamide;

N-(1-(1-(4-(dimethylamino)but-2-enoyl)piperidin-3-yl)-1H-benzo[d]imidazol-2(3H)-ylidene)-5-(1H-pyrazol-4-yl)thiophene-2-carboxamide;

4-chloro-N-(1-(1-(2-cyano-4-methylpent-2-enoyl)piperidin-3-yl)-5-((((S)-3,3-dimethylbutan-2-yl)amino)methyl)-1H-benzo[d]imidazol-2(3H)-ylidene)benzamide;

N-(1-(1-(4-amino-2-cyano-4-methylpent-2-enoyl)piperidin-3-yl)-5-((((S)-3,3-dimethylbutan-2-yl)amino)methyl)-1H-benzo[d]imidazol-2(3H)-ylidene)-4-chlorobenzamide;

4-chloro-N-(1-(1-(2-cyano-4-methyl-4-(methylamino)pent-2-enoyl)piperidin-3-yl)-5-((((S)-3,3-dimethylbutan-2-yl)amino)methyl)-1H-benzo[d]imidazol-2-yl)benzamide;

4-chloro-N-(1-(1-(2-cyano-4-(dimethylamino)-4-methylpent-2-enoyl)piperidin-3-yl)-5-((((S)-3,3-dimethylbutan-2-yl)amino)methyl)-1H-benzo[d]imidazol-2-yl)benzamide;

N-(1-(1-acryloylpiperidin-3-yl)-5-((((S)-3,3-dimethylbutan-2-yl)amino)methyl)-1H-benzo[d]imidazol-2-yl)-4-chlorobenzamide;

4-chloro-N-(1-((1-(2-cyano-4-methylpent-2-enoyl)pyrrolidin-2-yl)methyl)-5-((((S)-3,3-dimethylbutan-2-yl)amino)methyl)-1H-benzo[d]imidazol-2-yl)benzamide;

N-(1-((1-(4-amino-2-cyano-4-methylpent-2-enoyl)pyrrolidin-2-yl)methyl)-5-((((S)-3,3-dimethylbutan-2-yl)amino)methyl)-1H-benzo[d]imidazol-2-yl)-4-chlorobenzamide;

4-chloro-N-(1-((1-(2-cyano-4-methyl-4-(methylamino)pent-2-enoyl)pyrrolidin-2-yl)methyl)-5-((((S)-3,3-dimethylbutan-2-yl)amino)methyl)-1H-benzo[d]imidazol-2-yl)benzamide;

4-chloro-N-(1-((1-(2-cyano-4-(dimethylamino)-4-methylpent-2-enoyl)pyrrolidin-2-yl)methyl)-5-((((S)-3,3-dimethylbutan-2-yl)amino)methyl)-1H-benzo[d]imidazol-2-yl)benzamide;

4-chloro-N-(1-((1-(2-cyano-4-ethoxy-4-methylpent-2-enoyl)pyrrolidin-2-yl)methyl)-5-((((S)-3,3-dimethylbutan-2-yl)amino)methyl)-1H-benzo[d]imidazol-2-yl)benzamide;

N-(1(1-acryloylpyrrolidin-2-yl)methyl)-5-((((S)-3,3-dimethylbutan-2-yl)amino)methyl)-1H-benzo[d]imidazol-2-yl)-4-chlorobenzamide;

N-(1-(((R)-1-acryloylpyrrolidin-2-yl)methyl)-5-((((S)-3,3-dimethylbutan-2-yl)amino)methyl)-1H-benzo[d]imidazol-2-yl)-4-chlorobenzamide;

4-chloro-N-(1-(1-(2-cyano-4,4-dimethylpent-2-enoyl)piperidin-3-yl)-5-((((S)-3,3-dimethylbutan-2-yl)amino)methyl)-1H-benzo[d]imidazol-2-yl)benzamide;

4-chloro-N-(1-((1-(2-cyano-4,4-dimethylpent-2-enoyl)pyrrolidin-2-yl)methyl)-5-((((S)-3,3-dimethylbutan-2-yl)amino)methyl)-1H-benzo[d]imidazol-2-yl)benzamide;

N-(1((1-acryloylpyrrolidin-2-yl)methyl)-5-((((S)-3,3-dimethylbutan-2-yl)amino)methyl)-1H-benzo[d]imidazol-2-yl)-4-(difluoromethyl)benzamide;

N-(1-((1-(2-cyano-4-methylpent-2-enoyl)pyrrolidin-2-yl)methyl)-5-((((S)-3,3-dimethylbutan-2-yl)amino)methyl)-1H-benzo[d]imidazol-2-yl)-4-(difluoromethyl)benzamide;

N-(1-((1-acryloylpyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide;

N-(1-((1-(2-cyano-4-methylpent-2-enoyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-1H-benzo[d]imidazol-2-yl)-5-(1H-pyrazol-4-yl)thiophene-2-carboxamide;

N-(1-((1-(2-cyano-4-methylpent-2-enoyl)azetidin-3-yl)methyl)-1H-benzo[d]imidazol-2-yl)-5-(1H-pyrazol-4-yl)thiophene-2-carboxamide;

(R)-N-(1-((1-(4-amino-2-cyano-4-methylpent-2-enoyl)pyrrolidin-2-yl)methyl)-1H-benzo[d]imidazol-2-yl)-5-(1H-pyrazol-4-yl)thiophene-2-carboxamide;

(R)-N-(1-((1-(2-cyano-4-methyl-4-morpholinopent-2-enoyl)pyrrolidin-2-yl)methyl)-1H-benzo[d]imidazol-2-yl)-5-(1H-pyrazol-4-yl)thiophene-2-carboxamide;

(S)-N-(1-((1-(2-cyano-4-methylpent-2-enoyl)pyrrolidin-2-yl)methyl)-1H-benzo[d]imidazol-2-yl)-5-(1H-pyrazol-4-yl)thiophene-2-carboxamide;

N-(1-((1-(4-amino-2-cyano-4-methylpent-2-enoyl)azetidin-3-yl)methyl)-1H-benzo[d]imidazol-2-yl)-5-(1H-pyrazol-4-yl)thiophene-2-carboxamide;

(S)-N-(1((1-(4-amino-2-cyano-4-methylpent-2-enoyl)pyrrolidin-2-yl)methyl)-1H-benzo[d]imidazol-2-yl)-5-(1H-pyrazol-4-yl)thiophene-2-carboxamide;

(S)-N-(1-((1-(2-cyano-4-methyl-4-morpholinopent-2-enoyl)pyrrolidin-2-yl)methyl)-1H-benzo[d]imidazol-2-yl)-5-(1H-pyrazol-4-yl)thiophene-2-carboxamide;

N-(1-(2-(2-cyano-4-methylpent-2-enamido)ethyl)-1H-benzo[d]imidazol-2-yl)-5-(1H-pyrazol-4-yl)thiophene-2-carboxamide;

N-(1-((1-(2-cyano-4-methyl-4-morpholinopent-2-enoyl)azetidin-3-yl)methyl)-1H-benzo[d]imidazol-2-yl)-5-(1H-pyrazol-4-yl)thiophene-2-carboxamide;

N-(1-(2-(4-amino-2-cyano-4-methylpent-2-enamido)ethyl)-1H-benzo[d]imidazol-2-yl)-5-(1H-pyrazol-4-yl)thiophene-2-carboxamide;

N-(1-(2-(2-cyano-4-methyl-4-morpholinopent-2-enamido)ethyl)-1H-benzo[d]imidazol-2-yl)-5-(1H-pyrazol-4-yl)thiophene-2-carboxamide;

(R)-N-(1-((1-(2-cyano-4-methylpent-2-enoyl)pyrrolidin-2-yl)methyl)-1H-benzo[d]imidazol-2-yl)-5-(difluoromethyl)thiophene-2-carboxamide;

(S)-N-(1-((1-(2-cyano-4-methylpent-2-enoyl)pyrrolidin-2-yl)methyl)-1H-benzo[d]imidazol-2-yl)-5-(difluoromethyl)thiophene-2-carboxamide;

N-(1-(2-(2-cyano-N,4-dimethylpent-2-enamido)ethyl)-1H-benzo[d]imidazol-2-yl)-5-(1H-pyrazol-4-yl)thiophene-2-carboxamide;

N-(1-(2-(2-cyano-N,4-dimethyl-4-morpholinopent-2-enamido)ethyl)-1H-benzo[d]imidazol-2-yl)-5-(1H-pyrazol-4-yl)thiophene-2-carboxamide;

N-(1-(((S)-1-acryloylpyrrolidin-2-yl)methyl)-5-((((S)-3,3-dimethylbutan-2-yl)amino)methyl)-1H-benzo[d]imidazol-2-yl)-4-chlorobenzamide;

N-(1-(((R)-1-acryloylpyrrolidin-2-yl)methyl)-5-((((S)-3,3-dimethylbutan-2-yl)amino)methyl)-1H-benzo[d]imidazol-2-yl)-4-chlorobenzamide;

N-(1-(((R)-1-acryloylpyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide;

N-(1-(((R)-1-(2-cyano-4-methylpent-2-enoyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide;

N-(1-(((R)-1-(2-cyano-4,4-dimethylpent-2-enoyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide;

N-(1-(((R)-1-(2-cyano-3-cyclopropylacryloyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide;

N-(1-(((R)-1-(2-cyano-3-(3-methyloxetan-3-yl)acryloyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide;

N-(1-(((R)-1-(2-cyano-4-ethoxy-4-methylpent-2-enoyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide;

(R)-N-(1-((1-(2-cyano-4,4-dimethylpent-2-enoyl)pyrrolidin-2-yl)methyl)-1H-benzo[d]imidazol-2-yl)-5-(difluoromethyl)thiophene-2-carboxamide;

(R)-N-(1-((1-(2-cyano-4-(dimethylamino)-4-methylpent-2-enoyl)pyrrolidin-2-yl)methyl)-1H-benzo[d]imidazol-2-yl)-5-(difluoromethyl)thiophene-2-carboxamide;

(R)-N-(1-acryloylpyrrolidin-2-yl)methyl)-1H-benzo[d]imidazol-2-yl)-5-(difluoromethyl)thiophene-2-carboxamide;

N-(1-(2-(2-cyano-N,4,4-trimethylpent-2-enamido)ethyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-1H-benzo[d]imidazol-2-yl)isoxazole-5-carboxamide;

(R)-N-(1-((1-(2-cyano-4-methylpent-2-enoyl)pyrrolidin-2-yl)methyl)-1H-benzo[d]imidazol-2-yl)-3-(difluoromethyl)benzamide;

(R)-N-(1-((1-(2-cyano-4-methylpent-2-enoyl)pyrrolidin-2-yl)methyl)-1H-benzo[d]imidazol-2-yl)-3-(trifluoromethyl)benzamide;

(R)-N-(1-((1-(2-cyano-4-methylpent-2-enoyl)pyrrolidin-2-yl)methyl)-1H-benzo[d]imidazol-2-yl)-3-methylbenzamide;

(R)-N-(1-((1-(2-cyano-4-methylpent-2-enoyl)pyrrolidin-2-yl)methyl)-1H-benzo[d]imidazol-2-yl)-3,4-difluorobenzamide;

(R)-N-(1-((1-(2-cyano-5-hydroxy-4,4-dimethylpent-2-enoyl)pyrrolidin-2-yl)methyl)-1H-benzo[d]imidazol-2-yl)-5-(difluoromethyl)thiophene-2-carboxamide.

(R)-N-(1-((1-(4-amino-2-cyano-4-methylpent-2-enoyl)pyrrolidin-2-yl)methyl)-1H-benzo[d]imidazol-2-yl)-5-(difluoromethyl)thiophene-2-carboxamide;

(S)-N-(1-(1-(4-amino-2-cyano-4-methylpent-2-enoyl)pyrrolidin-3-yl)-1H-benzo[d]imidazol-2-yl)-5-(difluoromethyl)thiophene-2-carboxamide;

N-(1-((1-(4-amino-2-cyano-4-methylpent-2-enoyl)azetidin-3-yl)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-1H-benzo[d]imidazol-2-yl)-5-(difluoromethyl)thiophene-2-carboxamide;

(S)-N-(1-((1-(2-cyano-4-methylpent-2-enoyl)pyrrolidin-2-yl)methyl)-1H-benzo[d]imidazol-2-yl)-5-(difluoromethyl)thiophene-2-carboxamide;

N-(1-(2-(2-cyano-N,4-dimethyl-4-morpholinopent-2-enamido)ethyl)-1H-benzo[d]imidazol-2-yl)-5-(difluoromethyl)thiophene-2-carboxamide;

N-(1-(2-(2-cyano-4-(dimethylamino)-N,4-dimethylpent-2-enamido)ethyl)-1H-benzo[d]imidazol-2-yl)-5-(difluoromethyl)thiophene-2-carboxamide;

N-(1-((1-(2-cyano-4-(dimethylamino)-4-methylpent-2-enoyl)azetidin-3-yl)methyl)-1H-benzo[d]imidazol-2-yl)-5-(difluoromethyl)thiophene-2-carboxamide;

N-(1-((1-(2-cyano-4-methyl-4-morpholinopent-2-enoyl)azetidin-3-yl)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-(hydroxymethyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-((neopentylamino)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-(morpholinomethyl)-1H-benzo[d]imidazol-2-yl)-5-(difluoromethyl)thiophene-2-carboxamide;

N-(1-(((R)-1-(2-cyano-4-methylpent-2-enoyl)pyrrolidin-2-yl)methyl)-5-((2,6-dimethylmorpholino)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-(((2,2,2-trifluoroethyl)amino)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-((4-methylpiperazin-1-yl)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-6-((neopentylamino)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-6-(morpholinomethyl)-1H-benzo[d]imidazol-2-yl)-5-(difluoromethyl)thiophene-2-carboxamide;

N-(1-(((R)-1-(2-cyano-4-methylpent-2-enoyl)pyrrolidin-2-yl)methyl)-6-((2,6-dimethylmorpholino)methyl)-1H-benzo[d]imidazol-2-yl)-5-(difluoromethyl)thiophene-2-carboxamide;

N-(1-(((R)-1-(2-cyano-4-methylpent-2-enoyl)pyrrolidin-2-yl)methyl)-6-((((S)-3,3-dimethylbutan-2-yl)amino)methyl)-1H-benzo[d]imidazol-2-yl)-5-(difluoromethyl)thiophene-2-carboxamide;

N-(1-(((R)-1-(2-cyano-4-methylpent-2-enoyl)pyrrolidin-2-yl)methyl)-6-((((R)-3,3-dimethylbutan-2-yl)amino)methyl)-1H-benzo[d]imidazol-2-yl)-5-(difluoromethyl)thiophene-2-carboxamide;

(R)-N-(1-((1-(5-amino-2-cyano-4,4-dimethylpent-2-enoyl)pyrrolidin-2-yl)methyl)-1H-benzo[d]imidazol-2-yl)-5-(difluoromethyl)thiophene-2-carboxamide;

(R)-N-(1-((1(2-cyano-4,4-dimethylpent-2-enoyl)pyrrolidin-2-yl)methyl)-5-((neopentylamino)methyl)-1H-benzo[d]imidazol-2-yl)-5-(difluoromethyl)thiophene-2-carboxamide;

(R)-N-(1-((1 (2-cyano-4,4-dimethylpent-2-enoyl)pyrrolidin-2-yl)methyl)-5-(morpholinomethyl)-1H-benzo[d]imidazol-2-yl)-5-(difluoromethyl)thiophene-2-carboxamide; 97

N-(1-(((R)-1-(2-cyano-4,4-dimethylpent-2-enoyl)pyrrolidin-2-yl)methyl)-5-((2,6-dimethylmorpholino)methyl)-1H-benzo[d]imidazol-2-yl)-5-(difluoromethyl)thiophene-2-carboxamide;

(R)-N-(1-((1-(2-cyano-3-(3-methyloxetan-3-yl)acryloyl)pyrrolidin-2-yl)methyl)-5-((neopentylamino)methyl)-1H-benzo[d]imidazol-2-yl)-5-(difluoromethyl)thiophene-2-carboxamide;

(R)-N-(1-((1-(2-cyano-3-(3-methyloxetan-3-yl)acryloyl)pyrrolidin-2-yl)methyl)-5-(morpholinomethyl)-1H-benzo[d]imidazol-2-yl)-5-(difluoromethyl)thiophene-2-carboxamide;

N-(1-(((R)-1-(2-cyano-3-(3-methyloxetan-3-yl)acryloyl)pyrrolidin-2-yl)methyl)-5-((2,6-dimethylmorpholino)methyl)-1H-benzo[d]imidazol-2-yl)-5-(difluoromethyl)thiophene-2-carboxamide, (R)-N-(1-((1-(2-cyano-4-methylpent-2-enoyl)pyrrolidin-2-yl)methyl)-5-((isobutylamino)methyl)-1H-benzo[d]imidazol-2-yl)-5-(difluoromethyl)thiophene-2-carboxamide;

(R)-N-(1-((1-(2-cyano-4,4-dimethylpent-2-enoyl)pyrrolidin-2-yl)methyl)-5-((isobutylamino)methyl)-1H-benzo[d]imidazol-2-yl)-5-(difluoromethyl)thiophene-2-carboxamide;

(R)-N-(1-((1-(2-cyano-3-(3-methyloxetan-3-yl)acryloyl)pyrrolidin-2-yl)methyl)-5-((isobutylamino)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-((((3-methyloxetan-3-yl)methyl)amino)methyl)-1H-benzo[d]imidazol-2-yl)-5-(difluoromethyl)thiophene-2-carboxamide;

(R)-N-(1-((1-(2-cyano-4,4-dimethylpent-2-enoyl)pyrrolidin-2-yl)methyl)-5-((((3-methyloxetan-3-yl)methyl)amino)methyl)-1H-benzo[d]imidazol-2-yl)-5-(difluoromethyl)thiophene-2-carboxamide;

(R)-N-(1-((1-(2-cyano-3-(3-methyloxetan-3-yl)acryloyl)pyrrolidin-2-yl)methyl)-5-((((3-methyloxetan-3-yl)methyl)amino)methyl)-1H-benzo[d]imidazol-2-yl)-5-(difluoromethyl)thiophene-2-carboxamide;

(R)-N-(5-(2-oxa-6-azaspiro[3.3]heptan-6-ylmethyl)-1-((1-(2-cyano-4-methylpent-2-enoyl)pyrrolidin-2-yl)methyl)-1H-benzo[d]imidazol-2-yl)-5-(difluoromethyl)thiophene-2-carboxamide;

N-(1-(((R)-1-(but-2-ynoyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide;

N-(1-(((R)-1-(but-2-ynoyl)pyrrolidin-2-yl)methyl)-5-((((S)-3,3-dimethylbutan-2-yl)amino)methyl)-1H-benzo[d]imidazol-2-yl)-4-chlorobenzamide;

N-(1-(1-(but-2-ynoyl)piperidin-3-yl)-5-((((S)-3,3-dimethylbutan-2-yl)amino)methyl)-1H-benzo[d]imidazol-2-yl)-5-(difluoromethyl)thiophene-2-carboxamide;

N-(1-(1-(but-2-ynoyl)piperidin-3-yl)-5-((((S)-3,3-dimethylbutan-2-yl)amino)methyl)-1H-benzo[d]imidazol-2-yl)-4-chlorobenzamide;

(R)-N-(1-((1-(2-cyano-3-(3-methyloxetan-3-yl)acryloyl)pyrrolidin-2-yl)methyl)-5-((neopentylamino)methyl)-1H-benzo[d]imidazol-2-yl)-5-(difluoromethyl)thiophene-2-carboxamide.

(R)-N-(1-((1-(5-amino-2-cyano-4,4-dimethylpent-2-enoyl)pyrrolidin-2-yl)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-6-((neopentylamino)-methyl)-1H-benzo[d]imidazol-2-yl)-5-(difluoromethyl)thiophene-2-carboxamide;

(R)-N-(1-((1-(2-cyano-3-(3-methyloxetan-3-yl)acryloyl)pyrrolidin-2-yl)methyl)-6-((neopentylamino)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-(((2-hydroxy-2-methylpropyl)amino)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-(((cyclopropylmethyl)amino)methyl)-1H-benzo[d]imidazol-2-yl)-5-(difluoromethyl)thiophene-2-carboxamide;

(R)-1-((1-(2-cyano-4-methylpent-2-enoyl)pyrrolidin-2-yl)methyl)-2-(5-(difluoromethyl)thiophene-2-carboxamido)-N-neopentyl-1H-benzo[d]imidazole-5-carboxamide;

(R)-1-((1-(2-cyano-3-(3-methyloxetan-3-yl)acryloyl)pyrrolidin-2-yl)methyl)-2-(5-(difluoromethyl)thiophene-2-carboxamido)-N-neopentyl-1H-benzo[d]imidazole-5-carboxamide;

(R)-N-(1-((1-(2-cyano-4-methylpent-2-enoyl)pyrrolidin-2-yl)methyl)-5-((3-(2-hydroxypropan-2-yl)azetidin-1-yl)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-((3-hydroxyazetidin-1-yl)methyl)-1H-benzo[d]imidazol-2-yl)-5-(difluoromethyl)thiophene-2-carboxamide;

(R)-N-(1-((1-(2-cyano-4-methylpent-2-enoyl)pyrrolidin-2-yl)methyl)-5-((4-(2-hydroxypropan-2-yl)piperidin- 1-yl)methyl)-1H-benzo[d]imidazol-2-yl)-5-(difluoromethyl)thiophene-2-carboxamide;
(R)-N-(1-(1-(2-cyano-4,4-dimethylpent-2-enoyl)piperidin-3-yl)-1H-benzo imidazol-2-yl)-5-(difluoromethyl)thiophene-2-carboxamide;
(S)-N-(1-(1-(2-cyano-4,4-dimethylpent-2-enoyl)piperidin-3-yl)-1H-benzo imidazol-2-yl)-5-(difluoromethyl)thiophene-2-carboxamide;
(R)-N-(1-((1-(2-cyano-4,4-dimethyl-5-morpholinopent-2-enoyl)pyrrolidin-2-yl)methyl)-5-(hydroxymethyl)-1H-benzo[d]imidazol-2-yl)-5-(difluoromethyl)thiophene-2-carboxamide;
(R)-1-((1-acryloylpyrrolidin-2-yl)methyl)-2-(5-(difluoromethyl)thiophene-2-carboxamido)-N-neopentyl-1H-benzo[d]imidazole-5-carboxamide;
N-(3-(((R)-1-(2-cyano-4-(2-methoxyethoxy)-4-methylpent-2-enoyl)pyrrolidin-2-yl)methyl)-6-((((S)-3,3-dimethylbutan-2-yl)amino)methyl)-3H-imidazo[4,5-b]pyridin-2-yl)-5-(difluoromethyl)thiophene-2-carboxamide;
1-(((R)-1-acryloylpyrrolidin-2-yl)methyl)-2-(5-(difluoromethyl)thiophene-2-carboxamido)-N-((S)-3,3-dimethylbutan-2-yl)-1H-benzo[d]imidazole-5-carboxamide;
(S)-N-(1-((1-(2-cyano-4,4-dimethylpent-2-enoyl)azetidin-3-yl)methyl)-5-(((3,3-dimethylbutan-2-yl)amino)methyl)-1H-benzo[d]imidazol-2-yl)-5-(difluoromethyl)thiophene-2-carboxamide;
1-(((R)-1-(2-cyano-4,4-dimethylpent-2-enoyl)pyrrolidin-2-yl)methyl)-2-(5-(difluoromethyl)thiophene-2-carboxamido)-N-((S)-3,3-dimethylbutan-2-yl)-1H-benzo[d]imidazole-5-carboxamide;
(R)-N-(1-((1-(2-cyano-4-methylpent-2-enoyl)pyrrolidin-2-yl)methyl)-5-(3-hydroxypentan-3-yl)-1H-benzo[d]imidazol-2-yl)-5-(difluoromethyl)thiophene-2-carboxamide;
N-(1-((1-(2-cyano-4,4-dimethylpent-2-enoyl)pyrrolidin-3-yl)methyl)-5-((((S)-3,3-dimethylbutan-2-yl)amino)methyl)-1H-benzo[d]imidazol-2-yl)-5-(difluoromethyl)thiophene-2-carboxamide;
(R)-N-(1-((1-(2-cyano-4-ethoxy-4-methylpent-2-enoyl)pyrrolidin-2-yl)methyl)-5-((neopentylamino)methyl)-1H-benzo[d]imidazol-2-yl)-5-(difluoromethyl)thiophene-2-carboxamide;
(R)-N-(1-((1-(2-cyano-4-methylpent-2-enoyl)pyrrolidin-2-yl)methyl)-5-((neopentylamino)-methyl)-1H-benzo[d]imidazol-2-yl)isoxazole-5-carboxamide;
(R)-N-(1-((1-(2-cyano-4,4-dimethylpent-2-enoyl)pyrrolidin-2-yl)methyl)-5-((neopentylamino)methyl)-1H-benz[d]imidazol-2-yl)isoxazole-5-carboxamide;
(R)-N-(1-((1-(2-cyano-3-(3-methyloxetan-3-yl)acryloyl)pyrrolidin-2-yl)methyl)-5-((neopentylamino)methyl)-1H-benzo[d]imidazol-2-yl)isoxazole-5-carboxamide;
(R)-N-(1-((1-(2-cyano-4-methylpent-2-enoyl)pyrrolidin-2-yl)methyl)-5-((neopentylamino)methyl)-1H-benzo[d]imidazol-2-yl)nicotinamide;
(R)-N-(1-((1-(2-cyano-4-methylpent-2-enoyl)pyrrolidin-2-yl)methyl)-5-((neopentylamino)methyl)-1H-benzo[d]imidazol-2-yl)-3-(difluoromethyl)benzamide;
N-(1-(((R)-1-(2-cyano-4,4-dimethylpent-2-enoyl)pyrrolidin-2-yl)methyl)-5-((((S)-3,3-dimethylbutan-2-yl)amino)methyl)-1H-benzo[d]imidazol-2-yl)isoxazole-5-carboxamide;
N-(1-(((R)-1-(2-cyano-4-ethoxy-4-methylpent-2-enoyl)pyrrolidin-2-yl)methyl)-5-((((S)-3,3-dimethylbutan-2-yl)amino)methyl)-1H-benzo[d]imidazol-2-yl)isoxazole-5-carboxamide;
N-(1-(((R)-1-(2-cyano-4,4-dimethylpent-2-enoyl)pyrrolidin-3-yl)methyl)-5-((((S)-3,3-dimethylbutan-2-yl)amino)methyl)-1H-benzo[d]imidazol-2-yl)isoxazole-5-carboxamide;
N-(1-(((R)-1-(2-cyano-4-ethoxy-4-methylpent-2-enoyl)pyrrolidin-3-yl)methyl)-5-((((S)-3,3-dimethylbutan-2-yl)amino)methyl)-1H-benzo[d]imidazol-2-yl)isoxazole-5-carboxamide;
N-(1-(((S)-1-(2-cyano-4,4-dimethylpent-2-enoyl)pyrrolidin-3-yl)methyl)-5-((((S)-3,3-dimethylbutan-2-yl)amino)methyl)-1H-benzo[d]imidazol-2-yl)isoxazole-5-carboxamide;
N-(1-(((S)-1-(2-cyano-4-ethoxy-4-methylpent-2-enoyl)pyrrolidin-3-yl)methyl)-5-((((S)-3,3-dimethylbutan-2-yl)amino)methyl)-1H-benzo[d]imidazol-2-yl)isoxazole-5-carboxamide;
N-(1-(((S)-1-(2-cyano-4,4-dimethylpent-2-enoyl)pyrrolidin-3-yl)methyl)-5-((((S)-3,3-dimethylbutan-2-yl)amino)methyl)-1H-benzo[d]imidazol-2-yl)-5-(difluoromethyl)thiophene-2-carboxamide;
N-(1-(((S)-1-(2-cyano-4-ethoxy-4-methylpent-2-enoyl)pyrrolidin-3-yl)methyl)-5-((((S)-3,3-dimethylbutan-2-yl)amino)methyl)-1H-benzo[d]imidazol-2-yl)-5-(difluoromethyl)thiophene-2-carboxamide;
N-(1-(((R)-1-(2-cyano-4,4-dimethylpent-2-enoyl)pyrrolidin-3-yl)methyl)-5-((((S)-3,3-dimethylbutan-2-yl)amino)methyl)-1H-benzo[d]imidazol-2-yl)-5-(difluoromethyl)thiophene-2-carboxamide;
N-(1-(((R)-1-(2-cyano-4-ethoxy-4-methylpent-2-enoyl)pyrrolidin-3-yl)methyl)-5-((((S)-3,3-dimethylbutan-2-yl)amino)methyl)-1H-benzo[d]imidazol-2-yl)-5-(difluoromethyl)thiophene-2-carboxamide; N-(1-(((R)-1-(2-cyano-4,4-dimethylpent-2-enoyl)pyrrolidin-2-yl)methyl)-5-((((S)-3,3-dimethylbutan-2-yl)amino)methyl)-1H-benzo[d]imidazol-2-yl)-3-(difluoromethyl)benzamide;
N-(1-(((R)-1-(2-cyano-4-methylpent-2-enoyl)pyrrolidin-2-yl)methyl)-5-((((S)-3,3-dimethylbutan-2-yl)amino)methyl)-1H-benzo[d]imidazol-2-yl)-3-(difluoromethyl)benzamide;
N-(1-(((R)-1-(2-cyano-4-ethoxy-4-methylpent-2-enoyl)pyrrolidin-2-yl)methyl)-5-((((S)-3,3-dimethylbutan-2-yl)amino)methyl)-1H-benzo[d]imidazol-2-yl)-3-(difluoromethyl)benzamide;
(R)-N-(1-(1-(2-cyano-4,4-dimethylpent-2-enoyl)piperidin-3-yl)-5-(hydroxymethyl)-1H-benzo[d]imidazol-2-yl)-5-(difluoromethyl)thiophene-2-carboxamide;
N-(1-((R)-1-(2-cyano-4-ethoxy-4-methylpent-2-enoyl)pyrrolidin-3-yl)-5-((((S)-3,3-dimethylbutan-2-yl)amino)methyl)-1H-benzo[d]imidazol-2-yl)-5-(difluoromethyl)thiophene-2-carboxamide;
N-(1-((R)-1-(2-cyano-4-methylpent-2-enoyl)pyrrolidin-3-yl)-5-((((S)-3,3-dimethylbutan-2-yl)amino)methyl)-1H-benzo[d]imidazol-2-yl)-5-(difluoromethyl)thiophene-2-carboxamide;
N-(3-(((R)-1-(2-cyano-4,4-dimethylpent-2-enoyl)pyrrolidin-2-yl)methyl)-6-((((S)-3,3-dimethylbutan-2-yl)amino)methyl)-3H-imidazo[4,5-b]pyridin-2-yl)-5-(difluoromethyl)thiophene-2-carboxamide;
N-(3-(((R)-1-(2-cyano-4-ethoxy-4-methylpent-2-enoyl)pyrrolidin-2-yl)methyl)-6-((((S)-3,3-dimethylbutan-2-yl)amino)methyl)-3H-imidazo[4,5-b]pyridin-2-yl)-5-(difluoromethyl)thiophene-2-carboxamide;
(R)-N-(3-((1-(2-cyano-4,4-dimethylpent-2-enoyl)pyrrolidin-2-yl)methyl)-6-((neopentylamino)methyl)-3H-imidazo[4,5-b]pyridin-2-yl)-5-(difluoromethyl)thiophene-2-carboxamide; and (R)-N-(3-((1-(2-cyano-4-ethoxy-4-methylpent-2-enoyl)
pyrrolidin-2-yl)methyl)-6-((neopentylamino)methyl)-
3H-imidazo[4,5-b]pyridin-2-yl)-5-(difluoromethyl)
thiophene-2-carboxamide;
an individual E or Z isomer thereof; or
a pharmaceutically acceptable salt of any of the above
compounds.

23. A pharmaceutical composition comprising a compound of claim 1 or a pharmaceutically acceptable salt thereof; and a pharmaceutically acceptable excipient.

24. A method of relieving or causing regression of asthma, allergic dermatitis, atopic dermatitis, or psoriasis in a patient which method comprises administering to the patient in need thereof, a pharmaceutical composition comprising a therapeutically effective amount of a compound of claim 1 or a pharmaceutically acceptable salt thereof, and a pharmaceutically acceptable excipient.

25. The compound or a pharmaceutically acceptable salt thereof of claim 3 wherein $R^b$ and $R^c$ are hydrogen.

26. The compound or a pharmaceutically acceptable salt thereof of claim 3 wherein $R^b$ is cyano and $R^c$ is alkyl, substituted alkyl, cycloalkyl, or 3 to 6 membered saturated monocyclic heterocyclyl containing one or two heteroatoms selected from N, O, or S and optionally substituted with one or two substituents independently selected from hydroxy, alkyl or fluoro.

27. The compound or a pharmaceutically acceptable salt thereof of claim 25 wherein —X—Y— is

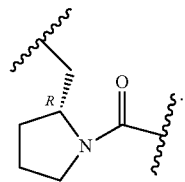

28. The compound or a pharmaceutically acceptable salt thereof of claim 27 wherein $R^2$ is hydrogen.

29. N-(1-(((R)-1-acryloylpyrrolidin-2-yl)methyl)-5-((((S)-3,3-dimethylbutan-2-yl)amino)-methyl)-1H-benzo[d]imidazol-2-yl)-5-(difluoromethyl)thiophene-2-carboxamide; or a pharmaceutically acceptable salt thereof.

30. A pharmaceutical composition comprising N-(1-(((R)-1-acryloylpyrrolidin-2-yl)methyl)-5-((((S)-3,3-dimethylbutan-2-yl)amino)-methyl)-1H-benzo[d]imidazol-2-yl)-5-(difluoromethyl)thiophene-2-carboxamide; or a pharmaceutically acceptable salt thereof and a pharmaceutically acceptable excipient.

31. The method of claim 24 wherein the pharmaceutical composition comprises N-(1-(((R)-1-acryloylpyrrolidin-2-yl)methyl)-5-((((S)-3,3-dimethylbutan-2-yl)amino)-methyl)-1H-benzo[d]imidazol-2-yl)-5-(difluoromethyl)thiophene-2-carboxamide; or a pharmaceutically acceptable salt thereof and a pharmaceutically acceptable excipient.

* * * * *